(12) United States Patent
Scanlan et al.

(10) Patent No.: US 7,560,537 B2
(45) Date of Patent: Jul. 14, 2009

(54) HUMAN SARCOMA-ASSOCIATED ANTIGENS

(75) Inventors: Matthew J. Scanlan, New York, NY (US); Sang-Yull Lee, New York, NY (US); Lloyd J. Old, New York, NY (US)

(73) Assignee: Ludwig Institute for Cancer Research, New York, NY (US)

(*) Notice: Subject to any disclaimer, the term of this patent is extended or adjusted under 35 U.S.C. 154(b) by 241 days.

(21) Appl. No.: 10/260,708

(22) Filed: Sep. 30, 2002

(65) Prior Publication Data

US 2004/0063101 A1     Apr. 1, 2004

(51) Int. Cl.
*C07H 21/02* (2006.01)
(52) U.S. Cl. .................................. 536/23.1
(58) Field of Classification Search ............... 536/23.1, 536/32.1
See application file for complete search history.

(56) References Cited

U.S. PATENT DOCUMENTS 6,392,019 B1 * 5/2002 Ford et al. ............... 530/387.9
6,783,961 B1 * 8/2004 Edwards et al. ............ 435/91.1
6,835,556 B2    12/2004 Attersand et al.

FOREIGN PATENT DOCUMENTS

WO     WO-01/40466 A2     6/2001
WO     WO-2004/031354 A2     4/2004

OTHER PUBLICATIONS

Westerhuis et al (J. Am. Soc. Nephrol., 1999, 10:770-778).*
Wildner et al. (Cancer Research, 1999, 59:5233-5238).*
Tockman et al (Cancer Res., 1992, 52:2711s-2718s).*
1997/1998 Stratagene catalog.*
Sequence comparison.*
Genbank Submission; NIH/NCBI, Accession No. AY211909. Lee et al. Mar. 23, 2003.
Genbank Submission; NIH/NCBI, Accession No. AY211910. Lee et al. Mar. 23, 2003.
Genbank Submission; NIH/NCBI, Accession No. AY211911. Lee et al. Mar. 23, 2003.
Genbank Submission; NIH/NCBI, Accession No. AY211912. Lee et al. Mar. 23, 2003.
Genbank Submission; NIH/NCBI, Accession No. AY211913. Lee et al. Mar. 23, 2003.
Genbank Submission; NIH/NCBI, Accession No. AY211914. Lee et al. Mar. 23, 2003.
Genbank Submission; NIH/NCBI, Accession No. AY211915. Lee et al. Mar. 23, 2003.
Genbank Submission; NIH/NCBI, Accession No. AY211916. Lee et al. Mar. 23, 2003.
Genbank Submission; NIH/NCBI, Accession No. AY211917. Lee et al. Mar. 23, 2003.
Genbank Submission; NIH/NCBI, Accession No. AY211918. Lee et al. Mar. 23, 2003.
Genbank Submission; NIH/NCBI, Accession No. AY211919. Lee et al. Mar. 23, 2003.
Genbank Submission; NIH/NCBI, Accession No. AY211920. Lee et al. Mar. 23, 2003.
Genbank Submission; NIH/NCBI, Accession No. AY211921. Lee et al. Mar. 23, 2003.
Genbank Submission; NIH/NCBI, Accession No. AY211922. Lee et al. Mar. 23, 2003.
Genbank Submission; NIH/NCBI, Accession No. AY211923. Lee et al. Mar. 23, 2003.
Genbank Submission; NIH/NCBI, Accession No. AY211924. Lee et al. Mar. 23, 2003.
Genbank Submission; NIH/NCBI, Accession No. AY211925. Lee et al. Mar. 23, 2003.
Genbank Submission; NIH/NCBI, Accession No. AY211926. Lee et al. Mar. 23, 2003.
Genbank Submission; NIH/NCBI, Accession No. AY211927. Lee et al. Mar. 23, 2003.
Genbank Submission; NIH/NCBI, Accession No. AY211928. Lee et al. Mar. 23, 2003.
Genbank Submission; NIH/NCBI, Accession No. AY211929. Lee et al. Mar. 23, 2003.
Genbank Submission; NIH/NCBI, Accession No. AY211930. Lee et al. Mar. 23, 2003.
Genbank Submission; NIH/NCBI, Accession No. AY211931. Lee et al. Mar. 23, 2003.
Genbank Submission; NIH/NCBI, Accession No. AA909915. Last updated May 19, 1998.
Genbank Submission; NIH/NCBI, Accession No. AW893050. Last updated Sep. 28, 2004
Genbank Submission; NIH/NCBI, Accession No. AK098602. Oshima et al. Sep. 14, 2006.
Genbank Submission; NIH/NCBI, Accession No. BI465380. Last updated Aug. 21, 2006.
Genbank Submission; NIH/NCBI, Accession No. BG771667. Last updated May 15, 2001.
Genbank Submission; NIH/NCBI, Accession No. AA906131. Last updated May 19, 1998.
Genbank Submission; NIH/NCBI, Accession No. BC034320. Strausberg et al. Jul. 17, 2006.
Genbank Submission; NIH/NCBI, Accession No. NM_152578. Lee et al. Nov. 17, 2006.
Genbank Submission; NIH/NCBI, Accession No. BX098898. Last updated Feb. 6, 2003.
Genbank Submission; NIH/NCBI, Accession No. CV024823. Last updated Aug. 20, 2004.
Genbank Submission; NIH/NCBI, Accession No. BP370444. Last updated Apr. 24, 2006.

(Continued)

*Primary Examiner*—Sean E Aeder
(74) *Attorney, Agent, or Firm*—Wolf, Greenfield & Sacks, P.C.

(57) ABSTRACT

The invention relates to sarcoma-associated antigens and the nucleic acid molecules that encode them. The invention further relates to the use of the nucleic acid molecules, polypeptides and fragments thereof associated with sarcoma in methods and compositions for the diagnosis and treatment of diseases, such as cancer. More specifically, the invention relates to the discovery of a novel cancer/testis (CT) antigen, NY-SAR-35.

14 Claims, 1 Drawing Sheet

OTHER PUBLICATIONS

Genbank Submission; NIH/NCBI, Accession No. DB482835. Last updated Mar. 30, 2006.
Genbank Submission; NIH/NCBI, Accession No. DB551686. Last updated Jul. 10, 2006.
Genbank Submission; NIH/NCBI, Accession No. DB450405. Last updated Apr. 13, 2006.
Genbank Submission; NIH/NCBI, Accession No. XM_098959. Last updated Aug. 1, 2002.
Genbank Submission; NIH/NCBI, Accession No. XP_150408. Feb. 24, 2003.
Genbank Submission; NIH/NCBI, Accession No. AY214130. Lee et al. Mar. 11, 2003.
Genbank Submission; NIH/NCBI, Accession No. NW_042622. Waterston et al. Apr. 28, 2006.
Cancer Immunome Database. SEREX-Sequence Information. Serex ID: 2356. Sequence Name: NY-SAR-36. Last updated Sep. 12, 2002. www2.licr.org/CancerImmunomeDB/SEREX_ShowSequence.php?SerexID=2356.
Cancer Immunome Database. SEREX-Sequence Information. Serex ID: 2368. Sequence Name: NY-SAR-48. Last updated Sep. 12, 2002. www2.licr.org/CancerImmunomeDB/SEREX_ShowSequence.php?SerexId=2368.
AHO et al., Isolation, expression, and chromosomal localization of the human mitochondrial capsule selenoprotein gene (MCSP). Genomics. Mar. 1, 1996;32(2):184-90.
Antonescu et al., MAGE antigen expression in monophasic and biphasic synovial sarcoma. Hum Pathol. Feb. 2002;33(2):225-9.
Boel et al., BAGE: a new gene encoding an antigen recognized on human melanomas by cytolytic T lymphocytes. Immunity. Feb. 1995;2(2):167-75.
Chen et al., A testicular antigen aberrantly expressed in human cancers detected by autologous antibody screening. Proc Natl Acad Sci U S A. Mar. 4, 1997;94(5):1914-8.
Chen et al., Identification of human tumor antigens by serological expression cloning. In: Principles and Practice of Biologic Therapy of Cancer. S.A. Rosenberg, ed. Philadelphia: Lippincott Williams & Wilkins. 2000:557-70.
Chen et al., Identification of multiple cancer/testis antigens by allogenic antibody screening of a melanoma cell line library. Proc Natl Acad Sci U S A. Jun. 9, 1998;95(12):6919-23.
Conrad et al., Differential expression of transforming growth factor beta 1 and interleukin 10 in progressing and regressing areas of primary melanoma. J Exp Clin Cancer Res. Jun. 1999;18(2):225-32.
Cox et al., Identification of a peptide recognized by five melanoma-specific human cytotoxic T cell lines. Science. Apr. 29, 1994;264(5159):716-9.
Domenjoud et al., Sequence of human protamine 2 cDNA. Nucleic Acids Res. Aug. 11, 1988;16(15):7733.
Garrido et al., MHC antigens and tumor escape from immune surveillance. Adv Cancer Res. 2001;83:117-58.
Gaugler et al., Human gene MAGE-3 codes for an antigen recognized on a melanoma by autologous cytolytic T lymphocytes. J Exp Med. Mar. 1, 1994;179(3):921-30.
Gure et al., SSX: a multigene family with several members transcribed in normal testis and human cancer. Int J Cancer. Sep. 17, 1997;72(6):965-71.
Hoffmann et al., The P-domain or trefoil motif: a role in renewal and pathology of mucous epithelia? Trends Biochem. Jul. 1993;18(7):239-43.
Jager et al., Identification of a tissue-specific putative transcription factor in breast tissue by serological screening of a breast cancer library. Cancer Res. Mar. 1, 2000;61(5):2055-61.
Jager et al., Serological cloning of a melanocyte rab guanosine 5'-triphosphate-binding protein and a chromosome condensation protein from a melanoma complementary DNA library. Cancer Res. Jul. 1, 2000;60(13):3584-91.
Jungbluth et al., Monophasic and biphasic synovial sarcomas abundantly express cancer/testis antigen NY-ESO-1 but not MAGE-A1 or CT7. Int J Cancer. Oct. 15, 2001;94(2):252-6.

Jungbluth et al., Immunohistochemical analysis of NY-ESO-1 antigen expression in normal and malignant human tissues. Int J Cancer. Jun. 15, 2001;92(6):856-60.
Jungbluth et al., Expression of MAGE-antigens in normal tissues and cancer. Int J Cancer. Feb. 15, 2000;85(4):460-5.
Kawakami et al., Cloning of the gene coding for a shared human melanoma antigen recognized by autologous T cells infiltrating into tumor. Proc Natl Acad Sci U S A. Apr. 26, 1994;91(9):3515-9.
Kiuru et al., Few FH mutations in sporadic counterparts of tumor types observed in hereditary leiomyomatosis and renal cell cancer families. Cancer Res. Aug. 15, 2002;62(16):4554-7.
Lee et al., Immunonomic analysis of human sarcoma. Proc Natl Acad Sci U S A. Mar. 4, 2003;100(5):2651-6.
Lethe et al., LAGE-1, a new gene with tumor specificity. Int J Cancer. Jun. 10, 1998;76(6):903-8.
Li et al., Molecular cloning of a novel tissue-specific gene from human nasopharyngeal epithelium. Gene. Sep. 3, 1999;237(1):235-40.
Pascolo et al., A MAGE-A1 HLA-A A*0201 epitope identified by mass spectrometry. Cancer Res. May 15, 2001;61(10):4072-7.
Sahin et al., Human neoplasms elicit multiple specific immune responses in the autologous host. Proc Natl Sci U S A. Dec. 5, 1995;92(25):11810-3.
Sahin et al., Expression of multiple cancer/testis (CT) antigens in breast cancer and melanoma: basis for polyvalent CT vaccine strategies. Int J Cancer. Oct. 29, 1998;78(3):387-9.
Scanlan et al., Characterization of human colon cancer antigens recognized by autologous antibodies. Int J Cancer. May 29, 1998;76(5):652-8.
Scanlan et al., Expression of cancer-testis antigens in lung cancer: definition of bromodomain testis-specific gene (BRDT) as a new CT gene, CT9. Cancer Lett. Mar. 31, 2000;150(2):155-64.
Scanlan et al., Cancer-related serological recognition of human colon cancer: identification of potential diagnostic and immunotherapeutic targets. Cancer Res. Jul. 15, 2002;62(14):4041-7.
Scanlan et al., Antigens recognized by autologous antibody in patients with renal-cell carcinoma. Int J Cancer. Nov. 12, 1999;83(4):456-64.
Scanlan et al., Humoral immunity to human breast cancer:antigen definition and quantitative analysis of mRNA expression. Cancer Immun. Mar. 30, 2001;1:4.
Skipper et al., An HLA-A2-restricted tyrosinase antigen on melanoma cells results from posttranslational modification and suggests a novel pathway for processing of membrane proteins. J Exp Med. Feb. 1, 1996;183(2):527-34.
Stockert et al., A survey of the humoral immune response of cancer patients to a panel of human tumor antigens. J Exp Med. Apr. 20, 1998;187(8):1349-54.
Tomlinson et al., Germline mutations in FH predispose to dominantly inherited uterine fibroids, skin leiomyomata and papillary renal cell cancer. Nat Genet. Apr. 2002;30(4):406-10.
Tureci et al., Expression of SSX genes in human tumors. Int J Cancer. Jul. 3, 1998;77(1):19-23.
Van Den Eynde et al., A new family of genes coding for an antigen recognized by autologous cytolytic T lymphocytes on a human melanoma. J Exp Med. Sep. 1, 1995;182(3):689-98.
Van Den Eynde et al., T cell defined tumor antigens. Curr Opin Immunol. Oct. 1997;9(5):684-93.
Van Der Bruggen et al., A gene encoding an antigen recognized by cytolytic T lymphocytes on a human melanoma. Science. Dec. 13, 1991;254(5038):1643-7.
GenBank Submission; NIH/NCBI; Accession No. AW593050, Mar. 22, 2000.
GenBank Submission; NIH/NCBI; Accession No. AX463882 (PAT Jul. 16, 2002).
UniGene Submission; NIH/NCBI; Accession No. HS.375082, Feb. 28, 2008.
UniGene Submission; NIH/NCBI; Accession No. HS.128580, Feb. 28, 2008.
Ayyoub et al., Proteasome-assisted identification of a SSX-2-derived epitope recognized by tumor-reactive CTL infiltrating metastatic melanoma. J Immunol. Feb. 15, 2002;168(4):1717-22.

Guillaudeux et al., Expression of HLA class I genes in meiotic and post-meiotic human spermatogenic cells. Biol Reprod. Jul. 1996;55(1):99-110.

Laprevotte et al., Nucleotide sequence of the gag gene and gag-pol junction of feline leukemia virus. J Virol. Jun. 1984;50(3):884-94.

Le Naour et al., Proteomics-based identification of RS/DJ-1 as a novel circulating tumor antigen in breast cancer. Clin Cancer Res. Nov. 2001;7(11):3328-35.

Lee et al., Immunomic analysis of human sarcoma. Proc Natl Acad Sci U S A. Mar. 4, 2003;100(5):2651-6. Epub Feb. 24, 2003.

Martelange et al., Identification on a human sarcoma of two new genes with tumor-specific expression. Cancer Res. Jul. 15, 2000;60(14):3848-55.

Naka et al., Expression of SSX genes in human osteosarcomas. Int J Cancer. Apr. 1, 2002;98(4):640-2.

Preuss et al., Analysis of the B-cell repertoire against antigens expressed by human neoplasms. Immunol Rev. Oct. 2002;188:43-50. Review.

Rosenberg et al., Progress in human tumour immunology and immunotherapy. Nature. May 17, 2001;411(6835):380-4. Review.

Scanlan et al., Cancer/testis antigens: an expanding family of targets for cancer immunotherapy. Immunol Rev. Oct. 2002;188:22-32. Review.

Scanlan et al., Humoral immunity to human breast cancer: antigen definition and quantative analysis of mRNA expression. Cancer Immun. Mar. 30, 2001;1:4.

Van Der Bruggen et al., Tumor-specific shared antigenic peptides recognized by human T cells. Immunol Rev. Oct. 2002;188:51-64. Review.

Yang et al., CML66, a broadly immunogenic tumor antigen, elicits a humoral immune response associated with remission of chronic myelogenous leukemia. Proc Natl Acad Sci U S A. Jun. 19, 2001;98(13):7492-7.

* cited by examiner

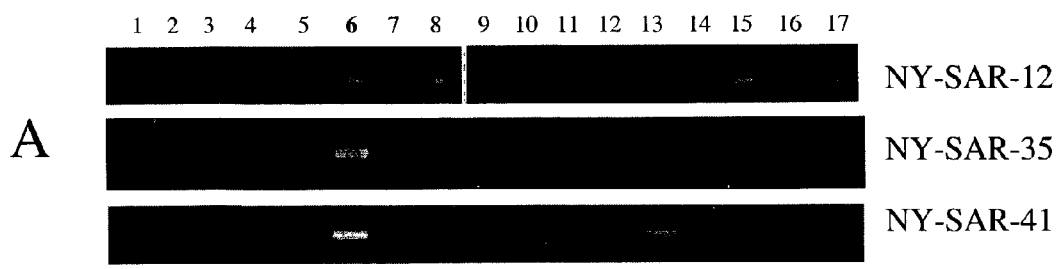
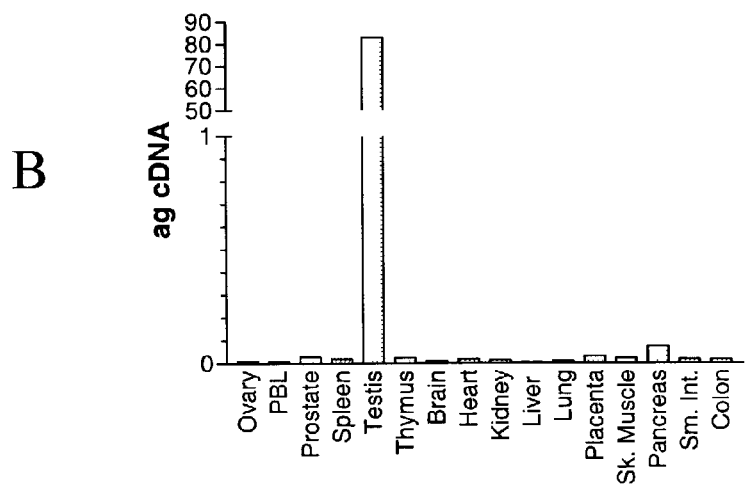
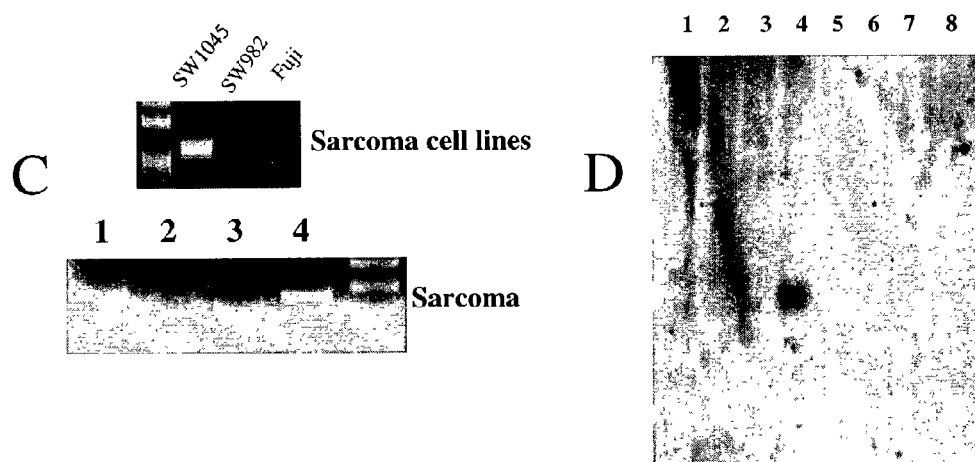

SEQUENCE LISTING

```
<160> NUMBER OF SEQ ID NOS: 96

<210> SEQ ID NO 1
<211> LENGTH: 1148
<212> TYPE: DNA
<213> ORGANISM: homo sapiens
<220> FEATURE:
<221> NAME/KEY: misc_feature
<222> LOCATION: (3)..(3)
<223> OTHER INFORMATION: n = a, c, g or t/u
<220> FEATURE:
<221> NAME/KEY: misc_feature
<222> LOCATION: (195)..(195)
<223> OTHER INFORMATION: n = a, c, g or t/u
<220> FEATURE:
<221> NAME/KEY: misc_feature
<222> LOCATION: (507)..(507)
<223> OTHER INFORMATION: n = a, c, g or t/u
<220> FEATURE:
<221> NAME/KEY: misc_feature
<222> LOCATION: (614)..(614)
<223> OTHER INFORMATION: n = a, c, g or t/u
<220> FEATURE:
<221> NAME/KEY: misc_feature
<222> LOCATION: (625)..(625)
<223> OTHER INFORMATION: n = a, c, g or t/u
<220> FEATURE:
<221> NAME/KEY: misc_feature
<222> LOCATION: (634)..(634)
<223> OTHER INFORMATION: n = a, c, g or t/u
<220> FEATURE:
<221> NAME/KEY: misc_feature
<222> LOCATION: (651)..(651)
<223> OTHER INFORMATION: n = a, c, g or t/u
<220> FEATURE:
<221> NAME/KEY: misc_feature
<222> LOCATION: (686)..(686)
<223> OTHER INFORMATION: n = a, c, g or t/u
<220> FEATURE:
<221> NAME/KEY: misc_feature
<222> LOCATION: (690)..(690)
<223> OTHER INFORMATION: n = a, c, g or t/u
<220> FEATURE:
<221> NAME/KEY: misc_feature
<222> LOCATION: (693)..(693)
<223> OTHER INFORMATION: n = a, c, g or t/u
<220> FEATURE:
<221> NAME/KEY: misc_feature
<222> LOCATION: (696)..(696)
<223> OTHER INFORMATION: n = a, c, g or t/u
<220> FEATURE:
```

-continued

```
<221> NAME/KEY: misc_feature
<222> LOCATION: (707)..(707)
<223> OTHER INFORMATION: n = a, c, g or t/u
<220> FEATURE:
<221> NAME/KEY: misc_feature
<222> LOCATION: (720)..(720)
<223> OTHER INFORMATION: n = a, c, g or t/u
<220> FEATURE:
<221> NAME/KEY: misc_feature
<222> LOCATION: (758)..(758)
<223> OTHER INFORMATION: n = a, c, g or t/u
<220> FEATURE:
<221> NAME/KEY: misc_feature
<222> LOCATION: (782)..(782)
<223> OTHER INFORMATION: n = a, c, g or t/u
<220> FEATURE:
<221> NAME/KEY: misc_feature
<222> LOCATION: (793)..(793)
<223> OTHER INFORMATION: n = a, c, g or t/u
<220> FEATURE:
<221> NAME/KEY: misc_feature
<222> LOCATION: (798)..(798)
<223> OTHER INFORMATION: n = a, c, g or t/u
<220> FEATURE:
<221> NAME/KEY: misc_feature
<222> LOCATION: (807)..(807)
<223> OTHER INFORMATION: n = a, c, g or t/u
<220> FEATURE:
<221> NAME/KEY: misc_feature
<222> LOCATION: (819)..(819)
<223> OTHER INFORMATION: n = a, c, g or t/u
<220> FEATURE:
<221> NAME/KEY: misc_feature
<222> LOCATION: (822)..(822)
<223> OTHER INFORMATION: n = a, c, g or t/u
<220> FEATURE:
<221> NAME/KEY: misc_feature
<222> LOCATION: (828)..(828)
<223> OTHER INFORMATION: n = a, c, g or t/u
<220> FEATURE:
<221> NAME/KEY: misc_feature
<222> LOCATION: (831)..(831)
<223> OTHER INFORMATION: n = a, c, g or t/u
<220> FEATURE:
<221> NAME/KEY: misc_feature
<222> LOCATION: (837)..(837)
<223> OTHER INFORMATION: n = a, c, g or t/u
<220> FEATURE:
<221> NAME/KEY: misc_feature
<222> LOCATION: (841)..(841)
<223> OTHER INFORMATION: n = a, c, g or t/u
<220> FEATURE:
<221> NAME/KEY: misc_feature
<222> LOCATION: (843)..(844)
<223> OTHER INFORMATION: n = a, c, g or t/u
<220> FEATURE:
<221> NAME/KEY: misc_feature
<222> LOCATION: (856)..(857)
<223> OTHER INFORMATION: n = a, c, g or t/u
<220> FEATURE:
<221> NAME/KEY: misc_feature
<222> LOCATION: (867)..(867)
<223> OTHER INFORMATION: n = a, c, g or t/u
<220> FEATURE:
<221> NAME/KEY: misc_feature
<222> LOCATION: (880)..(880)
<223> OTHER INFORMATION: n = a, c, g or t/u
<220> FEATURE:
<221> NAME/KEY: misc_feature
<222> LOCATION: (886)..(886)
<223> OTHER INFORMATION: n = a, c, g or t/u
<220> FEATURE:
<221> NAME/KEY: misc_feature
<222> LOCATION: (892)..(893)
<223> OTHER INFORMATION: n = a, c, g or t/u
<220> FEATURE:
<221> NAME/KEY: misc_feature
<222> LOCATION: (897)..(897)
<223> OTHER INFORMATION: n = a, c, g or t/u
```

```
<220> FEATURE:
<221> NAME/KEY: misc_feature
<222> LOCATION: (908)..(908)
<223> OTHER INFORMATION: n = a, c, g or t/u
<220> FEATURE:
<221> NAME/KEY: misc_feature
<222> LOCATION: (913)..(913)
<223> OTHER INFORMATION: n = a, c, g or t/u
<220> FEATURE:
<221> NAME/KEY: misc_feature
<222> LOCATION: (925)..(925)
<223> OTHER INFORMATION: n = a, c, g or t/u
<220> FEATURE:
<221> NAME/KEY: misc_feature
<222> LOCATION: (943)..(943)
<223> OTHER INFORMATION: n = a, c, g or t/u
<220> FEATURE:
<221> NAME/KEY: misc_feature
<222> LOCATION: (949)..(949)
<223> OTHER INFORMATION: n = a, c, g or t/u
<220> FEATURE:
<221> NAME/KEY: misc_feature
<222> LOCATION: (953)..(953)
<223> OTHER INFORMATION: n = a, c, g or t/u
<220> FEATURE:
<221> NAME/KEY: misc_feature
<222> LOCATION: (957)..(958)
<223> OTHER INFORMATION: n = a, c, g or t/u
<220> FEATURE:
<221> NAME/KEY: misc_feature
<222> LOCATION: (962)..(963)
<223> OTHER INFORMATION: n = a, c, g or t/u
<220> FEATURE:
<221> NAME/KEY: misc_feature
<222> LOCATION: (968)..(968)
<223> OTHER INFORMATION: n = a, c, g or t/u
<220> FEATURE:
<221> NAME/KEY: misc_feature
<222> LOCATION: (971)..(971)
<223> OTHER INFORMATION: n = a, c, g or t/u
<220> FEATURE:
<221> NAME/KEY: misc_feature
<222> LOCATION: (983)..(983)
<223> OTHER INFORMATION: n = a, c, g or t/u
<220> FEATURE:
<221> NAME/KEY: misc_feature
<222> LOCATION: (985)..(988)
<223> OTHER INFORMATION: n = a, c, g or t/u
<220> FEATURE:
<221> NAME/KEY: misc_feature
<222> LOCATION: (994)..(995)
<223> OTHER INFORMATION: n = a, c, g or t/u
<220> FEATURE:
<221> NAME/KEY: misc_feature
<222> LOCATION: (998)..(998)
<223> OTHER INFORMATION: n = a, c, g or t/u
<220> FEATURE:
<221> NAME/KEY: misc_feature
<222> LOCATION: (1003)..(1003)
<223> OTHER INFORMATION: n = a, c, g or t/u
<220> FEATURE:
<221> NAME/KEY: misc_feature
<222> LOCATION: (1008)..(1009)
<223> OTHER INFORMATION: n = a, c, g or t/u
<220> FEATURE:
<221> NAME/KEY: misc_feature
<222> LOCATION: (1012)..(1013)
<223> OTHER INFORMATION: n = a, c, g or t/u
<220> FEATURE:
<221> NAME/KEY: misc_feature
<222> LOCATION: (1020)..(1021)
<223> OTHER INFORMATION: n = a, c, g or t/u
<220> FEATURE:
<221> NAME/KEY: misc_feature
<222> LOCATION: (1029)..(1029)
<223> OTHER INFORMATION: n = a, c, g or t/u
<220> FEATURE:
<221> NAME/KEY: misc_feature
<222> LOCATION: (1033)..(1033)
```

```
<223> OTHER INFORMATION: n = a, c, g or t/u
<220> FEATURE:
<221> NAME/KEY: misc_feature
<222> LOCATION: (1035)..(1036)
<223> OTHER INFORMATION: n = a, c, g or t/u
<220> FEATURE:
<221> NAME/KEY: misc_feature
<222> LOCATION: (1043)..(1043)
<223> OTHER INFORMATION: n = a, c, g or t/u
<220> FEATURE:
<221> NAME/KEY: misc_feature
<222> LOCATION: (1050)..(1052)
<223> OTHER INFORMATION: n = a, c, g or t/u
<220> FEATURE:
<221> NAME/KEY: misc_feature
<222> LOCATION: (1057)..(1057)
<223> OTHER INFORMATION: n = a, c, g or t/u
<220> FEATURE:
<221> NAME/KEY: misc_feature
<222> LOCATION: (1062)..(1062)
<223> OTHER INFORMATION: n = a, c, g or t/u
<220> FEATURE:
<221> NAME/KEY: misc_feature
<222> LOCATION: (1065)..(1065)
<223> OTHER INFORMATION: n = a, c, g or t/u
<220> FEATURE:
<221> NAME/KEY: misc_feature
<222> LOCATION: (1069)..(1069)
<223> OTHER INFORMATION: n = a, c, g or t/u
<220> FEATURE:
<221> NAME/KEY: misc_feature
<222> LOCATION: (1071)..(1071)
<223> OTHER INFORMATION: n = a, c, g or t/u
<220> FEATURE:
<221> NAME/KEY: misc_feature
<222> LOCATION: (1074)..(1074)
<223> OTHER INFORMATION: n = a, c, g or t/u
<220> FEATURE:
<221> NAME/KEY: misc_feature
<222> LOCATION: (1077)..(1077)
<223> OTHER INFORMATION: n = a, c, g or t/u
<220> FEATURE:
<221> NAME/KEY: misc_feature
<222> LOCATION: (1083)..(1083)
<223> OTHER INFORMATION: n = a, c, g or t/u
<220> FEATURE:
<221> NAME/KEY: misc_feature
<222> LOCATION: (1086)..(1086)
<223> OTHER INFORMATION: n = a, c, g or t/u
<220> FEATURE:
<221> NAME/KEY: misc_feature
<222> LOCATION: (1090)..(1090)
<223> OTHER INFORMATION: n = a, c, g or t/u
<220> FEATURE:
<221> NAME/KEY: misc_feature
<222> LOCATION: (1092)..(1092)
<223> OTHER INFORMATION: n = a, c, g or t/u
<220> FEATURE:
<221> NAME/KEY: misc_feature
<222> LOCATION: (1094)..(1094)
<223> OTHER INFORMATION: n = a, c, g or t/u
<220> FEATURE:
<221> NAME/KEY: misc_feature
<222> LOCATION: (1096)..(1096)
<223> OTHER INFORMATION: n = a, c, g or t/u
<220> FEATURE:
<221> NAME/KEY: misc_feature
<222> LOCATION: (1099)..(1099)
<223> OTHER INFORMATION: n = a, c, g or t/u
<220> FEATURE:
<221> NAME/KEY: misc_feature
<222> LOCATION: (1102)..(1102)
<223> OTHER INFORMATION: n = a, c, g or t/u
<220> FEATURE:
<221> NAME/KEY: misc_feature
<222> LOCATION: (1107)..(1107)
<223> OTHER INFORMATION: n = a, c, g or t/u
<220> FEATURE:
<221> NAME/KEY: misc_feature
```

<222> LOCATION: (1113)..(1113)
<223> OTHER INFORMATION: n = a, c, g or t/u
<220> FEATURE:
<221> NAME/KEY: misc_feature
<222> LOCATION: (1115)..(1115)
<223> OTHER INFORMATION: n = a, c, g or t/u
<220> FEATURE:
<221> NAME/KEY: misc_feature
<222> LOCATION: (1136)..(1137)
<223> OTHER INFORMATION: n = a, c, g or t/u
<220> FEATURE:
<221> NAME/KEY: misc_feature
<222> LOCATION: (1139)..(1139)
<223> OTHER INFORMATION: n = a, c, g or t/u
<220> FEATURE:
<221> NAME/KEY: misc_feature
<222> LOCATION: (1142)..(1144)
<223> OTHER INFORMATION: n = a, c, g or t/u

<400> SEQUENCE: 1

| | | | | | |
|---|---|---|---|---|---|
| ttnggacagg | ggaactgtgt | tcagaaccag | ctcgatgaga | gccagcaaga | acggaatgac | 60 |
| ctgatgcagc | tgaagctaca | gctggaggga | caggtgacag | agctgaggag | ccgagtgcag | 120 |
| gagctcgaga | gggctctggc | aactgccagg | caggagcaca | ctggagctga | tggaacagta | 180 |
| caagggggatt | tcccnggtcc | catggggaga | tcacagaaga | gagggacatc | ctgagccggc | 240 |
| aacaggagaa | ccatgtggca | cgcatcctgg | agctagagga | tgacatccag | accatcagtg | 300 |
| agaaagtgct | gacgaaggaa | gtggagcctg | acaggcttaa | gagacacagt | gaaggccctg | 360 |
| actcgggaac | aagagaagct | ccttgggcaa | ctgaaagaag | tacaagcaga | caaggagcaa | 420 |
| agtgaggctg | agctccaagt | ggcacaacag | gagaaccatc | acttaaattt | ggacctgaag | 480 |
| gaggcgaaga | gctggcaaga | ggagcanagt | gctcaggctc | agcgactgaa | agacaaggtg | 540 |
| gcccagatga | aggacaccct | atgccaggcc | cagcagcggg | tggcccagct | ggagcccttg | 600 |
| aaggagcagc | ttcnaggggc | ccaangagcc | ttgncagcct | caagccagca | naaagccacc | 660 |
| ctttcttggg | gaggagtttg | ccagcngcan | cancanccag | ggacccntcc | atatgccgan | 720 |
| ctacaccgga | gccgtcctgg | aagtggctga | agttaacngc | aaggtggctg | acctcgtttt | 780 |
| gnctttgaag | ganaaaantc | ccatggncca | aggaccggnc | anggctgntc | ncaatgngga | 840 |
| ngnncaaaag | acaaanncctt | gaactcnatg | caaaatcctn | tattgnaaaa | gnncttngga | 900 |
| ggaaagancc | aanccagtgt | caaangactg | gccggaaaag | atnttcctng | tcnattnnca | 960 |
| annaatcngg | nattccaaat | ttngnnnncc | tgtnngtnca | aangaaannc | gnnccctgggn | 1020 |
| naccgaatnt | tancnntaaa | acnaagcccn | nngaagnggc | anaancggnt | ngtnccncac | 1080 |
| agntgngccn | tngntnatnc | cncttanaca | agnanccaaa | atagtccctg | gctgtnngna | 1140 |
| cnnntttt | | | | | | 1148 |

<210> SEQ ID NO 2
<211> LENGTH: 914
<212> TYPE: DNA
<213> ORGANISM: homo sapiens
<220> FEATURE:
<221> NAME/KEY: misc_feature
<222> LOCATION: (10)..(10)
<223> OTHER INFORMATION: n = a, c, g or t/u
<220> FEATURE:
<221> NAME/KEY: misc_feature
<222> LOCATION: (239)..(239)
<223> OTHER INFORMATION: n = a, c, g or t/u
<220> FEATURE:
<221> NAME/KEY: misc_feature
<222> LOCATION: (863)..(863)
<223> OTHER INFORMATION: n = a, c, g or t/u
<220> FEATURE:

<221> NAME/KEY: misc_feature
<222> LOCATION: (900)..(900)
<223> OTHER INFORMATION: n = a, c, g or t/u
<220> FEATURE:
<221> NAME/KEY: misc_feature
<222> LOCATION: (912)..(912)
<223> OTHER INFORMATION: n = a, c, g or t/u

<400> SEQUENCE: 2

```
ggagctcgcn cgcctgcagg tcgacactag tggatccaaa gaattcggca cgaggcgcca      60
gcgtccccac cgtcctcagc ttggcaaacg tttcccgaag aggattccga ctccccgcag     120
tttcgaagac gggcacacac gttcagccac ccacctttcaa gcacaaagag aaagctgaat    180
ttgcaggatg ggagggctca gggtgtgcgt tcccctctgc tgaggcagag ctccagtcna    240
acagtgcagt gatggagaag ggagaaaaag gacctcatct acctgcagca atgagtccct    300
aagtgtggga ggaacctctg tcactcctcg ccggatctcc tggcggcagc gcattttcct    360
cagggttgct tctcccatga acaaatctcc ctcagcaatg caacagcaag atggattgga    420
caggaacgag ctgctgccac tgtccccct ctctccaacc atggaggagg aaccgctggt     480
tgtattcctg tctggggagg atgacccaga aaagattgaa gaaagaaaga aatcaaaaga    540
actgaggagc ttgtggagaa aagctataca ccaacaaatc ttgttacttc gaatggaaaa    600
agaaaaccag aaacttgaag caagcagaga tgaactccag tccagaaaag ttaaattaga    660
ctatgaagaa gttggtgcat gtcagaaaga ggtcttaata acttgggata agaagttgtt    720
aaactgcaga gctaaaatca gatgtgatat ggaagatatt catactcttc ttaagaagga    780
gttcccaaag tcgacgagga gaatttggca gtttctggct tacagtaccg actcaacaca    840
gattgcctaa taacaacagc ctnctgacta ttcttaagga ctttgagcag ctactgctan    900
cagcatgcga tntt                                                      914
```

<210> SEQ ID NO 3
<211> LENGTH: 891
<212> TYPE: DNA
<213> ORGANISM: homo sapiens
<220> FEATURE:
<221> NAME/KEY: misc_feature
<222> LOCATION: (9)..(9)
<223> OTHER INFORMATION: n = a, c, g or t/u
<220> FEATURE:
<221> NAME/KEY: misc_feature
<222> LOCATION: (677)..(677)
<223> OTHER INFORMATION: n = a, c, g or t/u
<220> FEATURE:
<221> NAME/KEY: misc_feature
<222> LOCATION: (775)..(775)
<223> OTHER INFORMATION: n = a, c, g or t/u
<220> FEATURE:
<221> NAME/KEY: misc_feature
<222> LOCATION: (785)..(785)
<223> OTHER INFORMATION: n = a, c, g or t/u
<220> FEATURE:
<221> NAME/KEY: misc_feature
<222> LOCATION: (807)..(807)
<223> OTHER INFORMATION: n = a, c, g or t/u
<220> FEATURE:
<221> NAME/KEY: misc_feature
<222> LOCATION: (847)..(847)
<223> OTHER INFORMATION: n = a, c, g or t/u
<220> FEATURE:
<221> NAME/KEY: misc_feature
<222> LOCATION: (858)..(858)
<223> OTHER INFORMATION: n = a, c, g or t/u
<220> FEATURE:
<221> NAME/KEY: misc_feature
<222> LOCATION: (879)..(879)
<223> OTHER INFORMATION: n = a, c, g or t/u -continued

<400> SEQUENCE: 3

| ggagctcgng cgcctgcagg tcgacactag tggatccaaa gaattcggca cgaggggcac | 60 |
| gggcgcgtc gggcccgcag gtggggaacg ctctgggcag cctggagcca ctgcgctgga | 120 |
| tgctgcgctc gcccttcgac cgcaacgtgc cggtcaacct ggagcttcag gagttgctgc | 180 |
| tggactacag cttccagcac ctgggtgtct cctcacaggg ctgtgttgat catcccatag | 240 |
| ttttgacaga agctgtgtgc aacccactgt attcacggca aatgatgtct gagcttcttt | 300 |
| ttgagtgcta cgggattccc aaggttgcct atggaataga cagcctcttc agcttctacc | 360 |
| acaataagcc aaagaactcg atgtgcagtg ggctaatcat ttcatctgga taccagtgta | 420 |
| cgcatgtttt acccatctta aagggagat tagatgctaa aaactgcaag cgcatcaatc | 480 |
| ttggaggaag ccaagcagct ggttacctcc agcgtctcct ccagctgaag taccctgggc | 540 |
| acctggcagc catcaccctc agccgcatgg aggagattct gcatgagcac agctacatcg | 600 |
| ctgaggatta tgtggaagaa ttacacaaat ggcggtgtcc tgattattat gagaataatg | 660 |
| tccacaagat gcagctncca ttttccagca agctcctggg cagcactctg acctctgagg | 720 |
| agaaacaaga aaggcggcag cagcaattgc ggcggctgca ggagctcaat gcccngcggc | 780 |
| gggangagaa gctgcagctt ggatcangag cgtctggacc gactgctata tgtgcaggaa | 840 |
| cttctanagg atggccanat ggatcagttt acaaagctnt gatgagctga t | 891 |

<210> SEQ ID NO 4
<211> LENGTH: 880
<212> TYPE: DNA
<213> ORGANISM: homo sapiens
<220> FEATURE:
<221> NAME/KEY: misc_feature
<222> LOCATION: (654)..(654)
<223> OTHER INFORMATION: n = a, c, g or t/u
<220> FEATURE:
<221> NAME/KEY: misc_feature
<222> LOCATION: (693)..(693)
<223> OTHER INFORMATION: n = a, c, g or t/u
<220> FEATURE:
<221> NAME/KEY: misc_feature
<222> LOCATION: (698)..(698)
<223> OTHER INFORMATION: n = a, c, g or t/u
<220> FEATURE:
<221> NAME/KEY: misc_feature
<222> LOCATION: (784)..(784)
<223> OTHER INFORMATION: n = a, c, g or t/u
<220> FEATURE:
<221> NAME/KEY: misc_feature
<222> LOCATION: (803)..(803)
<223> OTHER INFORMATION: n = a, c, g or t/u
<220> FEATURE:
<221> NAME/KEY: misc_feature
<222> LOCATION: (813)..(813)
<223> OTHER INFORMATION: n = a, c, g or t/u
<220> FEATURE:
<221> NAME/KEY: misc_feature
<222> LOCATION: (842)..(842)
<223> OTHER INFORMATION: n = a, c, g or t/u
<220> FEATURE:
<221> NAME/KEY: misc_feature
<222> LOCATION: (867)..(867)
<223> OTHER INFORMATION: n = a, c, g or t/u

<400> SEQUENCE: 4

| ggcacgaggc ggcggcggcg gcggcggcag cggcagccag aggactccca gcggctggag | 60 |
| cagaagtgtt agcggccaga gctcccagac ccctacccac agccaggcgg gacgcgcaca | 120 |
| gtccctccac gcggaaagaa gtaccttcgc cggtcaccgg ctcctgcagg gtgcaaatat | 180 |

```
atacagagct tcataatcag cccaagacca catagagcaa acatgaatga tatttcccaa    240
aaggctgaga ttctgctttc ttcatctaaa cctgtcccaa aaacctatgt accaaaactt    300
ggcaagggtg atgtaaagga taagtttgaa gccatgcaga gagccaggga agaaagaaat    360
caaaggagat ctagagacga aaaacaaaga agaaaagaac aatatattag agagagagaa    420
tggaacagga gaaagcagga gattaaagaa atgcttgctt ctgatgatga ggaagatgta    480
tcttctaaag tagaaaaggc ttatgttcca aaattaacag gaactgtgaa gggtagattt    540
gctgaaatgg agaaacaaag acaagaggaa caaaggaaga aacggagga ggaacgaaaa    600 cgcagaattg agcaggatat gttagaaaag aggaaaatac agcgtgaatt agcnaaaagg    660
gctgaacagg aaggagatga ttcactactt atnactgngg tacctgtcaa tcatataaac    720
atctggaaaa tgaaaagaat tttgagatct agaaaaagac gtgaagagaa gaaagatcca    780
gtcnaggaga taaagattag atntgagaca cgncctctct caggagcaag ggcttcttag    840
tntggtgtga ataaaaggga gcaaaanatc cttctccca                           880

<210> SEQ ID NO 5
<211> LENGTH: 924
<212> TYPE: DNA
<213> ORGANISM: homo sapiens
<220> FEATURE:
<221> NAME/KEY: misc_feature
<222> LOCATION: (754)..(754)
<223> OTHER INFORMATION: n = a, c, g or t/u
<220> FEATURE:
<221> NAME/KEY: misc_feature
<222> LOCATION: (772)..(772)
<223> OTHER INFORMATION: n = a, c, g or t/u
<220> FEATURE:
<221> NAME/KEY: misc_feature
<222> LOCATION: (783)..(783)
<223> OTHER INFORMATION: n = a, c, g or t/u
<220> FEATURE:
<221> NAME/KEY: misc_feature
<222> LOCATION: (799)..(799)
<223> OTHER INFORMATION: n = a, c, g or t/u
<220> FEATURE:
<221> NAME/KEY: misc_feature
<222> LOCATION: (873)..(875)
<223> OTHER INFORMATION: n = a, c, g or t/u
<220> FEATURE:
<221> NAME/KEY: misc_feature
<222> LOCATION: (898)..(898)
<223> OTHER INFORMATION: n = a, c, g or t/u
<220> FEATURE:
<221> NAME/KEY: misc_feature
<222> LOCATION: (918)..(918)
<223> OTHER INFORMATION: n = a, c, g or t/u
<220> FEATURE:
<221> NAME/KEY: misc_feature
<222> LOCATION: (920)..(920)
<223> OTHER INFORMATION: n = a, c, g or t/u

<400> SEQUENCE: 5
ctggagctcg cgcgcctgca ggtcgacact agtggatcca agaattcgg cacgaggctc     60 actgctcaca gctgcccagc tgaaagccaa gggggagctg agctttgaac aggaccagct   120
ggtggctggg ggccagctgg gcgagctgca caacgggaca cagtatcgtg aggtccgcca   180
gttctgctcg ggctctggcc accaccttgt gcgcttctac ttcctcactc gtgtttactc   240
cgagtacctt gaggatgttc tggaagagct gacatatgga cctgccccgg acctggtgat   300
catcaactcc tgcctctggg atctctccag atatggtcgc tgctcaatgg agagctaccg   360
ggagaacctg gagcgggtgt tgtgcgcat ggaccaagta ttgccagact cctgcctgct   420
ggtgtggaac atggcgatgc ccctcgggga acgtatcact gggggtttcc tcctgccaga   480
```

```
gctccagccc ctggcaggct ccctgcggcg ggatgtggtt gaagggaact tctacagtgc    540
tacgctggcc ggggaccact gctttgatgt cctagacctc cactttcact tccggcatgc    600
agtacagcac cgtcatcggg atggtgtcca ctgggaccag catgcacacc gccacctctc    660
acacctgctt ctgacccatg tggctgacgc ctggggcgtg gagctgccca agcgtggcta    720 tcccctgac ccgtggattg aggactgggc aganatgaat catccattcc anggaagcca    780
tangcagacc caaacttcng ggagacctgg gccttgctcc accccacttc ttcttgctct    840
ccatgccttt tcctaccggt tctaggcctg cannnttcct tttccaccct gccagganac    900 cctttccag gcagcctncn ccca                                            924
```

<210> SEQ ID NO 6
<211> LENGTH: 929
<212> TYPE: DNA
<213> ORGANISM: homo sapiens
<220> FEATURE:
<221> NAME/KEY: misc_feature
<222> LOCATION: (11)..(11)
<223> OTHER INFORMATION: n = a, c, g or t/u
<220> FEATURE:
<221> NAME/KEY: misc_feature
<222> LOCATION: (640)..(640)
<223> OTHER INFORMATION: n = a, c, g or t/u
<220> FEATURE:
<221> NAME/KEY: misc_feature
<222> LOCATION: (672)..(672)
<223> OTHER INFORMATION: n = a, c, g or t/u
<220> FEATURE:
<221> NAME/KEY: misc_feature
<222> LOCATION: (715)..(715)
<223> OTHER INFORMATION: n = a, c, g or t/u
<220> FEATURE:
<221> NAME/KEY: misc_feature
<222> LOCATION: (724)..(724)
<223> OTHER INFORMATION: n = a, c, g or t/u
<220> FEATURE:
<221> NAME/KEY: misc_feature
<222> LOCATION: (768)..(768)
<223> OTHER INFORMATION: n = a, c, g or t/u
<220> FEATURE:
<221> NAME/KEY: misc_feature
<222> LOCATION: (782)..(782)
<223> OTHER INFORMATION: n = a, c, g or t/u
<220> FEATURE:
<221> NAME/KEY: misc_feature
<222> LOCATION: (795)..(795)
<223> OTHER INFORMATION: n = a, c, g or t/u
<220> FEATURE:
<221> NAME/KEY: misc_feature
<222> LOCATION: (800)..(800)
<223> OTHER INFORMATION: n = a, c, g or t/u
<220> FEATURE:
<221> NAME/KEY: misc_feature
<222> LOCATION: (813)..(813)
<223> OTHER INFORMATION: n = a, c, g or t/u
<220> FEATURE:
<221> NAME/KEY: misc_feature
<222> LOCATION: (818)..(818)
<223> OTHER INFORMATION: n = a, c, g or t/u
<220> FEATURE:
<221> NAME/KEY: misc_feature
<222> LOCATION: (820)..(820)
<223> OTHER INFORMATION: n = a, c, g or t/u
<220> FEATURE:
<221> NAME/KEY: misc_feature
<222> LOCATION: (827)..(827)
<223> OTHER INFORMATION: n = a, c, g or t/u
<220> FEATURE:
<221> NAME/KEY: misc_feature
<222> LOCATION: (829)..(829)
<223> OTHER INFORMATION: n = a, c, g or t/u
<220> FEATURE:

```
<221> NAME/KEY: misc_feature
<222> LOCATION: (840)..(840)
<223> OTHER INFORMATION: n = a, c, g or t/u
<220> FEATURE:
<221> NAME/KEY: misc_feature
<222> LOCATION: (846)..(846)
<223> OTHER INFORMATION: n = a, c, g or t/u
<220> FEATURE:
<221> NAME/KEY: misc_feature
<222> LOCATION: (849)..(849)
<223> OTHER INFORMATION: n = a, c, g or t/u
<220> FEATURE:
<221> NAME/KEY: misc_feature
<222> LOCATION: (852)..(852)
<223> OTHER INFORMATION: n = a, c, g or t/u
<220> FEATURE:
<221> NAME/KEY: misc_feature
<222> LOCATION: (862)..(862)
<223> OTHER INFORMATION: n = a, c, g or t/u
<220> FEATURE:
<221> NAME/KEY: misc_feature
<222> LOCATION: (873)..(873)
<223> OTHER INFORMATION: n = a, c, g or t/u
<220> FEATURE:
<221> NAME/KEY: misc_feature
<222> LOCATION: (875)..(875)
<223> OTHER INFORMATION: n = a, c, g or t/u
<220> FEATURE:
<221> NAME/KEY: misc_feature
<222> LOCATION: (887)..(887)
<223> OTHER INFORMATION: n = a, c, g or t/u
<220> FEATURE:
<221> NAME/KEY: misc_feature
<222> LOCATION: (889)..(889)
<223> OTHER INFORMATION: n = a, c, g or t/u
<220> FEATURE:
<221> NAME/KEY: misc_feature
<222> LOCATION: (903)..(903)
<223> OTHER INFORMATION: n = a, c, g or t/u
<220> FEATURE:
<221> NAME/KEY: misc_feature
<222> LOCATION: (909)..(909)
<223> OTHER INFORMATION: n = a, c, g or t/u
<220> FEATURE:
<221> NAME/KEY: misc_feature
<222> LOCATION: (913)..(913)
<223> OTHER INFORMATION: n = a, c, g or t/u
<220> FEATURE:
<221> NAME/KEY: misc_feature
<222> LOCATION: (928)..(928)
<223> OTHER INFORMATION: n = a, c, g or t/u

<400> SEQUENCE: 6
gcggtcacct ngtggatcca agaattcggc acgaggcttg tcttgcattt gaatcaattg      60
gaaggaaata aggaaaagtt tgaaaaacag ttaagaaga aatctgaaga ggtatattgt      120
ttacagaaag agctaaagat aaaaaatcac agtcttcaag agacttctga gcaaaacgtt     180
attctacagc atactcttca gcaacagcag caaatgttac aacaagagac aattagaaat     240
ggagagctag aagatactca aactaaactt gaaaaacagg tgtcaaaact ggaacaagaa     300
cttcaaaaac aaagggaaag ttcagctgaa agttgagaa aatgggagga gaaatgtgaa      360
tcagctgcac atgaagcaga tttgaaaagg caaaaagtga ttgagcttac tggcactgcc     420
aggcaagtaa agattgagat ggatcagtac aagaagagc tgtctaaaat ggaaaaggaa      480
ataatgcacc taaacgaga tggagaaaat aaagcaatgc acctctctca attagatatg      540
atcttagatc agacaaagac agagctagaa aagaaaacca atgctgtaaa ggagttagaa     600
aagttacagc acagtactga aactgaacta acagaagccn tgcaaaacgg gaagtacttg     660
agactgacta cnaaatgctc atgggagatt taaaaagtac tttaagacaa ctccnggaat    720
tggngagatg tactacagaa ggctccattt tcattagagg aaaatacnct actataagga    780
```

```
tnccccgct ggacntaaaa aatgcaagat ggnattgnan acaaaancng gagctcctgn    840
aatggnccng cncttaagag anaattggga ctnangcaaa aacagcncng gtaccctttg    900
ganttgctnt tcnggacccg aggaaaang                                      929
```

```
<210> SEQ ID NO 7
<211> LENGTH: 935
<212> TYPE: DNA
<213> ORGANISM: homo sapiens
<220> FEATURE:
<221> NAME/KEY: misc_feature
<222> LOCATION: (1)..(1)
<223> OTHER INFORMATION: n = a, c, g or t/u
<220> FEATURE:
<221> NAME/KEY: misc_feature
<222> LOCATION: (792)..(792)
<223> OTHER INFORMATION: n = a, c, g or t/u
<220> FEATURE:
<221> NAME/KEY: misc_feature
<222> LOCATION: (799)..(799)
<223> OTHER INFORMATION: n = a, c, g or t/u
<220> FEATURE:
<221> NAME/KEY: misc_feature
<222> LOCATION: (820)..(820)
<223> OTHER INFORMATION: n = a, c, g or t/u
<220> FEATURE:
<221> NAME/KEY: misc_feature
<222> LOCATION: (856)..(856)
<223> OTHER INFORMATION: n = a, c, g or t/u
<220> FEATURE:
<221> NAME/KEY: misc_feature
<222> LOCATION: (872)..(872)
<223> OTHER INFORMATION: n = a, c, g or t/u
<220> FEATURE:
<221> NAME/KEY: misc_feature
<222> LOCATION: (875)..(875)
<223> OTHER INFORMATION: n = a, c, g or t/u
<220> FEATURE:
<221> NAME/KEY: misc_feature
<222> LOCATION: (886)..(886)
<223> OTHER INFORMATION: n = a, c, g or t/u
<220> FEATURE:
<221> NAME/KEY: misc_feature
<222> LOCATION: (899)..(899)
<223> OTHER INFORMATION: n = a, c, g or t/u
<220> FEATURE:
<221> NAME/KEY: misc_feature
<222> LOCATION: (904)..(904)
<223> OTHER INFORMATION: n = a, c, g or t/u
<220> FEATURE:
<221> NAME/KEY: misc_feature
<222> LOCATION: (906)..(906)
<223> OTHER INFORMATION: n = a, c, g or t/u
<220> FEATURE:
<221> NAME/KEY: misc_feature
<222> LOCATION: (922)..(922)
<223> OTHER INFORMATION: n = a, c, g or t/u
<220> FEATURE:
<221> NAME/KEY: misc_feature
<222> LOCATION: (926)..(927)
<223> OTHER INFORMATION: n = a, c, g or t/u
<220> FEATURE:
<221> NAME/KEY: misc_feature
<222> LOCATION: (935)..(935)
<223> OTHER INFORMATION: n = a, c, g or t/u

<400> SEQUENCE: 7
ngctggagct cgcgcgcctg caggtcgaca ctagtggatc caaagaattc ggcacgaggg     60
aaacataaag aagacaaaga tgataggcgg cacagagatg acaaaagaga ttccaagaaa    120
gagaaaaaac acagtagaag cagaagcaga gaaggaaac acagaagtag gagtcgaagt    180
agaaatgcag ggaaacgaag tagaagtaga agcaaagaga aatcaagtaa acataaaaat    240
```

```
gaaagtaaag aaaaatcaaa taaacgaagt cgaagtggca gtcaaggaag aactgacagt      300
gttgaaaaat caaaaaaacg ggaacatagt cccagcaaag aaaaatctag aaagcgtagt      360
agaagcaaag aacgttccca caaacgagat cacagtgata gtaaggacca gtcagacaaa      420
catgatcgtc gaaggagcca agtatagaa  caagagagcc aagaaaaaca gcataaaaac      480
aaagatgaga ctgtgtgaaa atattttgta aaagtggatc acattgaatc ctataaatga      540
ttaaatctgc ttttttcccc cacgttgaga ttgtgcagta gttcgcactc ctcaagctct      600
ccctgtaggc tgcattttca tttcctcttt cgtgtaggga agtgcctttg taattccatt      660
tattgcattg gtgttttcac ccaattgtta agtttgatac atgatgcaca gattggtctt      720 gcattttat  tgtttggttt tgaatgtaca gtctgtacta tgtcctgaaa tggtttattc      780
ctttggcatg gntgcctgnt ggttaatttg tataggcatn aactgcccta tctaaaaaaa      840
aaaaaaaaaa ctcgangtct ttaaagcggc gnggncctcg atttcnccgg ggggaccng      900 taangnccca tccccttag  gngcgnntaa atccn                                 935

<210> SEQ ID NO 8
<211> LENGTH: 943
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (741)..(741)
<223> OTHER INFORMATION: n = a, c, g or t/u
<220> FEATURE:
<221> NAME/KEY: misc_feature
<222> LOCATION: (796)..(796)
<223> OTHER INFORMATION: n = a, c, g or t/u
<220> FEATURE:
<221> NAME/KEY: misc_feature
<222> LOCATION: (823)..(823)
<223> OTHER INFORMATION: n = a, c, g or t/u
<220> FEATURE:
<221> NAME/KEY: misc_feature
<222> LOCATION: (842)..(842)
<223> OTHER INFORMATION: n = a, c, g or t/u
<220> FEATURE:
<221> NAME/KEY: misc_feature
<222> LOCATION: (857)..(857)
<223> OTHER INFORMATION: n = a, c, g or t/u
<220> FEATURE:
<221> NAME/KEY: misc_feature
<222> LOCATION: (869)..(869)
<223> OTHER INFORMATION: n = a, c, g or t/u
<220> FEATURE:
<221> NAME/KEY: misc_feature
<222> LOCATION: (873)..(873)
<223> OTHER INFORMATION: n = a, c, g or t/u
<220> FEATURE:
<221> NAME/KEY: misc_feature
<222> LOCATION: (898)..(898)
<223> OTHER INFORMATION: n = a, c, g or t/u
<220> FEATURE:
<221> NAME/KEY: misc_feature
<222> LOCATION: (911)..(911)
<223> OTHER INFORMATION: n = a, c, g or t/u
<220> FEATURE:
<221> NAME/KEY: misc_feature
<222> LOCATION: (915)..(916)
<223> OTHER INFORMATION: n = a, c, g or t/u

<400> SEQUENCE: 8
aaangctgga gctcgcgcgc ctgcaggtcg acactagtgg atccaaagaa ttcggcacga       60
ggcaagagtg atttcaagga gtatgaaaaa gaacaggata aaccacctaa tttggttctg      120
```

```
aaagataaag taaagcccaa acaggataca aaatacgatc ttatattaga tgagcaggcc    180
gaagactcaa aatcaagtca ctcacacaca agtaaaaaac acaagaagaa aacccatcac    240
tgttctgaag agaaagaaga tgaggactac atgccaatca aaaatactaa tcaggatatc    300
tatagagaaa tggggtttgg tcactatgaa gaagaagaaa gctgttggga gaaacaaaag    360
agtgaaaaga gagaccgaac tcagaaccga agtcgtagcc gatctcgaga gagggatggc    420
cattatagta atagtcataa atcaaaatac caaacagatc tttatgaaag agaaggagt     480 aaaaagagag accgaagcag aagtccaaag aagtccaaag ataaagaaaa atctaagtat    540
agatgaaaga tgaagaggca gaattgagag gctaacatat ttactcttgt ctaacttaag    600
agtgccagga aagcagatgc ttagattttg tgtcaaagct tgttatttttt ttcatactag   660 gattatggtc tttagattaa tactgattat atagagcacg gaaagataaa gaattgacat    720
tttctttgta tacttttttac nctaattttt atggtataca taatggtagt cttcattttt   780
gaagtcttca ttttcnctct tttttttatgg agtatttcta ctncaaaatc cttaacgttt   840 tntagggta ataatgnaat atctggtcnc tcncacttag atacgtgtgc gacttttnag    900
tccctaggcc nccnnccaa aatattttgga tttgggtggc ttg                      943
```

<210> SEQ ID NO 9
<211> LENGTH: 910
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (584)..(584)
<223> OTHER INFORMATION: n = a, c, g or t/u
<220> FEATURE:
<221> NAME/KEY: misc_feature
<222> LOCATION: (626)..(626)
<223> OTHER INFORMATION: n = a, c, g or t/u
<220> FEATURE:
<221> NAME/KEY: misc_feature
<222> LOCATION: (723)..(723)
<223> OTHER INFORMATION: n = a, c, g or t/u
<220> FEATURE:
<221> NAME/KEY: misc_feature
<222> LOCATION: (751)..(751)
<223> OTHER INFORMATION: n = a, c, g or t/u
<220> FEATURE:
<221> NAME/KEY: misc_feature
<222> LOCATION: (756)..(756)
<223> OTHER INFORMATION: n = a, c, g or t/u
<220> FEATURE:
<221> NAME/KEY: misc_feature
<222> LOCATION: (775)..(775)
<223> OTHER INFORMATION: n = a, c, g or t/u
<220> FEATURE:
<221> NAME/KEY: misc_feature
<222> LOCATION: (784)..(784)
<223> OTHER INFORMATION: n = a, c, g or t/u
<220> FEATURE:
<221> NAME/KEY: misc_feature
<222> LOCATION: (796)..(796)
<223> OTHER INFORMATION: n = a, c, g or t/u
<220> FEATURE:
<221> NAME/KEY: misc_feature
<222> LOCATION: (833)..(833)
<223> OTHER INFORMATION: n = a, c, g or t/u
<220> FEATURE:
<221> NAME/KEY: misc_feature
<222> LOCATION: (844)..(844)
<223> OTHER INFORMATION: n = a, c, g or t/u
<220> FEATURE:

```
<221> NAME/KEY: misc_feature
<222> LOCATION: (870)..(870)
<223> OTHER INFORMATION: n = a, c, g or t/u
<220> FEATURE:
<221> NAME/KEY: misc_feature
<222> LOCATION: (884)..(884)
<223> OTHER INFORMATION: n = a, c, g or t/u
<220> FEATURE:
<221> NAME/KEY: misc_feature
<222> LOCATION: (894)..(894)
<223> OTHER INFORMATION: n = a, c, g or t/u
<220> FEATURE:
<221> NAME/KEY: misc_feature
<222> LOCATION: (903)..(903)
<223> OTHER INFORMATION: n = a, c, g or t/u

<400> SEQUENCE: 9
aatngctgga gctcgcgcgc ctgcaggtcg acactagtgg atccaaagaa ttcggcacga      60
gggcgagctc ggcaacctcg gcgcagcgag cgcgggcggc cagccagggc caggggcgg     120 tggcggccaa ggtccgaccg ggtgccagct gttcccagcc cccgcctcgg gcccgccgcc    180
ggcgccgcca tgggcaagaa gcacaagaag cacaaggccg agtggcgctc gtcctacgag    240
gattatgccg acaagcccct ggagaagcct ctaaagctag tcctgaaggt cggaggaagt    300
gaagtgactg aactctcagg atccggccac gactccagtt actatgatga caggtcagac    360
catgagcgag agaggcacaa agaaaagaaa aagaagaaga agaagaagtc cgagaaggag    420
aagcatctgg acgatgagga aagaaggaag cgaaaggaag agaagaagcg gaagcgagag    480
agggagcact gtgacacgga gggagaggct gacgactttg atcctgggaa gaaggtggag    540
gtggagccgc ccccagatcg gccagtccga gcgtgccgga cacngccagc cgaaaatgag    600
agcacaccta ttcagcaact cctggnaaca cttcctccgc cagcttcaga gaaaagatcc    660
ccatggattt tttgcttttc ctgtcacgga tgcaattgct cctgggatat ccatgataa    720 tanaacctcc catggatttt ggcaccatga nagacnaaat tgtagctaat gaatncaagt    780
cagntacgga atttanggca attccacgct gatgtgtgat atgcatggac ttncataggc    840
cagntccgtg tactacagtt ggcaagagan cttcccgcag cttnaagatg atgngcaacc    900 gcngctcttt                                                           910

<210> SEQ ID NO 10
<211> LENGTH: 1082
<212> TYPE: DNA
<213> ORGANISM: homo sapiens

<400> SEQUENCE: 10
ggcttccatc ctaatacgac tcgctatagg gctcgagcgg ccgcccgggc aggtctgggc      60
cacggactgc cggaccgttg ggctgtgagg cagcgtctca gcgaggcggc acccggagcc    120
atgtcttcac ataggaggaa agcgaagggg aggaatagga gaagtcaccg tgccatgcgt    180
gtggctcact tagagctggc aacttatgag ttggcggcaa ctgagtcgaa tcccgagagc    240
agccatcctg gatacgaggc cgccatggct gacaggcctc agccaggatg gcgggaatct    300
ctaaagatgc gggtcagcaa acccttlggg atgctcatgc tctccatttg gatcctgctg    360
ttcgtgtgct actacctgtc ctactacctg tgctccgggt cctcatattt tgtgcttgca    420
aatggacata tcctgcccaa cagtgaaaat gctcatggcc aatctctgga agaagattcc    480
gcattggaag ctttgctgaa ttttttcttt ccaacaactt gcaatctgag gaaaatcag    540 gtggcaaagc cttgtaatga gctgcaagat cttagtgaga gtgaatgttt gagacacaaa    600
tgctgttttt catcatcggg gaccacgagc ttcaaatgtt ttgctccatt tagagatgtg    660
```

```
cctaaacaga tgatgcaaat gtttgggctt ggtgcgatca gccttatcct ggtatgtctg    720
cccatttatt gccgctctct tttctggagg agcgaaccgg ccgatgattt acaaaggcag    780
gacaacagag ttgtaacggg tttgaagaaa caaagaagga agcgaaagag gaagtctgaa    840
atgttacaga aagcagcaag aggacgtgag gaacatggtg acgagtagca agagaccaaa    900
gcattatttt cccctcaaga caacagaaac cattcagagc agaggggact gtctcagcca    960
tgcaaacctc atggagcatt ttggaaagtt aaaattgatt cttattttg tcatgtttac    1020 tttcaaacat gaaataaaat tgagttctgt tttcatgcat caaaaaaaaa aaaaaaaaa   1080 aa                                                                  1082
```

```
<210> SEQ ID NO 11
<211> LENGTH: 924
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (204)..(204)
<223> OTHER INFORMATION: n = a, c, g or t/u
<220> FEATURE:
<221> NAME/KEY: misc_feature
<222> LOCATION: (752)..(752)
<223> OTHER INFORMATION: n = a, c, g or t/u
<220> FEATURE:
<221> NAME/KEY: misc_feature
<222> LOCATION: (754)..(754)
<223> OTHER INFORMATION: n = a, c, g or t/u
<220> FEATURE:
<221> NAME/KEY: misc_feature
<222> LOCATION: (756)..(759)
<223> OTHER INFORMATION: n = a, c, g or t/u
<220> FEATURE:
<221> NAME/KEY: misc_feature
<222> LOCATION: (761)..(761)
<223> OTHER INFORMATION: n = a, c, g or t/u
<220> FEATURE:
<221> NAME/KEY: misc_feature
<222> LOCATION: (765)..(765)
<223> OTHER INFORMATION: n = a, c, g or t/u
<220> FEATURE:
<221> NAME/KEY: misc_feature
<222> LOCATION: (770)..(770)
<223> OTHER INFORMATION: n = a, c, g or t/u
<220> FEATURE:
<221> NAME/KEY: misc_feature
<222> LOCATION: (773)..(775)
<223> OTHER INFORMATION: n = a, c, g or t/u
<220> FEATURE:
<221> NAME/KEY: misc_feature
<222> LOCATION: (777)..(779)
<223> OTHER INFORMATION: n = a, c, g or t/u
<220> FEATURE:
<221> NAME/KEY: misc_feature
<222> LOCATION: (781)..(781)
<223> OTHER INFORMATION: n = a, c, g or t/u
<220> FEATURE:
<221> NAME/KEY: misc_feature
<222> LOCATION: (802)..(802)
<223> OTHER INFORMATION: n = a, c, g or t/u
<220> FEATURE:
<221> NAME/KEY: misc_feature
<222> LOCATION: (812)..(812)
<223> OTHER INFORMATION: n = a, c, g or t/u
<220> FEATURE:
<221> NAME/KEY: misc_feature
<222> LOCATION: (829)..(829)
<223> OTHER INFORMATION: n = a, c, g or t/u
<220> FEATURE:
```

<221> NAME/KEY: misc_feature
<222> LOCATION: (833)..(833)
<223> OTHER INFORMATION: n = a, c, g or t/u
<220> FEATURE:
<221> NAME/KEY: misc_feature
<222> LOCATION: (849)..(849)
<223> OTHER INFORMATION: n = a, c, g or t/u
<220> FEATURE:
<221> NAME/KEY: misc_feature
<222> LOCATION: (866)..(866)
<223> OTHER INFORMATION: n = a, c, g or t/u
<220> FEATURE:
<221> NAME/KEY: misc_feature
<222> LOCATION: (873)..(873)
<223> OTHER INFORMATION: n = a, c, g or t/u
<220> FEATURE:
<221> NAME/KEY: misc_feature
<222> LOCATION: (879)..(880)
<223> OTHER INFORMATION: n = a, c, g or t/u
<220> FEATURE:
<221> NAME/KEY: misc_feature
<222> LOCATION: (886)..(886)
<223> OTHER INFORMATION: n = a, c, g or t/u
<220> FEATURE:
<221> NAME/KEY: misc_feature
<222> LOCATION: (901)..(901)
<223> OTHER INFORMATION: n = a, c, g or t/u

<400> SEQUENCE: 11

```
aatngctgga gctcgcgcgc ctgcaggtcg acactagtgg atccaaagaa ttcggcacga      60
gggagaaaaa gagtttataa tgctacaaaa tgaacaggag ataagtcaac tgaaaaaga     120
aattgaaaga acacaacaaa ggatgaaaga aatggagagt gttatgaaag agcaagaaca    180
gtacattgcc actcagtaca aggnggccat agatttgggg caagaattga ggctgacccg    240
ggagcaggtg cagaactctc atacagaatt ggcagaggct cgtcatcagc aagtccaagc    300
acagagagaa atagaaaggc tctctagtga actggaggat atgaagcaac tctctaaaga    360
gaaagatgct catggaaacc atttagctga gaactgggg gcttctaaag tacgtgaagc    420
tcatttagaa gcaagaatgc aagcagaaat caagaaattg tcagcagaag tagaatctct    480
caaagaagct tatcatatgg agatgatttc acatcaagag aaccatgcaa agtggaagat    540
ttctgctgac tctcaaaagt cttctgttca gcaactaaac gaacagttag agaaggcaaa    600
attggaatta aagaagctc aggatactgt aagcaatttg catcaacaag tccaagatag    660
gaatgaagta attgaagctg caaatgaagc attacttact aaagtaagta aacatataaa    720
agtattaaag catatctatg aaaacaaaac cncncnnnnc ngccntcccn ccnnnannnc    780
ntctcgagag tacttctaaa gnggccgcgg gnccctccga tttcccccng ggngggtac    840
caggtaagng tacccaattc cccctntagg agncgtatnn aattcnctgg ccgccgttta    900
ncacctcgtg ctgggaaaac ctgg                                             924
```

<210> SEQ ID NO 12
<211> LENGTH: 917
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (745)..(745)
<223> OTHER INFORMATION: n = a, c, g or t/u
<220> FEATURE:
<221> NAME/KEY: misc_feature
<222> LOCATION: (784)..(784)
<223> OTHER INFORMATION: n = a, c, g or t/u

<400> SEQUENCE: 12

```
aaanctggag ctcgcgcgcc tgcaggtcga cactagtgga tccaaagaat tcggcacgag    60
ggggaaaatg gcggattcct cggggcgagg cgctgggaag cctgcaaccg gccccacaaa   120
ttctagcagt gccaagaaga aggataaaag agttcaaggt ggaagagtga ttgagtcccg   180
gtatctgcag tatgaaaaga agacaaccca aaaggctcct gcaggagatg ggtcacagac   240
ccgagggaag atgtctgaag gtggaaggaa atccagcctg ctccagaaaa gcaaagcaga   300
tagcagtggg gtcggaaagg gtgacctgca gtccacgttg ctggaagggc atggcacagc   360
tccacctgac ctggatctct ctgctattaa tgacaaaagc atcgtcaaaa agacgccaca   420
gttagcaaaa acaatatcaa agaaacctga gtcaacatca ttttctgccc ctcggaaaaa   480
gagcccggat ttatctgaag caatggaaat gatggagtct cagacactac tgctgacgct   540
actatccgta aagatggaga caatcttgc tgagtttgaa agaagggcag aaaagaattt    600
attaataatg tgtaaggaga aggagaagct acagaaaaag gcccacgagc tgaagcgcag   660
gcttctcctc tctcagagga agcgggagct ggcagatgtc ctggatgccc agatcgagat   720
gctcagcccc cttcgaggca gtggncacac gcttcaagga gcaatacagg acattcgcca   780
cggnccttgg acactaccag gcacgagctg cccgtgaggt ccatccacct ggagggagat   840
gggcagcagc tcttagacgc cctgcagcat gactggtgac cctcagcgcc tcctgggaaa   900
cttgatgttg gtgatcg                                                  917
```

```
<210> SEQ ID NO 13
<211> LENGTH: 921
<212> TYPE: DNA
<213> ORGANISM: homo sapiens
<220> FEATURE:
<221> NAME/KEY: misc_feature
<222> LOCATION: (4)..(4)
<223> OTHER INFORMATION: n = a, c, g or t/u
<220> FEATURE:
<221> NAME/KEY: misc_feature
<222> LOCATION: (742)..(742)
<223> OTHER INFORMATION: n = a, c, g or t/u
<220> FEATURE:
<221> NAME/KEY: misc_feature
<222> LOCATION: (808)..(808)
<223> OTHER INFORMATION: n = a, c, g or t/u
<220> FEATURE:
<221> NAME/KEY: misc_feature
<222> LOCATION: (822)..(822)
<223> OTHER INFORMATION: n = a, c, g or t/u
<220> FEATURE:
<221> NAME/KEY: misc_feature
<222> LOCATION: (842)..(842)
<223> OTHER INFORMATION: n = a, c, g or t/u
<220> FEATURE:
<221> NAME/KEY: misc_feature
<222> LOCATION: (858)..(858)
<223> OTHER INFORMATION: n = a, c, g or t/u
<220> FEATURE:
<221> NAME/KEY: misc_feature
<222> LOCATION: (895)..(895)
<223> OTHER INFORMATION: n = a, c, g or t/u
<220> FEATURE:
<221> NAME/KEY: misc_feature
<222> LOCATION: (912)..(912)
<223> OTHER INFORMATION: n = a, c, g or t/u
<220> FEATURE:
<221> NAME/KEY: misc_feature
<222> LOCATION: (918)..(918)
<223> OTHER INFORMATION: n = a, c, g or t/u
<220> FEATURE:
<221> NAME/KEY: misc_feature
<222> LOCATION: (920)..(920)
```

<223> OTHER INFORMATION: n = a, c, g or t/u

<400> SEQUENCE: 13

```
aatngctgga gctcgcgcgc ctgcaggtcg acactagtgg atccaaagaa ttcggcacga    60
ggtgagggc ttccggttgg ggtggcaggg tggtggatct gttggtcccg tttcccgtc    120
gcacgtggtg gccactgttg gcttctgaat ggtttgcaag gcggatatcc acgccaaggc   180
ctttggatcg gccgtgggta catccgtctg agccgttcct ttccatcgca gagcggcggc   240
ctccggcggc gctctccagt catggactac cggcggcttc tcatgagccg ggtggtcccc   300
gggcaattcg acgacgcgga ctcctctgac agtgaaaaca gagacttgaa gacagtcaaa   360
gagaaggatg acattctgtt tgaagacctt caagacaatg tgaatgagaa tggtgaaggt   420
gaaatagaag atgaggagga ggagggttat gacgatgatg atgatgactg ggactgggat   480
gaaggagttg gaaaactcgc caagggttat gtctggaatg gaggaagcaa cccacaggca   540
aatcgacaga cctccgacag cagttcagcc aaaatgtcta ctccagcaga caaggtctta   600
cggaaaattt gagaataaaa ttaatttaga taagctaaat gttactgatt ccgtcataaa   660
taaagtcacc gaaaagtcta gacaaaagga agcagatatg tatcgcatca agataaggc    720
agacagagca actgtagaac angtgttgga tcccagacca agaatgattt tattcaagat   780
gttgactaga ggaatcataa cagagataa tggctgcatt anccaggaaa aaagctaatg    840
tnaccatgct acccagcnaa tggagagagc agaccatcaa atttataaac ttctntttgg   900
ggttcaagat cnggatantn t                                             921
```

<210> SEQ ID NO 14
<211> LENGTH: 901
<212> TYPE: DNA
<213> ORGANISM: homo sapiens
<220> FEATURE:
<221> NAME/KEY: misc_feature
<222> LOCATION: (836)..(836)
<223> OTHER INFORMATION: n = a, c, g or t/u
<220> FEATURE:
<221> NAME/KEY: misc_feature
<222> LOCATION: (892)..(892)
<223> OTHER INFORMATION: n = a, c, g or t/u

<400> SEQUENCE: 14

```
gctggagctc gcgcgcctgc aggtcgacac tagtggatcc aaagaattcg gcacgaggaa   60
gacgctactt cccctatcat agaagagctt atcacctttc atgatcacgc cctcataatc   120
attttcctta tctgcttcct agtcctgtat gcccttttcc taacactcac aacaaaacta   180
actaatacta acatctcaga cgctcaggaa atagaaaccg tctgaactat cctgcccgcc   240
atcatcctag tcctcatcgc cctcccatcc ctacgcatcc tttacataac agacgaggtc   300
aacgatccct cccttaccat caaatcaatt ggccaccaat ggtactgaac ctacgagtac   360
accgactacg gcggactaat cttcaactcc tacatacttc cccattatt cctagaacca   420
ggcgacctgc gactccttga cgttgacaat cgagtagtac tcccgattga agcccccatt   480
cgtataataa ttcatcaca agacgtcttg cactcatgag ctgtccccac attaggctta   540
aaaacagatg caattcccgg acgtctaaac caaaccactt tcaccgctac acgaccgggg   600
gtatactacg gtcaatgctc tgaaatctgt ggagcaaacc acagttcat gcccatcgtc    660
ctagaattaa ttcccctaaa atctttgaa ataggacccg tatttaccct atagcaccc    720
ctctacccc tctagagcca aaaaaaaaa aaaaaactc gagactagtt ctctccggac     780
attcagactg agcgtgccta ccaaaagcag ccgaccatct ttcaaaacaa gaaganggtc   840
```

```
ctgctgggag aactggcaag gagaagctcc gcggtactac aagaacatcg gnctgggctt    900
c                                                                    901
```

<210> SEQ ID NO 15
<211> LENGTH: 1850
<212> TYPE: DNA
<213> ORGANISM: homo sapiens

<400> SEQUENCE: 15

```
cggcgccggg gcggcagcag aagtccggag tcagggcgtg tggctgagga gatgccacta     60
agcacagctg gcatcctgag ctcctcttct gccgcttcca acaggtcaag gaataaggct    120
cgctatcgga ccaaagccgt gagctctgag gtggatgaga gcctctttgg agatatcaag    180
tccccagccc agggccagag cgacagcccc attgtgctgc tccgagataa gcataccctt    240
caaaaaactc tcactgcttt gggcttggat cgcaagccag agaccatcca gctcatcacc    300
cgggacatgg tccgagaact cattgttccc acagaggatc cctccgggga gtccctaatc    360
atcagccctg aggagtttga gcgaatcaaa tgggcatccc atgtcctgac cagagaagaa    420
cttgaggcca gggaccaggc cttcaagaag gagaaggaag ccaccatgga tgcagtgatg    480
acacgaaaga gatcatgaa acagaaggag atggtgtgga acaacaacaa gaagctcagt    540
gacctggagg aggtggccaa ggaacgggcc cagaacctcc tgcagagagc caacaagctg    600
cggatggagc aggaggagga gctcaaggac atgagcaaga ttatcctcaa tgctaagtgc    660
catgccatcc gggatgccca atcctggag aagcagcaga tccaaaaaga actggacaca    720
gaagagaagc ggttggatca gatgatggaa gtggagcggc agaaatccat tcaaaggcag    780
gaggaactgg agaggaagag gagggaggaa agaattagag gaaggcggca aattgtggaa    840
cagatggaaa agaaccagga ggagcgatcg ctgcttgctg agcagcggga gcaggagaag    900
gagcagatgc tggaatatat ggaacagctc aagaggaaga tctaaagga catggaacga    960
aggcagcaac aaaaactgaa gatgcaagct gagattaagc gcatcaatga tgaaaaccag   1020
aaacagaaag cagaactgct ggctcaggag aagctggcag accagatggt gatggagttt   1080
accaagaaga gatggctcg agaagcagag tttgaggctg agcaggagag aatccggagg   1140
gagaaagaga aggagatcgc acgcttgagg gccatgcagg agaaggccca ggattaccag   1200
gcagaacagg atgccttgcg ggccaagcgc aaccaggagg ttgcagacag agagtggcgc   1260
agaaaggaaa aggaaaatgc gcggaagaag atggaaacag aggctgagct gcgaaaaagt   1320
cggctcgaac aggtggcttt caaggagcac gctctggctg ttcaggtgca cgggaccggg   1380
atgagttcga gaggattctt cgggctcaga gagaacagat tgagaaggag cggctggagg   1440
aggagaaaaa ggccacaggg cgcttacagc atgccaatga gctccggcgc caggtgcgcg   1500
agaaccagca gaaggaagtg cagaaccgga ttgccaccct tgaggggggc cggcgcctca   1560
aagaggaggc ccagaaacgc cgtgagcgca tcgatgagat caagaggaaa aagcttgaag   1620
agctgagagc cactgccctt cccgagaagt actgcattga agctgagcgc aaagctaaca   1680
tcctgccagc tacctctgtg aactgagggg agccttcgtg gccctcagga tgccttcggg   1740
ggacagattc tgcccagtct ctgggcatcc ataattgctg ctaacctaga catttcatag   1800
ttacagatta aatctacttg actaaaaaaa aaaaaaaaa aaaaaaaaaa                1850
```

<210> SEQ ID NO 16
<211> LENGTH: 1791
<212> TYPE: DNA

<213> ORGANISM: homo sapiens

<400> SEQUENCE: 16

```
cccagaaatt ctacccaagc tccctcagca ccatgtaccg agcacttcgg ctcctcgcgc      60
gctcgcgtcc cctcgtgcgg gctccagccg cagccttagc ttcggctccc ggcttgggtg     120
gcgcggccgt gccctcgttt tggcctccga acgcggctcg aatggcaagc caaaattcct     180
tccggataga atatgatacc tttggtgaac taaaggtgcc aaatgataag tattatggcg     240
cccagaccgt gagatctacg atgaacttta agattggagg tgtgacagaa cgcatgccaa     300
ccccagttat taaagctttt ggcatcttga agcgagcggc cgctgaagta aaccaggatt     360
atggtcttga tccaaagatt gctaatgcaa taatgaaggc agcagatgag gtagctgaag     420
gtaaattaaa tgatcatttt cctctcgtgg tatggcagac tggatcagga actcagacaa     480
atatgaatgt aaatgaagtc attagcaata gagcaattga atgttaggag gtgaacttg      540
gcagcaagat acctgtgcat cccaacgatc atgttaataa aagccagagc tcaaatgata     600
cttttcccac agcaatgcac attgctgctg caatagaagt tcatgaagta ctgttaccag     660
gactacagaa gttacatgat gctcttgatg caaaatccaa agagtttgca cagatcatca     720
agattggacg tactcatact caggatgctg ttccacttac tcttgggcag gaatttagtg     780
gttatgttca acaagtaaaa tatgcaatga caagaataaa agctgccatg ccaagaatct     840
atgagctcgc agctggaggc actgctgttg gtacaggttt aaatactaga attggctttg     900
cagaaaaggt tgctgcaaaa gtggctgcac ttacaggctt gccttttgtc actgctccga     960
ataaatttga agctctggct gctcatgacg ctctggttga gctcagtgga gccatgaaca    1020
ctactgcctg cagtctgatg aagatagcaa atgatattcg attttgggt tctggtcctc     1080
ggtcaggtct gggagaattg atcttgcctg aaaatgaacc aggaagcagt atcatgccag    1140
gcaaggtgaa ccctactcag tgtgaagcaa tgaccatggt tgcagcccaa gtcatgggga    1200
accatgttgc tgtcactgtc ggaggcagca atggacattt tgagttgaat gttttcaagc    1260
caatgatgat taaaaatgtg ttacactcag ccaggctgct gggggatgct tcagtttcct    1320
ttacagaaaa ctgcgtggtg ggaatccagg ccaatacaga aaggatcaac aagctgatga    1380
atgagtctct aatgttggtg acagctctca atcctcatat agggtatgac aaggcagcaa    1440
agattgctaa gacagcacac aaaaatggat caaccttaaa ggaaactgct atcgaacttg    1500
gctatctcac agcagagcag tttgacgaat gggtaaaacc taaggacatg ctgggtccaa    1560
agtgatttac ataaatttat aatgaaaata acatgtata aaatttaaaa aaacagactc      1620
ccatttctta aaaacggata agtttgaaag gaaactgcta ttgaacttaa gcatctctag    1680
cagagcaatt tgatcagtat ataaaaccct aggatgtgct aggtctaaga tggattaaac    1740
aagtataaaa taaatacat ttataaaata aaaggaaaa cagacttaaa a               1791
```

```
<210> SEQ ID NO 17
<211> LENGTH: 3258
<212> TYPE: DNA
<213> ORGANISM: homo sapiens
```

<400> SEQUENCE: 17

```
cggccgcgtg acggtggcgc acaagaaggc tccgccggcc ctgatcgacg agtgcatcga      60
gaagttcaat cacgtcagcg gcagccgggg gtccgagagc cccgcccca acccgcccca     120
tgccgcgccc acaggagcc aggagcctgt gcgcaggccc atgcgcaagt ccttctccca     180
gcccggcctg cgctcgctgg cctttaggaa ggagctgcag gatgggggcc tccgaagcag    240
```

| | |
|---|---|
| cggcttcttc agctccttcg aggagagcga cattgagaac cacctcatta gcggacacaa | 300 |
| tattgtgcag cccacagata tcgaggaaaa tcgaactatg ctcttcacga ttggccagtc | 360 |
| tgaagtttac ctcatcagtc ctgacaccaa aaaaatagca ttggagaaaa attttaagga | 420 |
| gatatccttt tgctctcagg gcatcagaca cgtggaccac tttgggttta tctgtcggga | 480 |
| gtcttccgga ggtggcggct ttcattttgt ctgttacgtg tttcagtgca caaatgaggc | 540 |
| tctggttgat gaaattatga tgaccctgaa acaggccttc acggtggccg cagtgcagca | 600 |
| gacagctaag gcgccagccc agctgtgtga gggctgcccc ctgcaaagcc tgcacaagct | 660 |
| ctgtgagagg atagagggaa tgaattcttc caaaacaaaa ctagaactgc aaaagcacct | 720 |
| gacgacatta accaatcagg agcaggcgac tatttttgaa gaggttcaga aattgagacc | 780 |
| gagaaatgag cagcgagaga tgaattgat tatttctttt ctgagatgtt tatatgaaga | 840 |
| gaaacagaaa gaacacatcc atattgggga gatgaagcag acatcgcaga tggcagcaga | 900 |
| gaatattgga agtgaattac cacccagtgc cactcgattt aggctagata tgctgaaaaa | 960 |
| caaagcaaag agatctttaa cagagtcttt agaaagtatt ttgtcccggg gtaataaagc | 1020 |
| cagaggcctg caggaacact ccatcagtgt ggatctggat agctccctgt ctagtacatt | 1080 |
| aagtaacacc agcaaagagc catctgtgtg tgaaaaggag gccttgccca tctctgagag | 1140 |
| ctcctttaag ctcctcggct cctcggagga cctgtccagt gactcggaga gtcatctccc | 1200 |
| agaagagcca gctccgctgt cgccccagca ggccttcagg aggcgagcaa acaccctgag | 1260 |
| tcacttcccc atcgaatgcc aggaacctcc acaacctgcc cgggggtccc cgggggtttc | 1320 |
| gcaaaggaaa cttatgaggt atcactcagt gagcacagag acgcctcatg aacgaaagga | 1380 |
| cttgaatcc aaagcaaacc atcttggtga ttctggtggg actcctgtga agacccggag | 1440 |
| gcattcctgg aggcagcaga tattcctccg agtagccacc ccgcagaagg cgtgcgattc | 1500 |
| ttccagcaga tatgaagatt attcagagct gggagagctt cccccacgat ctcctttaga | 1560 |
| accagtttgt gaagatgggc cctttggccc ccaccagag gaaaagaaaa ggacatctcg | 1620 |
| tgagctccga gagctgtggc aaaaggctat tcttcaacag atactgctgc ttagaatgga | 1680 |
| gaaggaaaat cagaagctcc aagcctctga aaatgatttg ctgaacaagc gcctgaagct | 1740 |
| cgattatgaa gaaattactc cctgtcttaa agaagtaact acagtgtggg aaaagatgct | 1800 |
| tagcactcca ggaagatcaa aaattaagtt tgacatggaa aaaatgcact cggctgttgg | 1860 |
| gcaaggtgtg ccacgtcatc accgaggtga atctggaaa tttctagctg agcaattcca | 1920 |
| ccttaaacac cagtttccca gcaaacagca gccaaaggat gtgccataca agaactctt | 1980 |
| aaagcagctg acttcccagc agcatgcgat tcttattgac cttgggcgaa cctttcctac | 2040 |
| acacccatac ttctctgccc agcttggagc aggacagcta tcgctttaca acattttgaa | 2100 |
| ggcctactca cttctagacc aggaagtggg atattgccaa ggtctcagct tgtagcagg | 2160 |
| cattttgctt cttcatatga gtgaggaaga ggcgtttaaa atgctcaagt ttctgatgtt | 2220 |
| tgacatgggg ctgcggaaac agtatcggcc agacatgatt attttacaga tccagatgta | 2280 |
| ccagctctcg aggttgcttc atgattacca cagagacctc tacaatcacc tggaggagca | 2340 |
| cgagatcggc cccagcctct acgctgcccc ctggttcctc accatgtttg cctcacagtt | 2400 |
| cccgctggga ttcgtagcca gagtctttga tatgattttt cttcagggaa cagaggtcat | 2460 |
| atttaaagtg gctttaagtc tgttgggaag ccataagccc ttgattctgc agcatgaaaa | 2520 |
| cctagaaaacc atagttgact ttataaaaag cacgctaccc aaccttggct tggtacagat | 2580 |

| | | |
|---|---|---|
| ggaaaagacc atcaatcagg tatttgaaat ggacatcgct aaacagttac aagcttatga | 2640 | |
| agttgagtac cacgtccttc aagaagaact tatcgattcc tctcctctca gtgacaacca | 2700 | |
| aagaatggat aaattagaga aaccaacag cagcttacgc aaacagaacc ttgacctcct | 2760 | |
| tgaacagttg caggtggcaa atggtaggat ccaaagcctt gaggccacca ttgagaagct | 2820 | |
| cctgagcagt gagagcaagc tgaagcaggc catgcttacc ttagaactgg agcggtcggc | 2880 | |
| cctgctgcag acgtggagg agctgcggcg gcggagcgca gagcccagcg accgggagcc | 2940 | |
| tgagtgcacg cagcccgagc ccacgggcga ctgacagctc tgcaggagag attgcaacac | 3000 | |
| catcccacac tgtccaggcc ttaactgaga gggacagaag acgctggaag gagagaagga | 3060 | |
| agcgggaagt gtgcttctca gggaggaaac cggcttgcca gcaagtagat tcttacgaac | 3120 | |
| tccaacttgc aattcagggg gcatgtccca gtgttttttt tgttgttttt agatactaaa | 3180 | |
| tcgtcccttc tccagtcctg attactgtac acagtagctt tagatggcgt ggacgtgaat | 3240 | |
| aaatgcaact tatgttttt | 3258 | |

<210> SEQ ID NO 18
<211> LENGTH: 3496
<212> TYPE: DNA
<213> ORGANISM: homo sapiens

<400> SEQUENCE: 18

| | | |
|---|---|---|
| gaattctatg gagtgtaatt tgtgtatga attatatttt taaaacattg aagagttttc | 60 | |
| agaaagaagg ctagtagagt tgattactga tactttatgc taagcagtac ttttttggta | 120 | |
| gtacaatatt ttgttaggcg tttctgataa cactagaaag gacaagtttt atcttgtgat | 180 | |
| aaattgatta atgtttacaa catgactgat aattatagct gaatagtcct taaatgatga | 240 | |
| acaggttatt tagttttaa atgcagtgta aaagtgtgc tgtggaaatt ttatggctaa | 300 | |
| ctaagtttat ggagaaaata ccttcagttg atcaagaata atagtggtat acaaagttag | 360 | |
| gaagaaagtc aacatgatgc tgcaggaaat ggaaacaaat acaaatgata tttaacaaag | 420 | |
| atagagttta cagttttga actttaagcc aaattcattt gacatcaagc actatagcag | 480 | |
| gcacaggttc aacaaagctt gtgggtattg acttcccca aaagttgtca gctgaagtaa | 540 | |
| tttagcccac ttaagtaaat actatgatga taagctgtgt gaacttagct tttaaatagt | 600 | |
| gtgaccatat gaaggtttta attactttg tttattggaa taaaatgaga ttttttgggt | 660 | |
| tgtcatgtta aagtgcttat agggaaagaa gcctgcatat aattttttac cttgtggcat | 720 | |
| aatcagtaat tggtctgtta ttcaggcttc atagcttgta accaaatata aataaaaggc | 780 | |
| ataatttagg tattctatag ttgcttagaa ttttgttaat ataaatctct gtgaaaaatc | 840 | |
| aaggagtttt aatattttca gaagtgcatc cacctttcag ggctttaagt tagtattact | 900 | |
| caagattatg aacaaatagc acttaggtta cctgaaagag ttactacaac cccaaagagt | 960 | |
| tgtgttctaa gtagtatctt ggaaattcag agagatactc atcctacctg aatataaaact | 1020 | |
| gagataaatc cagtaaagaa agtgtagtaa attctacata agagtctatc attgatttct | 1080 | |
| tttggtggta aaaatcttag ttcatgtgaa gaaatttcat gtgaatgttt tagctatcaa | 1140 | |
| acagcactgt cacctactca tgcacaaaac tgcctcccaa agactttttcc caggtccctc | 1200 | |
| gtatcaaaac attaagagta taatggaaga tagcacgatc ttgtcagatt ggacaaacag | 1260 | |
| caacaaacaa aaaatgaagt atgacttttc ctgtgaactc tacagaatgt ctacatattc | 1320 | |
| aactttcccc gccggggtgc ctgtctcaga aaggagtctt gctcgtgctg gtttttatta | 1380 | |
| tactggtgtg aatgacaagg tcaaatgctt ctgttgtggc ctgatgctgg ataactggaa | 1440 | |

```
actaggagac agtcctattc aaaagcataa acagctatat cctagctgta gctttattca   1500
gaatctggtt tcagctagtc tgggatccac ctctaagaat acgtctccaa tgagaaacag   1560
ttttgcacat tcattatctc ccaccttgga acatagtagc ttgttcagtg gttcttactc   1620
cagcctttct ccaaaccctc ttaattctag agcagttgaa gacatctctt catcgaggac   1680 taaccccctac agttatgcaa tgagtactga agaagccaga tttcttacct accatatgtg   1740
gccattaact tttttgtcac catcagaatt ggcaagagct ggttttatt atataggacc    1800 tggagatagg gtagcctgct ttgcctgtgg tgggaagctc agtaactggg aaccaaagga   1860
tgatgctatg tcagaacacc ggaggcattt tcccaactgt ccattttggg aaaattctct   1920
agaaactctg aggtttagca tttcaaatct gagcatgcag acacatgcag ctcgaatgag   1980
aacatttatg tactggccat ctagtgttcc agttcagcct gagcagcttg caagtgctgg   2040
tttttattat gtgggtcgca atgatgatgt caaatgcttt tgttgtgatg gtggcttgag   2100
gtgttgggaa tctggagatg atccatgggt agaacatgcc aagtggtttc caaggtgtga   2160
gttcttgata cgaatgaaag gccaagagtt tgttgatgag attcaaggta gatatcctca   2220
tcttcttgaa cagctgttgt caacttcaga taccactgga gaagaaaatg ctgacccacc   2280
aattattcat tttggacctg agaaagttc ttcagaagat gctgtcatga tgaatacacc    2340
tgtggttaaa tctgccttgg aaatgggctt taatagagac ctggtgaaac aaacagttca   2400
aagtaaaatc ctgacaactg gagagaacta taaaacagtt aatgatattg tgtcagcact   2460
tctaaatgct gaagatgaaa aaagagagga ggagaaggaa aaacaagctg aagaaatggc   2520
atcagatgat ttgtcattaa ttcggaagaa cagaatggct ctctttcaac aattgacatg   2580
tgtgcttcct atcctggata tcttttaaaa ggccaatgta attaataaac aggaacatga   2640
tattattaaa caaaaaacac agatacccttt acaagcgaga gaactgattg ataccatttt   2700
ggttaaagga aatgctgcgg ccaacatctt caaaaactgt ctaaaagaaa ttgactctac   2760
attgtataag aacttatttg tggataagaa tatgaagtat attccaacag aagatgtttc   2820
aggtctgtca ctggaagaac aattgaggag gttgcaagaa gaacgaactt gtaaagtgtg   2880
tatggacaaa gaagtttctg ttgtatttat tccttgtggt catctggtag tatgccagga   2940
atgtgcccct tctctaagaa aatgccctat ttgcaggggg ataatcaagg gtactgttcg   3000
tacatttctc tcttaaagaa aaatagtcta tattttaacc tgcataaaaa ggtctttaaa   3060
atattgttga acacttgaag ccatctaaag taaaaaggga attatgagtt tttcaattag   3120
taacattcat gttctagtct gctttggtac taataatctt gtttctgaaa agatggtatc   3180
atatatttaa tcttaatctg tttatttaca agggaagatt tatgtttggt gaactatatt   3240
agtatgtatg tgtacctaag ggagtagtgt cactgcttgt tatgcatcat ttcaggagtt   3300
actggatttg ttgttctttc agaaagcttt gaatactaaa ttatagtgta gaaaagaact   3360
ggaaaccagg aactctggag ttcatcagag ttatggtgcc gaattgtctt tggtgctttt   3420
cacttgtgtt ttaaaataag gattttctc ttatttctcc ccctagtttg tgagaaacat    3480
ctcaataaag tgcttt                                                  3496
```

<210> SEQ ID NO 19
<211> LENGTH: 1807
<212> TYPE: DNA
<213> ORGANISM: homo sapiens

<400> SEQUENCE: 19

| | |
|---|---|
| gaattctttc ttcagcccat gtaaacatga aaataagggt taaaaatgac ttcattatgg | 60 |
| ggaaaaggga caggatgcaa attgttcaaa ttccgggtgg ccgctgctcc ggcctccggg | 120 |
| gccttgcgga gactcacccc ttcagcgtcg ctgcccccag ctcagctctt actgcgggcc | 180 |
| gtccgacggc ggtcccatcc tgtcaggac tatgcggcgc aaacatctcc ttcgccaaaa | 240 |
| gcaggcgccg ccaccgggcg catcgtggcg gtcattggcg cagtggtgga cgtccagttt | 300 |
| gatgagggac taccaccaat tctaaatgcc ctggaagtgc aaggcaggga gaccagactg | 360 |
| gttttggagg tggcccagca tttgggtgag agcacagtaa ggactattgc tatggatggt | 420 |
| acagaaggct tggttagagg ccagaaagta ctggattctg tgcaccaat caaaattcct | 480 |
| gttggtcctg agactttggg cagaatcatg aatgtcattg gagaacctat tgatgaaaga | 540 |
| ggtcccatca aaaccaaaca atttgctccc attcatgctg aggctccaga gttcatggaa | 600 |
| atgagtgttg agcaggaaat tctggtgact ggtatcaagg ttgtcgatct gctagctccc | 660 |
| tatgccaagg gtggcaaaat tgggcttttt ggtggtgctg gagttggcaa gactgtactg | 720 |
| atcatggagt taatcaacaa tgtcgccaaa gcccatggtg gttactctgt gtttgctggt | 780 |
| gttggtgaga ggacccgtga aggcaatgat ttataccatg aaatgattga atctggtgtt | 840 |
| atcaacttaa aagatgccac ctctaaggta gcgctggtat atggtcaaat gaatcaacca | 900 |
| cctggtgctc gtgcccgggt agctctgact gggctgactg tggctgaata cttcagagac | 960 |
| caagaaggtc aagatgtact gctatttatt gataacatct ttcgcttcac ccaggctggt | 1020 |
| tcagaggtgt ctgcattatt gggccgaatc ccttctgctg tgggctatca gcctaccctg | 1080 |
| gccactgaca tgggcactat gcaggaaaga attaccacta ccaagaaggg atctatcacc | 1140 |
| tctgtacagg ctatctatgt gcctgctgat gacttgactg accctgcccc tgctactacg | 1200 |
| tttgcccatt tggatgctac cactgtactg tcgcgtgcca ttgctgagct gggcatctat | 1260 |
| ccagctgtgg atcctctaga ctccacctct cgtatcatgg atcccaacat tgttggcagt | 1320 |
| gagcattacg atgttgcccg tggggtgcaa aagatcctgc aggactacaa atccctccag | 1380 |
| gatatcattg ccatcctggg tatggatgaa ctttctgagg aagacaagtt gaccgtgtcc | 1440 |
| cgtgcacgga aaatacagcg tttcttgtct cagccattcc aggttgctga ggtcttcaca | 1500 |
| ggtcatatgg ggaagctggt acccctgaag gagaccatca aaggattcca gcagattttg | 1560 |
| gcaggtgaat atgaccatct cccagaacag gccttctata tggtgggacc cattgaagaa | 1620 |
| gctgtggcaa aagctgataa gctggctgaa gagcattcat cgtgagggggt ctttgtcctc | 1680 |
| tgtacttgtc tctctccttg cccctaaccc aaaaagcttc atttttctat ataggctgca | 1740 |
| caagagcctt gattgaagat atattctttc tgaacagtat ttaaggtttc caataaaatc | 1800 |
| ggaattc | 1807 |

<210> SEQ ID NO 20
<211> LENGTH: 2676
<212> TYPE: DNA
<213> ORGANISM: homo sapiens

<400> SEQUENCE: 20

| | |
|---|---|
| gttccggcga ggaggccgcg ccagtgacag cgatggcggc ggagtcggcg ctccaagttg | 60 |
| tggagaagct gcaggcgcgc ctggccgcga acccggaccc taagaagcta ttgaaatatt | 120 |
| tgaagaaact ctccaccctg cctattacag tagacattct tgcggagact ggggttggga | 180 |
| aaacagtaaa tagcttgcga aaacacgagc atgttggaag ctttgccagg gacctagtgg | 240 |
| cccagtggaa gaagctggtt cctgtggaac gaaatgctga gcctgatgaa caggactttg | 300 |

-continued

```
agaagagcaa ttcccgaaag cgccctcggg atgccctgca gaaggaggag gagatggagg      360
gggactacca agaaacctgg aaagccacgg ggagccgatc ctatagccct gaccacaggc      420
agaagaaaca taggaaactc tcggagctcg agagacctca caaagtgtct cacggtcatg      480
agaggagaga tgagagaaag aggtgtcaca gaatgtcacc aacttactct tcagaccctg      540
agtcttctga ttatggccat gttcaatccc ctccatcttg taccagtcct catcagatgt      600
acgtcgacca ctacagatcc ctggaggagg accaggagcc cattgtttca caccagaagc      660
ctgggaaagg ccacagcaat gcctttcagg acagactcgg ggccagccaa gaacgacacc      720
tgggtgaacc ccatgggaaa ggggttgtga gtcaaaacaa ggagcacaaa tcttcccaca      780
aggacaaacg ccccgtggat gccaagagtg atgagaaggc ctctgtggtg agcagagaga      840
aatcacacaa ggccctctcc aaagaggaga accgaaggcc accctcaggg gacaatgcaa      900
gggagaaacc gccctctagt ggcgtaaaga agagaaggga cagagagggc agcagcctga      960
agaagaagtg tttgcctccc tcagaggccg cttcagacaa ccacctgaaa aagccaaagc     1020
acagagaccc agagaaagcc aaattggaca aaagcaagca aggtctggac agctttgaca     1080
caggaaaagg agcaggagac ctgttgccca aggtaaaaga gaagggttct aacaacctaa     1140
agactccaga agggaaagtc aaaactaatt tggatagaaa gtcactgggc tccctcccta     1200
aagttgagga gacagatatg gaggatgaat tcgagcagcc aaccatgtct tttgaatcct     1260
acctcagcta tgaccagccc cggaagaaaa agaaaaagat tgtgaaaact tcagccacgg     1320
cacttggaga taaaggactt aaaaaaaatg actctaaaag cactggtaaa aacttggact     1380
cagttcagaa attacccaag gtgaacaaaa ccaagtcaga aagccggct ggagctgatt     1440 tagccaagct gagaaaggtg cctgatgtgt tgccagtgtt gccagacctc ccgttacccg     1500
cgatacaggc caattaccgt ccactgcctt ccctcgagct gatatcctcc ttccagccaa     1560
agcgaaaagc gttctcttca ccccaggaag aagaagaagc tggatttact gggcgcagaa     1620
tgaattccaa gatgcaggtg tattctggtt ccaagtgtgc ctatctccct aaaatgatga     1680
ccttgcacca gcaatgcatc cgagtactta aaaacaacat cgattcaatc tttgaagtgg     1740
gaggagtccc atactctgtt cttgaacccg ttttggagag gtgtacacct gatcagctgt     1800
atcgcataga ggaatacaat catgtattaa ttgaagaaac agatcaatta tggaaagttc     1860
attgtcaccg agactttaag gaagaaagac ccgaagagta tgagtcgtgg cgagagatgt     1920
acctgcggct tcaggacgcc cgagagcagc ggctacgagt actaacaaag aatatccagt     1980
tcgcacatgc caataagccc aaaggccgac aagcaaagat ggcctttgtc aactctgtgg     2040
ccaagccacc tcgtgacgtc cggaggaggc aggaaaagtt tggaacggga ggagcagctg     2100
tccctgagaa aatcaagatc aagccagccc cgtacccat gggaagcagc catgcttccg     2160
ccagtagcat cagctttaac cccagccctg aggagccggc ctatgatggc caagcacca      2220 gcagtgccca cttggcacca gtggtcagca gcactgtttc ctatgatcct aggaaaccca     2280
ctgtgaagaa aattgcccca atgatggcca agacaattaa agctttcaag aacagattct     2340
cccgacgata aactgaggac ttgccttgga aatggaatct ggggaggcag gaatacaagg     2400
acagtggggg ttggggaatg gaattctaca ggagactgga gtcttgcttt gtggatcctt     2460
ttggtctccg agtctgcagt ctgcaggtgc tgcccctggg aacctgcgtg ccacagcccc     2520
gcctccctgc ctggagcaca ctttagaatt ctgaagatgt gaagcctctg tctcactgag     2580 gatttttaaag gtcaattata cttttgttgt tcattagcat ctttgtaaac tataagacgt     2640
```

```
agttttaatt aataaatatt gcccccagat gttaaa                      2676
```

<210> SEQ ID NO 21
<211> LENGTH: 2961
<212> TYPE: DNA
<213> ORGANISM: homo sapiens

<400> SEQUENCE: 21

```
cggtgctggc cccggcgagg tagcttctgg aaggcgctgc tcttccggtt ctctgtcccg    60
gttcctgggg ttgcacagac agaccctgta aacatgtcag ggttcagtcc ggaactcatc   120
gactacttgg aagggaaaat ctcctttgag gagttcgaac ggcggagaga agagagaaaa   180
acccgcgaga agaaaagtct tcaggaaaaa ggcaagttat cagctgaaga aaatcccgat   240
gactctgaag ttccatcatc atcaggaatt aactctacca aatcccaaga caaagatgtc   300
aatgaaggag aaacatcaga tggagtgagg aagtcagttc acaaggtctt tgcttccatg   360
cttggagaga atgaagatga tgaggaggaa aggaagaaag aggaggagga ggaggaggag   420
gaagaaacac ctgagcaacc cactgcgggc gatgtatttg tattggagat ggttctcaat   480
cgtgaaacca gaaaatgat gaaagagaaa aggcctcgga gtaaacttcc cagagctctg   540
agaggtctca tgggtgaagc caacattcgt tttgctcgag gagaacgtga gaggcgata    600
ttgatgtgca tggaaatcat aagacaagct cctctggctt atgagccatt ctctactcta   660
gccatgatat atgaggacca aggtgacatg gaaaaatcat tgcagtttga gttgattgct   720
gcgcatttaa atcccagtga cacagaagaa tgggttagac tggcagaaat gtctctggaa   780
caagacaata ttaagcaggc tattttttgc tatacaaaag ctcttaaata tgaacctact   840
aatgtccgtt atctgtggga gcgatcaagc ctttatgaac agatgggtga tcataaaatg   900
gccatggatg gttataggcg tatttaaaac cttttgtctc catctgatgg cgaacgtttt   960
atgcagctgg ctagagatat ggcaaagagt tactatgaag ccaatgatgt tacttctgct  1020
attaacataa ttgatgaagc tttctcaaag caccagggcc tagtctccat ggaagatgtt  1080
aacatagcag ctgaactata tatttctaac aaacagtatg acaaagcttt ggagataatt  1140
acagatttt ctggaattgt gctggaaaaa aaaacttcag aagaaggcac ctcagaagag  1200
aataaagctc ctgagaatgt tacctgcact atacctgatg gcgtgccaat agatatcaca  1260
gtgaagttga tggtctgcct tgtacatctc aacattcttg aaccacttaa tcctctcttg  1320
acaacactag tagaacagaa tcctgaagat atgggagacc tatacctaga tgttgctgaa  1380
gcttttctgg atgttggtga atataattct gcacttcccc tcctcagtgc tcttgtttgc  1440
tctgaaagat acaaccttgc agtagtttgg cttcgtcatg cagaatgttt aaaggcctta  1500
ggctatatgg agcgagctgc tgaaagctat ggcaaggtgg ttgatctggc cccactccat  1560
ttggatgcaa ggatttcact ttctaccctt cagcagcagc tgggccagcc tgagaaagct  1620
ctggaagctc tggaaccaat gtatgatcca gatactttag cacaggatgc aaatgctgca  1680
cagcaggaac tgaagttatt gcttcatcgt tctactctgt tgttttcaca aggcaaaatg  1740
tatggttatg tggataccctt acttactatg ttagccatgc ttttaaaggt agcaatgaat  1800
cgagcccaag tttgtttgat atccagttcc aagtctggag agaggcatct ttatcttatt  1860
aaagtatcga gagacaaaat atcagacagc aatgaccaag agtcagcaaa ttgtgatgca  1920
aaagcaatat ttgctgtgct cacaagcgtc ttgacaaagg atgactggtg gaatcttctg  1980
ttgaaggcca tatactcctt atgtgaccta tcccgatttc aagaggctga gttgcttgta  2040
gattcctcat tggaatatta ctcatttttat gatgacaggc aaaaacgcaa agaactagaa  2100
```

-continued

```
tactttggtc tgtctgctgc aattctggac aaaaatttca gaaaggcata caactatatc    2160
aggataatgg taatggaaaa tgtcaataaa ccccagctct ggaacatttt caatcaagtt    2220
accatgcact cccaagatgt acgacatcat cgcttctgtc tccgtttgat gctgaaaaac    2280
ccagaaaatc atgccctatg tgtcttaaat ggacacaatg catttgtatc tggtagtttt    2340
aagcatgcgc ttggacagta tgtgcaagcc tttcgcactc accctgacga acctctctat    2400
agcttctgta taggcctaac ctttattcat atggcatctc agaagtatgt gttacggaga    2460
catgctctta ttgtacaggg cttttccttt cttaatcgat acctcagttt acgtgggccc    2520
tgccaggaat cattctacaa tttgggccgt ggccttcatc agttggggct gattcatctt    2580
gcaatccact attatcagaa ggccctggag ctccctccac ttgtggtaga gggtatagaa    2640
cttgaccagt tagacttacg aagagatatt gcctacaact tgtctctcat ctatcagagc    2700
agtgggaata ccggaatggc tcaaacgctt ttgtatacct attgttctat ataaagcacc    2760
gcaactgaga acagagcaat ggcagctgct gtgtgaggac cagtgtcttc tgtctcaggg    2820
cttattattt gtaactccaa aatagaaatg accatttcag aattacctaa caaacagtgt    2880
atttattttt aatatgtgat catgatcttg tggtatatat gcaaaattat tcctacaaaa    2940
aaaaaaaaaa aaaaaaaaa a                                               2961
```

<210> SEQ ID NO 22
<211> LENGTH: 5676
<212> TYPE: DNA
<213> ORGANISM: homo sapiens

<400> SEQUENCE: 22

```
ggatccttga gggcactggt gcgactttca ggtgaggtct tagcagatga aagcggctgg     60
ctgtggcccg cgccagtagt gctttctgct ccgcactcgc cgtgagccag gtgtgcaacc    120
ggatttgggg cgagggtcgc gctggctacc tcgcatgcgc agagccggaa gcccgctgac    180
cggactacag ctcccagaag agccttgtgg aggccgcaga cgcgaagccg ctggcgccat    240
cttgaaatct gatcctccat ccccgaggct ttgcgtctgc gcggccggcc gctgctgctc    300
cgggagccca gtctgctaaa aggggaggac gttgaggacg cggcggctgg cgggagagac    360
agctggggag agacatggca gggtcggagc gcggcctgcg cctctgtcac tcagcatcct    420
cttaggcgtt ccacgccccg ccccctgccc gaggggcggg gctgacggct ctggtacccg    480
gagtcggcgc gcggggcagg ggcgcgcccc tgcagagtgg gaccccact gggctgtgcc    540 atgctgaccg gagaccaccg aggcgggaga cagagcgcgg cgaagagcca ttgagtggtc    600
acccagtagc cgccgccgcc gccgcctcgg gaagcttgcc acccgctagg agggaagatg    660
aaggagattt gcaggatctg tgcccgagag ctgtgtggaa accagcggcg ctggatcttc    720
cacacggcgt ccaagctcaa tctccaggtt ctgcttttcgc acgtcttggg caaggatgtc    780
ccccgcgatg gcaaagccga gttcgcttgc agcaagtgtg ctttcatgct tgatcgaatc    840
tatcgattcg acacagttat tgcccggatt gaagcgcttt ctattgagcg cttgcaaaag    900
ctgctactgg agaaggatcg cctcaagttc tgcattgcca gtatgtatcg gaagaataac    960
gatgactctg gcgcggagat caaggcgggg aatgggacgg ttgacatgtc cgtcttaccc   1020
gatgcgagat actctgcact gctccaggag gacttcgcct attcagggtt tgagtgctgg   1080
gtggagaatg aggatcagat ccaggagcca cacagctgcc atggttcaga aggccctgga   1140
aaccgaccca ggagatgccg tggttgtgcc gctttgcggg ttgctgattc tgactatgaa   1200
```

```
gccatttgta aggtacctcg aaaggtggcc agaagtatct cctgcggccc ttctagcagg   1260
tggtcgacca gcatttgcac tgaagaacca gcgttgtctg aggttgggcc acccgactta   1320
gcaagcacaa aggtaccccc agatggaaaa agcatggagg aagagacgcc tggttcctct   1380
gtggaatctt tggatgcaag cgtccaggct agccctccac aacagaaaga tgaggagact   1440
gagagaagtg caaaggaact tggaaagtgt gactgttgtt cagatgatca ggctccgcag   1500
catgggtgta atcacaagct ggaattagct cttagcatga ttaaaggtct tgattataag   1560
cccatccaga gcccccgagg gagcaggctt ccgattccag tgaaatccag cctacctgga   1620
gccaagcctg gccctagcat gacagatgga gttagttccg gtttccttaa caggtctttg   1680
aaaccccttt acaagacacc tgtgagttat cccttggagc tttcagacct gcaggagctg   1740
tgggatgatc tctgtgaaga ttatttgccg ctccgggtcc agcccatgac tgaagagttg   1800
ctgaaacaac aaaagctgaa ttcacatgag accactataa ctcagcagtc tgtatctgat   1860
tcccacttgg cagaactcca ggaaaaaatc cagcaaacag aggccaccaa caagattctt   1920
caagagaaac ttaatgaaat gagctatgaa ctaaagtgtg ctcaggagtc gtctcaaaag   1980
caagatggta caattcagaa cctcaaggaa actctgaaaa gcagggaacg tgagactgag   2040
gagttgtacc aggtaattga aggtcaaaat gacacaatgg caaagcttcg agaaatgctg   2100
caccaaagcc agcttggaca acttcacagc tcagagggta cttctccagc tcagcaacag   2160
gtagctctgc ttgatcttca gagtgcttta ttctgcagcc aacttgaaat acagaagctc   2220
cagagggtgg tacgacagaa agagcgccaa ctggctgatg ccaaacaatg tgtgcaattt   2280
gtagaggctg cagcacacga gagtgaacag cagaaagagg cttcttggaa acataaccag   2340
gaattgcgaa aagccttgca gcagctacaa gaagaattgc agaataagag ccaacagctt   2400
cgtgcctggg aggctgaaaa atacaatgag attcgaaccc aggaacaaaa catccagcac   2460
ctaaaccata gtctgagtca caaggagcag ttgcttcagg aatttcggga gctcctacag   2520
tatcgagata actcagacaa aacccttgaa gcaaatgaaa tgttgcttga gaacttcgc   2580 cagcgaatac atgataaagc tgttgctctg gagcgggcta tagatgaaaa attctctgct   2640
ctagaagaga aagaaaaaga actgcgccag cttcgtcttg ctgtgagaga gcgagatcat   2700
gacttagaga gactgcgcga tgtcctctcc tccaatgaag ctactatgca agtatggag   2760 agtctcctga gggccaaagg cctggaagtg gaacagttat ctactacctg tcaaaacctc   2820
cagtggctga agaagaaat ggaaaccaaa tttagccgtt ggcagaagga caagagagt   2880 atcattcagc agttacagac gtctcttcat gataggaaca agaagtgga ggatcttagt   2940 gcaacactgc tctgcaaact tggaccaggg cagagtgaga tagcagagga gctgtgccag   3000
cgtctacagc gaaaggaaag gatgctgcag gaccttctaa gtgatcgaaa taaacaagtg   3060
ctggaacatg aaatggagat tcaaggcctg cttcagtctg tgagcaccag ggagcaggaa   3120
agccaagctg ctgcagagaa gttggtgcaa gccttaatgg aaagaaattc agaattacag   3180
gccctgcgcc aatatttagg agggagagac tccctgatgt cccaagcacc atctctaac   3240 caacaagctg aagttacccc cactggccgt cttggaaaac agactgatca aggttcaatg   3300
cagatacctt ccagagatga tagcacttca ttgactgcca agaggatgt cagcataccc   3360 agatccacat taggagactt ggacacagtt gcagggctgg aaaaagaact gagtaatgcc   3420
aaagaggaac ttgaactcat ggctaaaaaa gaaagagaaa gtcagatgga actttctgct   3480
ctacagtcca tgatggctgt gcaggaagaa gagctgcagg tgcaggctgc tgatatggag   3540
tctctgacca ggaacataca gattaaagaa gatctcataa aggacctgca aatgcaactg   3600
```

```
gttgatcctg aagacatacc agctatggaa cgcctgaccc aggaagtctt acttcttcgg   3660
gaaaaagttg cttcagtaga atcccagggt caagaaattt caggaaaccg aagacaacag   3720
ttgctgctga tgctagaagg actagtagat gaacggagtc ggctcaatga ggccttacaa   3780
gcagagagac agctctatag cagtctggtg aagttccatg cccatccaga gagctctgag   3840
agagaccgaa ctctgcaggt ggaactgaaa ggggctcagg tgttacgcag tcggctagaa   3900
gaagttcttg aagaagcttt ggagcgctta aacaggctgg agaccctggc cgccattgga   3960
ggtgcagctg caggggatga caccgaagat acaagcactg agttcactga cagtattgag   4020
gaggaggctg cacaccatag tcaccagcaa ctatagcttc agaagcattt ttacttgcaa   4080
gacgatggac acattcccct tgggcttttt gtaactgaaa cgcaccacag aagacaggga   4140
gtcatcgaag ggctgctcgg ggaggtggca gggcggagga cctgcttggg aagaaactcc   4200
aagaagattg gaatgcttcc aaagcaagaa tctttctcag tgaaatctca ttatacaaag   4260
agaaccttat gcaacctgac aaaccactga ggtcatggtg actcagtgat cagcagatgg   4320
tacttcaaca gcaatcccct gtcaaacctc agaacttgag gctgaaacat tgcttccacc   4380
caccatcagt gaagatgtaa ctagcatgtt acaagagtga ataatctgga cttcagagat   4440
taagtcacca atagtgatct cacaagcact caccggaact cctataatgt ctccactttg   4500
tccatgccat ttagcaatct catctcctaa atggactgtg cctatgattc ttaaggagaa   4560
agtgaatcat tggtagatat cctgcacaag cagctggact ttccagtaat agctttcttg   4620
gggctattag gaaaattaaa caagaaatga ggctttctgg gtctgcctgt atgtcttctg   4680
cataagacaa agaagagaca tcgaatcaac caataagaag agcccaaata agcatcctca   4740
aatcttttgg gatttggcac ttggggacat gagtagttgt ctgggatacg tcatattctc   4800
aacagtttct ttgtagtagt aggatcacct tcttataata ggatcacctt cttgttgcta   4860
tagctgtacc cgaccttccc ttctcccttg agtgcttgca tgagctccac ttttcctttt   4920
gcttgaacag cttctcctga gtcctcctta ccgatggttg tgactttaat tatatacatc   4980
tctgtccctc cagacagatc cctctgtcct cactctctga tttcattgag gatcttgggt   5040
gagagagagg gacctgcagg atgaacaaat gtctactcta agacagctag attgggaggt   5100
tggctggtca ctgatggtta taatgactgt gggacaggat taacttcaga ataaatgaac   5160
aggagacaca gatatgaaga aagtttctga ttgatatggt ctgaagtact cctggtattg   5220
caagtcattt gctctaattc tcaattgtag gcaaactgat ttgtaaattt gcttcttcag   5280
ccttctttcc tgtagcctag catggagaat ctgaccagac cccatttga gaaggtcagc    5340 ctacactgga atgaactttt tacattaggg catttgtatt tccctcacaa tacttgccac   5400
attacttggc ataggagaga tgcttagtgt aattataagt taacaagcct ttggatcagg   5460
gcttgactca tgatagacaa agtatatgcc tgctggatgg aagaatctct tgggcgagca   5520 ccattttct ttccatcacc tttccttgaa aatatatctt cagctttggg taggaggaat     5580
cttggtgtat gaaatcattg caaatttact tcatctttc tggagtttga agttgtgact    5640
ctcctgctac caattaaata aagcttactt tgccat                             5676
```

<210> SEQ ID NO 23
<211> LENGTH: 1866
<212> TYPE: DNA
<213> ORGANISM: homo sapiens

<400> SEQUENCE: 23

```
atggcggatt tcgaagagtt gaggaatatg gtttctagtt ttagggtttc tgaactacaa        60
gtattactag gctttgctgg acggaataaa agtggacgca agcatgacct cctgatgagg       120
gcgctgcatt tattgaagag cggctgcagc cctgcggttc agattaaaat ccgagaattg       180
tatagacgcc gatatccacg aactcttgaa ggactttctg atttatccac aatcaaatca       240
tcggttttca gtttggatgg tggctcatca cctgtagaac ctgacttggc cgtggctgga       300
atccactcgt tgccttccac ttcagttaca cctcactcac catcctctcc tgttggttct       360
gtgctgcttc aagatactaa gcccacattt gagatgcagc agccatctcc cccaattcct       420
cctgtccatc ctgatgtgca gttaaaaaat ctgcccttt atgatgtcct tgatgttctc       480
atcaagccca cgagtttagt tcaaagcagt attcagcgat tcaagagaa gtttttatt       540 tttgctttga cacctcaaca agttagagag atatgcatat ccagggattt tttgccaggt       600
ggtaggagag attatacagt ccaagttcag ttgagacttt gcctggcaga gacaagttgc       660
cctcaagaag ataactatcc aaatagtcta tgtataaaag taatgggaa gctatttcct       720 ttgcctggct atgcaccacc gcctaaaaat gggattgaac agaagcgccc tggacgcccc       780
ttgaatatta catctttagt taggttatct tcagctgtgc caaaccaaat ttccatttct       840
tgggcatcag aaattgggaa gaattactct atgtctgtat atcttgtacg gcagcttaca       900
tcagccatgt tattacagag attaaaaatg aaaggtatta gaaaccctga tcattccaga       960
gcactaatta agaaaaaact tactgcagat cctgatagtg aaattgctac aactagcctt      1020
cgggtatcct tgatgtgccc tttaggaaaa atgaggctga caatcccatg ccgtgcagtg      1080
acttgtacac atctgcagtg ttttgatgct gccctctatc tacaaatgaa tgagaaaaag      1140
cccacctgga tttgtcctgt gtgtgacaaa aaagctgcct atgaaagtct aatattagat      1200 gggctttta tggaaattct caatgactgt tctgatgtag atgagatcaa attccaagaa      1260
gatggttctt ggtgtccaat gagaccgaag aaagaagcta tgaaagtatc cagccaaccg      1320
tgtacaaaaa tagaaagttc aagcgtcctc agtaagcctt gttcagtgac tgtagccagt      1380
gaggcaagca agaagaaagt agatgttatt gatcttacaa tagaaagctc ttctgacgaa      1440
gaggaagacc ctcctgccaa aggaaatgc atctttatgt cagaaacaca aagcagccca      1500
accaaagggg ttctcatgta tcagccatct tctgtaaggg tgcccagtgt gacttcggtt      1560
gatcctgctg ctattccgcc ttcattaaca gactactcag taccattcca ccatacgcca      1620
atatcaagca tgtcatcaga tttgccaggt ttggatttc tttcccttat tccagttgat      1680
ccccagtact gtcctcctat gttttggat agtctcacct cacccttaac agcaagcagt      1740
acgtctgtca ccaccaccag ctcccatgaa agcagtactc atgttagttc atccagcagc      1800
aggagtgaga caggggtcat aaccagcagt ggaagtaaca ttcctgaaat catctcattg      1860
gactaa                                                                  1866
```

<210> SEQ ID NO 24
<211> LENGTH: 2972
<212> TYPE: DNA
<213> ORGANISM: homo sapiens
<400> SEQUENCE: 24

```
gcgcgcggct ccgatgggaa gcatgacccg ggtggcggga caagacttgc ttcccggcca        60
cgcgcgctcg gccggccgtg gggcggggca taggcgtgac gtggtgtcgc gtatcgagtc       120 tccgcccct tccgcctcc ccgtatataa gacttgccg agcactctca ctcgcacaag       180
tggaccgggg tgttgggtgc tagtcggcac cagaggcaag ggtgcgagga ccacggccgg       240
```

```
ctcggacgtg tgaccgcgcc taggggggtgg cagcgggcag tgcggggcgg caaggcgacc    300
atggarcttt tgcggactat cacctaccag ccagccgcca gcaccaaaat gtgcgagcag    360
gcgctgggca agggttgcgg aggggactcg aagaagaagc ggccgccgca gcccccccgag   420
gaatcgcagc cacctcagtc ccaggcgcaa gtgcccccgg cggcccctca ccaccatcac    480
caccattcgc actcggggcc ggagatctcg cggattatcg tcgacccccac gactgggaag   540
cgctactgcc ggggcaaagt gctgggaaag ggtggctttg caaaatgtta cgagatgaca    600
gatttgacaa ataacaaagt ctacgccgca aaaattattc ctcacagcag agtagctaaa    660
cctcatcaaa gggaaaagat tgacaaagaa atagagcttc acagaattct tcatcataag    720
catgtagtgc agttttacca ctacttcgag gacaaagaaa acatttacat tctcttggaa    780
tactgcagta gaaggtcaat ggctcatatt ttgaaagcaa gaaggtgtt gacagagcca     840
gaagttcgat actacctcag gcagattgtg tctggactga ataccttca tgaacaagaa     900
atcttgcaca gagatctcaa actagggaac ttttttatta tgaagccat ggaactaaaa     960
gttggggact tcggtctggc agccaggcta gaacccytgg aacacagaag gagaacgata   1020
tgtggtaccc caaattatct ctctcctgaa gtcctcaaca acaaggaca tggctgtgaa   1080
tcagacattt gggccctggg ctgtgtaatg tatacaatgt tactagggag gcccccattt   1140
gaaactacaa atctcaaaga aacttatagg tgcataaggg aagcaaggta tacaatgccg   1200
tcctcattgc tggctcctgc caagcactta attgctagta tgttgtccaa aaacccagag   1260
gatcgtccca gtttggatga catcattcga catgactttt ttttgcaggg cttcactccg   1320
gacagactgt cttctagctg ttgtcataca gttccagatt tccacttatc aagcccagct   1380
aagaatttct ttaagaaagc agctgctgct cttttttggtg gcaaaaaaga caaagcaaga   1440
tatattgaca cacataatag agtgtctaaa gaagatgaag acatctacaa gcttaggcat   1500
gatttgaaaa agacttcaat aactcagcaa cccagcaaac acaggacaga tgaggagctc   1560
cagccaccta ccaccacagt tgccaggtct ggaacacccg cagtagaaaa caagcagcag   1620
attggggatg ctattcggat gatagtcaga gggactcttg gcagctgtag cagcagcagt   1680
gaatgccttg aagacagtac catgggaagt gttgcagaca cagtggcaag ggttcttcgg   1740
ggatgtctgg aaaacatgcc ggaagctgat tgcattccca aagagcagct gagcacatca   1800
tttcagtggg tcaccaaatg ggttgattac tctaacaaat atggctttgg gtaccagctc   1860
tcagaccaca ccgtcggtgt ccttttcaac aatggtgctc acatgagcct ccttccagac   1920
aaaaaaacag ttcactatta cgcagagctt ggccaatgct cagttttccc agcaacagat   1980
gctcctgagc aatttattag tcaagtgacg gtgctgaaat acttttctca ttacatggag   2040
gagaacctca tggatggtgg agatctgcct agtgttactg atattcgaag acctcggctc   2100
tacctccttc agtggctaaa atctgataag gccctaatga tgctctttaa tgatggcacc   2160
tttcaggtga atttctacca tgatcataca aaaatcatca tctgtagcca aaatgaagaa   2220
taccttctca cctacatcaa tgaggatagg atatctacaa cttctcaggct gacaactctg   2280
ctgatgtctg gctgttcatc agaattaaaa aatcgaatgg aatatgccct gaacatgctc   2340
ttacaaagat gtaactgaaa gacttttcga atggaccccta tgggactcct cttttccact   2400
gtgagatcta cagggaagcc aaaagaatga tctagagtat gttgaagaag atggacatgt   2460
ggtggtacga aaacaattcc cctgtggcct gctggactgg gtggaaccca gaaccaggct    2520
aaggcataca gttcttgact ttggacaatc ccaagagtga accagaatgc agttttcctt   2580
```

```
gagatacctg tttttaaaagg tttttcagac aattttgcag aaaggtgcat tgattcttaa    2640
attctctctg ttgagagcat ttcagccaga ggactttgga actgtgaata tacttcctga    2700
aggggaggga aagggagga agctcccatg ttgtttaaag gctgtaattg gagcagcttt    2760
tggctgcgta actgtgaact atggccatat ataatttttt ttcattaatt tttgaagata    2820
cttgtggctg gaaaagtgca ttccttgtta ataaactttt tatttattac agcccaaaga    2880
gcagtattta ttatcaaaat gtcttttttt ttatgttgac cattttaaac cgttggcaat    2940
aaagagtatg aaaacgcaaa aaaaaaaaaa aa                                  2972
```

<210> SEQ ID NO 25
<211> LENGTH: 2805
<212> TYPE: DNA
<213> ORGANISM: homo sapiens

<400> SEQUENCE: 25

```
gctgagctgg acttggcggt gggagccgga gcctgcttgt tgcagctgtg ggtgaggacg      60
gctctagcta ggtgagcggc tccggccagt tccctttag actatggcga catacctgga     120
gttcatccag cagaatgaag aacgggatgg tgtgcgtttt agttggaacg tgtggccttc     180
cagccggctg gaggctacaa gaatggttgt acccctggct tgtctcctta ctcctttgaa     240
agaacgtcca gacctacctc ctgtacaata tgaacctgtg ctttgcagca ggccaacttg     300
taaagctgtt ctcaacccac tttgtcaggt tgattatcga gcaaaacttt gggcctgtaa     360
tttctgtttt caaagaaatc agtttcctcc agcttatgga ggcatatctg aggtgaatca     420
acctgccgaa ttgatgcccc agttttctac aattgagtac gtgatacagc gaggtgctca     480
gtcccctctg atctttctct atgtggttga cacatgcctg gaggaagatg accttcaagc     540
actcaaagag tccctgcaga tgtccctgag tcttcttcct ccagatgctc tggtgggtct     600
gatcacattt ggaaggatgg tgcaggttca tgagctaagc tgtgaaggaa tctccaaaag     660
ttatgtcttc cgagggacca aggatttaac tgcaaagcaa atacaggata tgttgggcct     720
gaccaagcca gccatgccca tgcagcaagc acgacctgca caaccacagg agcacccttt     780
tgcttcaagc agatttctgc agcctgttca caagattgat atgaacctca ctgatcttct     840
tggggagcta cagagggacc catggccagt aactcagggg aagagacctt tgcgatccac     900
tggtgtggct ttgtccattg ctgttggctt gctggagggc acttttccaa acacaggagc     960
caggatcatg ctgtttactg gaggtcccc tacccaaggg cctggcatgg tggttggaga    1020
tgaattaaag attcctattc gttcttggca tgatattgag aaagataatg cacgattcat    1080
gaaaaaggca accaagcact atgagatgct tgctaatcga acagctgcaa atggtcactg    1140
cattgatatt tatgcttgtg cccttgatca aactggactt ttggagatga agtgttgtgc    1200
aaatcttact ggaggctaca tggtaatggg agattctttc aacacttctc tcttcaagca    1260
gacattccaa agaatcttta ctaaagattt taatggagat ttccgaatgg catttggtgc    1320
tactttggac gtaaagacct ctcgggaact gaagattgca ggagccattg gtccatgcgt    1380
atctctgaat gtgaaaggac cgtgtgtgtc agaaaatgag cttggtgttg gtggcacgag    1440
tcagtggaaa atctgtggcc tagatcctac atctacactt ggcatctatt ttgaagttgt    1500
caatcagcac aacaccccga tcccccaagg aggcagagga ccatccagt ttgtcacgca    1560 ttatcagcac tccagcaccc agagacgcat ccgcgtgacc accatcgccc gaattgggc    1620 agatgtacag agtcagctca ggcacataga agcagcattt gaccaggagg ctgcggcagt    1680
gttgatggca cggcttgggg tgttccgagc ggagtcagag gaggggcccg atgtgctccg    1740
```

```
gtggctggac cgacaactca tccgactgtg tcaaaagttt ggacagtata acaaagaaga    1800
ccccacttct tttaggttat cagattcctt ttctctatat cctcagttta tgttccatct    1860
gagaagatct ccatttcttc aagtgtttaa caacagtcct gatgagtcgt catattacag    1920
acatcatttt gcccggcagg acctgaccca gtccctcatc atgatccagc ccattctcta    1980
ctcttactcc tttcatgggc caccagagcc agtactcttg gatagcagca gcattctagc    2040
tgacagaatt ttgctgatgg atactttctt tcaaattgtc atttatcttg gtgagaccat    2100
agcccagtgg cgtaaagctg gctaccagga catgcccgag tatgaaaact tcaagcacct    2160
tctgcaggca ccactggatg atgctcaaga aattctgcaa gcacgcttcc cgatgccacg    2220
ttacatcaac acggagcatg aggcagtca ggctcgattc cttttgtcca aagtgaaccc     2280
atctcagaca cacaataacc tgtatgcttg gggacaggaa actggagcac ccatcctaac    2340
tgatgatgtt agcctgcagg tgttcatgga ccatttgaag aagctggctg tctccagtgc    2400
ctgttaagct gaggatacaa ccaggaaatg caacggtgtc agattgtgtt caaaatgtct    2460
agaaaggctt gataacattc ctgttacttt tctagcagat tttaacaaat aatcaaggac    2520
attttatatg taactcttta gattataatt tatttgtatt cctgtctttg tccttttttct   2580 tgcactataa aattataagg tcataaatgt tttggtactt gtagatgttt atgtgctttt    2640
tgtatcctaa cttttagaat ctaaataaaa tcagaggtaa tgtattttgg cagcttgttt    2700
aggtgagaat cttaatgatc ataaaaggaa ataaatctag atgcagaaag tactggctaa    2760
aatattgcta atacaaatgt gatttcctga aaaaaaaaaa aaaaa                    2805

<210> SEQ ID NO 26
<211> LENGTH: 766
<212> TYPE: DNA
<213> ORGANISM: homo sapiens

<400> SEQUENCE: 26
cactttgtca ccaactgctg ccaactcgcc accactgctg ccgcaatcgc aaccactgct      60
ttgtctctga agtgagactg ctcctggtgc catgaacgga gacgcacctt ttgcaaagag     120
acccagggat gatgctaaag catcagagaa gagaagcaag gcctttgatg atattgccac     180
atacttctct aagaaagagt ggaaaaagat gaaatactcg gagaaaatca gctatgtgta     240
tatgaagaga actataagg ccatgactaa actaggtttc aaagtcaccc tcccacctttt     300 catgtgtaat aaacaggcca cagacttcca ggggaatgat tttgataatg accataaccg     360
caggattcag gttgaacatc ctcagatgac tttcggcagg ctccacagaa tcatcccgaa     420
gatcatgccc aagaagccag cagaggacga aaatgattcg aagggagtgt cagaagcatc     480
tggcccacaa acgatggga acaactgca ccccccagga aaagcaaata tttctgagaa      540
gattaataag agatctggac ccaaaagggg gaaacatgcc tggacccaca gactgcgtga    600
gagaaagcag ctggtgattt atgaagagat cagtgaccct gaggaagatg acgagtaact    660
cccctggggg atacgacaca tgcccttgat gagaagcaga acgtggtgac ctttcacgaa    720
catgggcatg gctgcggctc cctcgtcatc aggtgcatag caagtg                   766

<210> SEQ ID NO 27
<211> LENGTH: 3432
<212> TYPE: DNA
<213> ORGANISM: homo sapiens
<220> FEATURE:
<221> NAME/KEY: misc_feature
<222> LOCATION: (2741)..(2741)
```

<223> OTHER INFORMATION: n = a, c, g or t/u

<400> SEQUENCE: 27

```
ctcgtcatgc gcaatgtggc gctgcggcgg gcggcagggc ctgtgtgtgc tgaggcggct      60
gagcggcgga catgcacacc acagagcgtg gcgatggaac agtaaccggg cttgtgagag     120
ggctctgcag tataaactag gagacaagat ccatggattc accgtaaacc aggtgacatc     180
tgttcccgag ctgttcctga ctgcagtgaa gctcacccat gatgacacag gagccaggta     240
tttacacctg gccagagaag acacgaataa tctgttcagc gtgcagttcc gtaccactcc     300
catggacagt actggtgttc ctcacattct tgagcatacc gtcctttgtg ggtctcaaaa     360
atatccgtgc agaaaccctt tcttcaaaat gttgaaccgg tccctctcca cgttcatgaa     420
cgccttcaca gctagtgatt atactctgta tccattttcc acacaaaatc caaggactt     480
tcagaatctc ctctcggtgt atttggatgc ccacctttcc ccatgtttac gcgagctgga     540
tttctggcag gaaggatggc ggctggaaca tgagaatccg agcgaccccc agacgccctt     600
ggtctttaaa ggagtcgtct ttaatgagat gaagggagcg tttacagaca atgagaggat     660
attctcccag caccttcaga acagacttct tcccgaccac acgtactcag tggtctccgg     720
gggtgaccca ctgtgcatcc cggagcttac atgggagcag cttaagcagt tcatgccac      780
tcactatcac ccaagcaatg ctaggttctt cacgtacgga aattttccat tagaacagca     840
tctgaaacaa attcacgagg aagcactgag caaattccag aaaattgaac caagcaccgt     900
ggtgccagct cagacaccct gggacaagcc tagggaattc cagataacat gtggcccgga     960
ttcatttgct acagatccct ctaaacaaac aaccgtcagc gttagcttcc tcttaccgga    1020
catcaccgac acatttgaag ccttcacatt aagtcttctg tcttcactct tgacttctgg    1080
gcccaattct ccctttaca aagccttgat tgaatctggc cttggcacag aattttctcc     1140
tgatgttgga tataatggct acacgaggga ggcctacttt agtgtcggcc tccaagggat    1200
tgtggagaaa gacattgaga ccgtcagaag cctcatagac agaacgattg atgaagtagt    1260
tgagacaagg attgaagatg atcgaattga ggctttactt cataaaattg aaatacagat    1320
gaaacatcag tctaccagct ttgggctgat gctgacatca tacatagctt cttgctggaa    1380
ccatgatggg gaccctgtgg agctcttgaa gttgggaaat cagttagcta aattcagaca    1440
gtgcctgcag gaaaatccaa aattttttgca agaaaaagta aaacagtatt ttaagaataa    1500
ccagcataag ctgactttat cgatgaggcc agatgacaag tatcacgaga agcaggcaca    1560
ggtggaagcc acgaagctca agcagaaggt cgaggctctg tcccccggag acaggcagca    1620
gatctacgag aaaggtctag aattacggag tcaacaaagc aaacctcaag atgcctcttg    1680
tctgccagcg ttgaaagttt ccgatattga acccaccata cctgtcacag agttggacgt    1740
ggtcctgaca gctggagata tccctgttca gtactgcgcc cagcccacca atggcatggt    1800
gtatttccgg gccttctcca gcctgaacac actccccgag gagctgaggc ctatgtgcc     1860
cctcttctgc agcatcctca ccaagctggg ctgcggcctt cttgactacc gggagcaggc    1920
tcagcagata gaattgaaga ccggagggat gagtgcttct ccccacgtgc tccccgacga    1980
ctcacacatg gacacctacg agcaggtagg tgtgcttttc tcctctctct gcctggatcg    2040
aaacctgcca gacatgatgc agctatggag tgaaatattt aacaaccgt gctttgaaga     2100
agaggagcac ttcaaggtgc tggtgaagat gccgcccag gagctcgcca atggaattcc     2160
tgactctggg cacctgtacg catccatcag ggcaggccgg accctcacgc cgcagggga     2220
cctgcaggag accttcagcg ggatggatca ggtgcggctg atgaagagga ttgcagaaat    2280
```

```
gacagatatc aaacccatcc tgaggaagct cccgcgtatc aagaaacact tgttaaatgg    2340
tgataatatg aggtgttcag tgaatgcgac tcctcagcag atgcctcaga cagaaaaagc    2400
ggtcgaagac ttccttagaa gcatcggtcg gagtaaaaag gaacggaggc ctgtgcgccc    2460
acacacggtc gagaaacctg tgcccagcag ctctggtgga gatgcccacg ttccccatgg    2520
ctcccaggtc attaggaagc tggtcatgga acccaccttc aagccctggc agatgaagac    2580
tcacttcctg atgcccttcc cggtgaatta cgtgggtgaa tgcatccgaa ctgtccccta    2640
cacggaccca gatcatgcca gtcttaaaat ccttgcacgt ttgatgactg ccaaattctt    2700
gcatacagaa attcgagaaa aggcggtgc ttatggtgga ngcgcaaaac tcagccacaa     2760
tgggattttc acccttact cttacaggga cccaaataca atagagacgc tccagtcttt     2820
tgggaaggct gtcgactggg ctaagtctgg aaaattcaca cagcaagaca cgacgaagc     2880 caaactttct gtcttctcaa ccgtagatgc tcctgtcgct ccttcagaca aggaatgga    2940 ccacttcttg tacggcctct cggatgagat gaagcaggcc cacagagagc agctctttgc    3000
tgtcagccac gacaagctcc tggccgtgag cgataggtac ctcggcactg gaagagcac    3060 acacggcctg gccatcctcg gacccgagaa cccgaaaatt gccaaggacc atcctggat    3120 catccgatga gcagccgtgg cgctcgactg cacaggagcc cgagacaata cacctccaag    3180
ctgaatatga aaagtcagaa atgctactgc ttttccaag aatattatgt cattgagtgt    3240
cgccaaagcc cttgactggc gagtcaaaaa ctcagatcta tcttaagagt gaccaggaag    3300
aggttcattg aaataatcat gcatgaagcg ccaaagatgc accatgtaga attttcactt    3360
tgtactggca ggctcgtttt acctgattct agaatattta agaatctaaa ataaagggc    3420 aactctgact ta                                                        3432

<210> SEQ ID NO 28
<211> LENGTH: 1232
<212> TYPE: DNA
<213> ORGANISM: homo sapiens

<400> SEQUENCE: 28
tttcccgaga tcaccaagat gctgggcgcc gagtggagca agctgcagcc aacggaaaag      60
cagcggtacc tggatgaggc cgagagagag aagcagcagt acatgaagga gctgcgggcg    120
taccagcagt ctgaagccta agatgtgc acggagaaga tccaggagaa aagatcaag      180 aaagaagact cgagctctgg gctcatgaac actctcctga atggacacaa gggtggggac    240
tgcgatggct tctccacctt cgatgttccc atcttcactg aagagttctt ggaccaaaac    300
aaagcgcgtg aggcggagct tcggcgcttg cggaagatga atgtggcctt cgaggagcag    360
aacgcggtac tgcagaggca aaacgcagag catgagcagc gcgcgcgagc gtctggagca    420
ggagctggcg ctggaggagc ggaggacgct ggcgctgcag cagcagctcc aggccgtgcg    480
ccaggcgctc accgccagct tcgcctcact gccggtgccg ggcacgggcg aaacgcccac    540
gctgggcact ctggacttct acatggcccg gcttcacgga gccatcgagc gcgacccgc    600 ccagcacgag aagctcatcg tccgcatcaa ggaaatcctg gcccaggtcg ccagcgagca    660
cctgtgagga gtgggcgggc ccacgatgca gaggagaagc tgtgggcgcg ccctgccac    720 accccacccc gtggacgaga ggctgggggt ccacccttg gggcctggtc ccatcctgca     780
cctttggggg ctccagcccc cctaaaatta aatttctgca gcatcccttt agctttcaat    840
ctccccagcc ccctgaaccc ggaaaaagca ctcgctgcgc gatacaccca gaagaacctc    900
```

| | |
|---|---|
| acagccgagg gtgcccctcc tcggaggaca gccacgcgct acactggctc tccgggccac | 960 |
| ccccaggaca cagggcagac gaaacccacc cccagcacac ggcaggaccc cccaaattac | 1020 |
| tcactacggg gggctgtgcc ataggccaca caggaagctg ccttgtgggg acttacctgg | 1080 |
| ggtgtccccc gcatgcctgt accccagatg ggtgggggcc ggctttgccc atcctgctct | 1140 |
| cctccagccg agggaccctg gtggggtgg ctccttctca ctgctggatc cggacttttt | 1200 |
| aaataaaaac aagtaaaatt tgtgttttaa aa | 1232 |

<210> SEQ ID NO 29
<211> LENGTH: 1313
<212> TYPE: DNA
<213> ORGANISM: homo sapiens

<400> SEQUENCE: 29

| | |
|---|---|
| aattggagga gttgttgtta ggccgtcccg agacccggt cgggagggag aaggtggca | 60 |
| agatggtgtt ggaaagcact atggtgtgtg tggacaacag tgagtatatg cggaatggag | 120 |
| acttcttacc caccaggctg caggcccagc aggatgctgt caacatagtt tgtcattcaa | 180 |
| agacccgcag caaccctgag aacaacgtgg gccttatcac actggctaat gactgtgaag | 240 |
| tgctgaccac actcaccccca gacactggcc gtatcctgtc caagctacat actgtccaac | 300 |
| ccaagggcaa gatcaccttc tgcacgggca tccgcgtggc ccatctggct ctgaagcacc | 360 |
| gacaaggcaa gaatcacaag atgcgcatca ttgcctttgt gggaagccca gtggaggaca | 420 |
| atgagaagga tctggtgaaa ctggctaaac gcctcaagaa ggagaaagta atgttgaca | 480 |
| ttatcaattt tggggaagag gaggtgaaca cagaaaagct gacagccttt gtaaacacgt | 540 |
| tgaatggcaa agatggaacc ggttctcatc tggtgacagt gcctcctggg cccagtttgg | 600 |
| ctgatgctct catcagttct ccgattttgg ctggtgaagg tggtgccatg ctgggtcttg | 660 |
| gtgccagtga cttttgaattt ggagtagatc ccagtgctga tcctgagctg gccttggccc | 720 |
| ttcgtgtatc tatggaagag cagcggcagc ggcaggagga ggaggcccgg cgggcagctg | 780 |
| cagcttctgc tgctgaggcc gggattgcta cgactgggac tgaagactca gacgatgccc | 840 |
| tgctgaagat gaccatcagc cagcaagagt ttggccgcac tgggcttcct gacctaagca | 900 |
| gtatgactga ggaagagcag attgcttatg ccatgcagat gtccctgcag ggagcagagt | 960 |
| ttggccaggc ggaatcagca gacattgatg ccagctcagc tatggacaca tctgagccag | 1020 |
| ccaaggagga ggatgattac gacgtgatgc aggacccccga gttccttcag agtgtcctag | 1080 |
| agaacctccc aggtgtggat cccaacaatg aagccattcg aaatgctatg ggctccctgg | 1140 |
| cctcccaggc caccaaggac ggcaagaagg acaagaagga ggaagacaag aagtgagact | 1200 |
| ggagggaaag ggtagctgag tctgcttagg ggactgcatg ggaagcacgg aatataggt | 1260 |
| tagatgtgtg ttatctgtaa ccattacagc ctaaataaag cttggcaact ttt | 1313 |

<210> SEQ ID NO 30
<211> LENGTH: 1682
<212> TYPE: DNA
<213> ORGANISM: homo sapiens

<400> SEQUENCE: 30

| | |
|---|---|
| cctgctgagg ccaagctcgg atccggtgcc gagccaagcg gggccgtgcg tcgccggcct | 60 |
| tcgctcgcgt gacctccgcc gtcctcccca accctcgtcc tctgcgcctg cggccgcagc | 120 |
| cccagcgccc ctcgcctaac ctcccgcggg gccgcgcctc ctcctcctcc tgctcccgc | 180 |
| cgcttccgtt tctcgaggga aaggctgctg cctcctgctc tgtcctcatc cccggcttag | 240 |

```
ctgacggccc agaggtgggt gccaattcca ccagcagctg caactgaaaa gcaaggttca      300
gaaatgtcag atatcctccg ggagctgctc tgtgtctctg agaaggctgc taacattgcc      360
cgggcgtgca gacagcagga agccctcttc cagctgctga tcgaagaaaa gaaagaggga      420
gaaaagaaca gaagtttgc agttgacttc aagactctgg ctgatgtact ggtacaggaa       480
gttataaaac agaatatgga gaacaagttt ccaggcttgg aaaaaaatat ttttggagaa      540
gaatccaatg agtttactaa tgactggggg gaaaagatta ccttgaggtt gtgttcaaca      600
gaggaagaaa cagcagagct tcttagcaaa gtcctcaatg gtaacaaggt agcatctgaa      660
gcattagcca gggttgttca tcaggatgtt gcctttactg acccaactct ggattccaca      720
gagatcaatg ttccacagga cattttggga atttgggtgg accccataga ttcaacttat      780
cagtatataa aaggttctgc tgacattaaa tccaaccagg gaatcttccc ctgtggactt      840
cagtgtgtca ccattttaat tggtgtctat gacatacaga cagggggttcc cctgatggga      900
gtcatcaatc aaccttttgt gtcacgagat ccaaacaccc tcaggtggaa aggacagtgc      960
tattggggcc tttcttacat ggggaccaac atgcattcac tacagctcac catctctaga     1020
agaaacggca gtgaaacaca cactggaaac accggctctg aggcagcatt ctcccccagt     1080
ttttcagccg taattagtac aagtgaaaag gagactatca agctgcattt gtcacgtgtg     1140
tgtggagatc gcatatttgg ggcagctggg gctggttata gagcctatg tgttgtccaa      1200
ggcctcgttg acatttacat cttttcagaa gataccacat tcaaatggga ctcttgtgct     1260
gctcatgcca tactgcgggc catgggtggg ggaatagtag acttgaaaga atgcttagaa     1320
agaaatccag aaacagggct tgatttgcca cagttggtgt accacgtgga aaatgagggt     1380
gctgctgggg tggatcggtg ggccaacaag ggaggactca ttgcatacag atccaggaag     1440
cggctggaga cattcctgag cctcctggtc caaaacctgg cacctgcaga gacgcatacc     1500
tagaggaact ctaaccccgg tgtacctgta taaactgaac tgtgaaactg tttcggttat     1560
ctctgtcttt tgaggatggc tttgtcctgt tgctggttaa cattcacctt cctcttttga     1620
ggagtatttt tccattatgt attcataata atgttaattt caataaatga cattcatgca     1680
gc                                                                   1682
```

<210> SEQ ID NO 31
<211> LENGTH: 1511
<212> TYPE: DNA
<213> ORGANISM: homo sapiens

<400> SEQUENCE: 31

```
cgacgcggga gccgcacgcg ccggacgagg ctcgctgcgc tccctgttgc ccagcgcggg       60
cccgttgagg cggagccctc agttcccggc caggacacgg tctgggccgc cgaatctccg      120
gccgaagagc ggcggcggca gcggcgggaa aaaaatgaag aatgaaattg ctgccgttgt      180
cttcttttc acaaggctag ttcgaaaaca tgataagttg aaaaaagagg cagttgagag       240
gtttgctgag aaattgaccc taatacttca agaaaaatat aaaatcact ggtatccaga      300
aaaccatcg aaaggacagg cctacagatg tattcgtgtc aataaatttc agagagttga      360
tcctgatgtc ctgaaagcct gtgaaaacag ctgcatcttg tatagtgacc tgggcttgcc      420
aaaggagctc actctctggg tggacccatg tgaggtgtgt tgtcgtagag atggggtttc      480
accatgttgg ccagactgct ctcaaactct tgacctcgtg atccgcccgc cttggcctcc      540
caaagcgctg gattacaggc gtgagccact gcgcccggcc tcctcctttt tgattatgta      600
```

-continued

```
tggagagaaa aacaatgcat tcattgttgc cagctttgaa aataaagatg agaacaagga      660
tgagatctcc aggaaagtta ccagggccct tgataaggtt acctctgatt atcattcagg      720
atcctcttct tcagatgaag aaacaagtaa ggaaatggaa gtgaaaccca gttcggtgac      780
tgcagccgca agtcctgtgt accagatttc agaacttata tttccacctc ttccaatgtg      840 gcacccttg cccagaaaaa agccaggaat gtatcgaggg aatggccatc agaatcacta      900
tcctcctcct gttccatttg gttatccaaa tcagggaaga aaaataaac catatcgccc      960 aattccagtg acatgggtac ctcctcctgg aatgcattgt gaccggaatc actggattaa     1020
tcctcacatg ttagcacctc actaacttcg tttttgattg tgttggtgtc atgttgagaa     1080
aaaggtagaa taaaccttac tacacattaa agttaaaag ttcttactaa tagtagtgaa      1140
gttagatggg ccaaaccatc aaacttattt ttatagaagt tattgagaat aatctttctt     1200
aaaaaatata tgcactttag atattgatat agtttgagaa attttattaa agttagtcaa     1260
gtgcctaagt ttttaatatt ggacttgagt atttatatat tgtgcatcaa ctctgttgga     1320
tacgagaacc ctgtagaagt ggacgatttg ttttagcccc tttgagaatt tactttatgg     1380
agcgtatgta agttatttat atacaaggaa atctatttta tgtcgttgtt taagagaatt     1440
gtgtgaaatc atgtagttgc aaataaaaaa tagtttgagg caaaaaaaaa aaaaaaaaa     1500 aaaaaaaaaa a                                                         1511

<210> SEQ ID NO 32
<211> LENGTH: 1250
<212> TYPE: DNA
<213> ORGANISM: homo sapiens

<400> SEQUENCE: 32
acacgccgat ttgccctttt gattcttcca caatcagggt gagactgctc ccagtgccat       60
gaacggagac gacgcctttg caaggagacc cagggatgat gctcaaatat cagagaagtt      120
acgaaaggcc ttcgatgata ttgccaaata cttctctaag aaagagtggg aaaagatgaa      180
atcctcggag aaaatcgtct atgtgtatat gaagctaaac tatgaggtca tgactaaact      240
aggtttcaag gtcaccctcc cacctttcat gcgtagtaaa cgggctgcag acttccacgg      300
gaatgatttt ggtaacgatc gaaaccacag gaatcaggtt gaacgtcctc agatgacttt      360
cggcagcctc cagagaatct tcccgaagat catgcccaag aagccagcag aggaagaaaa      420
tggtttgaag gaagtgccag aggcatctgg cccacaaaat gatgggaaac agctgtgccc      480
cccgggaaat ccaagtacct tggagaagat caacaagaca tctggaccca aaggggggaa      540
acatgcctgg acccacagac tgcgtgagag aaagcagctg gtggtttatg aagagatcag      600
cgaccctgag gaagatgacg agtaactccc ctcggggata tgcacatgc ccatgatgag      660 aagcagaacg tggtgaccttt tcacgaacat gggcatggct gcggacccct cgtcatcagg      720
tgcatagcaa gtgaaagcaa gtgttcacaa cagtgaaaag ttgagcgtca ttttttcttag     780 tgtgccaaga gttcgatgtt ggcgtttccg ctgtattttc ttgcagtgtg ccattctgtt      840
agacattagc gttttcgctg atgagcaaga catgcttaat gcatatttcg gcttgtgtat      900
ccatgcacct acctcagaaa acaagtattg tcaggtattc tctccataga acagcactac      960
cctcctctct ccccagatgt gactactgag gggaggtctc agtgtttaat ttccgatttt     1020
ttcctctgca tttacacaca caccacacac gcacacacac acaccaagta ccagtataag     1080
catctcccat ctgcttttct ccattgccat gcgtcctggt caagcccccc tcactctgtt     1140
tcctgttcag catgtactcc cctcatccga ttccgttgta tcagtcactg acagttaata     1200
```
aacctttgca aacgttcaac aaaaaaaaaa aaaaaaaaaa aaaaaaaaaa        1250

<210> SEQ ID NO 33
<211> LENGTH: 6792
<212> TYPE: DNA
<213> ORGANISM: homo sapiens

<400> SEQUENCE: 33
ctccagtccg catgctcagt agctgctgcc ggccgggctg cggggcggcg tccgctgcgc        60
gcctacgggc tgcggtggcg gccgccgcgg caccggcag ggcccgccag tccccgcttc        120
cctgctccag agccgccgcc tgggccgggg cagggcgggc ccggggctcc tccatgctgc        180
cagccgccgg gctgcggagc cgaccaagtg gctcctgcga tggcggcgga agaggaggct        240
gcggcgggag gtaaagtgtt gagagaggag aaccagtgca ttgctcctgt ggtttccagc        300
cgcgtgagtc cagggacaag accaacagct atggggtctt tcagctcaca catgacagag        360
tttccacgaa aacgcaaagg aagtgattca gacccatccc aagtggaaga tggtgaacac        420
caagttaaaa tgaaggcctt cagagaagct catagccaaa ctgaaaagcg gaggagagat        480
aaaatgaata acctgattga agaactgtct gcaatgatcc ctcagtgcaa ccccatggcg        540
cgtaaactgg acaaacttac agttttaaga atggctgttc aacacttgag atctttaaaa        600
ggcttgacaa attcttatgt gggaagtaat tatagaccat catttcttca ggataatgag        660
ctcagacatt taatccttaa gactgcagaa ggcttcttat ttgtggttgg atgtgaaaga        720
ggaaaaattc tcttcgtttc taagtcagtc tccaaaatac ttaattatga tcaggctagt        780
ttgactggac aaagcttatt tgacttctta catccaaaag atgttgccaa agtaaaggaa        840
caactttctt cttttgatat ttcaccaaga gaaaagctaa tagatgccaa aactggtttg        900
caagttcaca gtaatctcca cgctggaagg acacgtgtgt attctggctc aagacgatct        960
tttttctgtc ggataaagag ttgtaaaatc tctgtcaaag aagagcatgg atgcttaccc        1020
aactcaaaga agaaagagca cagaaaattc tatactatcc attgcactgg ttacttgaga        1080
agctggcctc caaatattgt tggaatgtaa gaagaaagga acagtaagaa agacaacagt        1140
aattttacct gccttgtggc cattggaaga ttacagccat atattgttcc acagaacagt        1200
ggagagatta atgtgaaacc aactgaattt ataacccggt ttgcagtgaa tggaaaattt        1260
gtctatgtag atcaaagggc aacagcgatt ttaggatatc tgcctcagga acttttggga        1320
acttcttgtt atgaatattt tcatcaagat gaccacaata atttgactga caagcacaaa        1380
gcagttctac agagtaagga gaaaatactt acagattcct acaaattcag agcaaaagat        1440
ggctcttttg taactttaaa aagccaatgg tttagtttca caaatccttg gacaaaagaa        1500
ctggaatata ttgtatctgt caacactttta gttttgggac atagtgagcc tggagaagca        1560
tcatttttac cttgtagctc tcaatcatca gaagaatcct ctagacagtc ctgtatgagt        1620
gtacctggaa tgtctactgg aacagtactt ggtgctggta gtattggaac agatattgca        1680
aatgaaattc tggatttaca gaggttacag tcttcttcat accttgatga ttcgagtcca        1740
acaggtttaa tgaaagatac tcatactgta aactgcagga gtatgtcaaa taaggagttg        1800
tttccaccaa gtccttctga aatggggag ctagaggcta ccaggcaaaa ccagagtact        1860
gttgctgtcc acagccatga gccactcctc agtgatggtg cacagttgga tttcgatgcc        1920
ctatgtgaca atgatgacac agccatggct gcatttatga attacttaga agcagagggg        1980
ggcctgggag accctgggga cttcagtgac atccagtgga ccctctagcc tttgattttt        2040

```
aactccaaaa atgagaaaca ttttaaagca ttatttacga aaaaactgtc tcaactattc    2100
ttaagtactg tattgatatt gtttgtatct tttattaatg ttctaccact ttttatagat    2160
ttgcatcttc ctgtcacagg gatgtgggga aatacgtttt cctcccaaga gaaccaagtt    2220
tattatagac tcctttattc agtgaaatgg cttataatcc actagttgcc atattttgc     2280
taaaatattt ctaaccaaga atactactta catattgttt tggctttgtt ttattttga     2340
tgcagttttt tttagttgag gtaatgtaat atattgatgt tttcctttgt gtctaagatt    2400
gatttataat agtaggtttg tataatttgg aacattttcc atgccttgcg aatttcctta    2460
attgaggata gggcttacac actttaagaa aacagtgagt acttgaacat ttaaagggac    2520
agtgcaattt atagtcataa tcacattgaa tactgtattt gatctttgga gacttaggca    2580
agcacagagc tgggatattt atgctcagtt gagcacttta agatgaattt taagtgagat    2640
gatttcttgc ttaaaactca gaaagtcaaa agagtttcag ctttccttac agaaaaggaa    2700
ggatcttggg ccctagatct tggggattaa cctctgcata taagatttac tcttaatagg    2760
ccagacgtgg tgctcacgcc tgtaatccca gtactttggg aggctgagac gggcagatca    2820
cttgaggtca ggagttcaag accagcctgg ccaatatggt gaaacccgt ttctactaaa      2880
aatacaaaaa aaattaccca ggcactcact cttgaggtaa ctaaccaact cccacgataa    2940
tgacagtcca ttcatgagcg caaaggcctc atgacctaat ggcacacacc tgtaatccca    3000
actgcttggg aggctgaggc gagaggattg cttgaacctg ggaggcagag gttgcagtga    3060
gccgagatcg caccactgca ctccagtctg gcaacagag tgagacttca tctcaaaaaa     3120
agtaaaaaaa aagatttaat ataatcactg aagatctcta ttatagatag attaggtttt    3180
tgacattgga aacatactta gggatagatt tgtcctaaag gaaaaaagta ggcccgggca    3240
gattaaatgt cttgtgtaaa gtcacacatt aaattcagtc acacattaaa ttcatagagt    3300
tttaaatgtt taatgtatat aaaccagttt ctttatacac atttgggaaa acattggtct    3360
cacagattaa atgattaact aactgaccca ggaactagtt gtagctttct aagtaattag    3420
gcaattacag ttattgcctg taaccaaagg taataaaaca aaatgacaag tacatgttta    3480
aaattatgag gcaatgagaa ataatttaaa aaccaatttt ctagttataa tttaaaattt    3540
ggagagcatt tttaacagta attaatccag aggtggctca aattgagtat aagaattaag    3600
attatttaaa atactgcatg tctaccttct cggggatcat actttataac actttctgct    3660
tcagtagctc ttcatagctt gccaagtatg ctcccatatt ttctctctcg tgcctcgcaa    3720
atgaaagtca dataggctgg gaactcatgg ggcagccctc agacttcaat gtgggcttca    3780
aatccagttt cctgttctat atggtgctac atctttccag aaaatttccc tcagagcccc    3840
tcgccaaaac aaagcattat tttgaccctg catgctattt ctttagctgt aggtgataga    3900
ttagaacttc tgtcagacat gttaatgaca aacataccaa cagacaataa ccaaagcaaa    3960
tgtttccttc aagtgtgaaa tgtgcagggg ctcgtgggca aggatgtatt ggcacactgt    4020
cctcttgaac tgatagtgtc ccagcaatgt tggaggttgg caccattcct ggtccgacac    4080
ttgaggacct gagagacatc aggtttagaa tgagccaaag aaatcctaca agatggggag    4140
aattggtgtg cagcagccta agtgttatag ttaagtctaa agaagtatga aagatcccct    4200
gtgttctcta aattgagcag aggggcctgc ctaccaatat cacttttag gggactgaac      4260
cattgcaggt tagacttggc ttccaaagag tctgcctaag ccaggggtgg cagggtaggc    4320
catcatagct ggatgcctc aaaagcagat ggggcagac ttgccctcgt gatgccagga      4380
tttgagaggc agagtttcta gagggagacc agtgctgcct ctcacagtgg cagtttttc     4440
```

```
tctttgcaag aggaggggct gttcaattcc atagaccagt gggcagatag ccagttgaat    4500
actctgtgca tggtttgatc ctttattagt tcgctctaat attttctgt agatccttt     4560
gtcctggact caaaatctaa tccatgcatt gtatgatacc gtagctctcc taaggtttgt   4620
gtttccttca aaatgtttta gttttcttca actaaatttg attttgctg ttagaagtga    4680
catatttta tggtatacac tatgttcctt ttttctactg cgagtcaatt ttttgaattt    4740
tcgtgagaaa gaatatatct acaaattgca cgaaagtatc ataaaaacag tactctagag   4800
cagcgctgtc caatagaaat ataatctgag ccacatgtat aattttattt tcttctagcc   4860
acattaaaga agtaaaaaga tacaagtaga actaatttta atgttttaat tcagtatatc   4920
caaaatatca tttgaacatg taattaatat aaaattatta atgtgatatt ttacattctt   4980
ttggtaatac tagtcttcaa aatctggtat gtatcttaca ttgatagcac atctcacttt   5040
gtactagcca cattgcaagt gctcagtagc cacatgtggc tagtggctac tgcactggac   5100
agcacagttc taggttccac cctaacaccc aagtcctgtg gattagaatc ccagaatcag   5160
agctggaagt aaacatagag atcaaacctc cttttaaaaa tgaggacgct gaggcacaga   5220
gtttaaatgg cttgcatgag gtcatacagc taaattcagc ctcaacaggg tcttctgatt   5280
ccaggcactc ttcccactcc actacattac tgtagtggta attcttaggg ttaaaaaaag   5340
tgtagagtag gccgggcgca gtggctcatg cctgtaatcc cagcactttg ggaggccgaa   5400
gtgggcggat cacgaggtca ggagatcgag accatcctgg ccaacatggt gaaacccgt    5460
ctctactgaa aatacaaagc aaaattagcc aggtgtggtg cgggcgcct gtggtcccag    5520
ctgctctgga ggctgaggca gaatggcgtg aacccaggag gcagagatgg cagtgagcca   5580
agatcgcgcc actgcacccc agcctgggcg acagagcgag actccatctc aaaaaaaaaa   5640
aaaaaaaaaa aagaaaagaa aagaaagtc tagagaacat tatattaagt ggttattatt    5700
gaagtagacc aaagtttata ccataaggat attttccttt aaataccatg tttgaagaac   5760
aattatttat tgatccttga atctgtaaga tcaaataaca agtctctatc catgttacca   5820
aatttaacct tttgaaaata ataaacttta aaatatcaga tgtgttatta caggatgata   5880
cttggaatca agtgaaatga gttatatggt catcactaaa tttagaaatc tattgtgaaa   5940
caaagacaaa caggaaagta cagaatagag acttttagta aataaatgga atttaaaaga   6000
aagtgtttat ttacagtgtc acgacagaaa aggatgtctt tgttgtcata gtctttgagg   6060
gatctccgta aaatctgggg cacaggtaca agaaatagcc aatatttagt tcccagacca   6120
tgtttagtag tgtccagttt cagatcatgc tgccaagagg tatctccccc tcaggtgggt   6180
catcactgag ccctggaatt ggagactcat acttgcccag cacaatgtta cgggcagaca   6240
ggccgacatc tatgattagc tagaagccat aaagaaaagc tgctaagtgg ccactaggtg   6300
ccactttct gttttgtaa tgctttcatt agcagatctt ttttttccaa gctccatggg     6360
gcctatgaga ggcatttatg attttgtgc ctacaataag tcagcctgtc tggtgtgagt    6420
tgttttatga gaaatgcttt ccaagggagg tctaggaaga tcctgacaca taagaacttt   6480
ggcttagaga gctttccagg tgtagtgcca ataaaaactg acctggaaag aaaacctgcc   6540
cagcacggaa catgctttct gaactcactt gagagtgtat ggtgtatgtc acttctcata   6600
tattcttgag tttagatttg tcttttatac aattttttagc tcttttccag ttcacttgtg   6660
ctcgtctgta tattggtatt tttaaatttt tgtggtaaat aatgaaaaga gtgaaattat   6720
attttataat tactcatttg tagttttttt ttttaattta ataaacttcc tccaaaaagt   6780
```

-continued

| | |
|---|---|
| gctcccttaa aa | 6792 |

<210> SEQ ID NO 34
<211> LENGTH: 2946
<212> TYPE: DNA
<213> ORGANISM: homo sapiens

<400> SEQUENCE: 34

| | |
|---|---|
| tcctggaatt gcacgcgctt cctgaccacc aggctctggc ccttgagaag ccagcggggc | 60 |
| tttgtccctg ttgctctcct tgccaaaccc agtctctctg ctagtggtgg tttcggttgc | 120 |
| gacaccgtcc aggttcccag gcaggaaccg ctcggcctgg ctgcttagct acttttcact | 180 |
| gaggaggtgg tggaaggtgt cgcctgctct ggctgagtaa gggtggctgg ctgagccggc | 240 |
| agcccccgcc ctaggcctgg ctcttcccgg cctctgtact ttgccctcgc tgcctgacag | 300 |
| gttctgctgt gggctctgct gaatggaagt cgctggtagt ccttttccct ttctccagtc | 360 |
| ggcccacctt gggacacctt gactccaagc ccagcagtaa gtccaacatg attcggggcc | 420 |
| gcaactcagc cacctctgct gatgagcagc cccacattgg aaactaccgg ctcctcaaga | 480 |
| ccattggcaa gggtaatttt gccaaggtga agttggcccg acacatcctg actgggaaag | 540 |
| aggtagctgt gaagatcatt gacaagactc aactgaactc ctccagcctc cagaaactat | 600 |
| tccgcgaagt aagaataatg aaggttttga atcatcccaa catagttaaa ttatttgaag | 660 |
| tgattgagac tgagaaaacg ctctaccttg tcatggagta cgctagtggc ggagaggtat | 720 |
| ttgattacct agtggctcat ggcaggatga agaaaaaga gctcgagcc aaattccgcc | 780 |
| agatagtgtc tgctgtgcag tactgtcacc agaagtttat tgtccataga gacttaaagg | 840 |
| cagaaaacct gctcttggat gctgatatga acatcaagat tgcagacttt ggcttcagca | 900 |
| atgaattcac ctttgggaac aagctggaca ccttctgtgg cagtccccct tatgctgccc | 960 |
| cagaactctt ccagggcaaa aaatatgatg gacccgaggt ggatgtgtgg agcctaggag | 1020 |
| ttatcctcta tactggtc agcggatccc tgccttttga tggacagaac ctcaaggagc | 1080 |
| tgcgggaacg ggtactgagg gggaaatacc gtattccatt ctacatgtcc acggactgtg | 1140 |
| aaaacctgct taagaaattt ctcatcctta atcccagcaa gagaggcact ttagagcaaa | 1200 |
| tcatgaaaga tcgatggatg aatgtgggtc acgaagatga tgaactaaag ccttacgtgg | 1260 |
| agccactccc tgactacaag gacccccggc ggacagagct gatggtgtcc atgggttata | 1320 |
| cacgggaaga gatccaggac tcgctggtgg gccagagata caacgaggtg atggccacct | 1380 |
| atctgctcct gggctacaag agctccgagc tggaaggcga caccatcacc ctgaaacccc | 1440 |
| ggccttcagc tgatctaacc aatagcagcg cccaattccc atcccacaag gtacagcgaa | 1500 |
| gcgtgtcggc caatcccaag cagcggcgct tcagcgacca ggctggtcct gccattccca | 1560 |
| cctctaattc ttactctaag aagactcaga gtaacaacgc agaaaataag cggcctgagg | 1620 |
| aggaccggga gtcagggcgg aaagccagca gcacagccaa ggtgcctgcc agcccctgc | 1680 |
| ccggtctgga gaggaagaag accaccccaa cccctccac gaacagcgtc ctctccacca | 1740 |
| gcacaaatcg aagcaggaat tccccacttt tggagcgggc cagcctcggc caggcctcca | 1800 |
| tccagaatgg caaagacagc ctaaccatgc cagggtcccg ggcctccacg gcttctgctt | 1860 |
| ctgccgcagt tctgcgcc cggccccgcc agcaccagaa atccatgtcg gcctccgtgc | 1920 |
| accccaacaa ggcctctggg ctgcccccca cggagagtaa ctgtgaggtg ccgcggccca | 1980 |
| gcacagcccc ccagcgtgtc cctgttgcct cccatccgc ccacaacatc agcagcagtg | 2040 |
| gtggagcccc agaccgaact aacttccccc ggggtgtgtc cagccgaagc accttccatg | 2100 |

```
ctgggcagct ccgacaggtg cgggaccagc agaatttgcc ctacggtgtg accccagcct    2160
ctccctctgg ccacagccag ggccggcggg gggcctctgg gagcatcttc agcaagttca    2220
cctccaagtt tgtacgcagg aacctgaatg aacctgaaag caaagaccga gtggagacgc    2280
tcagacctca cgtggtgggc agtggcggca acgacaaaga aaaggaagaa tttcgggagg    2340
ccaagccccg ctccctccgc ttcacgtgga gtatgaagac cacgagctcc atggagccca    2400
acgagatgat gcgggagatc cgcaaggtgc tggacgcgaa cagctgccag agcgagctgc    2460
atgagaagta catgctgctg tgcatgcacg gcacgccggg ccacgaggac ttcgtgcagt    2520
gggagatgga ggtgtgcaaa ctgccgcggc tctctctcaa cggggttcga tttaagcgga    2580
tatcgggcac ctccatggcc ttcaaaaaca ttgcctccaa aatagccaac gagctgaagc    2640
tttaacaggc tgccaggagc gggggcggcg ggggcgggcc agctggacgg gctgccggcc    2700
gtgcgccgcc ccacctgggc gagactgcag cgatggattg gtgtgtctcc ctgctggcac    2760
ttctcccctc cctggccctt tcagttttc tcccacattc accctgccc agagattccc    2820 ccttctcctc tcccctactg gaggcaaagg aaggggaggg tggatggggg ggcagggctc    2880
cccctcggta ctgcggttgc acagagtatt tcgcctaaac caagaaattt tttattacca    2940
aaaaga                                                              2946

<210> SEQ ID NO 35
<211> LENGTH: 1792
<212> TYPE: DNA
<213> ORGANISM: homo sapiens

<400> SEQUENCE: 35
ctccggacag catgagcgtg ggcttcatcg gcgctggcca gctggctttt gccctggcca      60
agggcttcac agcagcaggc gtcttggctg cccacaagat aatggctagc tccccagaca     120
tggacctggc cacagtttct gctctcagga agatgggggt gaagttgaca ccccacaaca     180
aggagacggt gcagcacagt gatgtgctct tcctggctgt gaagccacac atcatcccct     240
tcatcctgga tgaaataggc gccgacattg aggacagaca cattgtggtg tcctgcgcgg     300
ccggcgtcac catcagctcc attgagaaga gctgtcagc gtttcggcca gcccccaggg     360
tcatccgctg catgaccaac actccagtcg tggtgcggga gggggccacc gtgtatgcca     420
caggcacgca cgcccaggtg gaggacggga ggctcatgga gcagctgctg agcacggtgg     480
gcttctgcac ggaggtggaa gaggacctga ttgatgccgt cacggggctc agtggcagcg     540
gccccgccta cgcattcaca gccctggatg ccctggctga tggggtgtg aagatgggac     600 ttccaaggcg cctggcagtc cgcctcgggg cccaggccct cctgggggct gccaagatgc     660
tgctgcactc agaacagcac ccaggccagc tcaaggacaa cgtcagctct cctggtgggg     720
ccaccatcca tgccttgcat gtgctggaga gtggggctt ccgctccctg ctcatcaacg     780
ctgtggaggc ctcctgcatc cgcacacggg agctgcagtc catggctgac caggagcagg     840
tgtcaccagc cgccatcaag aagaccatcc tggacaaggt gaagctggac tcccctgcag     900
ggaccgctct gtcgccttct ggccacacca agctgctccc ccgcagcctg ccccagcgg     960 gcaaggattg acacgtcctg cctgaccacc atcctgccac cacttctct tctcttgtca    1020 ctaggggac taggggtcc ccaaagtggc ccactttctg tggctctgat cagcgcaggg    1080
gccagccagg gacatagcca gggaggggcc acatcacttc ccactggaaa tctctgtggt    1140
ctgcaagtgc ttcccagccc agaacagggg tggattcccc aacctcaacc tcctttcttc    1200
```

| | |
|---|---|
| tctgctccca aaccatgtca ggaccacctt cctctagagc tcgggagccc ggagggtctt | 1260 |
| cacccactcc tactccagta tcagctggca cgggctcctt cctgagagca aaggtcaagg | 1320 |
| accccctctg tgaaggctca gcagaggtgg gatcccacgc ccctcccgg ccctccctg | 1380 |
| ccctccattc agggagaaac ctctccttcc cgtgtgagaa gggccagagg gtccaggcat | 1440 |
| cccaagtcca gcgtgaaggg ccacagcccc tcttggctgc caagcacgca gatcccatgg | 1500 |
| acatttgggg aaagggctcc ttgggctgct ggtgaacttc tgtggccacc acctcctgct | 1560 |
| cctgacctcc ctgggagggt gctatcagtt ctgtcctggc cctttcagtt ttataagttg | 1620 |
| gtttccagcc cccagtgtcc tgacttctgt ctgccacatg aggagggagg ccctgcctgt | 1680 |
| gtgggagggt ggttactgtg ggtggaatag tggaggcctt caactgatta gacaaggccc | 1740 |
| gcccacatct tggagggcat ctgccttact gattaaaatg tcaatgtaat ct | 1792 |

<210> SEQ ID NO 36
<211> LENGTH: 639
<212> TYPE: DNA
<213> ORGANISM: homo sapiens

<400> SEQUENCE: 36

| | |
|---|---|
| ccggacggac gctcgtcttc gcccgccatg gccgagagcg actgggacac ggtgacggtg | 60 |
| ctgcgcaaga agggccctac ggccgcccag gccaaatcca agcaggctat cttagcggca | 120 |
| cagagacgag gagaagatgt ggagacttcc aagaaatggg ctgctggcca gaacaaacaa | 180 |
| cattctatta ccaagaacac ggccaagctg gaccgggaga cagaggagct gcaccatgac | 240 |
| agggtgaccc tggaggtggg caaggtgatc cagcaaggtc ggcagagcaa ggggcttacg | 300 |
| cagaaggacc tggccacgaa aatcaatgag aagccacagg tgatcgcgga ctatgagagc | 360 |
| ggacgggcca tacccaataa ccaggtgctt ggcaaaatcg agcgggccat ggcctcaag | 420 |
| ctccggggaa aggacattgg aaagcccatc gagaaggggc ctagggcgaa atgaacacaa | 480 |
| agcctcgaaa tcagtgcgct ccagctgatc tcgttccgcc ggttcccctt ggccgccagt | 540 |
| tccgttctcc tcacgggccg aacgaacaa ggggtccagc ttgcggggga ccctccccag | 600 |
| cccattcctg ctgtcaaaca aacaaaacct tgcaaagcg | 639 |

<210> SEQ ID NO 37
<211> LENGTH: 1793
<212> TYPE: DNA
<213> ORGANISM: homo sapiens

<400> SEQUENCE: 37

| | |
|---|---|
| cgcgtccgcc ccgcgagcac agagcctcgc ctttgccgat ccgccgcccg tccacacccg | 60 |
| ccgccagctc accatggatg atgatatcgc cgcgctcgtc gtcgacaacg gctccggcat | 120 |
| gtgcaaggcc ggcttcgcgg gcgacgatgc ccccggggcc gtcttcccct ccatcgtggg | 180 |
| gcgcccagg caccagggcg tgatggtggg catgggtcag aaggattcct atgtgggcga | 240 |
| cgaggcccag agcaagagag gcatcctcac cctgaagtac cccatcgagc acggcatcgt | 300 |
| caccaactgg gacgacatgg agaaaatctg gcaccacacc ttctacaatg agctgcgtgt | 360 |
| ggctcccgag gagcaccccg tgctgctgac cgaggccccc ctgaacccca ggccaaccg | 420 |
| cgagaagatg acccagatca tgtttgagac cttcaacacc ccagccatgt acgttgctat | 480 |
| ccaggctgtg ctatccctgt acgcctctgg ccgtaccact ggcatcgtga tggactccgg | 540 |
| tgacgggtc acccacactg tgcccatcta cgaggggtat gccctccccc atgccatcct | 600 |
| gcgtctggac ctggctggcc gggacctgac tgactacctc atgaagatcc tcaccgagcg | 660 |

```
cggctacagc ttcaccacca cggccgagcg ggaaatcgtg cgtgacatta aggagaagct      720
gtgctacgtc gccctggact tcgagcaaga gatggccacg gctgcttcca gctcctccct      780
ggagaagagc tacgagctgc ctgacggcca ggtcatcacc attggcaatg agcggttccg      840
ctgccctgag cactcttcc agccttcctt cctgggcatg gagtcctgtg catccacga       900 aactaccttc aactccatca tgaagtgtga cgtggacatc cgcaaagacc tgtacgccaa      960
cacagtgctg tctggcggca ccaccatgta ccctggcatt gccgacagga tgcagaagga      1020
gatcactgcc ctggcaccca gcacaatgaa gatcaagatc attgctcctc ctgagcgcaa      1080
gtactccgtg tggatcggcg gctccatcct ggcctcgctg tccaccttcc agcagatgtg      1140
gatcagcaag caggagtatg acgagtccgg cccctccatc gtccaccgca atgcttcta      1200 ggcggactat gacttagttg cgttacaccc tttcttgaca aaacctaact tgcgcagaaa      1260
acaagatgag attggcatgg ctttatttgt tttttttgtt ttgttttggt ttttttttt      1320 tttttggctt gactcaggat ttaaaaactg gaacggtgaa ggtgacagca gtcggttgga      1380
gcgagcatcc cccaaagttc acaatgtggc cgaggacttt gattgcacat tgttgttttt      1440
ttaatagtca ttccaaatat gagatgcatt gttacaggaa gtcccttgcc atcctaaaag      1500
ccaccccact tctctctaag gagaatggcc cagtcctctc ccaagtccac acaggggagg      1560
tgatagcatt gctttcgtgt aaattatgta atgcaaaatt ttttaatctt cgccttaat      1620 acttttttat tttgttttat tttgaatgat gagccttcgt gccccccctt ccccttttt      1680 gtcccccaac ttgagatgta tgaaggcttt tggtctccct gggagtgggt ggaggcagcc      1740
agggcttacc tgtacactga cttgagacca gttgaataaa agtgcacacc tta           1793

<210> SEQ ID NO 38
<211> LENGTH: 1116
<212> TYPE: DNA
<213> ORGANISM: homo sapiens

<400> SEQUENCE: 38
gttatgtgtt cccgtccgta ctggaggcta gctcttgtcg cggccgcggc gagttaacat       60 cgttttttcca atctgtccgc ggctgccgcc acccaagaca gagccagaat gttcaggatg      120
ctgaacagca gttttgagga tgacccctc ttctctgagt ccattcttgc caccgagaa        180 aatatgcgac agatgataag aagtttttct gaacccttttg gaagagactt gctcagtatc      240
tctgatggta gagggagagc tcataatcgt agaggacata tgatggtga agattctttg       300 actcatacag atgtcagctc tttccagacc atggaccaaa tggtgtcaaa tatgagaaac      360
tatatgcaga aattagaaag aaacttcggt caactttcag tggatccaaa tggacattca      420
ttttgttctt cctcagttat gacttattcc aaaataggag atgaaccgcc aaaggttttt      480
caggcctcaa ctcaaactcg tcgagctcca ggaggaataa aggaaaccag gaaagcaatg      540
agagattctg acagtggact agaaaaaatg gctattggtc atcatatcca tgaccgagct      600
catgtcatta aaaagtcaaa gaacaagaag actggagatg aagaggtcaa ccaggagttc      660
atcaatatga atgaaagcga tgctcatgct tttgatgagg agtggcaaag tgaggttttg      720
aagtacaaac aggacgaca caatctagga aacactagaa tgagaagtgt tggccatgag      780
aatcctggct cccgagaact taaaagaagg gagaaacctc aacaaagtcc agccattgaa      840 catgaagga gatcaaatgt tttgggggac aaactccaca tcaaaggctc atctgtgaaa      900
agcaacaaaa aataaatagc catgcatttg atttgtttag ttttgattgt tttaacagtt      960
```

-continued

| | |
|---|---|
| agtaatggtg ctgggtaata agcataagac caatctcttg ctgttaaatc agttctgtcc | 1020 |
| ttggcaactt tcttctgata tctgaatgtt catgaaggtc ctagctttat attgtccctc | 1080 |
| ttttaggaat aaaattttga ttttcaacaa aaaaaa | 1116 |

<210> SEQ ID NO 39
<211> LENGTH: 3074
<212> TYPE: DNA
<213> ORGANISM: homo sapiens

<400> SEQUENCE: 39

| | |
|---|---|
| ccgctctccg ctgcggggga ggccatggcg gaaccttccc aggccccgac cccggccccg | 60 |
| gctgcgcagc cccggcccct tcagtcccca gcccctgccc caactccgac tcctgcaccc | 120 |
| agcccggctt cagccccgat tccgactccc accccgcac cagcccctgc cccagctgca | 180 |
| gccccagccg gcagcacagg gactgggggg cccggggtag gaagtggggg ggccgggagc | 240 |
| ggggggggatc cggctcggcc tggcctgagc cagcagcagc gcgccagtca gaggaaggcg | 300 |
| caagtccggg ggctgccccg cgccaagaag cttgagaagc taggggtctt ctcggcttgc | 360 |
| aaggccaatg gaacctgtaa gtgtaatggc tggaaaaacc ccaagccccc cactgcaccc | 420 |
| cgcatagatc tgcagcagcc agctgccaac ctgagtgagc tgtgccgcag ttgtgagcac | 480 |
| cccttggctg accacgtatc ccacttggag aatgtgtcag aggatgagat aaaccgactg | 540 |
| ctggggatgg tggtggatgt ggagaatctc ttcatgtctg ttcacaagga agaggacaca | 600 |
| gacaccaagc aggtctattt ctacctcttc aagctactgc ggaaatgcat cctgcagatg | 660 |
| acccggcctg tggtggaggg gtccctgggc agccctccat ttgagaaacc taatattgag | 720 |
| cagggtgtgc tgaactttgt gcagtacaag tttagtcacc tggctccccg ggagcggcag | 780 |
| acgatgttcg agctctcaaa gatgttcttg ctctgcctta actactggga gcttgagaca | 840 |
| cctgcccagt ttcggcagag gtctcaggct gaggacgtgg ctacctacaa ggtcaattac | 900 |
| accagatggc tctgttactg ccacgtgccc cagagctgtg atagcctccc ccgctacgaa | 960 |
| accactcatg tctttgggcg aagccttctc cggtccattt tcaccgttac ccgccggcag | 1020 |
| ctgctggaaa agttccgagt ggagaaggac aaattggtgc ccgagaagag gaccctcatc | 1080 |
| ctcactcact tccccaaatt cctgtccatg ctggaggagg agatctatgg ggcaaactct | 1140 |
| ccaatctggg agtcaggctt caccatgcca ccctcagagg ggacacagct ggttccccgg | 1200 |
| ccagcttcag tcagtgcagc ggttgttccc agcaccccca tcttcagccc cagcatgggt | 1260 |
| gggggcagca acagctccct gagtctggat tctgcagggg ccgagcctat gccaggcgag | 1320 |
| aagaggacgc tcccagagaa cctgaccctg gaggatgcca agcggctccg tgtgatgggt | 1380 |
| gacatcccca tggagctggt caatgaggtc atgctgacca tcactgaccc tgctgccatg | 1440 |
| ctggggcctg agacgagcct gctttcggcc aatgcggccc gggatgagac agcccgcctg | 1500 |
| gaggagcgcc gcggcatcat cgagttccat gtcatcggca actcactgac gcccaaggcc | 1560 |
| aaccggcggg tgttgctgtg gctcgtgggg ctgcagaatg tcttttccca ccagctgccg | 1620 |
| cgcatgccta aggagtatat cgcccgcctc gtctttgacc cgaagcacaa gactctggcc | 1680 |
| ttgatcaagg atgggcgggt catcggtggc atctgcttcc gcatgttttcc cacccagggc | 1740 |
| ttcacggaga ttgtcttctg tgctgtcacc tcgaatgagc aggtcaaggg ttatgggacc | 1800 |
| cacctgatga accacctgaa ggagtatcac atcaagcaca acattctcta cttcctcacc | 1860 |
| tacgccgacg agtacgccat cggctacttc aaaaagcagg gtttctccaa ggacatcaag | 1920 |
| gtgcccaaga gccgctacct gggctacatc aaggactacg agggagcgac gctgatggag | 1980 |

```
tgtgagctga atccccgcat cccctacacg gagctgtccc acatcatcaa gaagcagaaa    2040
gagatcatca agaagctgat tgagcgcaaa caggcccaga tccgcaaggt ctacccgggg    2100
ctcagctgct tcaaggaggg cgtgaggcag atccctgtgg agagcgttcc tggcattcga    2160
gagacaggct ggaagccatt ggggaaggag aaggggaagg agctgaagga ccccgaccag    2220
ctctacacaa ccctcaaaaa cctgctggcc caaatcaagt ctcacccag tgcctggccc     2280 ttcatggagc tgtgaagaa gtcggaggcc cctgactact acgaggtcat ccgcttcccc    2340
attgacctga agaccatgac tgagcggctg cgaagccgct actacgtgac ccggaagctc    2400
tttgtggccg acctgcagcg ggtcatcgcc aactgtcgcg agtacaaccc ccggacagc    2460 gagtactgcc gctgtgccag cgccctggag aagttcttct acttcaagct caaggaggga    2520
ggcctcattg acaagtaggc ccatctttgg gccgcagccc tgacctggaa tgtctccacc    2580
tcggattctg atctgatcct tagggggtgc cctggcccca cggacccgac tcagcttgag    2640
acactccagc caagggtcct ccggacccga tcctgcagct ctttctggac cttcaggcac    2700
ccccaagcgt gcagctctgt cccagccttc actgtgtgtg agaggtctcc tgggttgggg    2760 cccagccct ctagagtagc tggtggccag ggatgaacct tgcccagccg tggtggcccc     2820
caggcctggt ccccaagagc tttggaggct tggattcctg ggcctggccc aggtggctgt    2880
ttccctgagg accagaactg ctcatttag cttgagtgat ggcttcaggg gttggaagtt     2940
cagcccaaac tgaaggggc catgccttgt ccagcactgt tctgtcagtc tcccccaggg     3000 gtgggggta tgggaccat tcattccctg gcattaatcc cttagaggga ataataaagc       3060
tttttatttc tctg                                                       3074

<210> SEQ ID NO 40
<211> LENGTH: 2381
<212> TYPE: DNA
<213> ORGANISM: homo sapiens

<400> SEQUENCE: 40
gacgggagct ccccgggagc cgtttgtgcc cggggtaacc ccgttccggc caagccgctt      60
cagcggggga cgtagccatg aaggaagaga aggagcacag gcctaaggag aagcgagtaa     120
ccctgttaac ccccgccggg gccacaggca gcggtggtgg gacctcgggg gacagctcca     180 aggggggaaga taagcaggat cgcaacaagg agaagaaaga agcgctgagc aaggtggtaa    240
ttcgaagatt acctcccact ttgaccaagg agcagcttca ggaacatctt caacctatgc    300
ctgagcatga ttattttgag ttttttttcta atgatacgag tttgtatcct catatgtatg   360
ccagagcata catcaacttt aaaaaccaag aggacattat tttgttcagg atcgctttg     420 atggttatgt attccttgac aataaaggtc aggaatatcc cgctatagta gaatttgcac    480
cttttcaaaa agctgcaaaa aagaagacta agaaaagaga taccaaagtc gggactatcg    540
atgatgatcc agaatataga aagttttgg aaagttatgc cacagataat gagaaaatga    600
catctactcc agagacactg ctagaggaaa tagaagcaaa aatatagagaa ttaatagcta   660 aaagacaac cccactttg agcttcctga aaaacaagca gagaatgaga gaagaaaaga    720
gagaagaaag gaggaggaga gaaatagaaa gaaaaagaca aagagaagaa gagaggagga    780
aatggaaaga agaagagaaa cgaaaaagga agatataga aaagctaaag aagatagaca    840
gaattccaga aagggacaaa ttaaaggatg aaccaaagat taaggtacac aggtttctgt    900
tacaagctgt gaatcagaaa aatctgctca agaagccaga aaaaggagat gaaaagaat    960
```

```
tggacaaaag agaaaaagcc aagaaattgg acaaagagaa tctcagtgat gaaagagcca    1020
gtgggcaaag ttgtacattg cccaagcgtt ctgatagcga acttaaagat gaaaaaccaa    1080
agagacctga agatgagagc ggcagagact atagggagag ggaacgggaa tatgaacgag    1140
atcaggagcg catacttcga gaaagagaga ggctgaagcg gcaagaagaa gagcgccgta    1200
ggcagaagga gcgctatgag aaagagaaga cttttaagag aaaagaagaa gaaatgaaaa    1260
aagagaaaga cacacttcgg gataaaggaa agaaggctga aagtacagaa tcaataggca    1320
gctcagaaaa aactgaaaag aaagaagaag tggtcaagag agatcgaata agaaacaagg    1380
atcgtccagc gatgcagctt taccaaccag gagctcgaag ccgaaatcga ctctgtcccc    1440
ctgatgacag caccaagtct ggagattcag cagcagaaag gaagcaggaa agtggtatta    1500
gccatagaaa agaaggagga gaggagtgat aagtccagat ggccttaggt gtcctgactg    1560
tctaggcagc caaagagcac acgttaagca atccagaggt gccttcaggg caagaatag     1620 agagaaaggg agccgctgtg ctggtggggt acactgcaga ggagtaagtc ttgtgtcaaa    1680
gcaggaatct gatcagaggt tcagaattgg aagtacaatt tcattgcttt tgcaatttct    1740
acaaattaat tttaaagtgt cagaaaaagg tgacggcaag gacatgcatt gcaatttgca    1800
gggggaattg tcaagtgagg acttcatcac atatgacacg agagaaaagt aagagctggt    1860
tctaaaatca aaagctgttg ttcatcctga attgaatttt ctgaatttgg gtggagcaga    1920
gtcgctttga agccttgttc cgatctaatt ctattgtatt gttgatgata agtgttgaca    1980
ttgggtagtg tagaagcaac aagcatgtcc ttgtagtaca ggtacagtga aggatagaac    2040
acactttcgt tgatacaaaa atttaaatag ttatgttact tctgtatcca gtgtcctaaa    2100
gttttaggat tagtttttagt tttttgtttg cttatatgag cttagcgtaa agaatatttt    2160
taaacttcgt gttttgtcat cagcatcttt tctattaaga ggtaaaatgt agtccttgtt    2220
tgactcttga caatccagtg tgtttgatct taggtctcat gatctgagtg catacccctct   2280 ccaggaagga aactgcacca gtgtctattc ctgttaaata gcaacttttta gtctcagctt    2340 gtttcgtttt gatgtcaata aatagtaaca gcattcaagt g                        2381
```

<210> SEQ ID NO 41
<211> LENGTH: 5163
<212> TYPE: DNA
<213> ORGANISM: homo sapiens

<400> SEQUENCE: 41

```
ttaggggcag aaaaacattt gtaataatta atggctttga gagacacaag gctttgtttg     60
ccccagagta ttagttaacc cacctagtgc tcctaatcat acaatattaa ggattgggag    120
ggacattcat tgcctcactc tctatttgtt tcaccttctg taaaattggt agaataatag    180
tacccacttc atagcattgt atgatgatta aattggttaa tattttttaaa atgcttagaa    240 cacagattgg gcacataaca gcaagcacca catgtgttta agataaaat tcctttgtgt     300 tgccttccgt taaagtttaa ataagtaaat aaataaataa atacttgcat gacattttga    360
agtctctcta taacatctga gtaagtgcg gctgcgacaa tgctactgga gttccagaat     420
cgtgttggtg acaagattgt tcaccagcat atggtgtggt gaaaactcac taatttggaa    480
ttagttcaga ttattaagcc tgaataggtg aaaatcctga aatcaaggat ctttggaact    540
atttgaaatc agtatttat attttcctgt tgtattcatt aaagtgttgc aagtgttcta    600
tttgatggat taagtatatt taggatatac atgttcaatt tgtgattttg tatacttaat    660
tggaacaaga aagctaataa aggttttgat atggacatct attctttttaa gtaaacttca    720
```

-continued

```
atgaaaatat atgagtagag catatagaga tgtaaataat ttgtggacac accacagact    780
gaaatagcaa atttaaaaga aattgttgga agaatcaagt gtttgtggaa tgagtcctcc    840
tagtaaagtt cctgctcttg tgaataatta agcctcatgt ataattacta tagcaaaagg    900
aagcctaaga agtattagac tctacttgta tttaaattac attttacata atttatgtgt    960
atgaaaaatg ttttaaatgc ttattttcgt aagccatgag atagctcctt tatattttaa   1020
gaatttctga attaatttgc ttggatttta ttagtgcaaa tggcagagct agcaattcct   1080
ttttctgtgt tcccattcca tcctattcat ccctctttta ggaaactctg aactctggat   1140
tgtccttgtt tacatacctg cctcctgcat tggactatgt gtctctgagt gtagtatgac   1200
taattcattt gtttgtcaag gactctcaat gcatttgttg aacagcctaa ttagtaatgt   1260
ctgcaacaat gacattttac tgtatttaat aaagctctgg gaaagtagga tacacataag   1320
acaggtctag gtctaaattc tttacagaaa cttggatttt tagttcggtt tgaaatttga   1380
agatgtgagt atatttatct cagtttccca aaggacaagc taattggaat tatcatcctc   1440
tttcacttga ttggatcccc agaatgccat ttacgcatgc agcaggattt tataacagtt   1500
ttaaattctg tatatttgat gaagaggttt tatatttttg gattcaagcc tcttttaaaa   1560
cttctacaat atggtttaca ataattcctt atatcctgct tttgaaatac atattacaac   1620
tttttaagtt tggaaggcta tatttcaagg actgaagtta cagtatactc aagtgataca   1680
caagcctagc acccccacttt ccacatagtg ttcgataaag attgataaac tcgaaatcac   1740
agaccttta attcttaaga caaatagcag cagaaagaaa catctttggc ttatttctgg   1800
taaggttttt atgctctgta aaacaaagaa ttgtattcat ccgcgcagca cagattctat   1860
taaaaataaa tgtgagagtc gttaatgtag tactgctcat ttaccatcaa aattcacttt   1920
tcaggaataa tcccatcagt ttaaattgga tattggaatg agcattgatt acatttaact   1980
tggtagccca aaatttcttc atggggtttt gaactcggcg ggatttcaaa ggttttaaaa   2040
atgagttttt gattttttt aaaaccctca aatttcatta cctttaaact aggtcgaaac   2100
ggggcgcaag agattggatt aacaccatag taatacttat tttgttctta accatttcag   2160
ggcttcttga aatagaggct gtatggtgta atggaaaaaa cagccttgga atctgggagc   2220
ctgattcctg gattcagtcc cagttttgcg tgacctgggg caagttactt tacttctctg   2280
aatttccgtt tcctcctctg caaaatgagg atcgcaatag ccaccttgca accttgactg   2340
gagcgagcct cgcacacccc gcgccggcct ggaggaagag cagccatgat tacgccgcct   2400
tcgctccgct acccgcttgc ggctggcgcc ctcctccagc aggtgtaggc gctgccgcgc   2460
tgccccacgc ctttccgccg ctcgcgggcc tgcgcctcgg cgtccccgag gaggccgctg   2520
cgggctgagg tagcgcaccg gcctctcggc gtcccagtcc ggtcccgggc ggagggaaag   2580
cgggcgaccc acctccgagg cagaagccga ggcccggccc cgccgagtgc ggaggagcgc   2640
aggcagcccc cgcccctcgg ccctccccc ggccctcccg ccctccctc cgcccctcc    2700
gccctcgcgc gccgcccgcc cgggtcgccg cggggccgtg gtgtacgtgc agagcgcgca   2760
gagcgagtgg cgcccgtatg ccctgcgctc ctccacagcc tgggccgggc cgcccgggac   2820
gctgaggcgg cggcggcggc cgaggggcc ggtcttgcgc tccccaggcc cgcgcgcctg    2880
agcccaggtt gccattcgcc gcacaggccc tattctctca gccctcggcg gcgatgaggc   2940
gctgaggcgg ctgccggcgc tgcgccggag cttaggactc ggaagcggcc gggccgaggg   3000
cgtggggtgc cggcctccct gaggcgaggg tagcgggtgc atggcgcagt aacggcccct   3060
```

```
atctctctcc ccgctcccca gcctcgggcg aggccgtccg gccgctaccc ctcctgctcg    3120
gccgccgcag tcgccgtcgc cgccgccgcc gccgccatgg ccaatgacag cggcgggccc    3180
ggcgggccga gcccgagcga gcgagaccgg cagtactgcg agctgtgcgg gaagatggag    3240
aacctgctgc gctgcagccg ctgccgcagc tccttctact gctgcaagga gcaccagcgt    3300
caggactgga agaagcacaa gctcgtgtgc cagggcagcg agggcgccct cggccacgga    3360
gtgggcccac accagcattc cggccccgcg ccgccggctg cagtgccgcc gcccagggcc    3420
ggggcccggg agcccaggaa ggcagcggcg cgccgggaca cgcctccgg ggacgcggcc     3480 aagggaaaag taaaggccaa gccccgcc gacccagcgg cggccgcgtc gccgtgtcgt      3540
gcggccgccg gcggccaggg ctcggcggtg gctgccgaag ccgagcccgg caaggaggag    3600
ccgccggccc gctcatcgct gttccaggag aaggcgaacc tgtaccccc aagcaacacg     3660 cccggggatg cgctgagccc cggcggcggc ctgcggccca acgggcagac gaagcccctg    3720
ccggcgctga gctggcgct cgagtacatc gtgccgtgca tgaacaagca cggcatctgt    3780
gtggtggacg acttcctcgg caaggagacc ggacagcaga tcggcgacga ggtgcgcgcc    3840
ctgcacgaca ccgggaagtt cacggacggg cagctggtca gccagaagag tgactcgtcc    3900
aaggacatcc gaggcgataa gatcacctgg atcgagggca aggagcccgg ctgcgaaacc    3960
attgggctgc tcatgagcag catggacgac ctgatacgcc actgtaacgg gaagctgggc    4020
agctacaaaa tcaatggccg gacgaaagcc atggttgctt gttatccggg caatggaacg    4080
ggttatgtac gtcatgttga taatccaaat ggagatggaa gatgtgtgac atgtatatat    4140
tatcttaata aagactggga tgccaaggta agtggaggta tacttcgaat ttttccagaa    4200
ggcaaagccc agtttgctga cattgaaccc aaatttgata gactgctgtt tttctggtct    4260
gaccgtcgca accctcatga agtacaacca gcatatgcta caaggtacgc aataactgtt    4320 tggtatttg atgcagatga gagagcacga gctaaagtaa aatatctaac aggtgaaaaa    4380
ggtgtgaggg ttgaactcaa taaaccttca gattcggtcg gtaaagacgt cttctagagc    4440 cttgatcca gcaatacccc acttcaccta caatattgtt aactatttgt taacttgtga     4500
atacgaataa atgggataaa gaaaaataga caaccagttc gcattttaat aaggaaacag    4560
aaacaacttt ttgtgttgca tcaaacagaa gattttgact gctgtgactt tgtactgcat    4620
gatcaacttc aaatctgtga ttgcttacag gaggaagata agctactaat tgaaaatggt    4680
ttttacatct ggatatgaaa taagtgccct gtgtagaatt ttttcattc ttatattttg     4740 ccagatctgt tatctagctg agttcatttc atctctcct tttttatatc aagtttgaat     4800
ttgggataat ttttctatat taggtacaat ttatctaaac tgaattgaga aaaaattaca    4860
gtattattcc tcaaaataac atcaatctat ttttgtaaac ctgttcatac tattaaattt    4920
tgccctaaaa gacctcttaa taatgattgt tgccagtgac tgatgattaa ttttatttta    4980 cttaaaaataa gaaaaggagc actttaatta caactgaaaa atcagattgt tttgcagtcc   5040
ttccttacac taatttgaac tcttaaagat tgctgctttt ttttgacat tgtcaataac    5100 gaaacctaat tgtaaaacag tcaccattta ctaccaataa cttttagtta atgttttaca    5160
agg                                                                  5163
```

<210> SEQ ID NO 42
<211> LENGTH: 4506
<212> TYPE: DNA
<213> ORGANISM: homo sapiens

<400> SEQUENCE: 42

-continued

```
ggcggtggcg gcggcgccgg gacggggagg gggcgcgccg gaaccggaac cgacctgcgc        60
cggaaccgga acggagagcg ggttgccagg gcccgaagag ggctggctgc ggcggtctcg       120
ctcggctgtc cgttccttgc tggagaattt ggccacaaag agttgccaag atagctgggc       180
caggaagaaa gcgccgcagc cctgacccag acgctgttgc cgaccccggg gcactctggc       240
tgtcgaccaa gcggctcaag atgtctggcg gggccagtgc cacaggccca aggagagggc       300
ccccaggact ggaggacacc actagtaaga agaagcagaa ggatcgagca aaccaggaga       360
gcaaggatgg agatcctagg aaagagacag ggtctcgata tgttgcccag gctggtcttg       420
aacctctggc ctcaggtgat ccttctgcct cagcctccca tgcagctggg atcacaggct       480
cacgccaccg tacccggctg ttctttcctt catcgtcagg gtcagcatcc actcctcaag       540
aggagcagac caaagaggga gcttgtgaag accctcatga tctcttggct actcccactc       600
cagagttgtt gctcgattgg aggcagagtg cagaagaggt gattgtcaag cttcgtgtgg       660
gagtaggtcc cctgcagctg gaggatgtag atgctgcttt cacagataca gactgtgtgg       720
tgcggtttgc aggtggtcag cagtggggtg tgtcttcta tgctgagata aaaagctctt       780
gtgctaaagt gcaaacccgc aagggcagtc tcctgcacct gacactgccc aaaaaggtgc       840
ctatgctcac gtggccctcc ctcctggttg aggctgatga acagctttgc ataccaccgc       900
tgaactccca aacctgtctc ctgggctcag aggagaattt agccccttttg gcaggagaga       960 aagcagtgcc tcccgggaat gacccagtct ctccagccat ggtccggagc agaaaccctg      1020
ggaaagatga ctgtgccaag gaggagatgg cagtggcagc agatgctgca accttggtgg      1080
atgagcccga gtcgatggtg aacctggcgt ttgtcaagaa tgactcgtat gagaagggcc      1140
cggattcagt ggtggtgcac gtgtacgtga aggagatctg cagggacacc tcaagagtac      1200
ttttccgtga gcaggacttc acgctcatct tccagaccag ggatggaaac ttcctgaggc      1260
tgcacccggg ctgtgggccc cacaccacct tccgttggca ggtgaagctc aggaatctga      1320
ttgagccaga gcagtgcacc ttctgtttca cggcttctcg catcgacatc tgccttcgta      1380
agaggcagag tcagcgctgg gggggcctgg aggccccggc tgcacgaggt gcagtgggtg      1440
gtgcaaaggt tgccgtgccg acaggtccaa cccctctgga ttcaaccccca ccaggaggtg      1500 ctccccaccc cctgacaggc caggaggagg cccgggctgt ggagaaggat aaatccaagg      1560
cacgatctga ggacacaggg ctagacagtg tggcaacccg cacacccatg gagcatgtaa      1620 cccccaaagcc agagacacac ctggcctcgc ccaagcctac atgcatggtg cctcccatgc      1680
cccacagccc agttagtgga gacagcgtgg aggaggagga agaggaagag aagaaggtgt      1740
gtctgccagg cttcactggc cttgtcaatt taggcaacac ctgcttcatg aacagcgtca      1800
ttcagtctct gtccaacact cgggaactcc gggacttctt ccatgaccgc tcctttgagg      1860
ctgagatcaa ctacaacaac ccactaggga ctggtgggcg tctggccatt ggctttgccg      1920
tgctgcttcg ggcgctgtgg aagggcaccc accatgcctt ccagccttcc aagttgaagg      1980
ccattgtggc gagtaaggcc agccagttca caggctatgc acagcatgat gcccaggagt      2040
tcatggcttt cctgctggat gggctgcacg aggacctgaa tcgcattcag aacaagccct      2100
acacagagac cgtggattca gatgggcggc ccgatgaggt ggtagctgag gaagcatggc      2160
agcggcacaa gatgaggaat gactctttca tcgtggacct atttcagggg cagtacaagt      2220
cgaagctggt gtgccctgtg tgtgccaagg tctccatcac ttttgacccg tttctttatc      2280
tgccggtgcc cttgccacaa aagcaaaagg ttctccctgt cttttatttt gcccgagagc      2340
```

```
cccacagcaa gcccatcaag ttcctggtga gcgtcagcaa ggagaactcc actgcgagcg    2400
aagtattgga ctccctctct cagagtgttc atgtgaagcc tgagaacctg cgtttggcag    2460
aggtaattaa gaatcgtttt catcgtgtgt tcctaccctc ccactcactg gacactgtgt    2520
ccccatctga tacgctcctc tgctttgagc tgctatcctc agagttggct aaggagcggg    2580
tagtggtgct agaggtgcaa cagcgccccc aggtgcccag cgtccccatc tccaagtgtg    2640
cagcctgcca gcggaagcaa cagtcggagg atgaaaagct gaagcgctgt acccggtgct    2700
accgtgtggg ctactgcaac cagctctgcc agaaaaccca ctggcctgac cacaagggcc    2760
tctgccgacc tgagaacatt ggctacccct tcctggtcag tgtacctgcc tcacgcctca    2820
cttatgcccg cctcgctcag ttgctagagg gctatgcccg gtactctgtg agtgtattcc    2880
agccacccct tcagccaggc cgcatggcct tggagtctca gagccctggc tgcaccacac    2940
tgctctccac aggttccctg gaggctgggg acagcgagag agaccccatt cagccacctg    3000
agctccagct ggtgacccct atggctgagg ggacacagg gcttcccgg gtgtgggcag     3060
cccctgaccg gggtcctgtg cccagcacca gtggaatttc ttctgagatg ctggccagtg    3120
ggcccattga ggttggctcc ttgccagctg gcgagagggt gtcccgaccc gaagctgctg    3180
tgcctgggta ccagcatcca agtgaagcta tgaatgccca cacacccag ttcttcatct     3240
ataaaattga ttcatccaac cgagagcagc ggctagagga caaaggagac accccactgg    3300
agctgggtga cgactgtagc ctggctctcg tctggcggaa caatgagcgc ttgcaggagt    3360
ttgtgttggt agcctccaag gagctggaat gtgctgagga tccaggctct gccggtgagg    3420
ctgcccgggc cggccacttc accctggacc agtgcctcaa cctcttcaca cggcctgagg    3480
tgctggcacc cgaggaggcc tggtactgcc acagtgcaa acagcaccgt gaggcctcca     3540
agcagctgtt gctatggcgc ctgccaaatg ttctcatcgt gcagctcaag cgcttctcct    3600
ttcgtagttt tatctggcgt gacaagatca atgacttggt ggagttccct gttaggaacc    3660
tggacctgag caagttctgc attggtcaga agaggagca gctgcccagc tacgatctat     3720
atgctgtcat caaccactat ggaggcatga ttggtggcca ctacactgcc tgtgcacgcc    3780
tgcccaatga tcgtagcagt cagcgcagtg acgtgggctg gcgcttgttt gatgacagca    3840
cagtgacaac ggtagacgag agccaggttg tgacgcgtta tgcctatgta ctcttctacc    3900
gccggcggaa ctctcctgtg gagaggcccc ccagggcagg tcactctgag caccacccag    3960
acctaggccc tgcagctgag gctgctgcca gccaggcttc ccggatttgg caggagctgg    4020
aggctgagga ggagccggtg cctgagggt ctggccccct gggtccctgg gggcccaag     4080
actgggtggg cccctacca cgtgccccta ccacaccaga tgagggctgc ctccggtact    4140
ttgtcctggg caccgtggcg gctttggtgg ccctcgtgct caacgtgttc tatcctctgg    4200
tatcccagag tcgctggaga tgagctcgcc tgcaggcagc tgctgtgagc tggcctacct    4260
gcctgcccca ggccatgcct gcctttgttg tggggaacac ctctgggctt tgggcctcag    4320
cttatgcatc tggtgggaga gggtggggag gttgtggccc ctgcagggc agagtatcct     4380
agggtgtgta tccatctggc tgtctgtcca ttcatcctgc tgctctgacc cttggcctca    4440
ggcttggccc tgcccaagct acttcctgta cttaaaagtg ttaataaaac cagactattc    4500
aggccc                                                              4506
```

<210> SEQ ID NO 43
<211> LENGTH: 1542
<212> TYPE: DNA
<213> ORGANISM: homo sapiens

<400> SEQUENCE: 43

```
ccgacgcgac catcgtttgt cgacgccgct gccaccgcct gcctgagaga agtcgtcgcg      60
gccgaccccg tcgcctccgc cggctaccat gtccgcccag gcgcagatgc gggccctgct     120
ggaccagctc atgggcacgg ctcgggacgg agacgaaacc agacagaggg tcaagtttac     180
agatgaccgt gtctgcaaga gtcaccttct ggactgctgc ccccatgaca tcctggctgg     240
gacgcgcatg gatttaggag aatgtaccaa atccacgac ttggccctcc gagcagatta      300
tgagattgca agtaaagaaa gagacctgtt ttttgaatta gatgcaatgg atcacttgga     360
gtcctttatt gctgaatgtg atcggagaac tgagctcgcc aagaagcggc tggcagaaac     420
acaggaggaa atcagtgcgg aagtttctgc aaaggcagaa aaagtacatg agttaaatga     480
agaaatagga aaactccttg ctaaagccga acagctaggg gctgaaggta atgtggatga     540
atcccagaag attcttatgg aagtggaaaa agttcgtgcg aagaaaaaag aagctgagga     600
agaatacaga aattccatgc ctgcatccag ttttcagcag caaaagctgc gtgtctgcga     660
ggtctgttca gcctaccttg gtctccatga caatgaccgt cgcctggcag accacttcgg     720
tggcaagtta cacttggggt tcattcagat ccgagagaag cttgatcagt tgaggaaaac     780
tgtcgctgaa aagcaggaga agagaaatca ggatcgcttg aggaggagag aggagaggga     840
acgggaggag cgtctgagca ggaggtcggg atcaagaacc agagatcgca ggaggtcacg     900
ctcccgggat cggcgtcgga ggcggtcaag atctacctcc cgagagcgac ggaaattgtc     960
ccggtcccgg tccgagata gacatcgcg ccaccgcagc cgttcccgga gccacagccg     1020
gggacatcgt cgggcttccc gggaccgaag tgcgaaatac aagtaactac tctgactcct    1080
tcggtagctg caaccaggag tgagcccttc tctgtgttcc cagggtctgc tgagggccgt    1140
gtctggtggg gatggggctg ggctcaccct caggagtagg gctggggagt cgtgaacggg    1200
actcaggtgt gggaagaggc gagagggctg tggaggagct cgcacggcgc caggtgatgg    1260
gctgcacagg cactgtcccc tgcctgcgtc ctggggcctg tgcactgttg cgtccatgct    1320
cagagtggct gagacttgtg tcctgaccag gccctgctta cctctgtttt ggttttgtt     1380
tttgatattt ttttttccat tgtgttttta cgtagtgtca tgttctgtgc atatagtgtt    1440
gtattctcct ttgcactgtt tatgttacag tgaaggctct ccttattaaa aatcttcgca    1500
aaggtcaaaa aaaaaaaaa aaaaaaaaa aaaaaaaaa aa                          1542
```

<210> SEQ ID NO 44
<211> LENGTH: 968
<212> TYPE: DNA
<213> ORGANISM: homo sapiens

<400> SEQUENCE: 44

```
gggggaagtt gctggctgac tgggcttgcg aggaaaccgc ctcggagctg cagcgaaggc      60
caaggaatca ctgaagatcg gcgagggagg acagggggtt catcatgggt ggcttttttct    120
caagtatatt ttccagtctg tttggaactc ggggaatgag aattttaatt ttgggattag     180
atggagcagg aaaaaccaca attttgtaca gattacaagt gggagaagtt gttactacta     240
tacctaccat tggatttaat gtagagacgt tgacgtacaa aaaccttaaa ttccaagtct     300
gggatttagg aggacagaca agtatcaggc catactggag atgttactat tcaaacacag     360
atgcagtcat ttatgtagta gacagttgtg accgagaccg aattggcatt tccaaatcag     420
agttagttgc catgttggag gaagaagagc tgagaaaagc catttttagtg gtgtttgcaa    480
```

```
ataaacagga catggaacag gccatgactt cctcagagat ggcaaattca cttgggttac    540
ctgccttgaa ggaccgaaaa tggcagatat tcaaaacgtc agcaaccaaa ggcaccggcc    600
ttgatgaggc aatggaatgg ttagttgaaa cattaaaaag cagacagtaa ttcagtccat    660
tcttctcccc tgaaatgaag actacatcac ctctctccct tggaaacag tcaagtgtac     720 ttcacactac tagatgttaa aactatatga ttattggcat atactgactg actgcaatat    780
ttgtagtaaa tagggaaaat aagtatttag ttggagggat aatttgatcg aatcacctga    840
atgttctatg taatgtaaaa tattcttttc ttgctttctt gtgttaaggt atatattcta    900
tttgtatgga attcttattc aaatacagtt gtattaaaga gtatactcct attggatgaa    960
aaaaacct                                                              968

<210> SEQ ID NO 45
<211> LENGTH: 700
<212> TYPE: DNA
<213> ORGANISM: homo sapiens

<400> SEQUENCE: 45
gcggcgtgag aagccatgag cagcaaagtc tctcgcgaca ccctgtacga ggcggtgcgg     60
gaagtcctgc acgggaacca gcgcaagcgc cgcaagttcc tggagacggt ggagttgcag    120
atcagcttga agaactatga tccccagaag gacaagcgct tctcgggcac cgtcaggctt    180
aagtccactc cccgccctaa gttctctgtg tgtgtcctgg gggaccagca gcactgtgac    240
gaggctaagg ccgtggatat ccccccacatg gacatcgagg cgctgaaaaa actcaacaag    300
aataaaaaac tggtcaagaa gctggccaag aagtatgatg cgttttttggc ctcagagtct    360 ctgatcaaga gattccacg aatcctcggc ccaggtttaa ataaggcagg aaagttccct    420
tccctgctca cacacaacga aaacatggtg gccaaagtgg atgaggtgaa gtccacaatc    480
aagttccaaa tgaagaaggt gttatgtctg gctgtagctg ttggtcacgt gaagatgaca    540
gacgatgagc ttgtgtataa cattcacctg gctgtcaact tcttggtgtc attgctcaag    600
aaaaactggc agaatgtccg ggccttatat atcaagagca ccatgggcaa gccccagcgc    660
ctatattaag gcacatttga ataaattcta ttaccagttc                          700

<210> SEQ ID NO 46
<211> LENGTH: 145
<212> TYPE: PRT
<213> ORGANISM: homo sapiens
<220> FEATURE:
<221> NAME/KEY: MISC_FEATURE
<222> LOCATION: (65)..(65)
<223> OTHER INFORMATION: Xaa = any amino acid
<220> FEATURE:
<221> NAME/KEY: MISC_FEATURE
<222> LOCATION: (101)..(101)
<223> OTHER INFORMATION: Xaa = any amino acid
<220> FEATURE:
<221> NAME/KEY: MISC_FEATURE
<222> LOCATION: (105)..(105)
<223> OTHER INFORMATION: Xaa = any amino acid
<220> FEATURE:
<221> NAME/KEY: MISC_FEATURE
<222> LOCATION: (108)..(108)
<223> OTHER INFORMATION: Xaa = any amino acid
<220> FEATURE:
<221> NAME/KEY: MISC_FEATURE
<222> LOCATION: (113)..(113)
<223> OTHER INFORMATION: Xaa = any amino acid
<220> FEATURE:
<221> NAME/KEY: MISC_FEATURE
<222> LOCATION: (125)..(128)
<223> OTHER INFORMATION: Xaa = any amino acid
```

```
<220> FEATURE:
<221> NAME/KEY: MISC_FEATURE
<222> LOCATION: (132)..(132)
<223> OTHER INFORMATION: Xaa = any amino acid
<220> FEATURE:
<221> NAME/KEY: MISC_FEATURE
<222> LOCATION: (136)..(136)
<223> OTHER INFORMATION: Xaa = any amino acid

<400> SEQUENCE: 46
```

Arg Arg Lys Trp Ser Leu Asp Arg Leu Arg Asp Thr Val Lys Ala Leu
1               5                   10                  15

Thr Arg Glu Gln Glu Lys Leu Leu Gly Gln Leu Lys Glu Val Gln Ala
            20                  25                  30

Asp Lys Glu Gln Ser Glu Ala Glu Leu Gln Val Ala Gln Gln Glu Asn
        35                  40                  45

His His Leu Asn Leu Asp Leu Lys Glu Ala Lys Ser Trp Gln Glu Glu
    50                  55                  60

Xaa Ser Ala Gln Ala Gln Arg Leu Lys Asp Lys Val Ala Gln Met Lys
65                  70                  75                  80

Asp Thr Leu Cys Gln Ala Gln Gln Arg Val Ala Gln Leu Glu Pro Leu
                85                  90                  95

Lys Glu Gln Leu Xaa Gly Ala Gln Xaa Ala Leu Xaa Ala Ser Ser Gln
            100                 105                 110

Xaa Lys Ala Thr Leu Ser Trp Gly Gly Val Cys Gln Xaa Xaa Xaa Xaa
        115                 120                 125

Pro Gly Thr Xaa Pro Tyr Ala Xaa Leu His Arg Ser Arg Pro Gly Ser
    130                 135                 140

Gly
145

```
<210> SEQ ID NO 47
<211> LENGTH: 208
<212> TYPE: PRT
<213> ORGANISM: homosapiens
<220> FEATURE:
<221> NAME/KEY: MISC_FEATURE
<222> LOCATION: (6)..(6)
<223> OTHER INFORMATION: Xaa = any amino acid

<400> SEQUENCE: 47
```

Gly Arg Ala Pro Val Xaa Gln Cys Ser Asp Gly Glu Gly Arg Lys Arg
1               5                   10                  15

Thr Ser Thr Cys Ser Asn Glu Ser Leu Ser Val Gly Gly Thr Ser
            20                  25                  30

Val Thr Pro Arg Arg Ile Ser Trp Arg Gln Arg Ile Phe Leu Arg Val
            35                  40                  45

Ala Ser Pro Met Asn Lys Ser Pro Ser Ala Met Gln Gln Gln Asp Gly
        50                  55                  60

Leu Asp Arg Asn Glu Leu Leu Pro Leu Ser Leu Ser Pro Thr Met
65                  70                  75                  80

Glu Glu Glu Pro Leu Val Val Phe Leu Ser Gly Glu Asp Asp Pro Glu
                85                  90                  95

Lys Ile Glu Glu Arg Lys Lys Ser Lys Glu Leu Arg Ser Leu Trp Arg
            100                 105                 110

Lys Ala Ile His Gln Gln Ile Leu Leu Leu Arg Met Glu Lys Glu Asn
        115                 120                 125

Gln Lys Leu Glu Ala Ser Arg Asp Glu Leu Gln Ser Arg Lys Val Lys
    130                 135                 140

```
Leu Asp Tyr Glu Glu Val Gly Ala Cys Gln Lys Glu Val Leu Ile Thr
145                 150                 155                 160

Trp Asp Lys Lys Leu Leu Asn Cys Arg Ala Lys Ile Arg Cys Asp Met
            165                 170                 175

Glu Asp Ile His Thr Leu Leu Lys Lys Glu Phe Pro Lys Ser Thr Arg
            180                 185                 190

Arg Ile Trp Gln Phe Leu Ala Tyr Ser Thr Asp Ser Thr Gln Ile Ala
            195                 200                 205

<210> SEQ ID NO 48
<211> LENGTH: 256
<212> TYPE: PRT
<213> ORGANISM: homosapiens
<220> FEATURE:
<221> NAME/KEY: MISC_FEATURE
<222> LOCATION: (186)..(186)
<223> OTHER INFORMATION: Xaa = any amino acid
<220> FEATURE:
<221> NAME/KEY: MISC_FEATURE
<222> LOCATION: (219)..(219)
<223> OTHER INFORMATION: Xaa = any amino acid
<220> FEATURE:
<221> NAME/KEY: MISC_FEATURE
<222> LOCATION: (222)..(222)
<223> OTHER INFORMATION: Xaa = any amino acid
<220> FEATURE:
<221> NAME/KEY: MISC_FEATURE
<222> LOCATION: (230)..(230)
<223> OTHER INFORMATION: Xaa = any amino acid
<220> FEATURE:
<221> NAME/KEY: MISC_FEATURE
<222> LOCATION: (243)..(243)
<223> OTHER INFORMATION: Xaa = any amino acid
<220> FEATURE:
<221> NAME/KEY: MISC_FEATURE
<222> LOCATION: (247)..(247)
<223> OTHER INFORMATION: Xaa = any amino acid
<220> FEATURE:
<221> NAME/KEY: MISC_FEATURE
<222> LOCATION: (254)..(254)
<223> OTHER INFORMATION: Xaa = any amino acid

<400> SEQUENCE: 48

Met Leu Arg Ser Pro Phe Asp Arg Asn Val Pro Val Asn Leu Glu Leu
1               5                   10                  15

Gln Glu Leu Leu Leu Asp Tyr Ser Phe Gln His Leu Gly Val Ser Ser
            20                  25                  30

Gln Gly Cys Val Asp His Pro Ile Val Leu Thr Glu Ala Val Cys Asn
        35                  40                  45

Pro Leu Tyr Ser Arg Gln Met Met Ser Glu Leu Leu Phe Glu Cys Tyr
50                  55                  60

Gly Ile Pro Lys Val Ala Tyr Gly Ile Asp Ser Leu Phe Ser Phe Tyr
65                  70                  75                  80

His Asn Lys Pro Lys Asn Ser Met Cys Ser Gly Leu Ile Ile Ser Ser
            85                  90                  95

Gly Tyr Gln Cys Thr His Val Leu Pro Ile Leu Glu Gly Arg Leu Asp
        100                 105                 110

Ala Lys Asn Cys Lys Arg Ile Asn Leu Gly Gly Ser Gln Ala Ala Gly
        115                 120                 125

Tyr Leu Gln Arg Leu Leu Gln Leu Lys Tyr Pro Gly His Leu Ala Ala
        130                 135                 140

Ile Thr Leu Ser Arg Met Glu Glu Ile Leu His Glu His Ser Tyr Ile
145                 150                 155                 160
```

```
Ala Glu Asp Tyr Val Glu Glu Leu His Lys Trp Arg Cys Pro Asp Tyr
                165                 170                 175

Tyr Glu Asn Asn Val His Lys Met Gln Xaa Pro Phe Ser Ser Lys Leu
            180                 185                 190

Leu Gly Ser Thr Leu Thr Ser Glu Glu Lys Gln Glu Arg Arg Gln Gln
        195                 200                 205

Gln Leu Arg Arg Leu Gln Glu Leu Asn Ala Xaa Arg Arg Xaa Glu Lys
    210                 215                 220

Leu Gln Leu Gly Ser Xaa Ala Ser Gly Pro Thr Ala Ile Cys Ala Gly
225                 230                 235                 240

Thr Ser Xaa Gly Trp Pro Xaa Gly Ser Val Tyr Lys Ala Xaa Met Ser
            245                 250                 255

<210> SEQ ID NO 49
<211> LENGTH: 205
<212> TYPE: PRT
<213> ORGANISM: homosapiens
<220> FEATURE:
<221> NAME/KEY: MISC_FEATURE
<222> LOCATION: (144)..(144)
<223> OTHER INFORMATION: Xaa = any amino acid
<220> FEATURE:
<221> NAME/KEY: MISC_FEATURE
<222> LOCATION: (157)..(157)
<223> OTHER INFORMATION: Xaa = any amino acid
<220> FEATURE:
<221> NAME/KEY: MISC_FEATURE
<222> LOCATION: (159)..(159)
<223> OTHER INFORMATION: Xaa = any amino acid
<220> FEATURE:
<221> NAME/KEY: MISC_FEATURE
<222> LOCATION: (188)..(188)
<223> OTHER INFORMATION: Xaa = any amino acid
<220> FEATURE:
<221> NAME/KEY: MISC_FEATURE
<222> LOCATION: (194)..(194)
<223> OTHER INFORMATION: Xaa = any amino acid
<220> FEATURE:
<221> NAME/KEY: MISC_FEATURE
<222> LOCATION: (197)..(197)
<223> OTHER INFORMATION: Xaa = any amino acid

<400> SEQUENCE: 49

Met Asn Asp Ile Ser Gln Lys Ala Glu Ile Leu Leu Ser Ser Ser Lys
1               5                   10                  15

Pro Val Pro Lys Thr Tyr Val Pro Lys Leu Gly Lys Gly Asp Val Lys
            20                  25                  30

Asp Lys Phe Glu Ala Met Gln Arg Ala Arg Glu Arg Asn Gln Arg
        35                  40                  45

Arg Ser Arg Asp Glu Lys Gln Arg Arg Lys Glu Gln Tyr Ile Arg Glu
50                  55                  60

Arg Glu Trp Asn Arg Arg Lys Gln Glu Ile Lys Glu Met Leu Ala Ser
65                  70                  75                  80

Asp Asp Glu Glu Asp Val Ser Ser Lys Val Glu Lys Ala Tyr Val Pro
                85                  90                  95

Lys Leu Thr Gly Thr Val Lys Gly Arg Phe Ala Glu Met Glu Lys Gln
            100                 105                 110

Arg Gln Glu Glu Gln Arg Lys Arg Thr Glu Glu Arg Lys Arg Arg
        115                 120                 125

Ile Glu Gln Asp Met Leu Glu Lys Arg Lys Ile Gln Arg Glu Leu Xaa
        130                 135                 140

Lys Arg Ala Glu Gln Glu Gly Asp Asp Ser Leu Leu Xaa Thr Xaa Val
145                 150                 155                 160
```

```
Pro Val Asn His Ile Asn Ile Trp Lys Met Lys Arg Ile Leu Arg Ser
                165                 170                 175

Arg Lys Arg Arg Glu Glu Lys Lys Asp Pro Val Xaa Glu Ile Lys Ile
            180                 185                 190

Arg Xaa Glu Thr Xaa Pro Leu Ser Gly Ala Arg Ala Ser
        195                 200                 205

<210> SEQ ID NO 50
<211> LENGTH: 172
<212> TYPE: PRT
<213> ORGANISM: homosapiens
<220> FEATURE:
<221> NAME/KEY: MISC_FEATURE
<222> LOCATION: (136)..(136)
<223> OTHER INFORMATION: Xaa = any amino acid
<220> FEATURE:
<221> NAME/KEY: MISC_FEATURE
<222> LOCATION: (142)..(142)
<223> OTHER INFORMATION: Xaa = any amino acid
<220> FEATURE:
<221> NAME/KEY: MISC_FEATURE
<222> LOCATION: (146)..(146)
<223> OTHER INFORMATION: Xaa = any amino acid
<220> FEATURE:
<221> NAME/KEY: MISC_FEATURE
<222> LOCATION: (151)..(151)
<223> OTHER INFORMATION: Xaa = any amino acid

<400> SEQUENCE: 50

Met Glu Ser Tyr Arg Glu Asn Leu Glu Arg Val Phe Val Arg Met Asp
1               5                   10                  15

Gln Val Leu Pro Asp Ser Cys Leu Leu Val Trp Asn Met Ala Met Pro
                20                  25                  30

Leu Gly Glu Arg Ile Thr Gly Gly Phe Leu Leu Pro Glu Leu Gln Pro
            35                  40                  45

Leu Ala Gly Ser Leu Arg Arg Asp Val Val Glu Gly Asn Phe Tyr Ser
        50                  55                  60

Ala Thr Leu Ala Gly Asp His Cys Phe Asp Val Leu Asp Leu His Phe
65                  70                  75                  80

His Phe Arg His Ala Val Gln His Arg His Arg Asp Gly Val His Trp
                85                  90                  95

Asp Gln His Ala His Arg His Leu Ser His Leu Leu Leu Thr His Val
            100                 105                 110

Ala Asp Ala Trp Gly Val Glu Leu Pro Lys Arg Gly Tyr Pro Pro Asp
        115                 120                 125

Pro Trp Ile Glu Asp Trp Ala Xaa Met Asn His Pro Phe Xaa Gly Ser
    130                 135                 140

His Xaa Gln Thr Gln Thr Xaa Gly Arg Pro Gly Pro Cys Ser Thr Pro
145                 150                 155                 160

Leu Leu Leu Ala Leu His Ala Phe Ser Tyr Arg Phe
                165                 170

<210> SEQ ID NO 51
<211> LENGTH: 159
<212> TYPE: PRT
<213> ORGANISM: homosapiens
<220> FEATURE:
<221> NAME/KEY: MISC_FEATURE
<222> LOCATION: (143)..(143)
<223> OTHER INFORMATION: Xaa = any amino acid
<220> FEATURE:
<221> NAME/KEY: MISC_FEATURE
<222> LOCATION: (153)..(153)
```

<223> OTHER INFORMATION: Xaa = any amino acid

<400> SEQUENCE: 51

```
Met Leu Gln Gln Glu Thr Ile Arg Asn Gly Glu Leu Glu Asp Thr Gln
1               5                   10                  15

Thr Lys Leu Glu Lys Gln Val Ser Lys Leu Glu Gln Glu Leu Gln Lys
            20                  25                  30

Gln Arg Glu Ser Ser Ala Glu Lys Leu Arg Lys Met Glu Glu Lys Cys
        35                  40                  45

Glu Ser Ala Ala His Glu Ala Asp Leu Lys Arg Gln Lys Val Ile Glu
    50                  55                  60

Leu Thr Gly Thr Ala Arg Gln Val Lys Ile Glu Met Asp Gln Tyr Lys
65                  70                  75                  80

Glu Glu Leu Ser Lys Met Glu Lys Glu Ile Met His Leu Lys Arg Asp
                85                  90                  95

Gly Glu Asn Lys Ala Met His Leu Ser Gln Leu Asp Met Ile Leu Asp
            100                 105                 110

Gln Thr Lys Thr Glu Leu Glu Lys Lys Thr Asn Ala Val Lys Glu Leu
        115                 120                 125

Glu Lys Leu Gln His Ser Thr Glu Thr Glu Leu Thr Glu Ala Xaa Gln
    130                 135                 140

Asn Gly Lys Tyr Leu Arg Leu Thr Xaa Lys Cys Ser Trp Glu Ile
145                 150                 155
```

<210> SEQ ID NO 52
<211> LENGTH: 122
<212> TYPE: PRT
<213> ORGANISM: homosapiens

<400> SEQUENCE: 52

```
Met Ile Gly Gly Thr Glu Met Thr Lys Glu Ile Pro Arg Lys Arg Lys
1               5                   10                  15

Asn Thr Val Glu Ala Glu Ala Glu Lys Gly Asn Thr Glu Val Gly Val
            20                  25                  30

Glu Val Glu Met Gln Gly Asn Glu Val Glu Val Glu Ala Lys Arg Asn
        35                  40                  45

Gln Val Asn Ile Lys Met Lys Val Lys Lys Asn Gln Ile Asn Glu Val
    50                  55                  60

Glu Val Ala Val Lys Glu Glu Leu Thr Val Leu Lys Asn Gln Lys Asn
65                  70                  75                  80

Gly Asn Ile Val Pro Ala Lys Lys Asn Leu Glu Ser Val Val Glu Ala
                85                  90                  95

Lys Asn Val Pro Thr Asn Glu Ile Thr Val Ile Val Arg Thr Ser Gln
            100                 105                 110

Thr Asn Met Ile Val Glu Gly Ala Lys Val
        115                 120
```

<210> SEQ ID NO 53
<211> LENGTH: 127
<212> TYPE: PRT
<213> ORGANISM: homosapiens

<400> SEQUENCE: 53

```
Met Ser Arg Pro Lys Thr Gln Asn Gln Val Thr His Thr Gln Val Lys
1               5                   10                  15

Asn Thr Arg Arg Lys Pro Ile Thr Val Leu Lys Arg Lys Lys Met Arg
            20                  25                  30
```

```
Thr Thr Cys Gln Ser Lys Ile Leu Ile Arg Ile Ser Ile Glu Lys Trp
            35                  40                  45

Gly Leu Val Thr Met Lys Lys Lys Ala Val Gly Arg Asn Lys Arg
 50                  55                  60

Val Lys Arg Glu Thr Glu Leu Arg Thr Glu Val Val Ala Asp Leu Glu
 65                  70                  75                  80

Arg Gly Met Ala Ile Ile Val Ile Val Ile Asn Gln Asn Thr Lys Gln
                    85                  90                  95

Ile Phe Met Lys Glu Lys Gly Val Lys Arg Glu Thr Glu Ala Glu Val
                100                 105                 110

Gln Arg Ser Pro Lys Ile Lys Lys Asn Leu Ser Ile Asp Glu Arg
                115                 120                 125

<210> SEQ ID NO 54
<211> LENGTH: 175
<212> TYPE: PRT
<213> ORGANISM: homosapiens
<220> FEATURE:
<221> NAME/KEY: MISC_FEATURE
<222> LOCATION: (132)..(132)
<223> OTHER INFORMATION: Xaa = any amino acid
<220> FEATURE:
<221> NAME/KEY: MISC_FEATURE
<222> LOCATION: (146)..(146)
<223> OTHER INFORMATION: Xaa = any amino acid

<400> SEQUENCE: 54

Met Gly Lys Lys His Lys Lys His Lys Ala Glu Trp Arg Ser Ser Tyr
 1               5                  10                  15

Glu Asp Tyr Ala Asp Lys Pro Leu Glu Lys Pro Leu Lys Leu Val Leu
                20                  25                  30

Lys Val Gly Gly Ser Glu Val Thr Glu Leu Ser Gly Ser Gly His Asp
                35                  40                  45

Ser Ser Tyr Tyr Asp Asp Arg Ser Asp His Glu Arg Glu Arg His Lys
 50                  55                  60

Glu Lys Lys Lys Lys Lys Lys Ser Glu Lys Glu Lys His Leu
 65                  70                  75                  80

Asp Asp Glu Glu Arg Arg Lys Arg Lys Glu Lys Lys Arg Lys Arg
                    85                  90                  95

Glu Arg Glu His Cys Asp Thr Glu Gly Glu Ala Asp Phe Asp Pro
                100                 105                 110

Gly Lys Lys Val Glu Val Glu Pro Pro Asp Arg Pro Val Arg Ala
                115                 120                 125

Cys Arg Thr Xaa Pro Ala Glu Asn Glu Ser Thr Pro Ile Gln Gln Leu
            130                 135                 140

Leu Xaa Thr Leu Pro Pro Pro Ala Ser Glu Lys Arg Ser Pro Trp Ile
145                 150                 155                 160

Phe Cys Phe Ser Cys His Gly Cys Asn Cys Ser Trp Asp Ile Pro
                165                 170                 175

<210> SEQ ID NO 55
<211> LENGTH: 255
<212> TYPE: PRT
<213> ORGANISM: homosapiens

<400> SEQUENCE: 55

Met Ser Ser His Arg Arg Lys Ala Lys Gly Arg Asn Arg Arg Ser His
 1               5                  10                  15
```

```
Arg Ala Met Arg Val Ala His Leu Glu Leu Ala Thr Tyr Glu Leu Ala
            20                  25                  30

Ala Thr Glu Ser Asn Pro Glu Ser His Pro Gly Tyr Glu Ala Ala
        35                  40                  45

Met Ala Asp Arg Pro Gln Pro Gly Trp Arg Glu Ser Leu Lys Met Arg
 50                  55                  60

Val Ser Lys Pro Phe Gly Met Leu Met Leu Ser Ile Trp Ile Leu Leu
 65                  70                  75                  80

Phe Val Cys Tyr Tyr Leu Ser Tyr Tyr Leu Cys Ser Gly Ser Ser Tyr
                85                  90                  95

Phe Val Leu Ala Asn Gly His Ile Leu Pro Asn Ser Glu Asn Ala His
                100                 105                 110

Gly Gln Ser Leu Glu Glu Asp Ser Ala Leu Glu Ala Leu Leu Asn Phe
            115                 120                 125

Phe Phe Pro Thr Thr Cys Asn Leu Arg Glu Asn Gln Val Ala Lys Pro
130                 135                 140

Cys Asn Glu Leu Gln Asp Leu Ser Glu Ser Glu Cys Leu Arg His Lys
145                 150                 155                 160

Cys Cys Phe Ser Ser Ser Gly Thr Thr Ser Phe Lys Cys Phe Ala Pro
                165                 170                 175

Phe Arg Asp Val Pro Lys Gln Met Met Gln Met Phe Gly Leu Gly Ala
                180                 185                 190

Ile Ser Leu Ile Leu Val Cys Leu Pro Ile Tyr Cys Arg Ser Leu Phe
            195                 200                 205

Trp Arg Ser Glu Pro Ala Asp Asp Leu Gln Arg Gln Asp Asn Arg Val
210                 215                 220

Val Thr Gly Leu Lys Lys Gln Arg Arg Lys Arg Lys Ser Glu
225                 230                 235                 240

Met Leu Gln Lys Ala Ala Arg Gly Arg Glu Glu His Gly Asp Glu
                245                 250                 255

<210> SEQ ID NO 56
<211> LENGTH: 239
<212> TYPE: PRT
<213> ORGANISM: homosapiens
<220> FEATURE:
<221> NAME/KEY: MISC_FEATURE
<222> LOCATION: (42)..(42)
<223> OTHER INFORMATION: Xaa = any amino acid
<220> FEATURE:
<221> NAME/KEY: MISC_FEATURE
<222> LOCATION: (225)..(229)
<223> OTHER INFORMATION: Xaa = any amino acid
<220> FEATURE:
<221> NAME/KEY: MISC_FEATURE
<222> LOCATION: (231)..(234)
<223> OTHER INFORMATION: Xaa = any amino acid

<400> SEQUENCE: 56

Met Leu Gln Asn Glu Gln Glu Ile Ser Gln Leu Lys Lys Glu Ile Glu
 1               5                  10                  15

Arg Thr Gln Gln Arg Met Lys Glu Met Glu Ser Val Met Lys Glu Gln
            20                  25                  30

Glu Gln Tyr Ile Ala Thr Gln Tyr Lys Xaa Ala Ile Asp Leu Gly Gln
                35                  40                  45

Glu Leu Arg Leu Thr Arg Glu Gln Val Gln Asn Ser His Thr Glu Leu
        50                  55                  60

Ala Glu Ala Arg His Gln Gln Val Gln Ala Gln Arg Glu Ile Glu Arg
65                  70                  75                  80
```

```
Leu Ser Ser Glu Leu Glu Asp Met Lys Gln Leu Ser Lys Glu Lys Asp
                85                  90                  95

Ala His Gly Asn His Leu Ala Glu Glu Leu Gly Ala Ser Lys Val Arg
            100                 105                 110

Glu Ala His Leu Glu Ala Arg Met Gln Ala Glu Ile Lys Lys Leu Ser
        115                 120                 125

Ala Glu Val Glu Ser Leu Lys Glu Ala Tyr His Met Glu Met Ile Ser
    130                 135                 140

His Gln Glu Asn His Ala Lys Trp Lys Ile Ser Ala Asp Ser Gln Lys
145                 150                 155                 160

Ser Ser Val Gln Gln Leu Asn Glu Gln Leu Glu Lys Ala Lys Leu Glu
                165                 170                 175

Leu Glu Glu Ala Gln Asp Thr Val Ser Asn Leu His Gln Gln Val Gln
            180                 185                 190

Asp Arg Asn Glu Val Ile Glu Ala Asn Glu Ala Leu Leu Thr Lys
        195                 200                 205

Val Ser Lys His Ile Lys Val Leu Lys His Ile Tyr Glu Asn Lys Thr
    210                 215                 220

Xaa Xaa Xaa Xaa Xaa Pro Xaa Xaa Xaa Xaa Ser Arg Glu Tyr Phe
225                 230                 235

<210> SEQ ID NO 57
<211> LENGTH: 249
<212> TYPE: PRT
<213> ORGANISM: homosapiens
<220> FEATURE:
<221> NAME/KEY: MISC_FEATURE
<222> LOCATION: (226)..(226)
<223> OTHER INFORMATION: Xaa = any amino acid
<220> FEATURE:
<221> NAME/KEY: MISC_FEATURE
<222> LOCATION: (239)..(239)
<223> OTHER INFORMATION: Xaa = any amino acid

<400> SEQUENCE: 57

Met Ala Asp Ser Ser Gly Arg Gly Ala Gly Lys Pro Ala Thr Gly Pro
1               5                   10                  15

Thr Asn Ser Ser Ser Ala Lys Lys Lys Asp Lys Arg Val Gln Gly Gly
            20                  25                  30

Arg Val Ile Glu Ser Arg Tyr Leu Gln Tyr Glu Lys Lys Thr Thr Gln
        35                  40                  45

Lys Ala Pro Ala Gly Asp Gly Ser Gln Thr Arg Gly Lys Met Ser Glu
    50                  55                  60

Gly Gly Arg Lys Ser Ser Leu Leu Gln Lys Ser Lys Ala Asp Ser Ser
65                  70                  75                  80

Gly Val Gly Lys Gly Asp Leu Gln Ser Thr Leu Leu Glu Gly His Gly
                85                  90                  95

Thr Ala Pro Pro Asp Leu Asp Leu Ser Ala Ile Asn Asp Lys Ser Ile
            100                 105                 110

Val Lys Lys Thr Pro Gln Leu Ala Lys Thr Ile Ser Lys Lys Pro Glu
        115                 120                 125

Ser Thr Ser Phe Ser Ala Pro Arg Lys Lys Ser Pro Asp Leu Ser Glu
    130                 135                 140

Ala Met Glu Met Met Glu Ser Gln Thr Leu Leu Thr Leu Leu Ser
145                 150                 155                 160

Val Lys Met Glu Asn Asn Leu Ala Glu Phe Glu Arg Arg Ala Glu Lys
                165                 170                 175
```

```
Asn Leu Leu Ile Met Cys Lys Glu Lys Glu Lys Leu Gln Lys Lys Ala
                180                 185                 190

His Glu Leu Lys Arg Arg Leu Leu Ser Gln Arg Lys Arg Glu Leu
            195                 200                 205

Ala Asp Val Leu Asp Ala Gln Ile Glu Met Leu Ser Pro Leu Arg Gly
210                 215                 220

Ser Xaa His Thr Leu Gln Gly Ala Ile Gln Asp Ile Arg His Xaa Pro
225                 230                 235                 240

Trp Thr Leu Pro Gly Thr Ser Cys Pro
                245

<210> SEQ ID NO 58
<211> LENGTH: 116
<212> TYPE: PRT
<213> ORGANISM: homosapiens

<400> SEQUENCE: 58

Met Asp Tyr Arg Arg Leu Leu Met Ser Arg Val Val Pro Gly Gln Phe
1               5                   10                  15

Asp Asp Ala Asp Ser Ser Asp Ser Glu Asn Arg Asp Leu Lys Thr Val
                20                  25                  30

Lys Glu Lys Asp Asp Ile Leu Phe Glu Asp Leu Gln Asp Asn Val Asn
            35                  40                  45

Glu Asn Gly Glu Gly Glu Ile Glu Asp Glu Glu Glu Gly Tyr Asp
        50                  55                  60

Asp Asp Asp Asp Asp Trp Asp Trp Asp Glu Gly Val Gly Lys Leu Ala
65                  70                  75                  80

Lys Gly Tyr Val Trp Asn Gly Gly Ser Asn Pro Gln Ala Asn Arg Gln
                85                  90                  95

Thr Ser Asp Ser Ser Ser Ala Lys Met Ser Thr Pro Ala Asp Lys Val
            100                 105                 110

Leu Arg Lys Ile
        115

<210> SEQ ID NO 59
<211> LENGTH: 225
<212> TYPE: PRT
<213> ORGANISM: homo sapiens

<400> SEQUENCE: 59

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
                20                  25                  30

Leu Ile Cys Phe Leu Val Leu Tyr Ala Leu Phe Leu Thr Leu Thr Thr
            35                  40                  45

Lys Leu Thr Asn Thr Asn Ile Ser Asp Ala Gln Glu Met Val Trp Thr
        50                  55                  60

Ile Leu Pro Ala Ile Ile Leu Val Leu Ile Ala Leu Pro Ser Leu Arg
65                  70                  75                  80

Ile Leu Tyr Met Thr Asp Glu Val Asn Asp Pro Ser Leu Thr Ile Lys
                85                  90                  95

Ser Ile Gly His Gln Trp Tyr Trp Thr Tyr Glu Tyr Thr Asp Tyr Gly
            100                 105                 110

Gly Leu Ile Phe Asn Ser Tyr Met Leu Pro Pro Leu Phe Leu Glu Pro
        115                 120                 125
```

```
Gly Asp Leu Arg Leu Leu Asp Val Asp Asn Arg Val Leu Pro Ile
    130                 135                 140

Glu Ala Pro Ile Arg Met Met Ile Thr Ser Gln Asp Val Leu His Ser
145                 150                 155                 160

Trp Ala Val Pro Thr Leu Gly Leu Lys Thr Asp Ala Ile Pro Gly Arg
                165                 170                 175

Leu Asn Gln Thr Thr Phe Thr Ala Thr Arg Pro Gly Val Tyr Tyr Gly
            180                 185                 190

Gln Cys Ser Glu Ile Cys Gly Ala Asn His Ser Phe Met Pro Ile Val
                195                 200                 205

Leu Glu Leu Ile Pro Leu Lys Ile Phe Glu Met Gly Pro Val Phe Thr
    210                 215                 220

Leu
225

<210> SEQ ID NO 60
<211> LENGTH: 384
<212> TYPE: PRT
<213> ORGANISM: homo sapiens

<400> SEQUENCE: 60

Met Asp Ala Val Met Thr Arg Lys Lys Ile Met Lys Gln Lys Glu Met
1               5                   10                  15

Val Trp Asn Asn Asn Lys Lys Leu Ser Asp Leu Glu Glu Val Ala Lys
                20                  25                  30

Glu Arg Ala Gln Asn Leu Leu Gln Arg Ala Asn Lys Leu Arg Met Glu
            35                  40                  45

Gln Glu Glu Leu Lys Asp Met Ser Lys Ile Ile Leu Asn Ala Lys
    50                  55                  60

Cys His Ala Ile Arg Asp Ala Gln Ile Leu Glu Lys Gln Gln Ile Gln
65                  70                  75                  80

Lys Glu Leu Asp Thr Glu Glu Lys Arg Leu Asp Gln Met Met Glu Val
                85                  90                  95

Glu Arg Gln Lys Ser Ile Gln Arg Gln Glu Leu Glu Arg Lys Arg
            100                 105                 110

Arg Glu Glu Arg Ile Arg Gly Arg Arg Gln Ile Val Glu Gln Met Glu
        115                 120                 125

Lys Asn Gln Glu Glu Arg Ser Leu Leu Ala Glu Gln Arg Glu Gln Glu
    130                 135                 140

Lys Glu Gln Met Leu Glu Tyr Met Glu Gln Leu Gln Glu Glu Asp Leu
145                 150                 155                 160

Lys Asp Met Glu Arg Arg Gln Gln Gln Lys Leu Lys Met Gln Ala Glu
                165                 170                 175

Ile Lys Arg Ile Asn Asp Glu Asn Gln Lys Gln Lys Ala Glu Leu Leu
            180                 185                 190

Ala Gln Glu Lys Leu Ala Asp Gln Met Val Met Glu Phe Thr Lys Lys
        195                 200                 205

Lys Met Ala Arg Glu Ala Glu Phe Glu Ala Glu Gln Arg Ile Arg
    210                 215                 220

Arg Glu Lys Glu Lys Glu Ile Ala Arg Leu Arg Ala Met Gln Glu Lys
225                 230                 235                 240

Ala Gln Asp Tyr Gln Ala Glu Gln Asp Ala Leu Arg Ala Lys Arg Asn
                245                 250                 255

Gln Glu Val Ala Asp Arg Glu Trp Arg Arg Lys Glu Lys Glu Asn Ala
```

-continued

```
                260                 265                 270
Arg Lys Lys Met Glu Ala Glu Leu Arg Lys Ser Arg Leu Glu Gln Val
            275                 280                 285
Ala Phe Lys Glu His Ala Leu Ala Val Gln Val His Gly Thr Gly Met
            290                 295                 300
Ser Ser Arg Gly Phe Phe Gly Leu Arg Glu Asn Arg Leu Arg Arg Ser
305                 310                 315                 320
Gly Trp Arg Arg Lys Arg Pro Gln Gly Ala Tyr Ser Met Pro Met
            325                 330                 335
Ser Ser Gly Ala Arg Cys Ala Arg Thr Ser Arg Lys Cys Arg Thr
            340                 345                 350
Gly Leu Pro Pro Leu Arg Gly Ala Gly Ala Ser Lys Arg Pro Arg
            355                 360                 365
Asn Ala Val Ser Ala Ser Met Arg Ser Arg Gly Lys Ser Leu Lys Ser
            370                 375                 380

<210> SEQ ID NO 61
<211> LENGTH: 510
<212> TYPE: PRT
<213> ORGANISM: homo sapiens

<400> SEQUENCE: 61

Met Tyr Arg Ala Leu Arg Leu Leu Ala Arg Ser Arg Pro Leu Val Arg
1               5                   10                  15
Ala Pro Ala Ala Leu Ala Ser Ala Pro Gly Leu Gly Gly Ala Ala
            20                  25                  30
Val Pro Ser Phe Trp Pro Pro Asn Ala Ala Arg Met Ala Ser Gln Asn
            35                  40                  45
Ser Phe Arg Ile Glu Tyr Asp Thr Phe Gly Glu Leu Lys Val Pro Asn
        50                  55                  60
Asp Lys Tyr Tyr Gly Ala Gln Thr Val Arg Ser Thr Met Asn Phe Lys
65                  70                  75                  80
Ile Gly Gly Val Thr Glu Arg Met Pro Thr Pro Val Ile Lys Ala Phe
                85                  90                  95
Gly Ile Leu Lys Arg Ala Ala Ala Glu Val Asn Gln Asp Tyr Gly Leu
            100                 105                 110
Asp Pro Lys Ile Ala Asn Ala Ile Met Lys Ala Ala Asp Glu Val Ala
            115                 120                 125
Glu Gly Lys Leu Asn Asp His Phe Pro Leu Val Val Trp Gln Thr Gly
        130                 135                 140
Ser Gly Thr Gln Thr Asn Met Asn Val Asn Glu Val Ile Ser Asn Arg
145                 150                 155                 160
Ala Ile Glu Met Leu Gly Gly Glu Leu Gly Ser Lys Ile Pro Val His
                165                 170                 175
Pro Asn Asp His Val Asn Lys Ser Gln Ser Ser Asn Asp Thr Phe Pro
            180                 185                 190
Thr Ala Met His Ile Ala Ala Ile Glu Val His Glu Val Leu Leu
            195                 200                 205
Pro Gly Leu Gln Lys Leu His Asp Ala Leu Asp Ala Lys Ser Lys Glu
        210                 215                 220
Phe Ala Gln Ile Ile Lys Ile Gly Arg Thr His Thr Gln Asp Ala Val
225                 230                 235                 240
Pro Leu Thr Leu Gly Gln Glu Phe Ser Gly Tyr Val Gln Gln Val Lys
                245                 250                 255
```

```
Tyr Ala Met Thr Arg Ile Lys Ala Ala Met Pro Arg Ile Tyr Glu Leu
            260                 265                 270

Ala Ala Gly Gly Thr Ala Val Gly Thr Gly Leu Asn Thr Arg Ile Gly
        275                 280                 285

Phe Ala Glu Lys Val Ala Ala Lys Val Ala Ala Leu Thr Gly Leu Pro
    290                 295                 300

Phe Val Thr Ala Pro Asn Lys Phe Glu Ala Leu Ala Ala His Asp Ala
305                 310                 315                 320

Leu Val Glu Leu Ser Gly Ala Met Asn Thr Thr Ala Cys Ser Leu Met
                325                 330                 335

Lys Ile Ala Asn Asp Ile Arg Phe Leu Gly Ser Gly Pro Arg Ser Gly
            340                 345                 350

Leu Gly Glu Leu Ile Leu Pro Glu Asn Glu Pro Gly Ser Ser Ile Met
        355                 360                 365

Pro Gly Lys Val Asn Pro Thr Gln Cys Glu Ala Met Thr Met Val Ala
    370                 375                 380

Ala Gln Val Met Gly Asn His Val Ala Val Thr Val Gly Gly Ser Asn
385                 390                 395                 400

Gly His Phe Glu Leu Asn Val Phe Lys Pro Met Met Ile Lys Asn Val
                405                 410                 415

Leu His Ser Ala Arg Leu Leu Gly Asp Ala Ser Val Ser Phe Thr Glu
            420                 425                 430

Asn Cys Val Val Gly Ile Gln Ala Asn Thr Glu Arg Ile Asn Lys Leu
        435                 440                 445

Met Asn Glu Ser Leu Met Leu Val Thr Ala Leu Asn Pro His Ile Gly
    450                 455                 460

Tyr Asp Lys Ala Ala Lys Ile Ala Lys Thr Ala His Lys Asn Gly Ser
465                 470                 475                 480

Thr Leu Lys Glu Thr Ala Ile Glu Leu Gly Tyr Leu Thr Ala Glu Gln
                485                 490                 495

Phe Asp Glu Trp Val Lys Pro Lys Asp Met Leu Gly Pro Lys
            500                 505                 510

<210> SEQ ID NO 62
<211> LENGTH: 937
<212> TYPE: PRT
<213> ORGANISM: homo sapiens

<400> SEQUENCE: 62

Met Arg Lys Ser Phe Ser Gln Pro Gly Leu Arg Ser Leu Ala Phe Arg
1               5                   10                  15

Lys Glu Leu Gln Asp Gly Gly Leu Arg Ser Ser Gly Phe Phe Ser Ser
            20                  25                  30

Phe Glu Glu Ser Asp Ile Glu Asn His Leu Ile Ser Gly His Asn Ile
        35                  40                  45

Val Gln Pro Thr Asp Ile Glu Glu Asn Arg Thr Met Leu Phe Thr Ile
    50                  55                  60

Gly Gln Ser Glu Val Tyr Leu Ile Ser Pro Asp Thr Lys Lys Ile Ala
65                  70                  75                  80

Leu Glu Lys Asn Phe Lys Glu Ile Ser Phe Cys Ser Gln Gly Ile Arg
                85                  90                  95

His Val Asp His Phe Gly Phe Ile Cys Arg Glu Ser Ser Gly Gly Gly
            100                 105                 110

Gly Phe His Phe Val Cys Tyr Val Phe Gln Cys Thr Asn Glu Ala Leu
        115                 120                 125
```

-continued

```
Val Asp Glu Ile Met Met Thr Leu Lys Gln Ala Phe Thr Val Ala Ala
    130                 135                 140

Val Gln Gln Thr Ala Lys Ala Pro Ala Gln Leu Cys Glu Gly Cys Pro
145                 150                 155                 160

Leu Gln Ser Leu His Lys Leu Cys Glu Arg Ile Glu Gly Met Asn Ser
                165                 170                 175

Ser Lys Thr Lys Leu Glu Leu Gln Lys His Leu Thr Thr Leu Thr Asn
            180                 185                 190

Gln Glu Gln Ala Thr Ile Phe Glu Val Gln Lys Leu Arg Pro Arg
        195                 200                 205

Asn Glu Gln Arg Glu Asn Glu Leu Ile Ile Ser Phe Leu Arg Cys Leu
    210                 215                 220

Tyr Glu Glu Lys Gln Lys Glu His Ile His Ile Gly Glu Met Lys Gln
225                 230                 235                 240

Thr Ser Gln Met Ala Ala Glu Asn Ile Gly Ser Glu Leu Pro Pro Ser
                245                 250                 255

Ala Thr Arg Phe Arg Leu Asp Met Leu Lys Asn Lys Ala Lys Arg Ser
            260                 265                 270

Leu Thr Glu Ser Leu Glu Ser Ile Leu Ser Arg Gly Asn Lys Ala Arg
        275                 280                 285

Gly Leu Gln Glu His Ser Ile Ser Val Asp Leu Asp Ser Ser Leu Ser
    290                 295                 300

Ser Thr Leu Ser Asn Thr Ser Lys Glu Pro Ser Val Cys Glu Lys Glu
305                 310                 315                 320

Ala Leu Pro Ile Ser Glu Ser Ser Phe Lys Leu Leu Gly Ser Ser Glu
                325                 330                 335

Asp Leu Ser Ser Asp Ser Glu Ser His Leu Pro Glu Glu Pro Ala Pro
            340                 345                 350

Leu Ser Pro Gln Gln Ala Phe Arg Arg Ala Asn Thr Leu Ser His
        355                 360                 365

Phe Pro Ile Glu Cys Gln Glu Pro Gln Pro Ala Arg Gly Ser Pro
    370                 375                 380

Gly Val Ser Gln Arg Lys Leu Met Arg Tyr His Ser Val Ser Thr Glu
385                 390                 395                 400

Thr Pro His Glu Arg Lys Asp Phe Glu Ser Lys Ala Asn His Leu Gly
                405                 410                 415

Asp Ser Gly Gly Thr Pro Val Lys Thr Arg Arg His Ser Trp Arg Gln
            420                 425                 430

Gln Ile Phe Leu Arg Val Ala Thr Pro Gln Lys Ala Cys Asp Ser Ser
        435                 440                 445

Ser Arg Tyr Glu Asp Tyr Ser Glu Leu Gly Glu Leu Pro Pro Arg Ser
    450                 455                 460

Pro Leu Glu Pro Val Cys Glu Asp Gly Pro Phe Gly Pro Pro Glu
465                 470                 475                 480

Glu Lys Lys Arg Thr Ser Arg Glu Leu Arg Glu Leu Trp Gln Lys Ala
                485                 490                 495

Ile Leu Gln Gln Ile Leu Leu Arg Met Glu Lys Glu Asn Gln Lys
            500                 505                 510

Leu Gln Ala Ser Glu Asn Asp Leu Leu Asn Lys Arg Leu Lys Leu Asp
        515                 520                 525

Tyr Glu Glu Ile Thr Pro Cys Leu Lys Glu Val Thr Thr Val Trp Glu
    530                 535                 540
```

-continued

```
Lys Met Leu Ser Thr Pro Gly Arg Ser Lys Ile Lys Phe Asp Met Glu
545                 550                 555                 560

Lys Met His Ser Ala Val Gly Gln Gly Val Pro Arg His His Arg Gly
                565                 570                 575

Glu Ile Trp Lys Phe Leu Ala Glu Gln Phe His Leu Lys His Gln Phe
            580                 585                 590

Pro Ser Lys Gln Gln Pro Lys Asp Val Pro Tyr Lys Glu Leu Leu Lys
        595                 600                 605

Gln Leu Thr Ser Gln Gln His Ala Ile Leu Ile Asp Leu Gly Arg Thr
    610                 615                 620

Phe Pro Thr His Pro Tyr Phe Ser Ala Gln Leu Gly Ala Gly Gln Leu
625                 630                 635                 640

Ser Leu Tyr Asn Ile Leu Lys Ala Tyr Ser Leu Leu Asp Gln Glu Val
                645                 650                 655

Gly Tyr Cys Gln Gly Leu Ser Phe Val Ala Gly Ile Leu Leu Leu His
            660                 665                 670

Met Ser Glu Glu Glu Ala Phe Lys Met Leu Lys Phe Leu Met Phe Asp
        675                 680                 685

Met Gly Leu Arg Lys Gln Tyr Arg Pro Asp Met Ile Ile Leu Gln Ile
    690                 695                 700

Gln Met Tyr Gln Leu Ser Arg Leu Leu His Asp Tyr His Arg Asp Leu
705                 710                 715                 720

Tyr Asn His Leu Glu Glu His Glu Ile Gly Pro Ser Leu Tyr Ala Ala
                725                 730                 735

Pro Trp Phe Leu Thr Met Phe Ala Ser Gln Phe Pro Leu Gly Phe Val
            740                 745                 750

Ala Arg Val Phe Asp Met Ile Phe Leu Gln Gly Thr Glu Val Ile Phe
        755                 760                 765

Lys Val Ala Leu Ser Leu Leu Gly Ser His Lys Pro Leu Ile Leu Gln
    770                 775                 780

His Glu Asn Leu Glu Thr Ile Val Asp Phe Ile Lys Ser Thr Leu Pro
785                 790                 795                 800

Asn Leu Gly Leu Val Gln Met Glu Lys Thr Ile Asn Gln Val Phe Glu
                805                 810                 815

Met Asp Ile Ala Lys Gln Leu Gln Ala Tyr Glu Val Glu Tyr His Val
            820                 825                 830

Leu Gln Glu Glu Leu Ile Asp Ser Ser Pro Leu Ser Asp Asn Gln Arg
        835                 840                 845

Met Asp Lys Leu Glu Lys Thr Asn Ser Ser Leu Arg Lys Gln Asn Leu
    850                 855                 860

Asp Leu Leu Glu Gln Leu Gln Val Ala Asn Gly Arg Ile Gln Ser Leu
865                 870                 875                 880

Glu Ala Thr Ile Glu Lys Leu Leu Ser Glu Ser Lys Leu Lys Gln
                885                 890                 895

Ala Met Leu Thr Leu Glu Leu Glu Arg Ser Ala Leu Leu Gln Thr Val
            900                 905                 910

Glu Glu Leu Arg Arg Arg Ser Ala Glu Pro Ser Asp Arg Glu Pro Glu
        915                 920                 925

Cys Thr Gln Pro Glu Pro Thr Gly Asp
    930                 935
```

<210> SEQ ID NO 63
<211> LENGTH: 618
<212> TYPE: PRT

<213> ORGANISM: homo sapiens

<400> SEQUENCE: 63

```
Met His Lys Thr Ala Ser Gln Arg Leu Phe Pro Gly Pro Ser Tyr Gln
1               5                   10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Arg Thr Asn Pro
            165                 170                 175

Tyr Ser Tyr Ala Met Ser Thr Glu Glu Ala Arg Phe Leu Thr Tyr His
        180                 185                 190

Met Trp Pro Leu Thr Phe Leu Ser Pro Ser Glu Leu Ala Arg Ala Gly
    195                 200                 205

Phe Tyr Tyr Ile Gly Pro Gly Asp Arg Val Ala Cys Phe Ala Cys Gly
210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
    290                 295                 300

Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
            340                 345                 350

Pro His Leu Leu Glu Gln Leu Leu Ser Thr Ser Asp Thr Thr Gly Glu
        355                 360                 365

Glu Asn Ala Asp Pro Pro Ile Ile His Phe Gly Pro Gly Glu Ser Ser
    370                 375                 380

Ser Glu Asp Ala Val Met Met Asn Thr Pro Val Val Lys Ser Ala Leu
385                 390                 395                 400
```

-continued

```
Glu Met Gly Phe Asn Arg Asp Leu Val Lys Gln Thr Val Gln Ser Lys
                405                 410                 415
Ile Leu Thr Thr Gly Glu Asn Tyr Lys Thr Val Asn Asp Ile Val Ser
            420                 425                 430
Ala Leu Leu Asn Ala Glu Asp Glu Lys Arg Glu Glu Lys Glu Lys
        435                 440                 445
Gln Ala Glu Glu Met Ala Ser Asp Asp Leu Ser Leu Ile Arg Lys Asn
    450                 455                 460
Arg Met Ala Leu Phe Gln Gln Leu Thr Cys Val Leu Pro Ile Leu Asp
465                 470                 475                 480
Asn Leu Leu Lys Ala Asn Val Ile Asn Lys Gln Glu His Asp Ile Ile
                485                 490                 495
Lys Gln Lys Thr Gln Ile Pro Leu Gln Ala Arg Glu Leu Ile Asp Thr
            500                 505                 510
Ile Leu Val Lys Gly Asn Ala Ala Asn Ile Phe Lys Asn Cys Leu
        515                 520                 525
Lys Glu Ile Asp Ser Thr Leu Tyr Lys Asn Leu Phe Val Asp Lys Asn
    530                 535                 540
Met Lys Tyr Ile Pro Thr Glu Asp Val Ser Gly Leu Ser Leu Glu Glu
545                 550                 555                 560
Gln Leu Arg Arg Leu Gln Glu Glu Arg Thr Cys Lys Val Cys Met Asp
                565                 570                 575
Lys Glu Val Ser Val Val Phe Ile Pro Cys Gly His Leu Val Val Cys
            580                 585                 590
Gln Glu Cys Ala Pro Ser Leu Arg Lys Cys Pro Ile Cys Arg Gly Ile
        595                 600                 605
Ile Lys Gly Thr Val Arg Thr Phe Leu Ser
    610                 615

<210> SEQ ID NO 64
<211> LENGTH: 539
<212> TYPE: PRT
<213> ORGANISM: homo sapiens

<400> SEQUENCE: 64

Met Thr Ser Leu Trp Gly Lys Gly Thr Gly Cys Lys Leu Phe Lys Phe
1               5                   10                  15
Arg Val Ala Ala Ala Pro Ala Ser Gly Ala Leu Arg Arg Leu Thr Pro
            20                  25                  30
Ser Ala Ser Leu Pro Pro Ala Gln Leu Leu Arg Ala Val Arg Arg
        35                  40                  45
Arg Ser His Pro Val Arg Asp Tyr Ala Ala Gln Thr Ser Pro Ser Pro
    50                  55                  60
Lys Ala Gly Ala Ala Thr Gly Arg Ile Val Ala Val Ile Gly Ala Val
65                  70                  75                  80
Val Asp Val Gln Phe Asp Glu Gly Leu Pro Pro Ile Leu Asn Ala Leu
                85                  90                  95
Glu Val Gln Gly Arg Glu Thr Arg Leu Val Leu Glu Val Ala Gln His
            100                 105                 110
Leu Gly Glu Ser Thr Val Arg Thr Ile Ala Met Asp Gly Thr Glu Gly
        115                 120                 125
Leu Val Arg Gly Gln Lys Val Leu Asp Ser Gly Ala Pro Ile Lys Ile
    130                 135                 140
Pro Val Gly Pro Glu Thr Leu Gly Arg Ile Met Asn Val Ile Gly Glu
145                 150                 155                 160
```

```
Pro Ile Asp Glu Arg Gly Pro Ile Lys Thr Lys Gln Phe Ala Pro Ile
            165                 170                 175

His Ala Glu Ala Pro Glu Phe Met Glu Met Ser Val Glu Gln Glu Ile
            180                 185                 190

Leu Val Thr Gly Ile Lys Val Val Asp Leu Leu Ala Pro Tyr Ala Lys
            195                 200                 205

Gly Gly Lys Ile Gly Leu Phe Gly Gly Ala Gly Val Gly Lys Thr Val
            210                 215                 220

Leu Ile Met Glu Leu Ile Asn Asn Val Ala Lys Ala His Gly Gly Tyr
225                 230                 235                 240

Ser Val Phe Ala Gly Val Gly Glu Arg Thr Arg Glu Gly Asn Asp Leu
            245                 250                 255

Tyr His Glu Met Ile Glu Ser Gly Val Ile Asn Leu Lys Asp Ala Thr
            260                 265                 270

Ser Lys Val Ala Leu Val Tyr Gly Gln Met Asn Gln Pro Pro Gly Ala
            275                 280                 285

Arg Ala Arg Val Ala Leu Thr Gly Leu Thr Val Ala Glu Tyr Phe Arg
            290                 295                 300

Asp Gln Glu Gly Gln Asp Val Leu Leu Phe Ile Asp Asn Ile Phe Arg
305                 310                 315                 320

Phe Thr Gln Ala Gly Ser Glu Val Ser Ala Leu Leu Gly Arg Ile Pro
            325                 330                 335

Ser Ala Val Gly Tyr Gln Pro Thr Leu Ala Thr Asp Met Gly Thr Met
            340                 345                 350

Gln Glu Arg Ile Thr Thr Thr Lys Lys Gly Ser Ile Thr Ser Val Gln
            355                 360                 365

Ala Ile Tyr Val Pro Ala Asp Asp Leu Thr Asp Pro Ala Pro Ala Thr
            370                 375                 380

Thr Phe Ala His Leu Asp Ala Thr Thr Val Leu Ser Arg Ala Ile Ala
385                 390                 395                 400

Glu Leu Gly Ile Tyr Pro Ala Val Asp Pro Leu Asp Ser Thr Ser Arg
            405                 410                 415

Ile Met Asp Pro Asn Ile Val Gly Ser Glu His Tyr Asp Val Ala Arg
            420                 425                 430

Gly Val Gln Lys Ile Leu Gln Asp Tyr Lys Ser Leu Gln Asp Ile Ile
            435                 440                 445

Ala Ile Leu Gly Met Asp Glu Leu Ser Glu Glu Asp Lys Leu Thr Val
450                 455                 460

Ser Arg Ala Arg Lys Ile Gln Arg Phe Leu Ser Gln Pro Phe Gln Val
465                 470                 475                 480

Ala Glu Val Phe Thr Gly His Met Gly Lys Leu Val Pro Leu Lys Glu
            485                 490                 495

Thr Ile Lys Gly Phe Gln Gln Ile Leu Ala Gly Glu Tyr Asp His Leu
            500                 505                 510

Pro Glu Gln Ala Phe Tyr Met Val Gly Pro Ile Glu Glu Ala Val Ala
            515                 520                 525

Lys Ala Asp Lys Leu Ala Glu Glu His Ser Ser
530                 535

<210> SEQ ID NO 65
<211> LENGTH: 772
<212> TYPE: PRT
<213> ORGANISM: homo sapiens
```

```
<400> SEQUENCE: 65

Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
            20                  25                  30

Leu Ser Thr Leu Pro Ile Thr Val Asp Ile Leu Ala Glu Thr Gly Val
        35                  40                  45

Gly Lys Thr Val Asn Ser Leu Arg Lys His Glu His Val Gly Ser Phe
    50                  55                  60

Ala Arg Asp Leu Val Ala Gln Trp Lys Lys Leu Val Pro Val Glu Arg
65                  70                  75                  80

Asn Ala Glu Pro Asp Glu Gln Asp Phe Glu Lys Ser Asn Ser Arg Lys
                85                  90                  95

Arg Pro Arg Asp Ala Leu Gln Lys Glu Glu Met Glu Gly Asp Tyr
            100                 105                 110

Gln Glu Thr Trp Lys Ala Thr Gly Ser Arg Ser Tyr Ser Pro Asp His
        115                 120                 125

Arg Gln Lys Lys His Arg Lys Leu Ser Glu Leu Glu Arg Pro His Lys
    130                 135                 140

Val Ser His Gly His Glu Arg Arg Asp Glu Arg Lys Arg Cys His Arg
145                 150                 155                 160

Met Ser Pro Thr Tyr Ser Ser Asp Pro Glu Ser Ser Asp Tyr Gly His
                165                 170                 175

Val Gln Ser Pro Pro Ser Cys Thr Ser Pro His Gln Met Tyr Val Asp
            180                 185                 190

His Tyr Arg Ser Leu Glu Glu Asp Gln Glu Pro Ile Val Ser His Gln
        195                 200                 205

Lys Pro Gly Lys Gly His Ser Asn Ala Phe Gln Asp Arg Leu Gly Ala
    210                 215                 220

Ser Gln Glu Arg His Leu Gly Glu Pro His Gly Lys Gly Val Val Ser
225                 230                 235                 240

Gln Asn Lys Glu His Lys Ser Ser His Lys Asp Lys Arg Pro Val Asp
                245                 250                 255

Ala Lys Ser Asp Glu Lys Ala Ser Val Val Ser Arg Glu Lys Ser His
            260                 265                 270

Lys Ala Leu Ser Lys Glu Glu Asn Arg Arg Pro Pro Ser Gly Asp Asn
        275                 280                 285

Ala Arg Glu Lys Pro Pro Ser Ser Gly Val Lys Lys Gly Lys Asp Arg
    290                 295                 300

Glu Gly Ser Ser Leu Lys Lys Lys Cys Leu Pro Pro Ser Glu Ala Ala
305                 310                 315                 320

Ser Asp Asn His Leu Lys Lys Pro Lys His Arg Asp Pro Glu Lys Ala
                325                 330                 335

Lys Leu Asp Lys Ser Lys Gln Gly Leu Asp Ser Phe Asp Thr Gly Lys
            340                 345                 350

Gly Ala Gly Asp Leu Leu Pro Lys Val Lys Lys Gly Ser Asn Asn
        355                 360                 365

Leu Lys Thr Pro Glu Gly Lys Val Lys Thr Asn Leu Asp Arg Lys Ser
    370                 375                 380

Leu Gly Ser Leu Pro Lys Val Glu Glu Thr Asp Met Glu Asp Glu Phe
385                 390                 395                 400

Glu Gln Pro Thr Met Ser Phe Glu Ser Tyr Leu Ser Tyr Asp Gln Pro
                405                 410                 415
```

```
Arg Lys Lys Lys Lys Ile Val Lys Thr Ser Ala Thr Ala Leu Gly
            420                 425                 430

Asp Lys Gly Leu Lys Lys Asn Asp Ser Lys Ser Thr Gly Lys Asn Leu
            435                 440                 445

Asp Ser Val Gln Lys Leu Pro Lys Val Asn Lys Thr Lys Ser Glu Lys
            450                 455                 460

Pro Ala Gly Ala Asp Leu Ala Lys Leu Arg Lys Val Pro Asp Val Leu
465                 470                 475                 480

Pro Val Leu Pro Asp Leu Pro Leu Pro Ala Ile Gln Ala Asn Tyr Arg
                485                 490                 495

Pro Leu Pro Ser Leu Glu Leu Ile Ser Ser Phe Gln Pro Lys Arg Lys
            500                 505                 510

Ala Phe Ser Ser Pro Gln Glu Glu Glu Ala Gly Phe Thr Gly Arg
            515                 520                 525

Arg Met Asn Ser Lys Met Gln Val Tyr Ser Gly Ser Lys Cys Ala Tyr
            530                 535                 540

Leu Pro Lys Met Met Thr Leu His Gln Gln Cys Ile Arg Val Leu Lys
545                 550                 555                 560

Asn Asn Ile Asp Ser Ile Phe Glu Val Gly Val Pro Tyr Ser Val
                565                 570                 575

Leu Glu Pro Val Leu Glu Arg Cys Thr Pro Asp Gln Leu Tyr Arg Ile
            580                 585                 590

Glu Glu Tyr Asn His Val Leu Ile Glu Glu Thr Asp Gln Leu Trp Lys
            595                 600                 605

Val His Cys His Arg Asp Phe Lys Glu Glu Arg Pro Glu Glu Tyr Glu
            610                 615                 620

Ser Trp Arg Glu Met Tyr Leu Arg Leu Gln Asp Ala Arg Glu Gln Arg
625                 630                 635                 640

Leu Arg Val Leu Thr Lys Asn Ile Gln Phe Ala His Ala Asn Lys Pro
                645                 650                 655

Lys Gly Arg Gln Ala Lys Met Ala Phe Val Asn Ser Val Ala Lys Pro
            660                 665                 670

Pro Arg Asp Val Arg Arg Gln Glu Lys Phe Gly Thr Gly Gly Ala
            675                 680                 685

Ala Val Pro Glu Lys Ile Lys Ile Lys Pro Ala Pro Tyr Pro Met Gly
            690                 695                 700

Ser Ser His Ala Ser Ala Ser Ser Ile Ser Phe Asn Pro Ser Pro Glu
705                 710                 715                 720

Glu Pro Ala Tyr Asp Gly Pro Ser Thr Ser Ser Ala His Leu Ala Pro
                725                 730                 735

Val Val Ser Ser Thr Val Ser Tyr Asp Pro Arg Lys Pro Thr Val Lys
            740                 745                 750

Lys Ile Ala Pro Met Met Ala Lys Thr Ile Lys Ala Phe Lys Asn Arg
            755                 760                 765

Phe Ser Arg Arg
    770

<210> SEQ ID NO 66
<211> LENGTH: 886
<212> TYPE: PRT
<213> ORGANISM: homo sapiens

<400> SEQUENCE: 66

Met Ser Gly Phe Ser Pro Glu Leu Ile Asp Tyr Leu Glu Gly Lys Ile
```

-continued

```
1               5                   10                  15
Ser Phe Glu Glu Phe Glu Arg Arg Glu Arg Lys Thr Arg Glu
            20                  25                  30
Lys Lys Ser Leu Gln Glu Lys Gly Lys Leu Ser Ala Glu Glu Asn Pro
            35                  40                  45
Asp Asp Ser Glu Val Pro Ser Ser Gly Ile Asn Ser Thr Lys Ser
    50                  55                  60
Gln Asp Lys Asp Val Asn Gly Glu Thr Ser Asp Gly Val Arg Lys
65                  70                  75                  80
Ser Val His Lys Val Phe Ala Ser Met Leu Gly Glu Asn Glu Asp Asp
                85                  90                  95
Glu Glu Glu Glu Glu Glu Glu Glu Glu Glu Glu Glu Glu Glu Thr
                100                 105                 110
Pro Glu Gln Pro Thr Ala Gly Asp Val Phe Val Leu Glu Met Val Leu
            115                 120                 125
Asn Arg Glu Thr Lys Lys Met Met Lys Glu Lys Arg Pro Arg Ser Lys
            130                 135                 140
Leu Pro Arg Ala Leu Arg Gly Leu Met Gly Glu Ala Asn Ile Arg Phe
145                 150                 155                 160
Ala Arg Gly Glu Arg Glu Ala Ile Leu Met Cys Met Glu Ile Ile
                165                 170                 175
Arg Gln Ala Pro Leu Ala Tyr Glu Pro Phe Ser Thr Leu Ala Met Ile
            180                 185                 190
Tyr Glu Asp Gln Gly Asp Met Glu Lys Ser Leu Gln Phe Glu Leu Ile
            195                 200                 205
Ala Ala His Leu Asn Pro Ser Asp Thr Glu Glu Trp Val Arg Leu Ala
210                 215                 220
Glu Met Ser Leu Glu Gln Asp Asn Ile Lys Gln Ala Ile Phe Cys Tyr
225                 230                 235                 240
Thr Lys Ala Leu Lys Tyr Glu Pro Thr Asn Val Arg Tyr Leu Trp Glu
            245                 250                 255
Arg Ser Ser Leu Tyr Glu Gln Met Gly Asp His Lys Met Ala Met Asp
            260                 265                 270
Gly Tyr Arg Arg Ile Leu Asn Leu Leu Ser Pro Ser Asp Gly Glu Arg
            275                 280                 285
Phe Met Gln Leu Ala Arg Asp Met Ala Lys Ser Tyr Tyr Glu Ala Asn
            290                 295                 300
Asp Val Thr Ser Ala Ile Asn Ile Ile Asp Glu Ala Phe Ser Lys His
305                 310                 315                 320
Gln Gly Leu Val Ser Met Glu Asp Val Asn Ile Ala Ala Glu Leu Tyr
            325                 330                 335
Ile Ser Asn Lys Gln Tyr Asp Lys Ala Leu Glu Ile Ile Thr Asp Phe
            340                 345                 350
Ser Gly Ile Val Leu Glu Lys Lys Thr Ser Glu Glu Gly Thr Ser Glu
            355                 360                 365
Glu Asn Lys Ala Pro Glu Asn Val Thr Cys Thr Ile Pro Asp Gly Val
            370                 375                 380
Pro Ile Asp Ile Thr Val Lys Leu Met Val Cys Leu Val His Leu Asn
385                 390                 395                 400
Ile Leu Glu Pro Leu Asn Pro Leu Leu Thr Thr Leu Val Glu Gln Asn
            405                 410                 415
Pro Glu Asp Met Gly Asp Leu Tyr Leu Asp Val Ala Glu Ala Phe Leu
            420                 425                 430
```

```
Asp Val Gly Glu Tyr Asn Ser Ala Leu Pro Leu Leu Ser Ala Leu Val
            435                 440                 445

Cys Ser Glu Arg Tyr Asn Leu Ala Val Val Trp Leu Arg His Ala Glu
        450                 455                 460

Cys Leu Lys Ala Leu Gly Tyr Met Glu Arg Ala Ala Glu Ser Tyr Gly
465                 470                 475                 480

Lys Val Val Asp Leu Ala Pro Leu His Leu Asp Ala Arg Ile Ser Leu
                485                 490                 495

Ser Thr Leu Gln Gln Gln Leu Gly Gln Pro Glu Lys Ala Leu Glu Ala
            500                 505                 510

Leu Glu Pro Met Tyr Asp Pro Asp Thr Leu Ala Gln Asp Ala Asn Ala
        515                 520                 525

Ala Gln Gln Glu Leu Lys Leu Leu His Arg Ser Thr Leu Leu Phe
        530                 535                 540

Ser Gln Gly Lys Met Tyr Gly Tyr Val Asp Thr Leu Leu Thr Met Leu
545                 550                 555                 560

Ala Met Leu Leu Lys Val Ala Met Asn Arg Ala Gln Val Cys Leu Ile
                565                 570                 575

Ser Ser Ser Lys Ser Gly Glu Arg His Leu Tyr Leu Ile Lys Val Ser
            580                 585                 590

Arg Asp Lys Ile Ser Asp Ser Asn Asp Gln Glu Ser Ala Asn Cys Asp
        595                 600                 605

Ala Lys Ala Ile Phe Ala Val Leu Thr Ser Val Leu Thr Lys Asp Asp
610                 615                 620

Trp Trp Asn Leu Leu Leu Lys Ala Ile Tyr Ser Leu Cys Asp Leu Ser
625                 630                 635                 640

Arg Phe Gln Glu Ala Glu Leu Leu Val Asp Ser Ser Leu Glu Tyr Tyr
                645                 650                 655

Ser Phe Tyr Asp Asp Arg Gln Lys Arg Lys Glu Leu Glu Tyr Phe Gly
            660                 665                 670

Leu Ser Ala Ala Ile Leu Asp Lys Asn Phe Arg Lys Ala Tyr Asn Tyr
        675                 680                 685

Ile Arg Ile Met Val Met Glu Asn Val Asn Lys Pro Gln Leu Trp Asn
690                 695                 700

Ile Phe Asn Gln Val Thr Met His Ser Gln Asp Val Arg His His Arg
705                 710                 715                 720

Phe Cys Leu Arg Leu Met Leu Lys Asn Pro Glu Asn His Ala Leu Cys
                725                 730                 735

Val Leu Asn Gly His Asn Ala Phe Val Ser Gly Ser Phe Lys His Ala
            740                 745                 750

Leu Gly Gln Tyr Val Gln Ala Phe Arg Thr His Pro Asp Glu Pro Leu
        755                 760                 765

Tyr Ser Phe Cys Ile Gly Leu Thr Phe Ile His Met Ala Ser Gln Lys
770                 775                 780

Tyr Val Leu Arg Arg His Ala Leu Ile Val Gln Gly Phe Ser Phe Leu
785                 790                 795                 800

Asn Arg Tyr Leu Ser Leu Arg Gly Pro Cys Gln Glu Ser Phe Tyr Asn
                805                 810                 815

Leu Gly Arg Gly Leu His Gln Leu Gly Leu Ile His Leu Ala Ile His
            820                 825                 830

Tyr Tyr Gln Lys Ala Leu Glu Leu Pro Pro Leu Val Val Glu Gly Ile
        835                 840                 845
```

```
Glu Leu Asp Gln Leu Asp Leu Arg Arg Asp Ile Ala Tyr Asn Leu Ser
    850                 855                 860

Leu Ile Tyr Gln Ser Ser Gly Asn Thr Gly Met Ala Gln Thr Leu Leu
865                 870                 875                 880

Tyr Thr Tyr Cys Ser Ile
                885

<210> SEQ ID NO 67
<211> LENGTH: 1130
<212> TYPE: PRT
<213> ORGANISM: homo sapiens

<400> SEQUENCE: 67

Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Ser His Val Leu Gly Lys Asp Val Pro Arg Asp Gly Lys Ala Glu
        35                  40                  45

Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Ile Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Ala Glu Ile Lys Ala Gly Asn
            100                 105                 110

Gly Thr Val Asp Met Ser Val Leu Pro Asp Ala Arg Tyr Ser Ala Leu
        115                 120                 125

Leu Gln Glu Asp Phe Ala Tyr Ser Gly Phe Glu Cys Trp Val Glu Asn
    130                 135                 140

Glu Asp Gln Ile Gln Glu Pro His Ser Cys His Gly Ser Glu Gly Pro
145                 150                 155                 160

Gly Asn Arg Pro Arg Arg Cys Arg Gly Cys Ala Ala Leu Arg Val Ala
                165                 170                 175

Asp Ser Asp Tyr Glu Ala Ile Cys Lys Val Pro Arg Lys Val Ala Arg
            180                 185                 190

Ser Ile Ser Cys Gly Pro Ser Ser Arg Trp Ser Thr Ser Ile Cys Thr
        195                 200                 205

Glu Glu Pro Ala Leu Ser Glu Val Gly Pro Pro Asp Leu Ala Ser Thr
    210                 215                 220

Lys Val Pro Pro Asp Gly Glu Ser Met Glu Glu Thr Pro Gly Ser
225                 230                 235                 240

Ser Val Glu Ser Leu Asp Ala Ser Val Gln Ala Ser Pro Pro Gln Gln
                245                 250                 255

Lys Asp Glu Glu Thr Glu Arg Ser Ala Lys Glu Leu Gly Lys Cys Asp
            260                 265                 270

Cys Cys Ser Asp Asp Gln Ala Pro Gln His Gly Cys Asn His Lys Leu
        275                 280                 285

Glu Leu Ala Leu Ser Met Ile Lys Gly Leu Asp Tyr Lys Pro Ile Gln
    290                 295                 300

Ser Pro Arg Gly Ser Arg Leu Pro Ile Pro Val Lys Ser Ser Leu Pro
305                 310                 315                 320

Gly Ala Lys Pro Gly Pro Ser Met Thr Asp Gly Val Ser Ser Gly Phe
                325                 330                 335
```

-continued

```
Leu Asn Arg Ser Leu Lys Pro Leu Tyr Lys Thr Pro Val Ser Tyr Pro
            340                 345                 350

Leu Glu Leu Ser Asp Leu Gln Glu Leu Trp Asp Asp Leu Cys Glu Asp
            355                 360                 365

Tyr Leu Pro Leu Arg Val Gln Pro Met Thr Glu Glu Leu Leu Lys Gln
            370                 375                 380

Gln Lys Leu Asn Ser His Glu Thr Thr Ile Thr Gln Gln Ser Val Ser
385                 390                 395                 400

Asp Ser His Leu Ala Glu Leu Gln Glu Lys Ile Gln Gln Thr Glu Ala
                405                 410                 415

Thr Asn Lys Ile Leu Gln Glu Lys Leu Asn Glu Met Ser Tyr Glu Leu
            420                 425                 430

Lys Cys Ala Gln Glu Ser Ser Gln Lys Gln Asp Gly Thr Ile Gln Asn
                435                 440                 445

Leu Lys Glu Thr Leu Lys Ser Arg Glu Arg Glu Thr Glu Glu Leu Tyr
            450                 455                 460

Gln Val Ile Glu Gly Gln Asn Asp Thr Met Ala Lys Leu Arg Glu Met
465                 470                 475                 480

Leu His Gln Ser Gln Leu Gly Gln Leu His Ser Ser Glu Gly Thr Ser
                485                 490                 495

Pro Ala Gln Gln Gln Val Ala Leu Leu Asp Leu Gln Ser Ala Leu Phe
            500                 505                 510

Cys Ser Gln Leu Glu Ile Gln Lys Leu Gln Arg Val Val Arg Gln Lys
                515                 520                 525

Glu Arg Gln Leu Ala Asp Ala Lys Gln Cys Val Gln Phe Val Glu Ala
            530                 535                 540

Ala Ala His Glu Ser Glu Gln Lys Glu Ala Ser Trp Lys His Asn
545                 550                 555                 560

Gln Glu Leu Arg Lys Ala Leu Gln Gln Leu Gln Glu Glu Leu Gln Asn
            565                 570                 575

Lys Ser Gln Gln Leu Arg Ala Trp Glu Ala Glu Lys Tyr Asn Glu Ile
                580                 585                 590

Arg Thr Gln Glu Gln Asn Ile Gln His Leu Asn His Ser Leu Ser His
            595                 600                 605

Lys Glu Gln Leu Leu Gln Glu Phe Arg Glu Leu Leu Gln Tyr Arg Asp
            610                 615                 620

Asn Ser Asp Lys Thr Leu Glu Ala Asn Glu Met Leu Leu Glu Lys Leu
625                 630                 635                 640

Arg Gln Arg Ile His Asp Lys Ala Val Ala Leu Glu Arg Ala Ile Asp
                645                 650                 655

Glu Lys Phe Ser Ala Leu Glu Glu Lys Glu Lys Glu Leu Arg Gln Leu
            660                 665                 670

Arg Leu Ala Val Arg Glu Arg Asp His Asp Leu Glu Arg Leu Arg Asp
                675                 680                 685

Val Leu Ser Ser Asn Glu Ala Thr Met Gln Ser Met Glu Ser Leu Leu
            690                 695                 700

Arg Ala Lys Gly Leu Glu Val Glu Gln Leu Ser Thr Thr Cys Gln Asn
705                 710                 715                 720

Leu Gln Trp Leu Lys Glu Met Lys Phe Ser Arg Trp Gln Lys Glu
            725                 730                 735

Gln Glu Ser Ile Ile Gln Gln Leu Gln Thr Ser Leu His Asp Arg Asn
            740                 745                 750
```

-continued

```
Lys Glu Val Glu Asp Leu Ser Ala Thr Leu Leu Cys Lys Leu Gly Pro
            755                 760                 765

Gly Gln Ser Glu Ile Ala Glu Leu Cys Gln Arg Leu Gln Arg Lys
        770                 775                 780

Glu Arg Met Leu Gln Asp Leu Ser Asp Arg Asn Lys Gln Val Leu
785                 790                 795                 800

Glu His Glu Met Glu Ile Gln Gly Leu Leu Gln Ser Val Ser Thr Arg
            805                 810                 815

Glu Gln Glu Ser Gln Ala Ala Glu Lys Leu Val Gln Ala Leu Met
        820                 825                 830

Glu Arg Asn Ser Glu Leu Gln Ala Leu Arg Gln Tyr Leu Gly Gly Arg
        835                 840                 845

Asp Ser Leu Met Ser Gln Ala Pro Ile Ser Asn Gln Gln Ala Glu Val
    850                 855                 860

Thr Pro Thr Gly Arg Leu Gly Lys Gln Thr Asp Gln Gly Ser Met Gln
865                 870                 875                 880

Ile Pro Ser Arg Asp Asp Ser Thr Ser Leu Thr Ala Lys Glu Asp Val
                885                 890                 895

Ser Ile Pro Arg Ser Thr Leu Gly Asp Leu Asp Thr Val Ala Gly Leu
            900                 905                 910

Glu Lys Glu Leu Ser Asn Ala Lys Glu Glu Leu Glu Leu Met Ala Lys
        915                 920                 925

Lys Glu Arg Glu Ser Gln Met Glu Leu Ser Ala Leu Gln Ser Met Met
    930                 935                 940

Ala Val Gln Glu Glu Glu Leu Gln Val Gln Ala Ala Asp Met Glu Ser
945                 950                 955                 960

Leu Thr Arg Asn Ile Gln Ile Lys Glu Asp Leu Ile Lys Asp Leu Gln
                965                 970                 975

Met Gln Leu Val Asp Pro Glu Asp Ile Pro Ala Met Glu Arg Leu Thr
            980                 985                 990

Gln Glu Val Leu Leu Leu Arg Glu Lys Val Ala Ser Val Glu Ser Gln
        995                 1000                1005

Gly Gln Glu Ile Ser Gly Asn Arg Arg Gln Gln Leu Leu Leu Met
    1010                1015                1020

Leu Glu Gly Leu Val Asp Glu Arg Ser Arg Leu Asn Glu Ala Leu
    1025                1030                1035

Gln Ala Glu Arg Gln Leu Tyr Ser Ser Leu Val Lys Phe His Ala
    1040                1045                1050

His Pro Glu Ser Ser Glu Arg Asp Arg Thr Leu Gln Val Glu Leu
    1055                1060                1065

Glu Gly Ala Gln Val Leu Arg Ser Arg Leu Glu Glu Val Leu Gly
    1070                1075                1080

Arg Ser Leu Glu Arg Leu Asn Arg Leu Glu Thr Leu Ala Ala Ile
    1085                1090                1095

Gly Gly Ala Ala Ala Gly Asp Asp Thr Glu Asp Thr Ser Thr Glu
    1100                1105                1110

Phe Thr Asp Ser Ile Glu Glu Glu Ala Ala His His Ser His Gln
    1115                1120                1125

Gln Leu
    1130

<210> SEQ ID NO 68
<211> LENGTH: 621
<212> TYPE: PRT
```

<213> ORGANISM: homo sapiens

<400> SEQUENCE: 68

```
Met Ala Asp Phe Glu Glu Leu Arg Asn Met Val Ser Ser Phe Arg Val
1               5                   10                  15

Ser Glu Leu Gln Val Leu Leu Gly Phe Ala Gly Arg Asn Lys Ser Gly
            20                  25                  30

Arg Lys His Asp Leu Leu Met Arg Ala Leu His Leu Leu Lys Ser Gly
        35                  40                  45

Cys Ser Pro Ala Val Gln Ile Lys Ile Arg Glu Leu Tyr Arg Arg Arg
50                  55                  60

Tyr Pro Arg Thr Leu Glu Gly Leu Ser Asp Leu Ser Thr Ile Lys Ser
65                  70                  75                  80

Ser Val Phe Ser Leu Asp Gly Gly Ser Ser Pro Val Glu Pro Asp Leu
                85                  90                  95

Ala Val Ala Gly Ile His Ser Leu Pro Ser Thr Ser Val Thr Pro His
            100                 105                 110

Ser Pro Ser Ser Pro Val Gly Ser Val Leu Leu Gln Asp Thr Lys Pro
        115                 120                 125

Thr Phe Glu Met Gln Gln Pro Ser Pro Ile Pro Pro Val His Pro
130                 135                 140

Asp Val Gln Leu Lys Asn Leu Pro Phe Tyr Asp Val Leu Asp Val Leu
145                 150                 155                 160

Ile Lys Pro Thr Ser Leu Val Gln Ser Ser Ile Gln Arg Phe Gln Glu
                165                 170                 175

Lys Phe Phe Ile Phe Ala Leu Thr Pro Gln Gln Val Arg Glu Ile Cys
            180                 185                 190

Ile Ser Arg Asp Phe Leu Pro Gly Gly Arg Arg Asp Tyr Thr Val Gln
        195                 200                 205

Val Gln Leu Arg Leu Cys Leu Ala Glu Thr Ser Cys Pro Gln Glu Asp
210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Lys Asn Gly Ile Glu Gln Lys Arg
                245                 250                 255

Pro Gly Arg Pro Leu Asn Ile Thr Ser Leu Val Arg Leu Ser Ser Ala
            260                 265                 270

Val Pro Asn Gln Ile Ser Ile Ser Trp Ala Ser Glu Ile Gly Lys Asn
        275                 280                 285

Tyr Ser Met Ser Val Tyr Leu Val Arg Gln Leu Thr Ser Ala Met Leu
290                 295                 300

Leu Gln Arg Leu Lys Met Lys Gly Ile Arg Asn Pro Asp His Ser Arg
305                 310                 315                 320

Ala Leu Ile Lys Glu Lys Leu Thr Ala Asp Pro Asp Ser Glu Ile Ala
                325                 330                 335

Thr Thr Ser Leu Arg Val Ser Leu Met Cys Pro Leu Gly Lys Met Arg
            340                 345                 350

Leu Thr Ile Pro Cys Arg Ala Val Thr Cys Thr His Leu Gln Cys Phe
        355                 360                 365

Asp Ala Ala Leu Tyr Leu Gln Met Asn Glu Lys Lys Pro Thr Trp Ile
370                 375                 380

Cys Pro Val Cys Asp Lys Lys Ala Ala Tyr Glu Ser Leu Ile Leu Asp
385                 390                 395                 400
```

```
Gly Leu Phe Met Glu Ile Leu Asn Asp Cys Ser Asp Val Asp Glu Ile
                405                 410                 415
Lys Phe Gln Glu Asp Gly Ser Trp Cys Pro Met Arg Pro Lys Lys Glu
            420                 425                 430
Ala Met Lys Val Ser Ser Gln Pro Cys Thr Lys Ile Glu Ser Ser Ser
        435                 440                 445
Val Leu Ser Lys Pro Cys Ser Val Thr Val Ala Ser Glu Ala Ser Lys
    450                 455                 460
Lys Lys Val Asp Val Ile Asp Leu Thr Ile Glu Ser Ser Asp Glu
465                 470                 475                 480
Glu Glu Asp Pro Pro Ala Lys Arg Lys Cys Ile Phe Met Ser Glu Thr
                485                 490                 495
Gln Ser Ser Pro Thr Lys Gly Val Leu Met Tyr Gln Pro Ser Ser Val
            500                 505                 510
Arg Val Pro Ser Val Thr Ser Val Asp Pro Ala Ala Ile Pro Pro Ser
        515                 520                 525
Leu Thr Asp Tyr Ser Val Pro Phe His His Thr Pro Ile Ser Ser Met
    530                 535                 540
Ser Ser Asp Leu Pro Gly Leu Asp Phe Leu Ser Leu Ile Pro Val Asp
545                 550                 555                 560
Pro Gln Tyr Cys Pro Pro Met Phe Leu Asp Ser Leu Thr Ser Pro Leu
                565                 570                 575
Thr Ala Ser Ser Thr Ser Val Thr Thr Thr Ser Ser His Glu Ser Ser
            580                 585                 590
Thr His Val Ser Ser Ser Ser Arg Ser Glu Thr Gly Val Ile Thr
        595                 600                 605
Ser Ser Gly Ser Asn Ile Pro Glu Ile Ile Ser Leu Asp
    610                 615                 620

<210> SEQ ID NO 69
<211> LENGTH: 685
<212> TYPE: PRT
<213> ORGANISM: homo sapiens

<400> SEQUENCE: 69

Met Glu Leu Leu Arg Thr Ile Thr Tyr Gln Pro Ala Ala Ser Thr Lys
1               5                   10                  15
Met Cys Glu Gln Ala Leu Gly Lys Gly Cys Gly Gly Asp Ser Lys Lys
            20                  25                  30
Lys Arg Pro Pro Gln Pro Glu Glu Ser Gln Pro Gln Ser Gln
        35                  40                  45
Ala Gln Val Pro Pro Ala Ala Pro His His His His His Ser His
    50                  55                  60
Ser Gly Pro Glu Ile Ser Arg Ile Ile Val Asp Pro Thr Thr Gly Lys
65                  70                  75                  80
Arg Tyr Cys Arg Gly Lys Val Leu Gly Lys Gly Phe Ala Lys Cys
                85                  90                  95
Tyr Glu Met Thr Asp Leu Thr Asn Asn Lys Val Tyr Ala Ala Lys Ile
            100                 105                 110
Ile Pro His Ser Arg Val Ala Lys Pro His Gln Arg Glu Lys Ile Asp
        115                 120                 125
Lys Glu Ile Glu Leu His Arg Ile Leu His His Lys His Val Val Gln
    130                 135                 140
Phe Tyr His Tyr Phe Glu Asp Lys Glu Asn Ile Tyr Ile Leu Leu Glu
145                 150                 155                 160
```

-continued

```
Tyr Cys Ser Arg Arg Ser Met Ala His Ile Leu Lys Ala Arg Lys Val
            165                 170                 175

Leu Thr Glu Pro Glu Val Arg Tyr Tyr Leu Arg Gln Ile Val Ser Gly
            180                 185                 190

Leu Lys Tyr Leu His Glu Gln Glu Ile Leu His Arg Asp Leu Lys Leu
            195                 200                 205

Gly Asn Phe Phe Ile Asn Glu Ala Met Glu Leu Lys Val Gly Asp Phe
            210                 215                 220

Gly Leu Ala Ala Arg Leu Glu Pro Leu Glu His Arg Arg Thr Ile
225                 230                 235                 240

Cys Gly Thr Pro Asn Tyr Leu Ser Pro Glu Val Leu Asn Lys Gln Gly
            245                 250                 255

His Gly Cys Glu Ser Asp Ile Trp Ala Leu Gly Cys Val Met Tyr Thr
            260                 265                 270

Met Leu Leu Gly Arg Pro Pro Phe Glu Thr Thr Asn Leu Lys Glu Thr
            275                 280                 285

Tyr Arg Cys Ile Arg Glu Ala Arg Tyr Thr Met Pro Ser Ser Leu Leu
            290                 295                 300

Ala Pro Ala Lys His Leu Ile Ala Ser Met Leu Ser Lys Asn Pro Glu
305                 310                 315                 320

Asp Arg Pro Ser Leu Asp Asp Ile Ile Arg His Asp Phe Phe Leu Gln
            325                 330                 335

Gly Phe Thr Pro Asp Arg Leu Ser Ser Ser Cys Cys His Thr Val Pro
            340                 345                 350

Asp Phe His Leu Ser Ser Pro Ala Lys Asn Phe Phe Lys Lys Ala Ala
            355                 360                 365

Ala Ala Leu Phe Gly Gly Lys Lys Asp Lys Ala Arg Tyr Ile Asp Thr
            370                 375                 380

His Asn Arg Val Ser Lys Glu Asp Glu Asp Ile Tyr Lys Leu Arg His
385                 390                 395                 400

Asp Leu Lys Lys Thr Ser Ile Thr Gln Gln Pro Ser Lys His Arg Thr
            405                 410                 415

Asp Glu Glu Leu Gln Pro Pro Thr Thr Val Ala Arg Ser Gly Thr
            420                 425                 430

Pro Ala Val Glu Asn Lys Gln Gln Ile Gly Asp Ala Ile Arg Met Ile
            435                 440                 445

Val Arg Gly Thr Leu Gly Ser Cys Ser Ser Ser Glu Cys Leu Glu
            450                 455                 460

Asp Ser Thr Met Gly Ser Val Ala Asp Thr Val Ala Arg Val Leu Arg
465                 470                 475                 480

Gly Cys Leu Glu Asn Met Pro Glu Ala Asp Cys Ile Pro Lys Glu Gln
            485                 490                 495

Leu Ser Thr Ser Phe Gln Trp Val Thr Lys Trp Val Asp Tyr Ser Asn
            500                 505                 510

Lys Tyr Gly Phe Gly Tyr Gln Leu Ser Asp His Thr Val Gly Val Leu
            515                 520                 525

Phe Asn Asn Gly Ala His Met Ser Leu Leu Pro Asp Lys Lys Thr Val
            530                 535                 540

His Tyr Tyr Ala Glu Leu Gly Gln Cys Ser Val Phe Pro Ala Thr Asp
545                 550                 555                 560

Ala Pro Glu Gln Phe Ile Ser Gln Val Thr Val Leu Lys Tyr Phe Ser
            565                 570                 575
```

```
His Tyr Met Glu Glu Asn Leu Met Asp Gly Gly Asp Leu Pro Ser Val
            580                 585                 590

Thr Asp Ile Arg Arg Pro Arg Leu Tyr Leu Leu Gln Trp Leu Lys Ser
        595                 600                 605

Asp Lys Ala Leu Met Met Leu Phe Asn Asp Gly Thr Phe Gln Val Asn
    610                 615                 620

Phe Tyr His Asp His Thr Lys Ile Ile Ile Cys Ser Gln Asn Glu Glu
625                 630                 635                 640

Tyr Leu Leu Thr Tyr Ile Asn Glu Asp Arg Ile Ser Thr Thr Phe Arg
            645                 650                 655

Leu Thr Thr Leu Leu Met Ser Gly Cys Ser Ser Glu Leu Lys Asn Arg
                660                 665                 670

Met Glu Tyr Ala Leu Asn Met Leu Leu Gln Arg Cys Asn
            675                 680                 685

<210> SEQ ID NO 70
<211> LENGTH: 767
<212> TYPE: PRT
<213> ORGANISM: homo sapiens

<400> SEQUENCE: 70

Met Ala Thr Tyr Leu Glu Phe Ile Gln Gln Asn Glu Glu Arg Asp Gly
1               5                   10                  15

Val Arg Phe Ser Trp Asn Val Trp Pro Ser Ser Arg Leu Glu Ala Thr
            20                  25                  30

Arg Met Val Val Pro Leu Ala Cys Leu Leu Thr Pro Leu Lys Glu Arg
        35                  40                  45

Pro Asp Leu Pro Pro Val Gln Tyr Glu Pro Val Leu Cys Ser Arg Pro
    50                  55                  60

Thr Cys Lys Ala Val Leu Asn Pro Leu Cys Gln Val Asp Tyr Arg Ala
65                  70                  75                  80

Lys Leu Trp Ala Cys Asn Phe Cys Phe Gln Arg Asn Gln Phe Pro Pro
                85                  90                  95

Ala Tyr Gly Gly Ile Ser Glu Val Asn Gln Pro Ala Glu Leu Met Pro
            100                 105                 110

Gln Phe Ser Thr Ile Glu Tyr Val Ile Gln Arg Gly Ala Gln Ser Pro
        115                 120                 125

Leu Ile Phe Leu Tyr Val Val Asp Thr Cys Leu Glu Glu Asp Asp Leu
    130                 135                 140

Gln Ala Leu Lys Glu Ser Leu Gln Met Ser Leu Ser Leu Leu Pro Pro
145                 150                 155                 160

Asp Ala Leu Val Gly Leu Ile Thr Phe Gly Arg Met Val Gln Val His
                165                 170                 175

Glu Leu Ser Cys Glu Gly Ile Ser Lys Ser Tyr Val Phe Arg Gly Thr
            180                 185                 190

Lys Asp Leu Thr Ala Lys Gln Ile Gln Asp Met Leu Gly Leu Thr Lys
        195                 200                 205

Pro Ala Met Pro Met Gln Gln Ala Arg Pro Ala Gln Pro Gln Glu His
    210                 215                 220

Pro Phe Ala Ser Ser Arg Phe Leu Gln Pro Val His Lys Ile Asp Met
225                 230                 235                 240

Asn Leu Thr Asp Leu Leu Gly Glu Leu Gln Arg Asp Pro Trp Pro Val
                245                 250                 255

Thr Gln Gly Lys Arg Pro Leu Arg Ser Thr Gly Val Ala Leu Ser Ile
            260                 265                 270
```

-continued

```
Ala Val Gly Leu Leu Glu Gly Thr Phe Pro Asn Thr Gly Ala Arg Ile
            275                 280                 285
Met Leu Phe Thr Gly Gly Pro Pro Thr Gln Gly Pro Gly Met Val Val
        290                 295                 300
Gly Asp Glu Leu Lys Ile Pro Ile Arg Ser Trp His Asp Ile Glu Lys
305                 310                 315                 320
Asp Asn Ala Arg Phe Met Lys Lys Ala Thr Lys His Tyr Glu Met Leu
                325                 330                 335
Ala Asn Arg Thr Ala Ala Asn Gly His Cys Ile Asp Ile Tyr Ala Cys
            340                 345                 350
Ala Leu Asp Gln Thr Gly Leu Leu Glu Met Lys Cys Cys Ala Asn Leu
        355                 360                 365
Thr Gly Gly Tyr Met Val Met Gly Asp Ser Phe Asn Thr Ser Leu Phe
    370                 375                 380
Lys Gln Thr Phe Gln Arg Ile Phe Thr Lys Asp Phe Asn Gly Asp Phe
385                 390                 395                 400
Arg Met Ala Phe Gly Ala Thr Leu Asp Val Lys Thr Ser Arg Glu Leu
                405                 410                 415
Lys Ile Ala Gly Ala Ile Gly Pro Cys Val Ser Leu Asn Val Lys Gly
            420                 425                 430
Pro Cys Val Ser Glu Asn Glu Leu Gly Val Gly Gly Thr Ser Gln Trp
        435                 440                 445
Lys Ile Cys Gly Leu Asp Pro Thr Ser Thr Leu Gly Ile Tyr Phe Glu
    450                 455                 460
Val Val Asn Gln His Asn Thr Pro Ile Pro Gln Gly Gly Arg Gly Ala
465                 470                 475                 480
Ile Gln Phe Val Thr His Tyr Gln His Ser Thr Gln Arg Ile
                485                 490                 495
Arg Val Thr Thr Ile Ala Arg Asn Trp Ala Asp Val Gln Ser Gln Leu
            500                 505                 510
Arg His Ile Glu Ala Ala Phe Asp Gln Glu Ala Ala Val Leu Met
        515                 520                 525
Ala Arg Leu Gly Val Phe Arg Ala Glu Ser Glu Glu Gly Pro Asp Val
    530                 535                 540
Leu Arg Trp Leu Asp Arg Gln Leu Ile Arg Leu Cys Gln Lys Phe Gly
545                 550                 555                 560
Gln Tyr Asn Lys Glu Asp Pro Thr Ser Phe Arg Leu Ser Asp Ser Phe
                565                 570                 575
Ser Leu Tyr Pro Gln Phe Met Phe His Leu Arg Arg Ser Pro Phe Leu
            580                 585                 590
Gln Val Phe Asn Asn Ser Pro Asp Glu Ser Ser Tyr Arg His His
        595                 600                 605
Phe Ala Arg Gln Asp Leu Thr Gln Ser Leu Ile Met Ile Gln Pro Ile
    610                 615                 620
Leu Tyr Ser Tyr Ser Phe His Gly Pro Pro Glu Pro Val Leu Leu Asp
625                 630                 635                 640
Ser Ser Ser Ile Leu Ala Asp Arg Ile Leu Leu Met Asp Thr Phe Phe
                645                 650                 655
Gln Ile Val Ile Tyr Leu Gly Glu Thr Ile Ala Gln Trp Arg Lys Ala
            660                 665                 670
Gly Tyr Gln Asp Met Pro Glu Tyr Glu Asn Phe Lys His Leu Leu Gln
        675                 680                 685
```

```
Ala Pro Leu Asp Asp Ala Gln Glu Ile Leu Gln Ala Arg Phe Pro Met
    690                 695                 700

Pro Arg Tyr Ile Asn Thr Glu His Gly Gly Ser Gln Ala Arg Phe Leu
705                 710                 715                 720

Leu Ser Lys Val Asn Pro Ser Gln Thr His Asn Asn Leu Tyr Ala Trp
                725                 730                 735

Gly Gln Glu Thr Gly Ala Pro Ile Leu Thr Asp Asp Val Ser Leu Gln
            740                 745                 750

Val Phe Met Asp His Leu Lys Lys Leu Ala Val Ser Ser Ala Cys
        755                 760                 765
```

<210> SEQ ID NO 71
<211> LENGTH: 188
<212> TYPE: PRT
<213> ORGANISM: homo sapiens

<400> SEQUENCE: 71

```
Met Asn Gly Asp Asp Thr Phe Ala Lys Arg Pro Arg Asp Asp Ala Lys
1               5                   10                  15

Ala Ser Glu Lys Arg Ser Lys Ala Phe Asp Asp Ile Ala Thr Tyr Phe
            20                  25                  30

Ser Lys Lys Glu Trp Lys Lys Met Lys Tyr Ser Glu Lys Ile Ser Tyr
        35                  40                  45

Val Tyr Met Lys Arg Asn Tyr Lys Ala Met Thr Lys Leu Gly Phe Lys
    50                  55                  60

Val Thr Leu Pro Pro Phe Met Cys Asn Lys Gln Ala Thr Asp Phe Gln
65                  70                  75                  80

Gly Asn Asp Phe Asp Asn Asp His Asn Arg Arg Ile Gln Val Glu His
                85                  90                  95

Pro Gln Met Thr Phe Gly Arg Leu His Arg Ile Ile Pro Lys Ile Met
            100                 105                 110

Pro Lys Lys Pro Ala Glu Asp Glu Asn Asp Ser Lys Gly Val Ser Glu
        115                 120                 125

Ala Ser Gly Pro Gln Asn Asp Gly Lys Gln Leu His Pro Pro Gly Lys
    130                 135                 140

Ala Asn Ile Ser Glu Lys Ile Asn Lys Arg Ser Gly Pro Lys Arg Gly
145                 150                 155                 160

Lys His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185
```

<210> SEQ ID NO 72
<211> LENGTH: 1038
<212> TYPE: PRT
<213> ORGANISM: homo sapiens
<220> FEATURE:
<221> NAME/KEY: MISC_FEATURE
<222> LOCATION: (910)..(910)
<223> OTHER INFORMATION: Xaa = any amino acid

<400> SEQUENCE: 72

```
Met Trp Arg Cys Gly Gly Arg Gln Gly Leu Cys Val Leu Arg Arg Leu
1               5                   10                  15

Ser Gly Gly His Ala His His Arg Ala Trp Arg Trp Asn Ser Asn Arg
            20                  25                  30

Ala Cys Glu Arg Ala Leu Gln Tyr Lys Leu Gly Asp Lys Ile His Gly
        35                  40                  45
```

```
Phe Thr Val Asn Gln Val Thr Ser Val Pro Glu Leu Phe Leu Thr Ala
    50                  55                  60
Val Lys Leu Thr His Asp Asp Thr Gly Ala Arg Tyr Leu His Leu Ala
65                  70                  75                  80
Arg Glu Asp Thr Asn Asn Leu Phe Ser Val Gln Phe Arg Thr Thr Pro
                85                  90                  95
Met Asp Ser Thr Gly Val Pro His Ile Leu Glu His Thr Val Leu Cys
            100                 105                 110
Gly Ser Gln Lys Tyr Pro Cys Arg Asn Pro Phe Phe Lys Met Leu Asn
        115                 120                 125
Arg Ser Leu Ser Thr Phe Met Asn Ala Phe Thr Ala Ser Asp Tyr Thr
    130                 135                 140
Leu Tyr Pro Phe Ser Thr Gln Asn Pro Lys Asp Phe Gln Asn Leu Leu
145                 150                 155                 160
Ser Val Tyr Leu Asp Ala Thr Phe Ser Pro Cys Leu Arg Glu Leu Asp
                165                 170                 175
Phe Trp Gln Glu Gly Trp Arg Leu Glu His Glu Asn Pro Ser Asp Pro
            180                 185                 190
Gln Thr Pro Leu Val Phe Lys Gly Val Val Phe Asn Glu Met Lys Gly
        195                 200                 205
Ala Phe Thr Asp Asn Glu Arg Ile Phe Ser Gln His Leu Gln Asn Arg
    210                 215                 220
Leu Leu Pro Asp His Thr Tyr Ser Val Val Ser Gly Gly Asp Pro Leu
225                 230                 235                 240
Cys Ile Pro Glu Leu Thr Trp Glu Gln Leu Lys Gln Phe His Ala Thr
                245                 250                 255
His Tyr His Pro Ser Asn Ala Arg Phe Phe Thr Tyr Gly Asn Phe Pro
            260                 265                 270
Leu Glu Gln His Leu Lys Gln Ile His Glu Glu Ala Leu Ser Lys Phe
        275                 280                 285
Gln Lys Ile Glu Pro Ser Thr Val Val Pro Ala Gln Thr Pro Trp Asp
    290                 295                 300
Lys Pro Arg Glu Phe Gln Ile Thr Cys Gly Pro Asp Ser Phe Ala Thr
305                 310                 315                 320
Asp Pro Ser Lys Gln Thr Thr Val Ser Val Ser Phe Leu Leu Pro Asp
                325                 330                 335
Ile Thr Asp Thr Phe Glu Ala Phe Thr Leu Ser Leu Leu Ser Ser Leu
            340                 345                 350
Leu Thr Ser Gly Pro Asn Ser Pro Phe Tyr Lys Ala Leu Ile Glu Ser
        355                 360                 365
Gly Leu Gly Thr Glu Phe Ser Pro Asp Val Gly Tyr Asn Gly Tyr Thr
    370                 375                 380
Arg Glu Ala Tyr Phe Ser Val Gly Leu Gln Gly Ile Val Glu Lys Asp
385                 390                 395                 400
Ile Glu Thr Val Arg Ser Leu Ile Asp Arg Thr Ile Asp Glu Val Val
                405                 410                 415
Glu Thr Arg Ile Glu Asp Asp Arg Ile Glu Ala Leu Leu His Lys Ile
            420                 425                 430
Glu Ile Gln Met Lys His Gln Ser Thr Ser Phe Gly Leu Met Leu Thr
        435                 440                 445
Ser Tyr Ile Ala Ser Cys Trp Asn His Asp Gly Asp Pro Val Glu Leu
    450                 455                 460
```

-continued

```
Leu Lys Leu Gly Asn Gln Leu Ala Lys Phe Arg Gln Cys Leu Gln Glu
465                 470                 475                 480

Asn Pro Lys Phe Leu Gln Glu Lys Val Lys Gln Tyr Phe Lys Asn Asn
                485                 490                 495

Gln His Lys Leu Thr Leu Ser Met Arg Pro Asp Asp Lys Tyr His Glu
            500                 505                 510

Lys Gln Ala Gln Val Glu Ala Thr Lys Leu Lys Gln Lys Val Glu Ala
        515                 520                 525

Leu Ser Pro Gly Asp Arg Gln Gln Ile Tyr Glu Lys Gly Leu Glu Leu
    530                 535                 540

Arg Ser Gln Gln Ser Lys Pro Gln Asp Ala Ser Cys Leu Pro Ala Leu
545                 550                 555                 560

Lys Val Ser Asp Ile Glu Pro Thr Ile Pro Val Thr Glu Leu Asp Val
                565                 570                 575

Val Leu Thr Ala Gly Asp Ile Pro Val Gln Tyr Cys Ala Gln Pro Thr
            580                 585                 590

Asn Gly Met Val Tyr Phe Arg Ala Phe Ser Ser Leu Asn Thr Leu Pro
        595                 600                 605

Glu Glu Leu Arg Pro Tyr Val Pro Leu Phe Cys Ser Ile Leu Thr Lys
    610                 615                 620

Leu Gly Cys Gly Leu Leu Asp Tyr Arg Glu Gln Ala Gln Gln Ile Glu
625                 630                 635                 640

Leu Lys Thr Gly Gly Met Ser Ala Ser Pro His Val Leu Pro Asp Asp
                645                 650                 655

Ser His Met Asp Thr Tyr Glu Gln Val Gly Val Leu Phe Ser Ser Leu
            660                 665                 670

Cys Leu Asp Arg Asn Leu Pro Asp Met Met Gln Leu Trp Ser Glu Ile
        675                 680                 685

Phe Asn Asn Pro Cys Phe Glu Glu Glu His Phe Lys Val Leu Val
    690                 695                 700

Lys Met Thr Ala Gln Glu Leu Ala Asn Gly Ile Pro Asp Ser Gly His
705                 710                 715                 720

Leu Tyr Ala Ser Ile Arg Ala Gly Arg Thr Leu Thr Pro Ala Gly Asp
                725                 730                 735

Leu Gln Glu Thr Phe Ser Gly Met Asp Gln Val Arg Leu Met Lys Arg
            740                 745                 750

Ile Ala Glu Met Thr Asp Ile Lys Pro Ile Leu Arg Lys Leu Pro Arg
        755                 760                 765

Ile Lys Lys His Leu Leu Asn Gly Asp Asn Met Arg Cys Ser Val Asn
    770                 775                 780

Ala Thr Pro Gln Gln Met Pro Gln Thr Glu Lys Ala Val Glu Asp Phe
785                 790                 795                 800

Leu Arg Ser Ile Gly Arg Ser Lys Lys Glu Arg Arg Pro Val Arg Pro
                805                 810                 815

His Thr Val Glu Lys Pro Val Pro Ser Ser Gly Gly Asp Ala His
            820                 825                 830

Val Pro His Gly Ser Gln Val Ile Arg Lys Leu Val Met Glu Pro Thr
        835                 840                 845

Phe Lys Pro Trp Gln Met Lys Thr His Phe Leu Met Pro Phe Pro Val
    850                 855                 860

Asn Tyr Val Gly Glu Cys Ile Arg Thr Val Pro Tyr Thr Asp Pro Asp
865                 870                 875                 880

His Ala Ser Leu Lys Ile Leu Ala Arg Leu Met Thr Ala Lys Phe Leu
```

-continued

```
                    885                 890                 895
His Thr Glu Ile Arg Glu Lys Gly Gly Ala Tyr Gly Gly Xaa Ala Lys
                900                 905                 910

Leu Ser His Asn Gly Ile Phe Thr Leu Tyr Ser Tyr Arg Asp Pro Asn
            915                 920                 925

Thr Ile Glu Thr Leu Gln Ser Phe Gly Lys Ala Val Asp Trp Ala Lys
        930                 935                 940

Ser Gly Lys Phe Thr Gln Gln Asp Ile Asp Glu Ala Lys Leu Ser Val
945                 950                 955                 960

Phe Ser Thr Val Asp Ala Pro Val Ala Pro Ser Asp Lys Gly Met Asp
                965                 970                 975

His Phe Leu Tyr Gly Leu Ser Asp Glu Met Lys Gln Ala His Arg Glu
            980                 985                 990

Gln Leu Phe Ala Val Ser His Asp Lys Leu Leu Ala Val Ser Asp Arg
        995                1000                1005

Tyr Leu Gly Thr Gly Lys Ser Thr His Gly Leu Ala Ile Leu Gly
   1010                1015                1020

Pro Glu Asn Pro Lys Ile Ala Lys Asp Pro Ser Trp Ile Ile Arg
   1025                1030                1035
```

<210> SEQ ID NO 73
<211> LENGTH: 341
<212> TYPE: PRT
<213> ORGANISM: homo sapiens

<400> SEQUENCE: 73

```
Met Leu Gly Ala Glu Trp Ser Lys Leu Gln Pro Thr Glu Lys Gln Arg
1               5                   10                  15

Tyr Leu Asp Glu Ala Glu Arg Glu Lys Gln Gln Tyr Met Lys Glu Leu
                20                  25                  30

Arg Ala Tyr Gln Gln Ser Glu Ala Tyr Lys Met Cys Thr Glu Lys Ile
            35                  40                  45

Gln Glu Lys Lys Ile Lys Lys Glu Asp Ser Ser Ser Gly Leu Met Asn
        50                  55                  60

Thr Leu Leu Asn Gly His Lys Gly Gly Asp Cys Asp Gly Phe Ser Thr
65                  70                  75                  80

Phe Asp Val Pro Ile Phe Thr Glu Glu Phe Leu Asp Gln Asn Lys Ala
                85                  90                  95

Arg Glu Ala Glu Leu Arg Arg Leu Arg Lys Met Asn Val Ala Phe Glu
                100                 105                 110

Glu Gln Asn Ala Val Leu Gln Arg Gln Asn Ala Glu His Glu Gln Arg
            115                 120                 125

Ala Arg Ala Ser Gly Ala Gly Ala Gly Ala Gly Ala Glu Asp Ala
        130                 135                 140

Gly Ala Ala Ala Ala Pro Gly Arg Ala Pro Gly Ala His Arg Gln
145                 150                 155                 160

Leu Arg Leu Thr Ala Gly Ala Gly His Gly Arg Asn Ala His Ala Gly
                165                 170                 175

His Ser Gly Leu Leu His Gly Pro Ala Ser Arg Ser His Arg Ala Arg
            180                 185                 190

Pro Arg Pro Ala Arg Glu Ala His Arg Pro His Gln Gly Asn Pro Gly
        195                 200                 205

Pro Gly Arg Gln Arg Ala Pro Val Arg Ser Gly Arg Ala His Asp Ala
    210                 215                 220
```

```
Glu Lys Leu Trp Ala Arg Pro Cys His Thr Pro Pro Arg Gly Arg
225                 230                 235                 240

Glu Ala Gly Gly Pro Pro Phe Gly Ala Trp Ser His Pro Ala Pro Leu
            245                 250                 255

Gly Ala Pro Ala Pro Leu Lys Leu Asn Phe Cys Ser Ile Pro Leu Ala
            260                 265                 270

Phe Asn Leu Pro Ser Pro Leu Asn Pro Glu Lys Ala Leu Ala Ala Arg
            275                 280                 285

Tyr Thr Gln Lys Asn Leu Thr Ala Glu Gly Ala Pro Pro Arg Arg Thr
            290                 295                 300

Ala Thr Arg Tyr Thr Gly Ser Pro Gly His Pro Gln Asp Thr Gly Gln
305                 310                 315                 320

Thr Lys Pro Thr Pro Ser Thr Arg Gln Asp Pro Pro Asn Tyr Ser Leu
                325                 330                 335

Arg Gly Ala Val Pro
            340

<210> SEQ ID NO 74
<211> LENGTH: 377
<212> TYPE: PRT
<213> ORGANISM: homo sapiens

<400> SEQUENCE: 74

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
    210                 215                 220

Glu Glu Gln Arg Gln Arg Gln Glu Glu Ala Arg Arg Ala Ala Ala
225                 230                 235                 240

Ala Ser Ala Ala Glu Ala Gly Ile Ala Thr Thr Gly Thr Glu Asp Ser
                245                 250                 255
```

```
Asp Asp Ala Leu Leu Lys Met Thr Ile Ser Gln Gln Glu Phe Gly Arg
            260                 265                 270

Thr Gly Leu Pro Asp Leu Ser Ser Met Thr Glu Glu Glu Gln Ile Ala
            275                 280                 285

Tyr Ala Met Gln Met Ser Leu Gln Gly Ala Glu Phe Gly Gln Ala Glu
            290                 295                 300

Ser Ala Asp Ile Asp Ala Ser Ser Ala Met Asp Thr Ser Glu Pro Ala
305                 310                 315                 320

Lys Glu Glu Asp Asp Tyr Asp Val Met Gln Asp Pro Glu Phe Leu Gln
                    325                 330                 335

Ser Val Leu Glu Asn Leu Pro Gly Val Asp Pro Asn Asn Glu Ala Ile
            340                 345                 350

Arg Asn Ala Met Gly Ser Leu Ala Ser Gln Ala Thr Lys Asp Gly Lys
            355                 360                 365

Lys Asp Lys Lys Glu Glu Asp Lys Lys
            370                 375
```

<210> SEQ ID NO 75
<211> LENGTH: 399
<212> TYPE: PRT
<213> ORGANISM: homo sapiens

<400> SEQUENCE: 75

```
Met Ser Asp Ile Leu Arg Glu Leu Leu Cys Val Ser Glu Lys Ala Ala
1               5                   10                  15

Asn Ile Ala Arg Ala Cys Arg Gln Gln Glu Ala Leu Phe Gln Leu Leu
            20                  25                  30

Ile Glu Glu Lys Lys Glu Gly Glu Lys Asn Lys Lys Phe Ala Val Asp
            35                  40                  45

Phe Lys Thr Leu Ala Asp Val Leu Val Gln Glu Val Ile Lys Gln Asn
    50                  55                  60

Met Glu Asn Lys Phe Pro Gly Leu Glu Lys Asn Ile Phe Gly Glu Glu
65                  70                  75                  80

Ser Asn Glu Phe Thr Asn Asp Trp Gly Glu Lys Ile Thr Leu Arg Leu
                85                  90                  95

Cys Ser Thr Glu Glu Thr Ala Glu Leu Leu Ser Lys Val Leu Asn
            100                 105                 110

Gly Asn Lys Val Ala Ser Glu Ala Leu Ala Arg Val Val His Gln Asp
            115                 120                 125

Val Ala Phe Thr Asp Pro Thr Leu Asp Ser Thr Glu Ile Asn Val Pro
    130                 135                 140

Gln Asp Ile Leu Gly Ile Trp Val Asp Pro Ile Asp Ser Thr Tyr Gln
145                 150                 155                 160

Tyr Ile Lys Gly Ser Ala Asp Ile Lys Ser Asn Gln Gly Ile Phe Pro
                165                 170                 175

Cys Gly Leu Gln Cys Val Thr Ile Leu Ile Gly Val Tyr Asp Ile Gln
            180                 185                 190

Thr Gly Val Pro Leu Met Gly Val Ile Asn Gln Pro Phe Val Ser Arg
            195                 200                 205

Asp Pro Asn Thr Leu Arg Trp Lys Gly Gln Cys Tyr Trp Gly Leu Ser
    210                 215                 220

Tyr Met Gly Thr Asn Met His Ser Leu Gln Leu Thr Ile Ser Arg Arg
225                 230                 235                 240

Asn Gly Ser Glu Thr His Thr Gly Asn Thr Gly Ser Glu Ala Ala Phe
```

```
                245                 250                 255
Ser Pro Ser Phe Ser Ala Val Ile Ser Thr Ser Glu Lys Glu Thr Ile
            260                 265                 270

Lys Ala Ala Leu Ser Arg Val Cys Gly Asp Arg Ile Phe Gly Ala Ala
        275                 280                 285

Gly Ala Gly Tyr Lys Ser Leu Cys Val Val Gln Gly Leu Val Asp Ile
    290                 295                 300

Tyr Ile Phe Ser Glu Asp Thr Thr Phe Lys Trp Asp Ser Cys Ala Ala
305                 310                 315                 320

His Ala Ile Leu Arg Ala Met Gly Gly Ile Val Asp Leu Lys Glu
            325                 330                 335

Cys Leu Glu Arg Asn Pro Glu Thr Gly Leu Asp Leu Pro Gln Leu Val
            340                 345                 350

Tyr His Val Glu Asn Glu Gly Ala Ala Gly Val Asp Arg Trp Ala Asn
            355                 360                 365

Lys Gly Gly Leu Ile Ala Tyr Arg Ser Arg Lys Arg Leu Glu Thr Phe
        370                 375                 380

Leu Ser Leu Leu Val Gln Asn Leu Ala Pro Ala Glu Thr His Thr
385                 390                 395

<210> SEQ ID NO 76
<211> LENGTH: 296
<212> TYPE: PRT
<213> ORGANISM: homo sapiens

<400> SEQUENCE: 76

Met Lys Asn Glu Ile Ala Ala Val Val Phe Phe Thr Arg Leu Val
1               5                   10                  15

Arg Lys His Asp Lys Leu Lys Lys Glu Ala Val Glu Arg Phe Ala Glu
            20                  25                  30

Lys Leu Thr Leu Ile Leu Gln Glu Lys Tyr Lys Asn His Trp Tyr Pro
        35                  40                  45

Glu Lys Pro Ser Lys Gly Gln Ala Tyr Arg Cys Ile Arg Val Asn Lys
    50                  55                  60

Phe Gln Arg Val Asp Pro Asp Val Leu Lys Ala Cys Glu Asn Ser Cys
65                  70                  75                  80

Ile Leu Tyr Ser Asp Leu Gly Leu Pro Lys Glu Leu Thr Leu Trp Val
                85                  90                  95

Asp Pro Cys Glu Val Cys Cys Arg Arg Asp Gly Val Ser Pro Cys Trp
            100                 105                 110

Pro Asp Cys Ser Gln Thr Pro Asp Leu Val Ile Arg Pro Pro Trp Pro
        115                 120                 125

Pro Lys Ala Leu Asp Tyr Arg Arg Glu Pro Leu Arg Pro Ala Ser Ser
    130                 135                 140

Phe Leu Ile Met Tyr Gly Glu Lys Asn Asn Ala Phe Ile Val Ala Ser
145                 150                 155                 160

Phe Glu Asn Lys Asp Glu Asn Lys Asp Glu Ile Ser Arg Lys Val Thr
                165                 170                 175

Arg Ala Leu Asp Lys Val Thr Ser Asp Tyr His Ser Gly Ser Ser Ser
            180                 185                 190

Ser Asp Glu Glu Thr Ser Lys Glu Met Glu Val Lys Pro Ser Ser Val
        195                 200                 205

Thr Ala Ala Ala Ser Pro Val Tyr Gln Ile Ser Glu Leu Ile Phe Pro
    210                 215                 220
```

```
Pro Leu Pro Met Trp His Pro Leu Pro Arg Lys Lys Pro Gly Met Tyr
225                 230                 235                 240

Arg Gly Asn Gly His Gln Asn His Tyr Pro Pro Val Pro Phe Gly
            245                 250                 255

Tyr Pro Asn Gln Gly Arg Lys Asn Lys Pro Tyr Arg Pro Ile Pro Val
        260                 265                 270

Thr Trp Val Pro Pro Gly Met His Cys Asp Arg Asn His Trp Ile
    275                 280                 285

Asn Pro His Met Leu Ala Pro His
    290                 295
```

<210> SEQ ID NO 77
<211> LENGTH: 188
<212> TYPE: PRT
<213> ORGANISM: homo sapiens

<400> SEQUENCE: 77

```
Met Asn Gly Asp Asp Ala Phe Ala Arg Arg Pro Arg Asp Asp Ala Gln
1               5                   10                  15

Ile Ser Glu Lys Leu Arg Lys Ala Phe Asp Asp Ile Ala Lys Tyr Phe
            20                  25                  30

Ser Lys Lys Glu Trp Glu Lys Met Lys Ser Ser Glu Lys Ile Val Tyr
        35                  40                  45

Val Tyr Met Lys Leu Asn Tyr Glu Val Met Thr Lys Leu Gly Phe Lys
    50                  55                  60

Val Thr Leu Pro Pro Phe Met Arg Ser Lys Arg Ala Ala Asp Phe His
65                  70                  75                  80

Gly Asn Asp Phe Gly Asn Asp Arg Asn His Arg Asn Gln Val Glu Arg
                85                  90                  95

Pro Gln Met Thr Phe Gly Ser Leu Gln Arg Ile Phe Pro Lys Ile Met
            100                 105                 110

Pro Lys Lys Pro Ala Glu Glu Glu Asn Gly Leu Lys Glu Val Pro Glu
        115                 120                 125

Ala Ser Gly Pro Gln Asn Asp Gly Lys Gln Leu Cys Pro Pro Gly Asn
    130                 135                 140

Pro Ser Thr Leu Glu Lys Ile Asn Lys Thr Ser Gly Pro Lys Arg Gly
145                 150                 155                 160

Lys His Ala Trp Thr His Arg Leu Arg Glu Arg Lys Gln Leu Val Val
                165                 170                 175

Tyr Glu Glu Ile Ser Asp Pro Glu Asp Asp Glu
            180                 185
```

<210> SEQ ID NO 78
<211> LENGTH: 602
<212> TYPE: PRT
<213> ORGANISM: homo sapiens

<400> SEQUENCE: 78

```
Met Ala Ala Glu Glu Ala Ala Ala Gly Gly Lys Val Leu Arg Glu
1               5                   10                  15

Glu Asn Gln Cys Ile Ala Pro Val Val Ser Ser Arg Val Ser Pro Gly
            20                  25                  30

Thr Arg Pro Thr Ala Met Gly Ser Phe Ser Ser His Met Thr Glu Phe
        35                  40                  45

Pro Arg Lys Arg Lys Gly Ser Asp Ser Asp Pro Ser Gln Val Glu Asp
    50                  55                  60
```

-continued

```
Gly Glu His Gln Val Lys Met Lys Ala Phe Arg Ala His Ser Gln
65                  70                  75                  80

Thr Glu Lys Arg Arg Asp Lys Met Asn Asn Leu Ile Glu Glu Leu
                85                  90                  95

Ser Ala Met Ile Pro Gln Cys Asn Pro Met Ala Arg Lys Leu Asp Lys
            100                 105                 110

Leu Thr Val Leu Arg Met Ala Val Gln His Leu Arg Ser Leu Lys Gly
            115                 120                 125

Leu Thr Asn Ser Tyr Val Gly Ser Asn Tyr Arg Pro Ser Phe Leu Gln
        130                 135                 140

Asp Asn Glu Leu Arg His Leu Ile Leu Lys Thr Ala Glu Gly Phe Leu
145                 150                 155                 160

Phe Val Val Gly Cys Glu Arg Gly Lys Ile Leu Phe Val Ser Lys Ser
                165                 170                 175

Val Ser Lys Ile Leu Asn Tyr Asp Gln Ala Ser Leu Thr Gly Gln Ser
            180                 185                 190

Leu Phe Asp Phe Leu His Pro Lys Asp Val Ala Lys Val Lys Glu Gln
            195                 200                 205

Leu Ser Ser Phe Asp Ile Ser Pro Arg Glu Lys Leu Ile Asp Ala Lys
        210                 215                 220

Thr Gly Leu Gln Val His Ser Asn Leu His Ala Gly Arg Thr Arg Val
225                 230                 235                 240

Tyr Ser Gly Ser Arg Arg Ser Phe Phe Cys Arg Ile Lys Ser Cys Lys
                245                 250                 255

Ile Ser Val Lys Glu Glu His Gly Cys Leu Pro Asn Ser Lys Lys Lys
            260                 265                 270

Glu His Arg Lys Phe Tyr Thr Ile His Cys Thr Gly Tyr Leu Arg Ser
        275                 280                 285

Trp Pro Pro Asn Ile Val Gly Met Glu Glu Arg Asn Ser Lys Lys
290                 295                 300

Asp Asn Ser Asn Phe Thr Cys Leu Val Ala Ile Gly Arg Leu Gln Pro
305                 310                 315                 320

Tyr Ile Val Pro Gln Asn Ser Gly Glu Ile Asn Val Lys Pro Thr Glu
                325                 330                 335

Phe Ile Thr Arg Phe Ala Val Asn Gly Lys Phe Val Tyr Val Asp Gln
            340                 345                 350

Arg Ala Thr Ala Ile Leu Gly Tyr Leu Pro Gln Glu Leu Leu Gly Thr
        355                 360                 365

Ser Cys Tyr Glu Tyr Phe His Gln Asp Asp His Asn Asn Leu Thr Asp
    370                 375                 380

Lys His Lys Ala Val Leu Gln Ser Lys Glu Lys Ile Leu Thr Asp Ser
385                 390                 395                 400

Tyr Lys Phe Arg Ala Lys Asp Gly Ser Phe Val Thr Leu Lys Ser Gln
                405                 410                 415

Trp Phe Ser Phe Thr Asn Pro Trp Lys Glu Leu Glu Tyr Ile Val
            420                 425                 430

Ser Val Asn Thr Leu Val Leu Gly His Ser Glu Pro Gly Glu Ala Ser
            435                 440                 445

Phe Leu Pro Cys Ser Ser Gln Ser Ser Glu Glu Ser Ser Arg Gln Ser
        450                 455                 460

Cys Met Ser Val Pro Gly Met Ser Thr Gly Thr Val Leu Gly Ala Gly
465                 470                 475                 480

Ser Ile Gly Thr Asp Ile Ala Asn Glu Ile Leu Asp Leu Gln Arg Leu
```

-continued

```
                485                 490                 495
Gln Ser Ser Ser Tyr Leu Asp Asp Ser Ser Pro Thr Gly Leu Met Lys
            500                 505                 510

Asp Thr His Thr Val Asn Cys Arg Ser Met Ser Asn Lys Glu Leu Phe
            515                 520                 525

Pro Pro Ser Pro Ser Glu Met Gly Glu Leu Glu Ala Thr Arg Gln Asn
            530                 535                 540

Gln Ser Thr Val Ala Val His Ser His Glu Pro Leu Leu Ser Asp Gly
545                 550                 555                 560

Ala Gln Leu Asp Phe Asp Ala Leu Cys Asp Asn Asp Asp Thr Ala Met
                565                 570                 575

Ala Ala Phe Met Asn Tyr Leu Glu Ala Glu Gly Gly Leu Gly Asp Pro
            580                 585                 590

Gly Asp Phe Ser Asp Ile Gln Trp Thr Leu
            595                 600

<210> SEQ ID NO 79
<211> LENGTH: 745
<212> TYPE: PRT
<213> ORGANISM: homo sapiens

<400> SEQUENCE: 79

Met Ile Arg Gly Arg Asn Ser Ala Thr Ser Ala Asp Glu Gln Pro His
1               5                   10                  15

Ile Gly Asn Tyr Arg Leu Leu Lys Thr Ile Gly Lys Gly Asn Phe Ala
                20                  25                  30

Lys Val Lys Leu Ala Arg His Ile Leu Thr Gly Lys Glu Val Ala Val
            35                  40                  45

Lys Ile Ile Asp Lys Thr Gln Leu Asn Ser Ser Ser Leu Gln Lys Leu
        50                  55                  60

Phe Arg Glu Val Arg Ile Met Lys Val Leu Asn His Pro Asn Ile Val
65                  70                  75                  80

Lys Leu Phe Glu Val Ile Glu Thr Glu Lys Thr Leu Tyr Leu Val Met
                85                  90                  95

Glu Tyr Ala Ser Gly Gly Glu Val Phe Asp Tyr Leu Val Ala His Gly
            100                 105                 110

Arg Met Lys Glu Lys Glu Ala Arg Ala Lys Phe Arg Gln Ile Val Ser
        115                 120                 125

Ala Val Gln Tyr Cys His Gln Lys Phe Ile Val His Arg Asp Leu Lys
    130                 135                 140

Ala Glu Asn Leu Leu Leu Asp Ala Asp Met Asn Ile Lys Ile Ala Asp
145                 150                 155                 160

Phe Gly Phe Ser Asn Glu Phe Thr Phe Gly Asn Lys Leu Asp Thr Phe
                165                 170                 175

Cys Gly Ser Pro Pro Tyr Ala Ala Pro Glu Leu Phe Gln Gly Lys Lys
            180                 185                 190

Tyr Asp Gly Pro Glu Val Asp Val Trp Ser Leu Gly Val Ile Leu Tyr
        195                 200                 205

Thr Leu Val Ser Gly Ser Leu Pro Phe Asp Gly Gln Asn Leu Lys Glu
    210                 215                 220

Leu Arg Glu Arg Val Leu Arg Gly Lys Tyr Arg Ile Pro Phe Tyr Met
225                 230                 235                 240

Ser Thr Asp Cys Glu Asn Leu Leu Lys Lys Phe Leu Ile Leu Asn Pro
                245                 250                 255
```

-continued

```
Ser Lys Arg Gly Thr Leu Glu Gln Ile Met Lys Asp Arg Trp Met Asn
            260                 265                 270

Val Gly His Glu Asp Glu Leu Lys Pro Tyr Val Glu Pro Leu Pro
        275                 280                 285

Asp Tyr Lys Asp Pro Arg Thr Glu Leu Met Val Ser Met Gly Tyr
    290                 295                 300

Thr Arg Glu Glu Ile Gln Asp Ser Leu Val Gly Gln Arg Tyr Asn Glu
305                 310                 315                 320

Val Met Ala Thr Tyr Leu Leu Leu Gly Tyr Lys Ser Ser Glu Leu Glu
                325                 330                 335

Gly Asp Thr Ile Thr Leu Lys Pro Arg Pro Ser Ala Asp Leu Thr Asn
                340                 345                 350

Ser Ser Ala Gln Phe Pro Ser His Lys Val Gln Arg Ser Val Ser Ala
            355                 360                 365

Asn Pro Lys Gln Arg Arg Phe Ser Asp Gln Ala Gly Pro Ala Ile Pro
    370                 375                 380

Thr Ser Asn Ser Tyr Ser Lys Lys Thr Gln Ser Asn Asn Ala Glu Asn
385                 390                 395                 400

Lys Arg Pro Glu Glu Asp Arg Glu Ser Gly Arg Lys Ala Ser Ser Thr
                405                 410                 415

Ala Lys Val Pro Ala Ser Pro Leu Pro Gly Leu Glu Arg Lys Lys Thr
                420                 425                 430

Thr Pro Thr Pro Ser Thr Asn Ser Val Leu Ser Thr Ser Thr Asn Arg
            435                 440                 445

Ser Arg Asn Ser Pro Leu Leu Glu Arg Ala Ser Leu Gly Gln Ala Ser
    450                 455                 460

Ile Gln Asn Gly Lys Asp Ser Leu Thr Met Pro Gly Ser Arg Ala Ser
465                 470                 475                 480

Thr Ala Ser Ala Ser Ala Ala Val Ser Ala Ala Arg Pro Arg Gln His
                485                 490                 495

Gln Lys Ser Met Ser Ala Ser Val His Pro Asn Lys Ala Ser Gly Leu
            500                 505                 510

Pro Pro Thr Glu Ser Asn Cys Glu Val Pro Arg Pro Ser Thr Ala Pro
            515                 520                 525

Gln Arg Val Pro Val Ala Ser Pro Ser Ala His Asn Ile Ser Ser Ser
            530                 535                 540

Gly Gly Ala Pro Asp Arg Thr Asn Phe Pro Arg Gly Val Ser Ser Arg
545                 550                 555                 560

Ser Thr Phe His Ala Gly Gln Leu Arg Gln Val Arg Asp Gln Gln Asn
                565                 570                 575

Leu Pro Tyr Gly Val Thr Pro Ala Ser Pro Ser Gly His Ser Gln Gly
                580                 585                 590

Arg Arg Gly Ala Ser Gly Ser Ile Phe Ser Lys Phe Thr Ser Lys Phe
            595                 600                 605

Val Arg Arg Asn Leu Asn Glu Pro Glu Ser Lys Asp Arg Val Glu Thr
            610                 615                 620

Leu Arg Pro His Val Val Gly Ser Gly Asn Asp Lys Glu Lys Glu
625                 630                 635                 640

Glu Phe Arg Glu Ala Lys Pro Arg Ser Leu Arg Phe Thr Trp Ser Met
                645                 650                 655

Lys Thr Thr Ser Ser Met Glu Pro Asn Glu Met Met Arg Glu Ile Arg
            660                 665                 670

Lys Val Leu Asp Ala Asn Ser Cys Gln Ser Glu Leu His Glu Lys Tyr
```

```
              675                 680                 685
Met Leu Leu Cys Met His Gly Thr Pro Gly His Glu Asp Phe Val Gln
    690                 695                 700

Trp Glu Met Glu Val Cys Lys Leu Pro Arg Leu Ser Leu Asn Gly Val
705                 710                 715                 720

Arg Phe Lys Arg Ile Ser Gly Thr Ser Met Ala Phe Lys Asn Ile Ala
                725                 730                 735

Ser Lys Ile Ala Asn Glu Leu Lys Leu
                740                 745

<210> SEQ ID NO 80
<211> LENGTH: 319
<212> TYPE: PRT
<213> ORGANISM: homo sapiens

<400> SEQUENCE: 80

Met Ser Val Gly Phe Ile Gly Ala Gly Gln Leu Ala Phe Ala Leu Ala
1               5                   10                  15

Lys Gly Phe Thr Ala Ala Gly Val Leu Ala Ala His Lys Ile Met Ala
                20                  25                  30

Ser Ser Pro Asp Met Asp Leu Ala Thr Val Ser Ala Leu Arg Lys Met
            35                  40                  45

Gly Val Lys Leu Thr Pro His Asn Lys Glu Thr Val Gln His Ser Asp
    50                  55                  60

Val Leu Phe Leu Ala Val Lys Pro His Ile Ile Pro Phe Ile Leu Asp
65                  70                  75                  80

Glu Ile Gly Ala Asp Ile Glu Asp Arg His Ile Val Val Ser Cys Ala
                85                  90                  95

Ala Gly Val Thr Ile Ser Ser Ile Glu Lys Lys Leu Ser Ala Phe Arg
            100                 105                 110

Pro Ala Pro Arg Val Ile Arg Cys Met Thr Asn Thr Pro Val Val Val
        115                 120                 125

Arg Glu Gly Ala Thr Val Tyr Ala Thr Gly Thr His Ala Gln Val Glu
    130                 135                 140

Asp Gly Arg Leu Met Glu Gln Leu Leu Ser Thr Val Gly Phe Cys Thr
145                 150                 155                 160

Glu Val Glu Glu Asp Leu Ile Asp Ala Val Thr Gly Leu Ser Gly Ser
                165                 170                 175

Gly Pro Ala Tyr Ala Phe Thr Ala Leu Asp Ala Leu Ala Asp Gly Gly
            180                 185                 190

Val Lys Met Gly Leu Pro Arg Arg Leu Ala Val Arg Leu Gly Ala Gln
        195                 200                 205

Ala Leu Leu Gly Ala Ala Lys Met Leu Leu His Ser Glu Gln His Pro
    210                 215                 220

Gly Gln Leu Lys Asp Asn Val Ser Ser Pro Gly Gly Ala Thr Ile His
225                 230                 235                 240

Ala Leu His Val Leu Glu Ser Gly Gly Phe Arg Ser Leu Leu Ile Asn
                245                 250                 255

Ala Val Glu Ala Ser Cys Ile Arg Thr Arg Glu Leu Gln Ser Met Ala
            260                 265                 270

Asp Gln Glu Gln Val Ser Pro Ala Ala Ile Lys Lys Thr Ile Leu Asp
        275                 280                 285

Lys Val Lys Leu Asp Ser Pro Ala Gly Thr Ala Leu Ser Pro Ser Gly
    290                 295                 300
```

His Thr Lys Leu Leu Pro Arg Ser Leu Ala Pro Ala Gly Lys Asp
305                 310                 315

<210> SEQ ID NO 81
<211> LENGTH: 148
<212> TYPE: PRT
<213> ORGANISM: homo sapiens

<400> SEQUENCE: 81

Met Ala Glu Ser Asp Trp Asp Thr Val Thr Val Leu Arg Lys Lys Gly
1               5                   10                  15

Pro Thr Ala Ala Gln Ala Lys Ser Lys Gln Ala Ile Leu Ala Ala Gln
            20                  25                  30

Arg Arg Gly Glu Asp Val Glu Thr Ser Lys Lys Trp Ala Ala Gly Gln
        35                  40                  45

Asn Lys Gln His Ser Ile Thr Lys Asn Thr Ala Lys Leu Asp Arg Glu
    50                  55                  60

Thr Glu Glu Leu His His Asp Arg Val Thr Leu Glu Val Gly Lys Val
65                  70                  75                  80

Ile Gln Gln Gly Arg Gln Ser Lys Gly Leu Thr Gln Lys Asp Leu Ala
                85                  90                  95

Thr Lys Ile Asn Glu Lys Pro Gln Val Ile Ala Asp Tyr Glu Ser Gly
            100                 105                 110

Arg Ala Ile Pro Asn Asn Gln Val Leu Gly Lys Ile Glu Arg Ala Ile
        115                 120                 125

Gly Leu Lys Leu Arg Gly Lys Asp Ile Gly Lys Pro Ile Glu Lys Gly
    130                 135                 140

Pro Arg Ala Lys
145

<210> SEQ ID NO 82
<211> LENGTH: 375
<212> TYPE: PRT
<213> ORGANISM: homo sapiens

<400> SEQUENCE: 82

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 83
<211> LENGTH: 268
<212> TYPE: PRT
<213> ORGANISM: homo sapiens

<400> SEQUENCE: 83

Met Phe Arg Met Leu Asn Ser Ser Phe Glu Asp Asp Pro Phe Phe Ser
1               5                   10                  15

Glu Ser Ile Leu Ala His Arg Glu Asn Met Arg Gln Met Ile Arg Ser
            20                  25                  30

Phe Ser Glu Pro Phe Gly Arg Asp Leu Leu Ser Ile Ser Asp Gly Arg
        35                  40                  45

Gly Arg Ala His Asn Arg Gly His Asn Asp Gly Glu Asp Ser Leu
    50                  55                  60

Thr His Thr Asp Val Ser Ser Phe Gln Thr Met Asp Gln Met Val Ser
65                  70                  75                  80

Asn Met Arg Asn Tyr Met Gln Lys Leu Glu Arg Asn Phe Gly Gln Leu
                85                  90                  95

Ser Val Asp Pro Asn Gly His Ser Phe Cys Ser Ser Val Met Thr
            100                 105                 110

Tyr Ser Lys Ile Gly Asp Glu Pro Pro Lys Val Phe Gln Ala Ser Thr
        115                 120                 125

Gln Thr Arg Arg Ala Pro Gly Gly Ile Lys Glu Thr Arg Lys Ala Met
    130                 135                 140

Arg Asp Ser Asp Ser Gly Leu Glu Lys Met Ala Ile Gly His His Ile
145                 150                 155                 160

His Asp Arg Ala His Val Ile Lys Lys Ser Lys Asn Lys Lys Thr Gly
                165                 170                 175

Asp Glu Glu Val Asn Gln Glu Phe Ile Asn Met Asn Glu Ser Asp Ala
            180                 185                 190

His Ala Phe Asp Glu Glu Trp Gln Ser Glu Val Leu Lys Tyr Lys Pro
        195                 200                 205

Gly Arg His Asn Leu Gly Asn Thr Arg Met Arg Ser Val Gly His Glu
    210                 215                 220

Asn Pro Gly Ser Arg Glu Leu Lys Arg Arg Glu Lys Pro Gln Gln Ser
225                 230                 235                 240

Pro Ala Ile Glu His Gly Arg Arg Ser Asn Val Leu Gly Asp Lys Leu
                245                 250                 255

His Ile Lys Gly Ser Ser Val Lys Ser Asn Lys Lys
                260                 265

<210> SEQ ID NO 84
<211> LENGTH: 837
<212> TYPE: PRT
<213> ORGANISM: homo sapiens

<400> SEQUENCE: 84

Met Ala Glu Pro Ser Gln Ala Pro Thr Pro Ala Pro Ala Ala Gln Pro
1               5                   10                  15

Arg Pro Leu Gln Ser Pro Ala Pro Ala Pro Thr Pro Thr Pro Ala Pro
            20                  25                  30

Ser Pro Ala Ser Ala Pro Ile Pro Thr Pro Thr Pro Ala Pro Ala Pro
        35                  40                  45

Ala Pro Ala Ala Ala Pro Ala Gly Ser Thr Gly Thr Gly Gly Pro Gly
    50                  55                  60

Val Gly Ser Gly Gly Ala Gly Ser Gly Gly Asp Pro Ala Arg Pro Gly
65                  70                  75                  80

Leu Ser Gln Gln Gln Arg Ala Ser Gln Arg Lys Ala Gln Val Arg Gly
                85                  90                  95

Leu Pro Arg Ala Lys Lys Leu Glu Lys Leu Gly Val Phe Ser Ala Cys
            100                 105                 110

Lys Ala Asn Gly Thr Cys Lys Cys Asn Gly Trp Lys Asn Pro Lys Pro
        115                 120                 125

Pro Thr Ala Pro Arg Ile Asp Leu Gln Gln Pro Ala Ala Asn Leu Ser
    130                 135                 140

Glu Leu Cys Arg Ser Cys Glu His Pro Leu Ala Asp His Val Ser His
145                 150                 155                 160

Leu Glu Asn Val Ser Glu Asp Glu Ile Asn Arg Leu Leu Gly Met Val
                165                 170                 175

Val Asp Val Glu Asn Leu Phe Met Ser Val His Lys Glu Glu Asp Thr
            180                 185                 190

Asp Thr Lys Gln Val Tyr Phe Tyr Leu Phe Lys Leu Leu Arg Lys Cys
        195                 200                 205

Ile Leu Gln Met Thr Arg Pro Val Val Glu Gly Ser Leu Gly Ser Pro
    210                 215                 220

Pro Phe Glu Lys Pro Asn Ile Glu Gln Gly Val Leu Asn Phe Val Gln
225                 230                 235                 240

Tyr Lys Phe Ser His Leu Ala Pro Arg Glu Arg Gln Thr Met Phe Glu
                245                 250                 255

Leu Ser Lys Met Phe Leu Leu Cys Leu Asn Tyr Trp Glu Leu Glu Thr

-continued

```
                260                 265                 270
Pro Ala Gln Phe Arg Gln Arg Ser Gln Ala Glu Asp Val Ala Thr Tyr
            275                 280                 285
Lys Val Asn Tyr Thr Arg Trp Leu Cys Tyr Cys His Val Pro Gln Ser
            290                 295                 300
Cys Asp Ser Leu Pro Arg Tyr Glu Thr Thr His Val Phe Gly Arg Ser
305                 310                 315                 320
Leu Leu Arg Ser Ile Phe Thr Val Thr Arg Gln Leu Leu Glu Lys
                325                 330                 335
Phe Arg Val Glu Lys Asp Lys Leu Val Pro Glu Lys Arg Thr Leu Ile
            340                 345                 350
Leu Thr His Phe Pro Lys Phe Leu Ser Met Leu Glu Glu Ile Tyr
            355                 360                 365
Gly Ala Asn Ser Pro Ile Trp Glu Ser Gly Phe Thr Met Pro Pro Ser
            370                 375                 380
Glu Gly Thr Gln Leu Val Pro Arg Pro Ala Ser Val Ser Ala Ala Val
385                 390                 395                 400
Val Pro Ser Thr Pro Ile Phe Ser Pro Ser Met Gly Gly Gly Ser Asn
                405                 410                 415
Ser Ser Leu Ser Leu Asp Ser Ala Gly Ala Glu Pro Met Pro Gly Glu
                420                 425                 430
Lys Arg Thr Leu Pro Glu Asn Leu Thr Leu Glu Asp Ala Lys Arg Leu
            435                 440                 445
Arg Val Met Gly Asp Ile Pro Met Glu Leu Val Asn Glu Val Met Leu
            450                 455                 460
Thr Ile Thr Asp Pro Ala Ala Met Leu Gly Pro Glu Thr Ser Leu Leu
465                 470                 475                 480
Ser Ala Asn Ala Ala Arg Asp Glu Thr Ala Arg Leu Glu Glu Arg Arg
                485                 490                 495
Gly Ile Ile Glu Phe His Val Ile Gly Asn Ser Leu Thr Pro Lys Ala
            500                 505                 510
Asn Arg Arg Val Leu Leu Trp Leu Val Gly Leu Gln Asn Val Phe Ser
            515                 520                 525
His Gln Leu Pro Arg Met Pro Lys Glu Tyr Ile Ala Arg Leu Val Phe
            530                 535                 540
Asp Pro Lys His Lys Thr Leu Ala Leu Ile Lys Asp Gly Arg Val Ile
545                 550                 555                 560
Gly Gly Ile Cys Phe Arg Met Phe Pro Thr Gln Gly Phe Thr Glu Ile
                565                 570                 575
Val Phe Cys Ala Val Thr Ser Asn Glu Gln Val Lys Gly Tyr Gly Thr
                580                 585                 590
His Leu Met Asn His Leu Lys Glu Tyr His Ile Lys His Asn Ile Leu
            595                 600                 605
Tyr Phe Leu Thr Tyr Ala Asp Glu Tyr Ala Ile Gly Tyr Phe Lys Lys
            610                 615                 620
Gln Gly Phe Ser Lys Asp Ile Lys Val Pro Lys Ser Arg Tyr Leu Gly
625                 630                 635                 640
Tyr Ile Lys Asp Tyr Glu Gly Ala Thr Leu Met Glu Cys Glu Leu Asn
                645                 650                 655
Pro Arg Ile Pro Tyr Thr Glu Leu Ser His Ile Ile Lys Lys Gln Lys
            660                 665                 670
Glu Ile Ile Lys Lys Leu Ile Glu Arg Lys Gln Ala Gln Ile Arg Lys
            675                 680                 685
```

```
Val Tyr Pro Gly Leu Ser Cys Phe Lys Glu Gly Val Arg Gln Ile Pro
            690                 695                 700

Val Glu Ser Val Pro Gly Ile Arg Glu Thr Gly Trp Lys Pro Leu Gly
705                 710                 715                 720

Lys Glu Lys Gly Lys Glu Leu Lys Asp Pro Asp Gln Leu Tyr Thr Thr
            725                 730                 735

Leu Lys Asn Leu Leu Ala Gln Ile Lys Ser His Pro Ser Ala Trp Pro
            740                 745                 750

Phe Met Glu Pro Val Lys Lys Ser Glu Ala Pro Asp Tyr Tyr Glu Val
            755                 760                 765

Ile Arg Phe Pro Ile Asp Leu Lys Thr Met Thr Glu Arg Leu Arg Ser
            770                 775                 780

Arg Tyr Tyr Val Thr Arg Lys Leu Phe Val Ala Asp Leu Gln Arg Val
785                 790                 795                 800

Ile Ala Asn Cys Arg Glu Tyr Asn Pro Pro Asp Ser Glu Tyr Cys Arg
            805                 810                 815

Cys Ala Ser Ala Leu Glu Lys Phe Phe Tyr Phe Lys Leu Lys Glu Gly
            820                 825                 830

Gly Leu Ile Asp Lys
            835

<210> SEQ ID NO 85
<211> LENGTH: 483
<212> TYPE: PRT
<213> ORGANISM: homo sapiens

<400> SEQUENCE: 85

Met Lys Glu Glu Lys Glu His Arg Pro Lys Glu Lys Arg Val Thr Leu
1               5                   10                  15

Leu Thr Pro Ala Gly Ala Thr Gly Ser Gly Gly Gly Thr Ser Gly Asp
            20                  25                  30

Ser Ser Lys Gly Glu Asp Lys Gln Asp Arg Asn Lys Glu Lys Lys Glu
        35                  40                  45

Ala Leu Ser Lys Val Val Ile Arg Arg Leu Pro Pro Thr Leu Thr Lys
    50                  55                  60

Glu Gln Leu Gln Glu His Leu Gln Pro Met Pro Glu His Asp Tyr Phe
65                  70                  75                  80

Glu Phe Phe Ser Asn Asp Thr Ser Leu Tyr Pro His Met Tyr Ala Arg
                85                  90                  95

Ala Tyr Ile Asn Phe Lys Asn Gln Glu Asp Ile Ile Leu Phe Arg Asp
            100                 105                 110

Arg Phe Asp Gly Tyr Val Phe Leu Asp Asn Lys Gly Gln Glu Tyr Pro
        115                 120                 125

Ala Ile Val Glu Phe Ala Pro Phe Gln Lys Ala Lys Lys Lys Thr
    130                 135                 140

Lys Lys Arg Asp Thr Lys Val Gly Thr Ile Asp Asp Pro Glu Tyr
145                 150                 155                 160

Arg Lys Phe Leu Glu Ser Tyr Ala Thr Asp Asn Glu Lys Met Thr Ser
                165                 170                 175

Thr Pro Glu Thr Leu Leu Glu Glu Ile Glu Ala Lys Asn Arg Glu Leu
            180                 185                 190

Ile Ala Lys Lys Thr Thr Pro Leu Leu Ser Phe Leu Lys Asn Lys Gln
        195                 200                 205

Arg Met Arg Glu Glu Lys Arg Glu Glu Arg Arg Arg Arg Glu Ile Glu
```

```
              210                 215                 220
Arg Lys Arg Gln Arg Glu Glu Arg Lys Trp Lys Glu Glu
225                 230                 235                 240

Lys Arg Lys Arg Lys Asp Ile Glu Lys Leu Lys Lys Ile Asp Arg Ile
                245                 250                 255

Pro Glu Arg Asp Lys Leu Lys Asp Glu Pro Lys Ile Lys Val His Arg
                260                 265                 270

Phe Leu Leu Gln Ala Val Asn Gln Lys Asn Leu Leu Lys Lys Pro Glu
            275                 280                 285

Lys Gly Asp Glu Lys Glu Leu Asp Lys Arg Glu Lys Ala Lys Lys Leu
290                 295                 300

Asp Lys Glu Asn Leu Ser Asp Glu Arg Ala Ser Gly Gln Ser Cys Thr
305                 310                 315                 320

Leu Pro Lys Arg Ser Asp Ser Glu Leu Lys Asp Glu Lys Pro Lys Arg
                325                 330                 335

Pro Glu Asp Glu Ser Gly Arg Asp Tyr Arg Glu Arg Glu Arg Glu Tyr
                340                 345                 350

Glu Arg Asp Gln Glu Arg Ile Leu Arg Glu Arg Glu Arg Leu Lys Arg
                355                 360                 365

Gln Glu Glu Glu Arg Arg Gln Lys Glu Arg Tyr Glu Lys Glu Lys
            370                 375                 380

Thr Phe Lys Arg Lys Glu Glu Met Lys Lys Glu Lys Asp Thr Leu
385                 390                 395                 400

Arg Asp Lys Gly Lys Lys Ala Glu Ser Thr Glu Ser Ile Gly Ser Ser
                405                 410                 415

Glu Lys Thr Glu Lys Lys Glu Glu Val Val Lys Arg Asp Arg Ile Arg
                420                 425                 430

Asn Lys Asp Arg Pro Ala Met Gln Leu Tyr Gln Pro Gly Ala Arg Ser
                435                 440                 445

Arg Asn Arg Leu Cys Pro Pro Asp Asp Ser Thr Lys Ser Gly Asp Ser
            450                 455                 460

Ala Ala Glu Arg Lys Gln Glu Ser Gly Ile Ser His Arg Lys Glu Gly
465                 470                 475                 480

Gly Glu Glu

<210> SEQ ID NO 86
<211> LENGTH: 426
<212> TYPE: PRT
<213> ORGANISM: homo sapiens

<400> SEQUENCE: 86

Met Ala Asn Asp Ser Gly Gly Pro Gly Gly Pro Ser Pro Ser Glu Arg
1               5                   10                  15

Asp Arg Gln Tyr Cys Glu Leu Cys Gly Lys Met Glu Asn Leu Leu Arg
                20                  25                  30

Cys Ser Arg Cys Arg Ser Ser Phe Tyr Cys Cys Lys Glu His Gln Arg
            35                  40                  45

Gln Asp Trp Lys Lys His Lys Leu Val Cys Gln Gly Ser Glu Gly Ala
        50                  55                  60

Leu Gly His Gly Val Gly Pro His Gln His Ser Gly Pro Ala Pro Pro
65                  70                  75                  80

Ala Ala Val Pro Pro Pro Arg Ala Gly Ala Arg Glu Pro Arg Lys Ala
                85                  90                  95

Ala Ala Arg Arg Asp Asn Ala Ser Gly Asp Ala Ala Lys Gly Lys Val
```

-continued

```
                100                 105                 110
Lys Ala Lys Pro Pro Ala Asp Pro Ala Ala Ala Ser Pro Cys Arg
            115                 120                 125
Ala Ala Ala Gly Gly Gln Gly Ser Ala Val Ala Ala Glu Ala Glu Pro
        130                 135                 140
Gly Lys Glu Glu Pro Pro Ala Arg Ser Ser Leu Phe Gln Glu Lys Ala
145                 150                 155                 160
Asn Leu Tyr Pro Pro Ser Asn Thr Pro Gly Asp Ala Leu Ser Pro Gly
                165                 170                 175
Gly Gly Leu Arg Pro Asn Gly Gln Thr Lys Pro Leu Pro Ala Leu Lys
            180                 185                 190
Leu Ala Leu Glu Tyr Ile Val Pro Cys Met Asn Lys His Gly Ile Cys
                195                 200                 205
Val Val Asp Asp Phe Leu Gly Lys Glu Thr Gly Gln Gln Ile Gly Asp
        210                 215                 220
Glu Val Arg Ala Leu His Asp Thr Gly Lys Phe Thr Asp Gly Gln Leu
225                 230                 235                 240
Val Ser Gln Lys Ser Asp Ser Ser Lys Asp Ile Arg Gly Asp Lys Ile
                245                 250                 255
Thr Trp Ile Glu Gly Lys Glu Pro Gly Cys Glu Thr Ile Gly Leu Leu
            260                 265                 270
Met Ser Ser Met Asp Asp Leu Ile Arg His Cys Asn Gly Lys Leu Gly
                275                 280                 285
Ser Tyr Lys Ile Asn Gly Arg Thr Lys Ala Met Val Ala Cys Tyr Pro
            290                 295                 300
Gly Asn Gly Thr Gly Tyr Val Arg His Val Asp Asn Pro Asn Gly Asp
305                 310                 315                 320
Gly Arg Cys Val Thr Cys Ile Tyr Tyr Leu Asn Lys Asp Trp Asp Ala
                325                 330                 335
Lys Val Ser Gly Gly Ile Leu Arg Ile Phe Pro Glu Gly Lys Ala Gln
            340                 345                 350
Phe Ala Asp Ile Glu Pro Lys Phe Asp Arg Leu Leu Phe Phe Trp Ser
        355                 360                 365
Asp Arg Arg Asn Pro His Glu Val Gln Pro Ala Tyr Ala Thr Arg Tyr
    370                 375                 380
Ala Ile Thr Val Trp Tyr Phe Asp Ala Asp Glu Arg Ala Arg Ala Lys
385                 390                 395                 400
Val Lys Tyr Leu Thr Gly Glu Lys Gly Val Arg Val Glu Leu Asn Lys
                405                 410                 415
Pro Ser Asp Ser Val Gly Lys Asp Val Phe
            420                 425

<210> SEQ ID NO 87
<211> LENGTH: 1320
<212> TYPE: PRT
<213> ORGANISM: homo sapiens

<400> SEQUENCE: 87

Met Ser Gly Gly Ala Ser Ala Thr Gly Pro Arg Arg Gly Pro Pro Gly
1               5                   10                  15
Leu Glu Asp Thr Thr Ser Lys Lys Lys Gln Lys Asp Arg Ala Asn Gln
                20                  25                  30
Glu Ser Lys Asp Gly Asp Pro Arg Lys Glu Thr Gly Ser Arg Tyr Val
            35                  40                  45
```

```
Ala Gln Ala Gly Leu Glu Pro Leu Ala Ser Gly Asp Pro Ser Ala Ser
 50                  55                  60

Ala Ser His Ala Ala Gly Ile Thr Gly Ser Arg His Arg Thr Arg Leu
 65                  70                  75                  80

Phe Phe Pro Ser Ser Ser Gly Ser Ala Ser Thr Pro Gln Glu Glu Gln
                 85                  90                  95

Thr Lys Glu Gly Ala Cys Glu Asp Pro His Asp Leu Leu Ala Thr Pro
            100                 105                 110

Thr Pro Glu Leu Leu Leu Asp Trp Arg Gln Ser Ala Glu Glu Val Ile
            115                 120                 125

Val Lys Leu Arg Val Gly Val Gly Pro Leu Gln Leu Glu Asp Val Asp
130                 135                 140

Ala Ala Phe Thr Asp Thr Asp Cys Val Val Arg Phe Ala Gly Gly Gln
145                 150                 155                 160

Gln Trp Gly Gly Val Phe Tyr Ala Glu Ile Lys Ser Ser Cys Ala Lys
                165                 170                 175

Val Gln Thr Arg Lys Gly Ser Leu Leu His Leu Thr Leu Pro Lys Lys
            180                 185                 190

Val Pro Met Leu Thr Trp Pro Ser Leu Leu Val Glu Ala Asp Glu Gln
            195                 200                 205

Leu Cys Ile Pro Pro Leu Asn Ser Gln Thr Cys Leu Leu Gly Ser Glu
210                 215                 220

Glu Asn Leu Ala Pro Leu Ala Gly Glu Lys Ala Val Pro Pro Gly Asn
225                 230                 235                 240

Asp Pro Val Ser Pro Ala Met Val Arg Ser Arg Asn Pro Gly Lys Asp
                245                 250                 255

Asp Cys Ala Lys Glu Glu Met Ala Val Ala Ala Asp Ala Ala Thr Leu
            260                 265                 270

Val Asp Glu Pro Glu Ser Met Val Asn Leu Ala Phe Val Lys Asn Asp
            275                 280                 285

Ser Tyr Glu Lys Gly Pro Asp Ser Val Val His Val Tyr Val Lys
290                 295                 300

Glu Ile Cys Arg Asp Thr Ser Arg Val Leu Phe Arg Glu Gln Asp Phe
305                 310                 315                 320

Thr Leu Ile Phe Gln Thr Arg Asp Gly Asn Phe Leu Arg Leu His Pro
                325                 330                 335

Gly Cys Gly Pro His Thr Thr Phe Arg Trp Gln Val Lys Leu Arg Asn
                340                 345                 350

Leu Ile Glu Pro Glu Gln Cys Thr Phe Cys Phe Thr Ala Ser Arg Ile
            355                 360                 365

Asp Ile Cys Leu Arg Lys Arg Gln Ser Gln Arg Trp Gly Gly Leu Glu
            370                 375                 380

Ala Pro Ala Ala Arg Gly Ala Val Gly Gly Ala Lys Val Ala Val Pro
385                 390                 395                 400

Thr Gly Pro Thr Pro Leu Asp Ser Thr Pro Pro Gly Gly Ala Pro His
                405                 410                 415

Pro Leu Thr Gly Gln Glu Glu Ala Arg Ala Val Glu Lys Asp Lys Ser
            420                 425                 430

Lys Ala Arg Ser Glu Asp Thr Gly Leu Asp Ser Val Ala Thr Arg Thr
            435                 440                 445

Pro Met Glu His Val Thr Pro Lys Pro Glu Thr His Leu Ala Ser Pro
            450                 455                 460

Lys Pro Thr Cys Met Val Pro Pro Met Pro His Ser Pro Val Ser Gly
```

-continued

```
            465                 470                 475                 480
Asp Ser Val Glu Glu Glu Glu Glu Lys Lys Val Cys Leu Pro
                    485                 490                 495
Gly Phe Thr Gly Leu Val Asn Leu Gly Asn Thr Cys Phe Met Asn Ser
                500                 505                 510
Val Ile Gln Ser Leu Ser Asn Thr Arg Glu Leu Arg Asp Phe Phe His
            515                 520                 525
Asp Arg Ser Phe Glu Ala Glu Ile Asn Tyr Asn Asn Pro Leu Gly Thr
        530                 535                 540
Gly Gly Arg Leu Ala Ile Gly Phe Ala Val Leu Leu Arg Ala Leu Trp
545                 550                 555                 560
Lys Gly Thr His His Ala Phe Gln Pro Ser Lys Leu Lys Ala Ile Val
                565                 570                 575
Ala Ser Lys Ala Ser Gln Phe Thr Gly Tyr Ala Gln His Asp Ala Gln
                580                 585                 590
Glu Phe Met Ala Phe Leu Leu Asp Gly Leu His Glu Asp Leu Asn Arg
                595                 600                 605
Ile Gln Asn Lys Pro Tyr Thr Glu Thr Val Asp Ser Asp Gly Arg Pro
        610                 615                 620
Asp Glu Val Val Ala Glu Ala Trp Gln Arg His Lys Met Arg Asn
625                 630                 635                 640
Asp Ser Phe Ile Val Asp Leu Phe Gln Gly Gln Tyr Lys Ser Lys Leu
                645                 650                 655
Val Cys Pro Val Cys Ala Lys Val Ser Ile Thr Phe Asp Pro Phe Leu
                660                 665                 670
Tyr Leu Pro Val Pro Leu Pro Gln Lys Gln Lys Val Leu Pro Val Phe
                675                 680                 685
Tyr Phe Ala Arg Glu Pro His Ser Lys Pro Ile Lys Phe Leu Val Ser
                690                 695                 700
Val Ser Lys Glu Asn Ser Thr Ala Ser Glu Val Leu Asp Ser Leu Ser
705                 710                 715                 720
Gln Ser Val His Val Lys Pro Glu Asn Leu Arg Leu Ala Glu Val Ile
                725                 730                 735
Lys Asn Arg Phe His Arg Val Phe Leu Pro Ser His Ser Leu Asp Thr
                740                 745                 750
Val Ser Pro Ser Asp Thr Leu Leu Cys Phe Glu Leu Leu Ser Ser Glu
                755                 760                 765
Leu Ala Lys Glu Arg Val Val Leu Glu Val Gln Gln Arg Pro Gln
        770                 775                 780
Val Pro Ser Val Pro Ile Ser Lys Cys Ala Ala Cys Gln Arg Lys Gln
785                 790                 795                 800
Gln Ser Glu Asp Glu Lys Leu Lys Arg Cys Thr Arg Cys Tyr Arg Val
                805                 810                 815
Gly Tyr Cys Asn Gln Leu Cys Gln Lys Thr His Trp Pro Asp His Lys
                820                 825                 830
Gly Leu Cys Arg Pro Glu Asn Ile Gly Tyr Pro Phe Leu Val Ser Val
                835                 840                 845
Pro Ala Ser Arg Leu Thr Tyr Ala Arg Leu Ala Gln Leu Leu Glu Gly
        850                 855                 860
Tyr Ala Arg Tyr Ser Val Ser Val Phe Gln Pro Pro Phe Gln Pro Gly
865                 870                 875                 880
Arg Met Ala Leu Glu Ser Gln Pro Gly Cys Thr Thr Leu Leu Ser
                885                 890                 895
```

```
Thr Gly Ser Leu Glu Ala Gly Asp Ser Glu Arg Asp Pro Ile Gln Pro
            900                 905                 910

Pro Glu Leu Gln Leu Val Thr Pro Met Ala Glu Gly Asp Thr Gly Leu
        915                 920                 925

Pro Arg Val Trp Ala Ala Pro Asp Arg Gly Pro Val Pro Ser Thr Ser
    930                 935                 940

Gly Ile Ser Ser Glu Met Leu Ala Ser Gly Pro Ile Glu Val Gly Ser
945                 950                 955                 960

Leu Pro Ala Gly Glu Arg Val Ser Arg Pro Glu Ala Ala Val Pro Gly
            965                 970                 975

Tyr Gln His Pro Ser Glu Ala Met Asn Ala His Thr Pro Gln Phe Phe
        980                 985                 990

Ile Tyr Lys Ile Asp Ser Ser Asn Arg Glu Gln Arg Leu Glu Asp Lys
        995                 1000                1005

Gly Asp Thr Pro Leu Glu Leu Gly Asp Asp Cys Ser Leu Ala Leu
    1010                1015                1020

Val Trp Arg Asn Asn Glu Arg Leu Gln Glu Phe Val Leu Val Ala
    1025                1030                1035

Ser Lys Glu Leu Glu Cys Ala Glu Asp Pro Gly Ser Ala Gly Glu
    1040                1045                1050

Ala Ala Arg Ala Gly His Phe Thr Leu Asp Gln Cys Leu Asn Leu
    1055                1060                1065

Phe Thr Arg Pro Glu Val Leu Ala Pro Glu Glu Ala Trp Tyr Cys
    1070                1075                1080

Pro Gln Cys Lys Gln His Arg Glu Ala Ser Lys Gln Leu Leu Leu
    1085                1090                1095

Trp Arg Leu Pro Asn Val Leu Ile Val Gln Leu Lys Arg Phe Ser
    1100                1105                1110

Phe Arg Ser Phe Ile Trp Arg Asp Lys Ile Asn Asp Leu Val Glu
    1115                1120                1125

Phe Pro Val Arg Asn Leu Asp Leu Ser Lys Phe Cys Ile Gly Gln
    1130                1135                1140

Lys Glu Glu Gln Leu Pro Ser Tyr Asp Leu Tyr Ala Val Ile Asn
    1145                1150                1155

His Tyr Gly Gly Met Ile Gly Gly His Tyr Thr Ala Cys Ala Arg
    1160                1165                1170

Leu Pro Asn Asp Arg Ser Ser Gln Arg Ser Asp Val Gly Trp Arg
    1175                1180                1185

Leu Phe Asp Asp Ser Thr Val Thr Thr Val Asp Glu Ser Gln Val
    1190                1195                1200

Val Thr Arg Tyr Ala Tyr Val Leu Phe Tyr Arg Arg Arg Asn Ser
    1205                1210                1215

Pro Val Glu Arg Pro Pro Arg Ala Gly His Ser Glu His His Pro
    1220                1225                1230

Asp Leu Gly Pro Ala Ala Glu Ala Ala Ala Ser Gln Ala Ser Arg
    1235                1240                1245

Ile Trp Gln Glu Leu Glu Ala Glu Glu Glu Pro Val Pro Glu Gly
    1250                1255                1260

Ser Gly Pro Leu Gly Pro Trp Gly Pro Gln Asp Trp Val Gly Pro
    1265                1270                1275

Leu Pro Arg Gly Pro Thr Thr Pro Asp Glu Gly Cys Leu Arg Tyr
    1280                1285                1290
```

-continued

```
Phe Val Leu Gly Thr Val Ala Leu Val Ala Leu Val Leu Asn
    1295                1300                1305

Val Phe Tyr Pro Leu Val Ser Gln Ser Arg Trp Arg
    1310                1315                1320

<210> SEQ ID NO 88
<211> LENGTH: 325
<212> TYPE: PRT
<213> ORGANISM: homo sapiens

<400> SEQUENCE: 88

Met Ser Ala Gln Ala Gln Met Arg Ala Leu Leu Asp Gln Leu Met Gly
1               5                   10                  15

Thr Ala Arg Asp Gly Asp Glu Thr Arg Gln Arg Val Lys Phe Thr Asp
                20                  25                  30

Asp Arg Val Cys Lys Ser His Leu Leu Asp Cys Cys Pro His Asp Ile
            35                  40                  45

Leu Ala Gly Thr Arg Met Asp Leu Gly Glu Cys Thr Lys Ile His Asp
        50                  55                  60

Leu Ala Leu Arg Ala Asp Tyr Glu Ile Ala Ser Lys Glu Arg Asp Leu
65                  70                  75                  80

Phe Phe Glu Leu Asp Ala Met Asp His Leu Glu Ser Phe Ile Ala Glu
                85                  90                  95

Cys Asp Arg Arg Thr Glu Leu Ala Lys Lys Arg Leu Ala Glu Thr Gln
            100                 105                 110

Glu Glu Ile Ser Ala Glu Val Ser Ala Lys Ala Glu Lys Val His Glu
        115                 120                 125

Leu Asn Glu Glu Ile Gly Lys Leu Leu Ala Lys Ala Glu Gln Leu Gly
130                 135                 140

Ala Glu Gly Asn Val Asp Glu Ser Gln Lys Ile Leu Met Glu Val Glu
145                 150                 155                 160

Lys Val Arg Ala Lys Lys Glu Ala Glu Glu Tyr Arg Asn Ser
                165                 170                 175

Met Pro Ala Ser Ser Phe Gln Gln Gln Lys Leu Arg Val Cys Glu Val
            180                 185                 190

Cys Ser Ala Tyr Leu Gly Leu His Asp Asn Asp Arg Arg Leu Ala Asp
        195                 200                 205

His Phe Gly Gly Lys Leu His Leu Gly Phe Ile Gln Ile Arg Glu Lys
    210                 215                 220

Leu Asp Gln Leu Arg Lys Thr Val Ala Glu Lys Gln Glu Lys Arg Asn
225                 230                 235                 240

Gln Asp Arg Leu Arg Arg Arg Glu Glu Arg Glu Arg Glu Glu Arg Leu
                245                 250                 255

Ser Arg Arg Ser Gly Ser Arg Thr Arg Asp Arg Arg Ser Arg Ser
            260                 265                 270

Arg Asp Arg Arg Arg Arg Ser Arg Ser Thr Ser Arg Glu Arg Arg
        275                 280                 285

Lys Leu Ser Arg Ser Arg Ser Arg Asp Arg His Arg Arg His Arg Ser
    290                 295                 300

Arg Ser Arg Ser His Ser Arg Gly His Arg Arg Ala Ser Arg Asp Arg
305                 310                 315                 320

Ser Ala Lys Tyr Lys
            325

<210> SEQ ID NO 89
```

```
<211> LENGTH: 181
<212> TYPE: PRT
<213> ORGANISM: homo sapiens

<400> SEQUENCE: 89

Met Gly Gly Phe Ser Ser Ile Phe Ser Leu Phe Gly Thr Arg
1               5                   10                  15

Glu Met Arg Ile Leu Ile Leu Gly Leu Asp Gly Ala Gly Lys Thr Thr
                20                  25                  30

Ile Leu Tyr Arg Leu Gln Val Gly Glu Val Val Thr Thr Ile Pro Thr
                35                  40                  45

Ile Gly Phe Asn Val Glu Thr Val Thr Tyr Lys Asn Leu Lys Phe Gln
        50                  55                  60

Val Trp Asp Leu Gly Gly Gln Thr Ser Ile Arg Pro Tyr Trp Arg Cys
65                  70                  75                  80

Tyr Tyr Ser Asn Thr Asp Ala Val Ile Tyr Val Val Asp Ser Cys Asp
                85                  90                  95

Arg Asp Arg Ile Gly Ile Ser Lys Ser Glu Leu Val Ala Met Leu Glu
                100                 105                 110

Glu Glu Glu Leu Arg Lys Ala Ile Leu Val Val Phe Ala Asn Lys Gln
                115                 120                 125

Asp Met Glu Gln Ala Met Thr Ser Ser Glu Met Ala Asn Ser Leu Gly
        130                 135                 140

Leu Pro Ala Leu Lys Asp Arg Lys Trp Gln Ile Phe Lys Thr Ser Ala
145                 150                 155                 160

Thr Lys Gly Thr Gly Leu Asp Glu Ala Met Glu Trp Leu Val Glu Thr
                165                 170                 175

Leu Lys Ser Arg Gln
                180

<210> SEQ ID NO 90
<211> LENGTH: 217
<212> TYPE: PRT
<213> ORGANISM: homo sapiens

<400> SEQUENCE: 90

Met Ser Ser Lys Val Ser Arg Asp Thr Leu Tyr Glu Ala Val Arg Glu
1               5                   10                  15

Val Leu His Gly Asn Gln Arg Lys Arg Arg Lys Phe Leu Glu Thr Val
                20                  25                  30

Glu Leu Gln Ile Ser Leu Lys Asn Tyr Asp Pro Gln Lys Asp Lys Arg
                35                  40                  45

Phe Ser Gly Thr Val Arg Leu Lys Ser Thr Pro Arg Pro Lys Phe Ser
        50                  55                  60

Val Cys Val Leu Gly Asp Gln Gln His Cys Asp Glu Ala Lys Ala Val
65                  70                  75                  80

Asp Ile Pro His Met Asp Ile Glu Ala Leu Lys Lys Leu Asn Lys Asn
                85                  90                  95

Lys Lys Leu Val Lys Lys Leu Ala Lys Lys Tyr Asp Ala Phe Leu Ala
                100                 105                 110

Ser Glu Ser Leu Ile Lys Gln Ile Pro Arg Ile Leu Gly Pro Gly Leu
                115                 120                 125

Asn Lys Ala Gly Lys Phe Pro Ser Leu Leu Thr His Asn Glu Asn Met
        130                 135                 140

Val Ala Lys Val Asp Glu Val Lys Ser Thr Ile Lys Phe Gln Met Lys
145                 150                 155                 160
```

```
Lys Val Leu Cys Leu Ala Val Ala Val Gly His Val Lys Met Thr Asp
                165                 170                 175

Asp Glu Leu Val Tyr Asn Ile His Leu Ala Val Asn Phe Leu Val Ser
            180                 185                 190

Leu Leu Lys Lys Asn Trp Gln Asn Val Arg Ala Leu Tyr Ile Lys Ser
        195                 200                 205

Thr Met Gly Lys Pro Gln Arg Leu Tyr
    210                 215

<210> SEQ ID NO 91
<211> LENGTH: 24
<212> TYPE: DNA
<213> ORGANISM: Artificial Sequence
<220> FEATURE:
<223> OTHER INFORMATION: Primer

<400> SEQUENCE: 91
tggcgcagaa aggaaaagga aaat                                            24

<210> SEQ ID NO 92
<211> LENGTH: 23
<212> TYPE: DNA
<213> ORGANISM: Artificial Sequence
<220> FEATURE:
<223> OTHER INFORMATION: Primer

<400> SEQUENCE: 92
agaggtagct ggcaggatgt tag                                             23

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
cttggtgcga tcagccttat                                                 20

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
ttgatgcatg aaaacagaac tc                                              22

<210> SEQ ID NO 95
<211> LENGTH: 24
<212> TYPE: DNA
<213> ORGANISM: Artificial Sequence
<220> FEATURE:
<223> OTHER INFORMATION: Primer

<400> SEQUENCE: 95
agaattggca gaggctcgtc atca                                            24

<210> SEQ ID NO 96
<211> LENGTH: 24
<212> TYPE: DNA
<213> ORGANISM: Artificial Sequence
<220> FEATURE:
```

```
<223> OTHER INFORMATION: Primer

<400> SEQUENCE: 96
ttccaatttt gccttctcta actg                                              24
```

HUMAN SARCOMA-ASSOCIATED ANTIGENS

FIELD OF THE INVENTION

The invention relates to sarcoma-associated antigens and the nucleic acid molecules that encode them. The invention further relates to the use of the nucleic acid molecules, polypeptides and fragments thereof associated with sarcoma in methods and compositions for the diagnosis and treatment of diseases, such as cancer. More specifically, the invention relates to the discovery of a novel cancer/testis (CT) antigen, NY-SAR-35.

BACKGROUND OF THE INVENTION

The identification of human tumor antigens recognized by the autologous host is yielding new and promising target molecules for immunotherapy, diagnosis and monitoring of human cancer (1-4). Studies of the cellular and humoral immune response to cancer have revealed an extensive repertoire of tumor antigens recognized by the immune system, collectively termed the cancer immunome (5).

The immunome is composed largely of antigens defined by T-cell epitope cloning (1-3, 6, 7), MHC peptide elution (8-10), and serological expression cloning (SEREX, 4, 5, 11-14), and is catalogued in three databases: the peptide database of T-cell defined tumor antigens (authored by members of the Ludwig Institute for Cancer Research (LICR) that is available on the website of Cancer Immunity, Journal of the Academy of Cancer Immunology, cancerimmunity.org/peptidedatabase/Tcellepitopes); the SYFPEITHI database of MHC ligands and peptide motifs (available on the website of Biomedical Informatics-Heidelberg, bmi-heidelberg.com/syfpeithi/) and the SEREX database (available on the website of the LICR, licr.org/SEREX.html).

SEREX is a method of immunoscreening tumor-derived cDNA expression libraries with cancer patient sera in order to identify molecules recognized by high titered IgG antibodies (11) As archived in the SEREX database, approximately 1000 distinct antigens have been defined by SEREX analysis, including a number of etiologically and therapeutically significant cancer antigens, such as mutational antigens (e.g. p53, LKB1, BUB1; refs. 12-14), differentiation antigens (e.g. tyrosinase, NY-BR-1, rab 38; refs. 5, 11, 15), overexpressed gene products (e.g. Her2neu, TPD52, eIF4-gamma; refs. 14, 16) and cancer/testis antigens (e.g. MAGE-1, NY-ESO-1, SSX-2; refs. 4, 11).

Cancer/testis (CT) antigens represent a group of shared, tumor-specific antigens expressed exclusively in developing germ cells of the testis and fetal ovary, as well as in placental trophoblast, and most notably, in a proportion of human cancers of diverse origins (16). On the basis of tissue-restricted expression and immunogenicity, CT antigens are attractive targets for vaccine-based immunotherapies. In general, CT antigens are expressed in 20-40% of specimens from a given tumor type (17-19). One exception to this is synovial sarcoma, in which 80% of specimens express NY-ESO-1 (20) and MAGE antigens (21). Thus, identification of additional CT antigens and other genes having a tumor-associated expression profile is needed for the development of additional therapeutics and diagnostics to permit effective treatment and diagnosis of a broader group of cancer patients.

SUMMARY OF THE INVENTION

The humoral immune response of sarcoma patients to CT antigens was examined using the SEREX method. Sera from patients which showed a humoral immune response to CT antigens were subsequently used to screen cDNA libraries derived from CT-rich sarcoma cell lines, leading to the identification of antigens not before associated with cancer along with several novel antigens associated with a sarcoma-related immune response, including a novel CT antigen, NY-SAR-35.

According to one aspect of the invention, isolated nucleic acid molecules are provided. The isolated nucleic acid molecules are selected from the group consisting of (a) nucleic acid molecules which hybridize under high stringency conditions to a nucleic acid molecule comprising a nucleotide sequence selected from the group consisting of nucleotide sequences set forth as SEQ ID NOs: 1-14 and which code for a sarcoma-associated antigen, (b) nucleic acid molecules that differ from the nucleic acid molecules of (a) or (b) in codon sequence due to the degeneracy of the genetic code, and (c) complements of (a) or (b).

In some embodiments, the isolated nucleic acid molecule includes a nucleotide sequence selected from the group consisting of nucleotide sequences set forth as SEQ ID NOs: 1-14. Preferably the isolated nucleic acid molecule comprises a nucleotide sequence set forth as SEQ ID NO: 10.

According to another aspect of the invention, additional isolated nucleic acid molecules are provided. The isolated nucleic acid molecules are selected from the group consisting of: (a) unique fragments of a nucleotide sequence set forth as SEQ ID NO: 10, which encodes an immunogenic peptide and (b) complements of (a).

In certain embodiments, the isolated nucleic acid molecule includes a nucleotide sequence that is at least about 90% identical to a nucleotide sequence selected from the group consisting of SEQ ID NOs: 1-14; preferably the nucleotide sequence is at least about 95% identical, more preferably the nucleotide sequence is at least about 97% identical, still more preferably the nucleotide sequence is at least about 98% identical, and yet more preferably the nucleotide sequence is at least about 99% identical.

According to further aspects of the invention, expression vectors that include any of the foregoing isolated nucleic acid molecules operably linked to a promoter are provided, as are host cells transformed or transfected with these expression vectors. In certain embodiments, the host cell expresses a MHC molecule, and in some of these embodiments the MHC molecule is expressed recombinantly.

According to another aspect of the invention, isolated polypeptides are provided that are encoded by the foregoing isolated nucleic acid molecules. In certain embodiments, the isolated polypeptide includes an amino acid sequence as set forth in SEQ ID NOs: 46-60 or a fragment thereof that is at least eight amino acids in length.

Another aspect of the invention provides binding polypeptides that selectively binds to the foregoing isolated polypeptides. Preferably these binding polypeptides are isolated also. In preferred embodiments, the binding polypeptides are antibodies or antigen-binding fragments thereof.

According to another aspect of the invention, methods of diagnosing cancer in a subject are provided. The methods include obtaining a biological sample from the subject, and determining the presence of an antibody in the biological sample that binds specifically to one or more sarcoma-associated antigens encoded by a nucleotide sequence selected from the group consisting of SEQ ID NO: 5-7, 10-13 and 15-45. The presence of such antibodies indicates that the subject has cancer.

In some embodiments, the step of determining the presence of an antibody includes contacting the biological sample with one or more sarcoma-associated antigens that are specifically bound by the antibody and are encoded by a nucleic acid molecule comprising a nucleotide sequence selected from the group consisting of (1) nucleotide sequences set forth as SEQ ID NOs: 5-7, 10-13 and 15-45 and (2) nucleotide sequences that are at least 90% identical to the nucleotide sequences of (1), and then determining the binding of the antibody to the sarcoma-associated antigen.

In preferred embodiments, the nucleic acid molecule comprises a nucleotide sequence selected from the group consisting of nucleotide sequences set forth as SEQ ID NOs: 10, 11 and 15, and in particularly preferred embodiments the nucleic acid molecule includes the nucleotide sequence set forth as SEQ ID NO: 10.

In other embodiments, the sarcoma-associated antigen is a polypeptide that includes the amino acid sequence of any of SEQ ID NOs: 50-52, 55-58 and 60-90 or a fragment thereof that is at least eight amino acids in length.

In a particularly preferred embodiment, the sarcoma-associated antigen includes the amino acid sequence set forth as SEQ ID NO: 55 or a fragment thereof that is at least eight amino acids in length.

In certain embodiments, the biological sample is serum. In other embodiments, the one or more sarcoma-associated antigens are produced recombinantly, and/or the one or more sarcoma-associated antigens are bound to a substrate. In some embodiments, the step of determining the binding of the antibody with the one or more sarcoma-associated antigens is performed with an ELISA-based method.

According to still another aspect of the invention, methods for diagnosing cancer in a subject are provided. The methods include obtaining a biological sample from a subject, and determining the expression of a sarcoma-associated antigen or a nucleic acid molecule that encodes it. The nucleic acid molecule includes a nucleotide sequence selected from the group consisting of SEQ ID NOs: 5-7, 10-13 and 15-45 in the biological sample. The expression of the sarcoma-associated antigen or the nucleic acid molecule that encodes it in the sample is diagnostic for cancer in the subject.

In certain embodiments, the sarcoma-associated nucleic acid molecule comprises the nucleotide sequence selected from the group consisting of SEQ ID NOs: 10, 11 and 15. Preferably the sarcoma-associated nucleic acid molecule includes the nucleotide sequence set forth as SEQ ID NO: 10.

In other embodiments, the sarcoma-associated antigen comprises an amino acid sequence selected from the group consisting of SEQ ID NOs: 50-52, 55-58 and 60-90 or a fragment thereof that is at least eight amino acids in length. Preferably the sarcoma-associated antigen includes an amino acid sequence set forth as SEQ ID NO: 55 or a fragment thereof that is at least eight amino acids in length.

According to yet another aspect of the invention, methods for determining onset, progression, or regression of cancer in a subject are provided. The methods include obtaining from a subject a first biological sample, determining the expression of a sarcoma-associated antigen or the nucleic acid molecule that encodes it in the first sample, obtaining from the subject a second biological sample, determining the expression of the sarcoma-associated antigen or the nucleic acid molecule that encodes it in the second sample, and comparing the expression in the first sample to the expression in the second sample as a determination of the onset, progression, or regression of the cancer. The nucleic acid molecule comprises a nucleotide sequence selected from the group consisting of (1) nucleotide sequences set forth as SEQ ID NOs: 5-7, 10-13 and 15-45 and (2) nucleotide sequences that are at least 90% identical to the nucleotide sequences of (1).

In some preferred embodiments, the nucleic acid molecule that encodes the sarcoma-associated antigen includes a nucleotide sequence selected from the group consisting of SEQ ID NO: 10, 11 and 15. Preferably the nucleic acid molecule includes the nucleotide sequence of SEQ ID NO: 10. In other preferred embodiments, the sarcoma-associated antigen includes a polypeptide sequence selected from the group consisting of polypeptide sequences set forth as SEQ ID NOs: 50-52, 55-58 and 60-90 or a fragment thereof that is at least eight amino acids in length. Preferably the sarcoma-associated antigen includes the amino acid sequence of SEQ ID NO: 55 or a fragment thereof that is at least eight amino acids in length.

In some embodiments of the foregoing methods, the step of determining the expression of the sarcoma-associated antigen or the nucleic acid molecule that encodes it includes contacting the biological sample with an agent that selectively binds to the sarcoma-associated antigen or the nucleic acid molecule that encodes it. For methods in which the agent that selectively binds is a nucleic acid molecule, it is preferred that the expression of the sarcoma-associated nucleic acid molecule is determined by nucleic acid hybridization or nucleic acid amplification; particularly preferred embodiments of the methods utilize real-time RT-PCR or RT-PCR as methods of nucleic acid amplification, or use a nucleic acid microarray as a method for nucleic acid hybridization. For methods in which the agent that selectively binds is a polypeptide, the polypeptide preferably is an antibody or antigen-binding fragment thereof. More preferably, the antibody is a monoclonal antibody, particularly a a chimeric, human, or humanized antibody, a single chain antibody, or the antigen-binding fragment is a $F(ab')_2$, Fab, Fd, or Fv fragment. In certain embodiments, the antibody or antigen-binding fragment is labeled with a detectable label, preferably a fluorescent or radioactive label.

In certain embodiments of the foregoing methods, the sample is selected from the group consisting of tissue, cells, and blood. In some preferred embodiments, the cancer is a sarcoma.

In another aspect of the invention, kits for detecting antibodies reactive to a sarcoma-associated antigen in a biological sample are provided. The kits include one or more sarcoma-associated antigens encoded by a nucleic acid molecule comprising a nucleotide sequence selected from the group consisting of nucleotide sequences set forth as SEQ ID NOs: 5-7, 10-13 and 15-45, and instructions for the use of the sarcoma-associated antigens in the detection of antibodies in the biological sample. In a preferred embodiment, the sarcoma-associated nucleic acid molecule comprises the nucleotide sequence set forth as SEQ ID NO: 10. In other embodiments, the sarcoma-associated antigens are bound to a substrate. In further embodiments, the kit also includes a labeling reagent and labeling reagent substrate, and/or a blocking reagent. Additional kit embodiments include secondary antibodies for detection of the antibody bound to the antigen.

In a further aspect of the invention, other kits for the diagnosis of cancer in a subject are provided. The kits include one or more binding agents that specifically bind to a sarcoma-associated antigen or the nucleic acid molecule that encodes it. In this aspect, the nucleic acid molecule includes a nucleotide sequence selected from the group consisting of SEQ ID NOs: 5-7, 10-13 and 15-45. The kit also includes instructions for the use of the binding agents in the diagnosis of cancer. The one or more binding agents are nucleic acid molecules or polypeptides. If the latter, the polypeptides preferably are antibodies or antigen-binding fragments thereof. In other embodiments, the one or more agents are bound to a substrate. Further embodiments of the kits include one or more agents that bind specifically to a cancer-associated antigen other than those encoded by a nucleic acid molecule comprising a nucleotide sequence selected from the group consisting of SEQ ID NOs: 10, 11 and 15. In preferred embodiments, the kit is configured for diagnosis of sarcomas.

According to another aspect of the invention, methods for treating a subject with a disorder characterized by the aberrant expression of a sarcoma-associated antigen or the nucleic acid molecule that encodes it are provided. The methods include administering to a subject an effective amount of an antibody or antigen-binding fragment thereof that specifically binds to the sarcoma-associated antigen. In this aspect, the antigen includes an amino acid sequence selected from the group consisting of SEQ ID NOs: 50-52, 55-58 and 60-90 or a fragment thereof that is eight or more amino acids in length. In a preferred embodiment, the antibody or antigen-binding fragment thereof specifically binds to the extracellular domain of a sarcoma-associated antigen that includes the amino acid sequence of SEQ ID NO: 55 or a fragment thereof that is eight or more amino acids in length.

In certain preferred embodiments, the disorder is cancer, preferably sarcoma. In other embodiments, the antibody used in the methods is a monoclonal antibody, preferably a chimeric, human, or humanized antibody; a single chain antibody; or the antigen-binding fragment is a F(ab')$_2$, Fab, Fd, or Fv fragment.

In other preferred embodiments, the antibody or antigen-binding fragment thereof is bound to a cytotoxic agent. Preferred cytotoxic agents include: calicheamicin, esperamicin, methotrexate, doxorubicin, melphalan, chlorambucil, ARA-C, vindesine, mitomycin C, cisplatinum, etoposide, bleomycin and 5-fluorouracil. Other cytotoxic agents include radioisotopes, including those that emit $\alpha$, $\beta$, and/or $\gamma$ radiation. Preferred radioisotopes include: $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Bo, $^{64}$Cu, $^{212}$Pb, $^{224}$Ra and $^{223}$Ra.

According to another aspect of the invention, methods for treating a subject with a disorder characterized by the aberrant expression of a sarcoma-associated antigen or a nucleic acid molecule that encodes it are provided. The methods include administering an amount of an agent that selectively binds to the sarcoma-associated antigen or the nucleic acid molecule that encodes it effective to treat the disorder. The nucleic acid molecule comprises a nucleotide sequence selected from the group consisting of (a) an isolated nucleic acid molecule comprising a nucleotide sequence that is at least 90% identical to the nucleotide sequence selected from the group consisting of SEQ ID NOs: 5-7, 10-13 and 15-45, and (b) nucleic acid molecules that differ from the nucleic acid molecules of (a) in codon sequence due to the degeneracy of the genetic code. In certain embodiments the disorder is cancer, preferably sarcoma. In other embodiments the sarcoma-associated nucleic acid molecule comprises the nucleotide sequence selected from the group consisting of nucleotide sequences set forth as SEQ ID NOs: 10, 11 and 15. Preferably the sarcoma-associated nucleic acid molecule comprises the nucleotide sequence set forth as SEQ ID NO: 10. In still other embodiments the sarcoma-associated nucleic acid molecule codes for a sarcoma-associated antigen which comprises the polypeptide sequence selected from the group consisting of polypeptide sequences set forth as SEQ ID NOs: 50-52, 55-58 and 60-90 or a fragment thereof that is at least eight amino acids in length. Preferably the sarcoma-associated nucleic acid molecule codes for a sarcoma-associated antigen which comprises the polypeptide sequence set forth as SEQ ID NO: 55 or a fragment thereof that is at least eight amino acids in length.

In certain embodiments, the binding agent is an antisense or RNAi molecule. In other embodiments, the binding agent is a polypeptide, preferably an antibody or antigen-binding fragment thereof. Preferred antibodies include monoclonal antibodies, including chimeric, human, or humanized antibodies, and single chain antibodies; preferred antigen-binding fragments include F(ab')$_2$, Fab, Fd, or Fv fragments. In other embodiments, the antibody or antigen-binding fragment is bound to a cytotoxic agent.

According to yet another aspect of the invention, methods for treating a subject with a disorder characterized by the aberrant expression of a sarcoma-associated antigen or the nucleic acid molecule that encodes it are provided. The methods include administering to the subject an amount of an agent effective to stimulate an immune response to a sarcoma-associated antigen encoded by a nucleic acid molecule comprising a nucleotide sequence that is at least 90% identical to the nucleotide sequence selected from the group consisting of SEQ ID NOs: 5-7, 10-13 and 15-45. In preferred embodiments, the disorder is cancer, particularly sarcoma.

In other embodiments the sarcoma-associated nucleic acid molecule comprises the nucleotide sequence selected from the group consisting of nucleotide sequences set forth as SEQ ID NOs: 10, 11 and 15. Preferably the sarcoma-associated nucleic acid molecule comprises the nucleotide sequence set forth as SEQ ID NO: 10. In still other embodiments the sarcoma-associated antigen includes an amino acid sequence selected from the group consisting of SEQ ID NOs: 50-52, 55-58 and 60-90, or a fragment thereof that is at least eight amino acids in length. Preferably the sarcoma-associated antigen includes the amino acid sequence set forth as SEQ ID NO: 55, or a fragment thereof that is at least eight amino acids in length.

In some embodiments, the agent that stimulates an immune response is a nucleic acid that encodes a sarcoma-associated antigen operably linked to a promoter for expressing the sarcoma-associated antigen; a polypeptide comprising the sarcoma-associated antigen; or a host cell that expresses the sarcoma-associated antigen, particularly a host cell that also expresses a MHC molecule. In preferred embodiments, the agent which stimulates an immune response is a peptide fragment of the sarcoma-associated antigen, or is a complex of a peptide fragment of the sarcoma-associated antigen and a MHC molecule. In other preferred embodiments, the agent also includes an adjuvant or cytokine.

In another aspect of the invention, kits for diagnosing a disorder associated with the aberrant expression of a sarcoma-associated antigen or a nucleic acid molecule that encodes it are provided. The kits include one or more nucleic acid molecules that hybridize to the nucleic acid molecule that encodes the sarcoma-associated antigen comprising a nucleotide sequence selected from the group consisting of nucleotide sequences set forth as SEQ ID NOs: 5-7, 10-13 and 15-45 under high stringency conditions, and instructions for the use of the nucleic acid molecules in the diagnosis of a disorder associated with aberrant expression of the sarcoma-associated antigen or the nucleic acid molecule that encodes it. In some embodiments, the one or more nucleic acid molecules are detectably labeled. Preferably the nucleic acid molecule that encodes the sarcoma-associated antigen comprises the nucleotide sequence set forth as SEQ ID NO: 10.

In certain preferred embodiments, the one or more nucleic acid molecules consist of a first primer and a second primer, wherein the first primer and the second primer are constructed and arranged to selectively amplify at least a portion of a nucleic acid molecule that encodes the sarcoma-associated antigen and comprises a nucleotide sequence selected from the group consisting of SEQ ID NOs: 10, 11 and 15. In other embodiments, the nucleic acids in the kit are bound to a substrate.

In still another aspect of the invention, methods for identifying a cancer-associated antigen are provided. The methods include obtaining a biological sample from one or more subjects, determining the reactivity of the biological sample to one or more known cancer-associated antigens, using the reactive biological sample to screen an expression library to determine the presence of cancer-associated antigens reactive with the biological sample, and isolating a clone that encodes the cancer-associated antigen from the expression library. In certain embodiments the biological sample is serum. In some embodiments the expression library is derived from a tumor, preferably from a tumor cell line.

In still other embodiments, the methods also include determining the identity of the cancer-associated antigen encoded by the isolated clone, preferably by DNA sequencing.

The invention in a further aspect provides a composition including an agent that stimulates an immune response to a sarcoma-associated antigen. Preferred sarcoma-associated antigens are those encoded by a nucleic acid molecule selected from the group consisting of an isolated nucleic acid molecule comprising a nucleotide sequence that is at least 90% identical to the nucleotide sequence selected from the group consisting of SEQ ID NOs: 5-7, 10-13 and 15-45, and nucleic acid molecules that differ from the nucleic acid molecules of (a) in codon sequence due to the degeneracy of the genetic code. In particularly preferred embodiments, the nucleic acid molecule includes a nucleotide sequence selected from the group consisting of SEQ ID NOs: 10, 11 and 15. Most preferably, the the nucleic acid molecule includes the nucleotide sequence set forth as SEQ ID NO: 10.

In some embodiments, sarcoma-associated antigen comprises a polypeptide sequence selected from the group consisting of SEQ ID NOs: 50-52, 55-58 and 60-90 or a fragment thereof that is at least eight amino acids in length. Preferably the sarcoma-associated antigen includes the amino acid sequence of SEQ ID NO: 55 or a fragment thereof that is at least eight amino acids in length.

The agent, in some embodiments, is a nucleic acid that encodes a sarcoma-associated antigen operably linked to a promoter for expressing the sarcoma-associated antigen. In other embodiments, the agent is a polypeptide comprising the sarcoma-associated antigen. In still other embodiments, the agent is a host cell that expresses the sarcoma-associated antigen; preferably the host cell also expresses a MHC molecule. In yet other embodiments, the agent is a complex of a peptide derived from the sarcoma-associated antigen and a MHC molecule.

The composition also includes, in certain embodiments, an adjuvant or cytokine and/or one or more cytotoxic or chemotherapeutic agents. The compositions optionally includes a pharmaceutically acceptable carrier.

In another aspect of the invention, compositions are provided that include an agent that selectively binds to a sarcoma-associated antigen or a nucleic acid molecule that encodes it. The nucleic acid molecule includes a nucleotide sequence selected from the group consisting of: (a) an isolated nucleic acid molecule comprising a nucleotide sequence that is at least 90% identical to the nucleotide sequence selected from the group consisting of SEQ ID NOs: 5-7 and 10-13 and (b) nucleic acid molecules that differ from the nucleic acid molecules of (a) in codon sequence due to the degeneracy of the genetic code. Preferably the nucleic acid molecule includes a nucleotide sequence selected from the group consisting of SEQ ID NOs: 10 and 11; preferably the nucleic acid molecule includes the nucleotide sequence set forth as SEQ ID NO: 10. In other embodiments, the sarcoma-associated antigen includes the amino acid sequence set forth as SEQ ID NO: 55 or a fragment thereof that is at least eight amino acids in length. The agents in this aspect of the invention include nucleic acids and polypeptides, preferably antibodies or antigen-binding fragments thereof. Preferred antibodies include monoclonal antibodies (particularly chimeric, human, or humanized antibodies), and single chain antibodies; preferred antibody fragments include $F(ab')_2$, Fab, Fd, or Fv fragments.

In certain embodiments, the antibody or antigen-binding fragment is conjugated to cytotoxic or chemotherapeutic agent. In other embodiments, the composition includes one or more cytotoxic or chemotherapeutic agent. In still other embodiments, the composition includes a pharmaceutically acceptable carrier.

The invention also involves the use of the genes, gene products, fragments thereof, agents which bind thereto, and other compositions and molecules described herein in the preparation of medicaments. A particular medicament is for treating cancer.

These and other aspects of the invention will be described in further detail in connection with the detailed description of the invention.

BRIEF DESCRIPTION OF THE DRAWING

FIG. 1 provides the mRNA expression patterns of serologically defined sarcoma antigens. FIG. 1A shows the results of the RT-PCR analysis of NY-SAR-12, -35, and -41 in a panel of 17 normal tisues (Lanes 1, brain; 2, kidney; 3, liver; 4, pancreas; 5, placenta; 6, testis; 7, fetal brain; 8, small intestine; 9, heart; 10, prostate; 11, adrenal gland; 12, spleen; 13, colon; 14, stomach; 15, lung; 16, bladder; and 17, ovary). FIG. 1B provides the results of the quantitative real-time RT-PCR analysis of NY-SAR-35 in various normal tissues. FIG. 1C shows the results of the RT-PCR analysis of NY-SAR-35 expression in sarcoma cell lines and sarcoma tissue (Lane 1, fibrosarcoma; 2, rhabdomyosarcoma; 3, leiomyosarcoma; and 4, normal testis). FIG. 1D provides the results of the Northern blot analysis of NY-SAR-35 in various normal tissues (Lane 1, spleen; 2, thymus; 3, prostate; 4, testis; 5, ovary; 6, small intestine; 7, colon mucosa; and 8, peripheral blood leukocytes).

DETAILED DESCRIPTION OF THE INVENTION

The screening of cDNA expression libraries derived from human tumors with autologous antibody (SEREX) has proven to be a powerful method for defining the structure of tumor antigens recognized by the humoral immune system, and has led to the identification of new targets for cancer immunotherapy. The current study examined the humoral immune response of sarcoma patients to CT antigens. Sera from patients which showed a humoral immune response to CT antigens were subsequently used to screen cDNA libraries derived from CT-rich sarcoma cell lines, leading to the identification of antigens not before associated with cancer along with several novel antigens associated with a sarcoma-related immune response, including a novel CT antigen, NY-SAR-35.

Sarcoma-associated antigens were identified with an optimized SEREX analysis method. A cell line that is rich in CT antigen expression was chosen as the source of cDNA. Additionally, sera was obtained from a group of patients that were actively mounting a humoral immune response to a panel of known CT antigens. This optimized SEREX analysis led to the identification of 72 antigens reactive with serum IgG of 5 sarcoma patients. The antigens identified were further evaluated for cancer-restricted expression and the frequency of eliciting antibody responses in normal individuals as well as cancer patients.

Twenty-four of the 72 antigens (33%) had a serological profile that was not restricted to cancer patients, as evidenced by their reactivity with normal sera, while the remaining 48 antigens had a cancer-related serological profile, reacting only with sera from cancer patients. Notable antigens belonging to this latter category include the CT antigens, NY-SAR-36/SSX-1, NY-SAR-43/SSX-4 and NY-SAR-35. Although the antibody response to NY-SAR-4/FH was most frequent, occurring in 5/39 (13%) sarcoma patients, no individual antigen was serodominant. NY-SAR-4 is equivalent to fumarate hydratase (FH), an enzyme of the tricarboxylic acid cycle. This serological response to NY-SAR-4/FH may be of interest given the recent finding that germ line mutations in the FH gene are associated with a predisposition to uterine and cutaneous leiomyomata, and also renal cell carcinoma (37).

In addition, 6 tissue-restricted antigens, LAGE-1/NY-SAR-17, SSX1/NY-SAR-36, SSX4/NY-SAR-43, NESG1/NY-SAR-12, NY-SAR-35, and NY-SAR-41 were identified. Two of these antigens, NY-SAR-35, and NY-SAR-41 are novel gene products, and a third, NESG1/NY-SAR-12 (27), has not been previously studied in relation to cancer. NY-SAR-35 further represents a newly defined CT antigen expressed exclusively in normal testis, melanoma, sarcoma, lung cancer and breast cancer.

Table 1, below, provides a list of the sarcoma-associated antigens and their corresponding sequence identification numbers. The antigens listed include those that were found to be novel gene products as well as those sarcoma-associated antigens that exhibited cancer-restricted expression.

TABLE 1

Sarcoma-Associated Antigens (Novel Gene Products and Cancer-Restricted Expression)

| NY-SAR-Antigen | Sequence Identification Number (nucleotide and amino acid sequence, respectively) |
|---|---|
| 3 | SEQ ID NOs: 1 and 46 |
| 10 | SEQ ID NOs: 2 and 47 |
| 16 | SEQ ID NOs: 3 and 48 |
| 22 | SEQ ID NOs: 4 and 49 |
| 23 | SEQ ID NOs: 5 and 50 |
| 24 | SEQ ID NOs: 6 and 51 |
| 27 | SEQ ID NOs: 7 and 52 |
| 28 | SEQ ID NOs: 8 and 53 |
| 29 | SEQ ID NOs: 9 and 54 |
| 35 | SEQ ID NOs: 10 and 55 |
| 41 | SEQ ID NOs: 11 and 56 |
| 48 | SEQ ID NOs: 12 and 57 |
| 62 | SEQ ID NOs: 13 and 58 |
| 71 | SEQ ID NOs: 14 and 59 |
| 12 | SEQ ID NOs: 15 and 60 |
| 4 | SEQ ID NOs: 16 and 61 |
| 5 | SEQ ID NOs: 17 and 62 |
| 8 | SEQ ID NOs: 18 and 63 |
| 9 | SEQ ID NOs: 19 and 64 |
| 20 | SEQ ID NOs: 20 and 65 |
| 21 | SEQ ID NOs: 21 and 66 |
| 25 | SEQ ID NOs: 22 and 67 |
| 26 | SEQ ID NOs: 23 and 68 |

TABLE 1-continued

Sarcoma-Associated Antigens (Novel Gene Products and Cancer-Restricted Expression)

| NY-SAR-Antigen | Sequence Identification Number (nucleotide and amino acid sequence, respectively) |
|---|---|
| 30 | SEQ ID NOs: 24 and 69 |
| 34 | SEQ ID NOs: 25 and 70 |
| 36 | SEQ ID NOs: 26 and 71 |
| 37 | SEQ ID NOs: 27 and 72 |
| 38 | SEQ ID NOs: 28 and 73 |
| 39 | SEQ ID NOs: 29 and 74 |
| 40 | SEQ ID NOs: 30 and 75 |
| 42 | SEQ ID NOs: 31 and 76 |
| 43 | SEQ ID NOs: 32 and 77 |
| 46 | SEQ ID NOs: 33 and 78 |
| 49 | SEQ ID NOs: 34 and 79 |
| 50 | SEQ ID NOs: 35 and 80 |
| 51 | SEQ ID NOs: 36 and 81 |
| 52 | SEQ ID NOs: 37 and 82 |
| 56 | SEQ ID NOs: 38 and 83 |
| 57 | SEQ ID NOs: 39 and 84 |
| 59 | SEQ ID NOs: 40 and 85 |
| 60 | SEQ ID NOs: 41 and 86 |
| 63 | SEQ ID NOs: 42 and 87 |
| 67 | SEQ ID NOs: 43 and 88 |
| 69 | SEQ ID NOs: 44 and 89 |
| 70 | SEQ ID NOs: 45 and 90 |

The invention relates, in part, to the sarcoma-associated antigens defined herein and the nucleic acid molecules that encode them. The invention further relates to the use of the nucleic acid molecules, polypeptides and fragments thereof associated with sarcoma in methods and compositions for the diagnosis and treatment of diseases, such as cancer.

As used herein, the term "sarcoma-associated antigens" means polypeptides that elicit specific immune responses to the polypeptide when expressed by a tumor cell and thus, include sarcoma-associated polypeptides (including proteins) and fragments of sarcoma-associated polypeptides, that are recognized by the immune system (e.g., by antibodies and/or T lymphocytes). In part, the invention relates to sarcoma-associated antigens as well as the nucleic acid molecules that encode the sarcoma-associated antigens. As used herein, the "nucleic acid molecules that encode" means the nucleic acid molecules that code for the immunogenic sarcoma-associated polypeptides or immunogenic fragments thereof. These nucleic acid molecules may be DNA or may be RNA (e.g. mRNA). The sarcoma-associated nucleic acid molecules of the invention also encompass variants of the nucleic acid molecules described herein. These variants may be splice variants or allelic variants of certain sequences provided. Variants of the nucleic acid molecules of the invention are intended to include homologs and alleles which are described further below. Further, as used herein, the term "sarcoma-associated molecules" includes sarcoma-associated antigens (polypeptides and fragments thereof) as well as sarcoma-associated nucleic acids. In all embodiments, human sarcoma-associated antigens and the encoding nucleic acid molecules thereof, are preferred.

In one aspect, the invention provides isolated nucleic acid molecules that encode the sarcoma-associated antigens defined herein. The isolated nucleic acid molecules of this aspect of the invention comprise: (a) nucleotide sequences selected from the group consisting of nucleotide sequences set forth as SEQ ID NOs: 1-14, (b) isolated nucleic acid molecules which hybridize under highly stringent conditions to the nucleic acid molecules of (a) and which code for a sarcoma-associated antigen, (c) nucleic acid molecules that differ from (a) or (b) due to the degeneracy of the genetic code, and (d) complements of (a), (b) or (c).

As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The sarcoma-associated nucleic acid molecules of the invention also intended to encompass homologs and alleles which can be identified by conventional techniques. Identification of human and other organism homologs of sarcoma-associated polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode sarcoma-associated antigens identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH2PO4(pH 7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the sarcoma-associated nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or at least 95% amino acid identity to the sequences of sarcoma-associated nucleic acids and polypeptides, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In another aspect of the invention, unique fragments are provided which include unique fragments of the nucleotide sequences of the invention and complements thereof. The invention, in a preferred embodiment, provides unique fragments of SEQ ID NO: 10 and complements thereof. A unique fragment is one that is a 'signature' for the larger nucleic acid. It, for example, is long enough to assure that its precise sequence is not found in molecules outside of the nucleic acid molecules that encode the sarcoma-associated antigens defined above. Those of ordinary skill in the art may apply no more than routine procedures to determine if a fragment is unique within the human genome.

Unique fragments can be used as probes in Southern blot assays to identify such nucleic acid molecules, or can be used as probes in amplification assays such as those employing the polymerase chain reaction (PCR), including, but not limited to RT-PCR and RT-real-time PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of the sarcoma-associated polypeptides useful, for example, in the preparation of antibodies and in immunoassays.

In screening for sarcoma-associated antigen genes, a Southern blot may be performed using the foregoing conditions, together with a detectably labeled probe (e.g. radioactive or chemiluminescent probes). After washing the membrane to which the DNA is finally transferred, the membrane can be placed against X-ray film or analyzed using a phosphorimager device to detect the radioactive or chemiluminescent signal. In screening for the expression of sarcoma-associated antigen nucleic acids, Northern blot hybridizations using the foregoing conditions can be performed on samples taken from cancer patients or subjects suspected of having a condition characterized by abnormal cell proliferation or neoplasia. Amplification protocols such as polymerase chain reaction using primers that hybridize to the sequences presented also can be used for detection of the sarcoma-associated antigen genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library (e.g., testis). One also can use expression cloning utilizing the antisera described herein to identify nucleic acids that encode related antigenic proteins in humans or other species using the SEREX procedure to screen the appropriate expression libraries. (See: Sahin et al. Proc. Natl. Acad. Sci. USA 92:11810-11813, 1995).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating sarcoma-associated polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5; 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of activity or structural relation to the nucleic acids and/or polypeptides disclosed herein. As used herein the terms: "deletion", "addition", and "substitution" mean deletion, addition, and substitution changes to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acids of a sequence of the invention.

According to yet another aspect of the invention, an expression vector comprising any of the isolated nucleic acid molecules of the invention, preferably operably linked to a promoter is provided. In a related aspect, host cells transformed or transfected with such expression vectors also are provided. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., -galactosidase or alkaline phosphatase, and genes which visibly affect the phenotype of transformed or transfected cells, hosts, colonies or plaques, e.g., green fluorescent protein. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

It will also be recognized that the invention embraces the use of the sarcoma-associated nucleic acid molecules and genomic sequences in expression vectors, as well as to transfect host cells and cell lines, be these prokaryotic, e.g., *E. coli*, or eukaryotic, e.g., CHO cells, COS cells, yeast expression systems, and recombinant baculovirus expression in insect cells. Especially useful are mammalian cells such as human, mouse, hamster, pig, goat, primate, etc. They may be of a wide variety of tissue types, including mast cells, fibroblasts, oocytes, and lymphocytes, and may be primary cells and cell lines. Specific examples include dendritic cells, peripheral blood leukocytes, bone marrow stem cells and embryonic stem cells. The expression vectors require that the pertinent sequence, i.e., those nucleic acids described supra, be operably linked to a promoter.

The invention, in one aspect, also permits the construction of sarcoma-associated antigen gene "knock-outs" and "knock-ins" in cells and in animals, providing materials for studying certain aspects of cancer and immune system responses to cancer.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA or RNA encoding a sarcoma-associated antigen, a mutant sarcoma-associated antigen, fragments, or variants thereof. The heterologous DNA or RNA is placed under operable control of transcriptional elements to permit the expression of the heterologous DNA in the host cell.

Preferred systems for mRNA expression in mammalian cells are those such as pcDNA1.1 and pCDM8 (Invitrogen) that contain a selectable marker (which facilitates the selection of stably transfected cell lines) and contain the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1, which stimulates efficiently transcription in vitro. The plasmid is described by Mizushima and Nagata (Nuc. Acids Res. 18:5322, 1990), and its use in transfection experiments is disclosed by, for example, Demoulin (Mol. Cell. Biol. 16:4710-4716, 1996). Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is described by Warnier et al., in intradermal injection in mice for immunization against P1A (Int. J. Cancer, 67:303-310, 1996).

The invention also embraces kits termed expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also includes kits for amplification of a sarcoma-associated antigen nucleic acid, including at least one pair of amplification primers which hybridize to a sarcoma-associated nucleic acid. The primers preferably are 12-32 nucleotides in length and are non-overlapping to prevent formation of "primer-dimers". One of the primers will hybridize to one strand of the sarcoma-associated nucleic acid and the second primer will hybridize to the complementary strand of the sarcoma-associated nucleic acid, in an arrangement which permits amplification of the sarcoma-associated nucleic acid. Selection of appropriate primer pairs is standard in the art. For example, the selection can be made with assistance of a computer program designed for such a purpose, optionally followed by testing the primers for amplification specificity and efficiency.

The invention, in another aspect provides isolated polypeptides (including whole proteins and partial proteins) encoded by the foregoing sarcoma-associated nucleic acids. Examples of the amino acid sequences encoded by the foregoing sarcoma-associated nucleic acids are set forth as SEQ ID NOs: 46-90. The amino acids of the invention are also intended to encompass amino acid sequences that result from the translation of the nucleic acid sequences provided herein in a different reading frame. In one preferred embodiment of the invention a polypeptide is provided which comprises the polypeptide sequence set forth as SEQ ID NO: 55. Such polypeptides are useful, for example, alone or as fusion proteins to generate antibodies, and as components of an immunoassay or diagnostic assay. Immunogenic sarcoma-associated polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Fragments of the immunogenic sarcoma-associated polypeptides (including immunogenic peptides) also can be synthesized chemically using well-established methods of peptide synthesis. Thus, fragments of the disclosed polypeptides are useful for eliciting an immune response. In one embodiment fragments of a polypeptide which comprises SEQ ID NO: 55 that are at least eight amino acids in length and exhibit immunogenicity are provided.

Fragments of a polypeptide preferably are those fragments that retain a distinct functional capability of the polypeptide. Functional capabilities that can be retained in a fragment of a polypeptide include interaction with antibodies or MHC molecules (e.g. immunogenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment that can be used for inducing an immune response will depend upon factors such as whether the epitope recognized by an antibody is a linear epitope or a conformational epitope or the particular MHC molecule that binds to and presents the fragment (e.g. HLA class I or II). Thus, some immunogenic fragments of sarcoma-associated polypeptides will consist of longer segments while others will consist of shorter segments, (e.g. 5, 6, 7, 8, 9, 10, 11 or 12 or more amino acids long, including each integer up to the full length of the sarcoma-associated polypeptide). Those skilled in the art are well versed in methods for selecting immunogenic fragments of polypeptides.

The invention embraces variants of the sarcoma-associated polypeptides described above. As used herein, a "variant" of a sarcoma-associated antigen polypeptide is a polypeptide which contains one or more modifications to the primary amino acid sequence of a sarcoma-associated polypeptide. Modifications which create a sarcoma-associated antigen variant can be made to a sarcoma-associated polypeptide 1) to reduce or eliminate an activity of a sarcoma-associated polypeptide; 2) to enhance a property of a sarcoma-associated polypeptide, such as protein stability in an expression system or the stability of protein-protein binding; 3) to provide a novel activity or property to a sarcoma-associated polypeptide, such as addition of an antigenic epitope or addition of a detectable moiety; or 4) to provide equivalent or better binding to a MHC molecule.

Modifications to a sarcoma-associated polypeptide are typically made to the nucleic acid which encodes the sarcoma-associated polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the sarcoma-associated antigen amino acid sequence. One of skill in the art will be familiar with methods for predicting the effect on protein conformation of a change in protein sequence, and can thus "design" a variant sarcoma-associated polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a sarcoma-associated polypeptide can be proposed and tested to determine whether the variant retains a desired conformation.

In general, variants include sarcoma-associated polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a sarcoma-associated polypeptide by eliminating proteolysis by proteases in an expression system (e.g., dibasic amino acid residues in yeast expression systems in which KEX2 protease activity is present).

Mutations of a nucleic acid which encode a sarcoma-associated polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant sarcoma-associated polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a sarcoma-associated antigen gene or cDNA clone to enhance expression of the polypeptide. The activity of variants of sarcoma-associated polypeptides can be tested by cloning the gene encoding the variant sarcoma-associated polypeptide into a bacterial or mammalian expression vector, introducing the vector into an appropriate host cell, expressing the variant sarcoma-associated polypeptide, and testing for a functional capability of the sarcoma-associated polypeptides as disclosed herein. For example, the variant sarcoma-associated polypeptide can be tested for reaction with autologous or allogeneic sera as described in the Examples. Preparation of other variant polypeptides may favor testing of other activities, as will be known to one of ordinary skill in the art.

The skilled artisan will also realize that conservative amino acid substitutions may be made in immunogenic sarcoma-associated polypeptides to provide functionally equivalent variants, or homologs of the foregoing polypeptides, i.e., the variants retain the functional capabilities of the immunogenic sarcoma-associated polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants or homologs of the sarcoma-associated polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the sarcoma-associated antigens disclosed herein and retain the specific antibody-binding characteristics of the antigens.

Likewise, upon determining that a peptide derived from a sarcoma-associated polypeptide is presented by an MHC molecule and recognized by antibodies or T lymphocytes (e.g., helper T cells or CTLs), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03 182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.*

43:13-18, 1995; Drijfhout et al., *Human Immunol.* 43:1-12, 1995). The substituted peptides can then be tested for binding to the MHC molecule and recognition by antibodies or T lymphocytes when bound to MHC. These variants can be tested for improved stability and are useful, inter alia, in vaccine compositions.

Conservative amino-acid substitutions in the amino acid sequence of sarcoma-associated polypeptides to produce functionally equivalent variants of sarcoma-associated polypeptides typically are made by alteration of a nucleic acid encoding a sarcoma-associated polypeptide. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a gene encoding a sarcoma-associated polypeptide. Where amino acid substitutions are made to a small unique fragment of a sarcoma-associated polypeptide, such as an antigenic epitope recognized by autologous or allogeneic sera or T lymphocytes, the substitutions can be made by directly synthesizing the peptide. The activity of functionally equivalent variants of sarcoma-associated polypeptides can be tested by cloning the gene encoding the altered sarcoma-associated polypeptide into a bacterial or mammalian expression vector, introducing the vector into an appropriate host cell, expressing the altered polypeptide, and testing for a functional capability of the sarcoma-associated polypeptides as disclosed herein. Peptides that are chemically synthesized can be tested directly for function, e.g., for binding to antisera recognizing associated antigens.

The invention as described herein has a number of uses, some of which are described elsewhere herein. In one aspect of the invention a method of identifying cancer-associated antigens is provided. Novel cancer-associated antigens can be identified by obtaining a biological sample from a subject, determining the reactivity of the biological sample with one or more known cancer-associated antigens, and subsequently using the reactive biological sample to screen an expression library to identify novel cancer-associated antigens as well as proteins previously known but not previously associated with cancer.

As used herein, a "subject" is preferably a human, non-human primate, cow, horse, pig, sheep, goat, dog, cat or rodent. In all embodiments, human subjects are preferred. In some embodiments, the subject is suspected of having cancer or has been diagnosed with cancer. Cancers in which the sarcoma-associated nucleic acid or polypeptide are differentially expressed include sarcoma.

As used herein, a biological sample includes, but is not limited to: tissue, cells, or body fluid (e.g. serum, blood, lymph node fluid, etc.). The fluid sample may include cells and/or fluid. The tissue and cells may be obtained from a subject or may be grown in culture (e.g. from a cell line). As used herein, a biological sample is body fluid, tissue or cells obtained from a subject using methods well-known to those of ordinary skill in the related medical arts.

The invention in another aspect permits the isolation of the cancer-associated antigens described herein. A variety of methodologies well-known to the skilled practitioner can be utilized to obtain isolated cancer-associated antigens. The proteins may be purified from cells which naturally produce the protein by chromatographic means or immunological recognition. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce the protein. Those skilled in the art also can readily follow known methods for isolating cancer-associated antigens. These include, but are not limited to, chromatographic techniques such as immunochromatography, HPLC, size-exclusion chromatography, ion-exchange chromatography, and immune-affinity chromatography.

The invention also involves diagnosing or monitoring cancer in subjects by determining the presence of an immune response to one or more sarcoma-associated antigens of the invention. In preferred embodiments, this determination is performed by assaying a bodily fluid obtained from the subject, preferably serum, blood, or lymph node fluid for the presence of antibodies against the sarcoma-associated antigens described herein. This determination may also be performed by assaying a tissue or cells from the subject for the presence of one or more sarcoma-associated antigens (or nucleic acid molecules that encode these antigens) described herein. In another embodiment, the presence of antibodies against at least one additional cancer antigen is determined for diagnosis of cancer. The additional antigen may be a sarcoma-associated antigen as described herein or may be some other cancer-associated antigen. This determination may also be performed by assaying a tissue or cells from the subject for the presence of the sarcoma-associated antigens described herein.

Measurement of the immune response against one of the sarcoma-associated antigens over time by sequential determinations permits monitoring of the disease and/or the effects of a course of treatment. For example, a sample, such as serum, blood, or lymph node fluid, may be obtained from a subject, tested for an immune response to one of the sarcoma-associated antigens, and at a second, subsequent time, another sample, may be obtained from the subject and similarly tested. The results of the first and second (or subsequent) tests can be compared as a measure of the onset, regression or progression of cancer, or, if cancer treatment was undertaken during the interval between obtaining the samples, the effectiveness of the treatment may be evaluated by comparing the results of the two tests. In preferred embodiments the sarcoma-associated antigens are bound to a substrate. In other preferred embodiments the immune response of the biological sample to the sarcoma-associated antigens is determined with ELISA. Other methods will be apparent to one of skill in the art.

Diagnostic methods of the invention also involve determining the aberrant expression of one or more of the sarcoma-associated antigens described herein or the nucleic acid molecules that encode them. Such determinations can be carried out via any standard nucleic acid assay, including the polymerase chain reaction or assaying with hybridization probes, which may be labeled, or by assaying biological samples with binding partners (e.g., antibodies) for sarcoma-associated antigens.

The diagnostic methods of the invention can be used to detect the presence of a disorder associated with aberrant expression of a sarcoma-associated molecule, as well as to assess the progression and/or regression of the disorder such as in response to treatment (e.g., chemotherapy, radiation). According to this aspect of the invention, the method for diagnosing a disorder characterized by aberrant expression of a sarcoma-associated molecule involve: detecting expression of a sarcoma-associated molecule in a first biological sample obtained from a subject, wherein differential expression of the sarcoma-associated molecule compared to a control sample indicates that the subject has a disorder characterized by aberrant expression of a sarcoma-associated molecule, such as cancer.

As used herein, "aberrant expression" of a sarcoma-associated antigen is intended to include any expression that is statistically significant from the expected amount of expression. For example, expression of a sarcoma-associated molecule (i.e., the sarcoma-associated antigen or the nucleic acid molecules that encode it) in a tissue that is not expected to express the sarcoma-associated molecule would be included in the definition of "aberrant expression". Likewise, expression of the sarcoma-associated molecule that is determined to be expressed at a significantly higher or lower level than expected is also included. Therefore, a determination of the level of expression of one or more of the sarcoma-associated antigens and/or the nucleic acids that encode them is diagnostic of cancer if the level of expression is above a baseline level determined for that tissue type. The baseline level of expression can be determined using standard methods known to those of skill in the art. Such methods include, for example, assaying a number of histologically normal tissue samples from subjects that are clinically normal (i.e. do not have clinical signs of cancer in that tissue type) and determining the mean level of expression for the samples.

The level of expression of the nucleic acid molecules of the invention or the antigens they encode can indicate cancer in the tissue when the level of expression is significantly more in the tissue than in a control sample. In some embodiments, a level of expression in the tissues that is at least about 5%, 10%, 20%, 30%, 40%, 50%, 60%, 70%, 80%, 90%, 100%, 150%, 200%, 250%, 300%, 400%, or 500% more than the level of expression in the control tissue indicates cancer in the tissue.

As used herein the term "control" means predetermined values, and also means samples of materials tested in parallel with the experimental materials. Examples include samples from control populations or control samples generated through manufacture to be tested in parallel with the experimental samples.

As used herein the term "control" includes positive and negative controls which may be a predetermined value that can take a variety of forms. The control(s) can be a single cut-off value, such as a median or mean, or can be established based upon comparative groups, such as in groups having normal amounts of sarcoma-associated molecules of the invention and groups having abnormal amounts of sarcoma-associated molecules of the invention. Another example of a comparative group is a group having a particular disease, condition and/or symptoms and a group without the disease, condition and/or symptoms. Another comparative group is a group with a family history of a particular disease and a group without such a family history of the particular disease. The predetermined control value can be arranged, for example, where a tested population is divided equally (or unequally) into groups, such as a low-risk group, a medium-risk group and a high-risk group or into quadrants or quintiles, the lowest quadrant or quintile being individuals with the lowest risk or lowest expression levels of a sarcoma-associated molecule of the invention that is up-regulated in cancer and the highest quadrant or quintile being individuals with the highest risk or highest expression levels of a sarcoma-associated molecule of the invention that is up-regulated in cancer.

The predetermined value of a control will depend upon the particular population selected. For example, an apparently healthy population will have a different "normal" sarcoma-associated molecule expression level range than will a population which is known to have a condition characterized by aberrant expression of the sarcoma-associated molecule. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. As used herein, the term "increased expression" means a higher level of expression relative to a selected control.

The invention involves in some aspects diagnosing or monitoring cancer by determining the level of expression of one or more sarcoma-associated nucleic acid molecules and/or determining the level of expression of one or more sarcoma-associated polypeptides they encode. In some important embodiments, this determination is performed by assaying a tissue sample from a subject for the level of expression of one or more sarcoma-associated nucleic acid molecules or for the level of expression of one or more sarcoma-associated polypeptides encoded by the nucleic acid molecules of the invention.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

These methods of determining the presence and/or level of the molecules of the invention in cells and tissues may include use of labels to monitor the presence of the molecules of the invention. Such labels may include, but are not limited to radiolabels or chemiluminescent labels, which may be utilized to determine whether a molecule of the invention is expressed in a cell or tissue, and to determine the level of expression in the cell or tissue. For example, a fluorescently labeled or radiolabeled antibody that selectively binds to a polypeptide of the invention may be contacted with a tissue or cell to visualize the polypeptide in vitro or in vivo. These and other in vitro and in vivo imaging methods for determining the presence of the nucleic acid and polypeptide molecules of the invention are well known to those of ordinary skill in the art.

The invention, therefore, also involves the use of agents such as polypeptides that bind to sarcoma-associated antigens. Such agents can be used in methods of the invention including the diagnosis and/or treatment of cancer. Such binding agents can be used, for example, in screening assays to detect the presence or absence of sarcoma-associated antigens and can be used in quantitative binding assays to determine levels of expression in biological samples and cells. Such agents also may be used to inhibit the native activity of the sarcoma-associated polypeptides, for example, by binding to such polypeptides.

According to this aspect, the binding polypeptides bind to an isolated nucleic acid or protein of the invention, including unique fragments thereof. Preferably, the binding polypeptides bind to a sarcoma-associated polypeptide, or a unique fragment thereof.

In preferred embodiments, the binding polypeptide is an antibody or antibody fragment, more preferably, an Fab or F(ab)$_2$ fragment of an antibody. Typically, the fragment includes a CDR3 region that is selective for the sarcoma-associated antigen. Any of the various types of antibodies can be used for this purpose, including polyclonal antibodies, monoclonal antibodies, humanized antibodies, and chimeric antibodies.

Thus, the invention provides agents which bind to sarcoma-associated antigens encoded by sarcoma-associated nucleic acid molecules of the invention, and in certain embodiments preferably to unique fragments of the sarcoma-associated polypeptides. Such binding partners can be used in screening assays to detect the presence or absence of a sarcoma-associated antigen and in purification protocols to isolate such sarcoma-associated antigens. Likewise, such binding partners can be used to selectively target drugs, toxins or other molecules (including detectable diagnostic molecules) to cells which express sarcoma-associated antigens. In this manner, for example, cells present in solid or non-solid tumors which express sarcoma-associated proteins can be treated with cytotoxic compounds that are selective for the sarcoma-associated molecules (nucleic acids and/or antigens). Such binding agents also can be used to inhibit the native activity of the sarcoma-associated antigen, for example, to further characterize the functions of these molecules.

The antibodies of the present invention thus are prepared by any of a variety of methods, including administering a protein, fragments of a protein, cells expressing the protein or fragments thereof and the like to an animal to induce polyclonal antibodies. The present invention also provides methods of producing monoclonal antibodies to the sarcoma-associated molecules of the invention described herein. The production of monoclonal antibodies is according to techniques well known in the art. As detailed herein, such antibodies may be used for example to identify tissues expressing protein or to purify protein. Antibodies also may be coupled to specific labeling agents or imaging agents, including, but not limited to a molecule preferably selected from the group consisting of fluorescent, enzyme, radioactive, metallic, biotin, chemiluminescent, bioluminescent, chromophore, or colored, etc. In some aspects of the invention, a label may be a combination of the foregoing molecule types.

Significantly, as is well-known in the art, only a small portion of an antibody molecule, the paratope, is involved in the binding of the antibody to its epitope (see, in general, Clark, W. R. (1986) The Experimental Foundations of Modem Immunology Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to sarcoma-associated antigens. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

The sarcoma-associated antigens of the invention can be used to screen peptide libraries, including phage display libraries, to identify and select peptide binding partners of the sarcoma-assoc iated antigens of the invention. Such molecules can be used, as described, for screening assays, for diagnostic assays, for purification protocols or for targeting drugs, toxins and/or labeling agents (e.g., radioisotopes, fluorescent molecules, etc.) to cells which express sarcoma-associated molecules such as cancer cells which have aberrant sarcoma-associated expression.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the sarcoma-associated antigen. This process can be repeated through several cycles of reselection of phage that bind to the sarcoma-associated polypeptide. Repeated rounds lead to enrichment of phage bearing particular sequences. DNA sequence analysis can be conducted to identify the sequences of the expressed polypeptides. The minimal linear portion of the sequence that binds to the sarcoma-associated polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the sarcoma-associated antigens.

As detailed herein, the foregoing antibodies and other binding molecules may be used to identify tissues with normal or aberrant expression of a sarcoma-associated antigen. Antibodies also may be coupled to specific diagnostic labeling agents for imaging of cells and tissues with normal or aberrant sarcoma-associated antigen expression or to therapeutically useful agents according to standard coupling procedures. As used herein, "therapeutically useful agents" include any therapeutic molecule which desirably is targeted selectively to a cell or tissue selectively with an aberrant sarcoma-associated expression.

Diagnostic agents for in vivo use include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99, iodine-131 and indium-111, and nuclides for nuclear magnetic resonance such as fluorine and gadolinium. Other diagnostic agents useful in the invention will be apparent to one of ordinary skill in the art.

The antibodies of the present invention can also be used to therapeutically target sarcoma-associated antigens. In a preferred embodiment, antibodies can be used to target antigens expressed on the cell surface, such as NY-SAR-35. These antibodies can be linked not only to a detectable marker but also an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I, or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents that may be conjugated to the anti-PSMA antibodies of the present invention include dolastatins (U.S. Pat. Nos. 6,034,065 and 6,239,104) and derivatives thereof. Of particular interest is dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., *Anticancer Drug Des.* 13(4):243-277, 1998; Woyke, T. et al., *Antimicrob. Agents Chemother.* 45(12):3580-3584, 2001), and aurastatin E and the like. Toxins that are less preferred in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Other chemotherapeutic agents are known to those skilled in the art.

Agents that act on the tumor vasculature can include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein) and interferon inducible protein 10 (U.S. Pat. No. 5,994,292). A number of antiangiogenic agents currently in clinical trials are also contemplated. Agents currently in clinical trials include: 2ME2, Angiostatin, Angiozyme, Anti-VEGF RhuMAb, Apra (CT-2584), Avicine, Benefin, BMS275291, Carboxyamidotriazole, CC4047, CC5013, CC7085, CDC801, CGP-41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, Iressa (ZD1839), Marimastat, Metastat (Col-3), Neovastat, Octreotide, Paclitaxel, Penicillamine, Photofrin, Photopoint, PI-88, Prinomastat (AG-3340), PTK787 (ZK22584), R0317453, Solimastat, Squalamine, SU 101, SU 5416, SU-6668, Suradista (FCE 26644), Suramin (Metaret), Tetrathiomolybdate, Thalidomide, TNP-470 and Vitaxin additional antiangiogenic agents are described by Kerbel, J. Clin. Oncol. 19(18s):45s-51s, 2001, which is incorporated by reference herein. Immunomodulators suitable for conjugation to the antibodies include α-interferon, γ-interferon, and tumor necrosis factor alpha (TNFα).

The coupling of one or more toxin molecules to the antibody is envisioned to include many chemical mechanisms, for instance covalent binding, affinity binding, intercalation, coordinate binding, and complexation. The toxic compounds used to prepare the immunotoxins are attached to the antibodies or antigen-binding fragments thereof by standard protocols known in the art.

In other aspects of the invention, the sarcoma-associated molecules and the antibodies and other binding molecules, as described herein, can be used for the treatment of disorders. When "disorder" is used herein, it refers to any pathological condition where the sarcoma-associated antigens are aberrantly expressed. An example of such a disorder is cancer, with sarcoma as a particular example. For human cancers, additional particular examples include synovial sarcoma, liposarcoma, neurosarcoma, chondrosarcoma, fibrosarcoma, Ewing sarcoma, leimyosarcoma, osteosarcoma, rhabdomyosarcoma, malignant fibrous histocytoma, DFSP, leukemia, lymphoma, gastric cancer, glioma, bladder cancer, breast cancer, ovarian cancer, renal cancer, lung cancer, colon cancer, prostate cancer, esophageal cancer, melanoma and hepatoma.

Conventional treatment for cancer may include, but is not limited to: surgical intervention, chemotherapy, radiotherapy, and adjuvant systemic therapies. In one aspect of the invention, treatment may include administering binding polypeptides such as antibodies that specifically bind to the sarcoma-associated antigen. These binding polypeptides can be optionally linked to one or more detectable markers, antitumor agents or immunomodulators as described above.

Cancer treatment, in another aspect of the invention may include administering an antisense molecules or RNAi molecules to reduce expression level and/or function level of sarcoma-associated polypeptides of the invention in the subject in cancers where a sarcoma-associated molecule is up-regulated. The use of RNA interference or "RNAi" involves the use of double-stranded RNA (dsRNA) to block gene expression. (see: Sui, G, et al, Proc Natl. Acad. Sci U.S.A. 99:5515-5520,2002). Methods of applying RNAi strategies in embodiments of the invention would be understood by one of ordinary skill in the art.

Sarcoma-associated polypeptides as described herein, can also be used in one aspect of the invention to induce or enhance an immune response. Some therapeutic approaches based upon the disclosure are premised on a response by a subject's immune system, leading to lysis of antigen presenting cells, such as cancer cells which present one or more sarcoma-associated antigens of the invention. One such approach is the administration of autologous CTLs specific to a sarcoma-associated antigen/MHC complex to a subject with abnormal cells of the phenotype at issue. It is within the ability of one of ordinary skill in the art to develop such CTLs in vitro. An example of a method for T cell differentiation is presented in International Application number PCT/US96/05607. Generally, a sample of cells taken from a subject, such as blood cells, are contacted with a cell presenting the complex and capable of provoking CTLs to proliferate. The target cell can be a transfectant, such as a COS cell. These transfectants present the desired complex of their surface and, when combined with a CTL of interest, stimulate its proliferation. COS cells are widely available, as are other suitable host cells. Specific production of CTL clones is well known in the art. The clonally expanded autologous CTLs then are administered to the subject.

Another method for selecting antigen-specific CTL clones has recently been described (Altman et al., Science 274:94-96, 1996; Dunbar et al., Curr. Biol. 8:413-416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, J. Immunol. 136(5): 1917, 1986; Riddel et al., Science 257: 238, 1992; Lynch et al, Eur. J. Immunol. 21: 1403-1410,1991; Kast et al., Cell 59: 603-614, 1989), cells presenting the desired complex (e.g., dendritic cells) are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/cancer associated antigen complex. This can be determined very easily, as the art is very familiar with methods for identifying cells which present a particular HLA molecule, as well as how to identify cells expressing DNA of the pertinent sequences, in this case a sarcoma-associated antigen sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a sarcoma-associated antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex (i.e. the antigenic peptide and the presenting MHC molecule). Chen et al. (Proc. Natl. Acad. Sci. USA 88: 110-114,1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a sarcoma-associated polypeptide may be operably linked to promoter and enhancer sequences which direct expression of the sarcoma-associated antigen polypeptide in certain tissues or cell types. The nucleic acid may be incorporated into an expression vector.

Expression vectors may be unmodified extrachromosomal nucleic acids, plasmids or viral genomes constructed or modified to enable insertion of exogenous nucleic acids, such as those encoding sarcoma-associated antigen, as described elsewhere herein. Nucleic acids encoding a sarcoma-associated antigen also may be inserted into a retroviral genome, thereby facilitating integration of the nucleic acid into the genome of the target tissue or cell type. In these systems, the gene of interest is carried by a microorganism, e.g., a Vaccinia virus, pox virus, herpes simplex virus, retrovirus or adenovirus, and the materials de facto "infect" host cells. The cells which result present the complex of interest, and are recognized by autologous CTLs, which then proliferate.

A similar effect can be achieved by combining the sarcoma-associated polypeptide or a stimulatory fragment thereof with an adjuvant to facilitate incorporation into antigen presenting cells in vivo. The sarcoma-associated polypeptide is processed to yield the peptide partner of the MHC molecule while a sarcoma-associated fragment may be presented without the need for further processing. Generally, subjects can receive an intradermal injection of an effective amount of the sarcoma-associated antigen. Initial doses can be followed by booster doses, following immunization protocols standard in the art. Preferred sarcoma-associated antigens include those found to react with allogeneic cancer antisera, shown in the examples below.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models, can be used for testing of immunization against cancer using a sarcoma-associated nucleic acid. For example, human cancer cells can be introduced into a mouse to create a tumor, and one or more sarcoma-associated nucleic acids can be delivered by the methods described herein. The effect on the cancer cells (e.g., reduction of tumor size) can be assessed as a measure of the effectiveness of the sarcoma-associated nucleic acid immunization. Of course, testing of the foregoing animal model using more conventional methods for immunization include the administration of one or more sarcoma-associated polypeptides or fragments derived therefrom, optionally combined with one or more adjuvants and/or cytokines to boost the immune response.

Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more sarcoma-associated polypeptides or immunogenic fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of Salmonella minnesota Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., Mol. Cells 7:178-186, 1997); incomplete Freund's adjuvant; complete Freund's adjuvant; montamide; alum; CpG oligonucleotides (see e.g. Kreig et al., Nature 374:546-9, 1995); and various water-in-oil emulsions prepared from biodegradable oils such as squalene and/or tocopherol. Preferably, the antigens are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., Science 268:1432-1434, 1995), GM-CSF and IL-18. Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P., et al. Proc. Natl. Acad. Sci. USA 95 (11):6284-6289 (1998)).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., J. Immunol, 154:5637-5648 (1995)). Tumor cell transfection with B7 has ben discussed in relation to in vitro CTL expansion for adoptive transfer immunotherapy by Wang et al., (J. Immunol., 19:1-8 (1986)). Other delivery mechanisms for the B7 molecule would include nucleic acid (naked DNA) immunization (Kim J., et al. Nat. Biotechnol., 15:7:641-646 (1997)) and recombinant viruses such as adeno and pox (Wendtner et al., Gene Ther., 4:7:726-735 (1997)). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., Nature 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., J. Immunol., 158:637-642 (1997), Fenton et al., J. Immunother., 21:2:95-108 (1998)).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., J. Immunother., 21:2:95-108 (1998)). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., Nature, 393:474 (1998), Bennett et al., Nature, 393:478 (1998), Schoenberger et al., Nature, 393:480 (1998)). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor antigens which are normally encountered outside of an inflammatory context or are presented by non-professional APCs (tumor cells). In these situations Th help and B7 costimulation signals are not provided.

The invention contemplates delivery of nucleic acids, polypeptides or fragments thereof for vaccination. Delivery of polypeptides and fragments thereof can be accomplished according to standard vaccination protocols which are well known in the art. In another embodiment, the delivery of nucleic acid is accomplished by ex vivo methods, i.e. by removing a cell from a subject, genetically engineering the cell to include a sarcoma-associated polypeptide, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

A virus vector for delivering a nucleic acid encoding a sarcoma-associated polypeptide is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), and Ty virus-like particle (Allsopp et al., Eur. J. Immunol 26:1951-1959, 1996). A preferred virus vector is an adenovirus.

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a sarcoma-associated antigen, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

According to a further aspect of the invention, compositions containing the nucleic acid molecules, proteins, and binding polypeptides of the invention are provided. The compositions contain any of the foregoing therapeutic agents in an optional pharmaceutically acceptable carrier. Thus, in a related aspect, the invention provides a method for forming a medicament that involves placing a therapeutically effective amount of the therapeutic agent in the pharmaceutically acceptable carrier to form one or more doses. The effectiveness of treatment or prevention methods of the invention can be determined using standard diagnostic methods described herein.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral, intravenous, intratumoral, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712). Those of skill in the art can readily determine the various parameters and conditions for producing antibody aerosols without undue experimentation. When using antisense preparations of the invention, slow intravenous administration is preferred.

The compositions of the invention are administered in effective amounts. An "effective amount" is that amount of a sarcoma-associated polypeptide composition that alone, or together with further doses, produces the desired response, e.g. increases an immune response to the sarcoma-associated polypeptide. In the case of treating a particular disease or condition characterized by expression of one or more sarcoma-associated polypeptides, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of sarcoma-associated polypeptide or nucleic acid encoding sarcoma-associated polypeptide for producing the desired response in a unit of weight or volume suitable for administration to a patient. The response can, for example, be measured by determining the immune response following administration of the sarcoma-associated polypeptide composition via a reporter system by measuring downstream effects such as gene expression, or by measuring the physiological effects of the sarcoma-associated polypeptide composition, such as regression of a tumor or decrease of disease symptoms. Other assays will be known to one of ordinary skill in the art and can be employed for measuring the level of the response.

The doses of sarcoma-associated polypeptide compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of sarcoma-associated antigen are formulated and administered in doses between 1 ng and 1 mg, and preferably between 10 ng and 100 μg, according to any standard procedure in the art. Where nucleic acids encoding sarcoma-associated polypeptides or variants thereof are employed, doses of between 1 ng and 0.1 mg generally will be formulated and administered according to standard procedures. Other protocols for the administration of sarcoma-associated polypeptide compositions will be known to one of ordinary skill in the art, in which the dose amount, schedule of injections, sites of injections, mode of administration (e.g., intra-tumoral) and the like vary from the foregoing. Administration of sarcoma-associated polypeptide compositions to mammals other than humans, e.g. for testing purposes or veterinary therapeutic purposes, is carried out under substantially the same conditions as described above.

Where sarcoma-associated polypeptides are used for vaccination, modes of administration which effectively deliver the sarcoma-associated polypeptide and adjuvant, such that an immune response to the polypeptide is increased, can be used. For administration of a sarcoma-associated polypeptide in adjuvant, preferred methods include intradermal, intravenous, intramuscular and subcutaneous administration. Although these are preferred embodiments, the invention is not limited by the particular modes of administration disclosed herein. Standard references in the art (e.g., Remington's Pharmaceutical Sciences, 18th edition, 1990) provide modes of administration and formulations for delivery of immunogens with adjuvant or in a non-adjuvant carrier.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, and lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like.

The pharmaceutical agents of the invention may be administered alone, in combination with each other, and/or in combination with other anti-cancer drug therapies and/or treatments. These therapies and/or treatments may include, but are not limited to: surgical intervention, chemotherapy, radiotherapy, and adjuvant systemic therapies.

The invention also provides a pharmaceutical kit comprising one or more containers comprising one or more of the pharmaceutical compounds or agents of the invention. Additional materials may be included in any or all kits of the invention, and such materials may include, but are not limited to buffers, water, enzymes, tubes, control molecules, etc. The kit may also include instructions for the use of the one or more pharmaceutical compounds or agents of the invention for the treatment of cancer.

The invention includes kits for assaying the presence of sarcoma-associated antigens and/or antibodies that specifically bind to sarcoma-associated polypeptides. An example of such a kit may include the above-mentioned polypeptides bound to a substrate, for example a dipstick, which is dipped into a blood or body fluid sample of a subject. The surface of the substrate may then be processed using procedures well known to those of skill in the art, to assess whether specific binding occurred between the polypeptides and agents (e.g. antibodies) in the subject's sample. For example, procedures may include, but are not limited to, contact with a secondary antibody, or other method that indicates the presence of specific binding.

Another example of a kit may include an antibody or antigen-binding fragment thereof, that binds specifically to a sarcoma-associated antigen. The antibody or antigen-binding fragment thereof, may be applied to a tissue or cell sample from a patient with cancer and the sample then processed to assess whether specific binding occurs between the antibody and an antigen or other component of the sample. In addition, the antibody or antigen-binding fragment thereof, may be applied to a body fluid sample, such as serum, from a subject, either suspected of having cancer, diagnosed with cancer, or believed to be free of cancer. As will be understood by one of skill in the art, such binding assays may also be performed with a sample or object contacted with an antibody and/or sarcoma-associated antigen that is in solution, for example in a 96-well plate or applied directly to an object surface.

Another example of a kit of the invention is a kit that provides components necessary to determine the level of expression of one or more sarcoma-associated nucleic acid molecules of the invention. Such components may include primers useful for amplification of one or more sarcoma-associated nucleic acid molecules and/or other chemicals for PCR amplification.

Another example of a kit of the invention is a kit that provides components necessary to determine the level of expression of one or more sarcoma-associated nucleic acid molecules of the invention using a method of hybridization.

The foregoing kits can include instructions or other printed material on how to use the various components of the kits for diagnostic purposes.

The invention further includes nucleic acid or protein microarrays (including antibody arrays) for the analysis of expression of sarcoma-associated antigens or nucleic acids encoding such antigens. In this aspect of the invention, standard techniques of microarray technology are utilized to assess expression of the sarcoma-associated antigens and/or identify biological constituents that bind such antigens. The constituents of biological samples include antibodies, lymphocytes (particularly T lymphocytes), and the like. Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate. Nucleic acid probes preferably are linked using UV irradiation or heat.

Protein microarray technology, which is also known by other names including protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485):1760-1763, 2000.

Targets are peptides or proteins and may be natural or synthetic. The tissue may be obtained from a subject or may be grown in culture (e.g. from a cell line).

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid arrays, particularly arrays that bind sarcoma-associated antigens, also can be used for diagnostic applications, such as for identifying subjects that have a condition characterized by aberrant sarcoma-associated antigen expression. Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast, Nature Genetics*, Vol.21, January 1999, the entire contents of which is incorporated by reference herein.

According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of one or more of the sarcoma-associated nucleic acid molecules as described herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or oligonucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, nucleic acid probes are synthesized directly on the substrate in a predetermined grid pattern using methods such as light-directed chemical synthesis, photochemical deprotection, or delivery of nucleotide precursors to the substrate and subsequent probe production.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

EXAMPLES

Materials and Methods

Cell Lines, Tissues, Sera and RNA

SW1045, SW982, and Fuji synovial sarcoma cell lines were obtained from the cell repository of the Ludwig Institute for Cancer Research (LICR), New York Branch at the Memorial Sloan-Kettering Cancer Center. Tumor tissues and sera were obtained from Memorial Sloan-Kettering Cancer Center, Weill Medical College of Cornell University and Aichi Cancer Center Research Center, Nagoya Japan. Normal tissue RNA preparations were purchased from Clontech laboratories Incorporated (Palo Alto, Calif.) and Ambion Incorporated (Austin, Tex.). Total RNA from tumor tissues was prepared by the guanidinium thiocyanate method.

SEREX Analysis of cDNA Expression Libraries

Poly(A)+ RNA from two sarcoma cell lines, SW1045 and SW982, was prepared using the Fast Track mRNA Purification Kit (Invitrogen, Life Technologies, Carlsbad, Calif.). Two cDNA libraries, corresponding to the SW1045 and SW982 sarcoma cell lines, were constructed in the ZAP Express vector (Stragene, La Jolla, Calif.) according to THE manufacturer's instructions using 5 µg polyA+ mRNA. Libraries containing $1-2 \times 10^6$ primary recombinants were obtained and were not amplified for imunoscreening.

To remove serum antibodies reactive with vector-related antigens, sera was absorbed against *E. coli*/bacteriophage lysates prepared in the following manner. Wild-type lambda ZAP Express bacteriophage at a concentration of 5,000 pfu per 15 cm plate were amplified in *E. coli* XL1 Blue MRF' overnight in NZY/0.7% agarose. 10 ml of binding buffer (0.1M NaHCO3, pH 8.3) was then added to the plates, and the plates were gently agitated at 4° C. for 15 hours. The resultant supernatants were collected and residual *E. coli* were lysed by sonication. The lysates were then coupled to CNBr—Sepharose 4B (Amersham Pharmacia Biotech, Piscataway, N.J.) according to the manufacturer's instructions. Patient sera (1:10 dilution) were absorbed by batch absorption with Sepharose 4B coupled *E. coli* phage lysates, followed by a 15 hour incubation with nitrocellulose filters precoated with proteins derived from *E. coli* and *E. coli*/phage lysates. Library screenings were performed as previously described (Scanlan, M. J., Chen, Y. T., Williamson, B., Gure, A. O., Stockert, E., Gordan, J. D., Tureci, O., Sahin, U., Pfreundschuh, M., and Old, L. J. Characterization of human colon cancer antigens recognized by autologous antibodies. *Int. J. Cancer* 1998; 76: 652-8. Scanlan, M. J., Gordan, J. D., Williamson, B., Stockert, E., Bander, N. H., Jongeneel, V., Gure, A. O., Jäger, D., Jäger, E., Knuth, A., Chen, Y. -T., and Old, L. J. Antigens recognized by autologous antibody in patients with renal-cell carcinoma. *Int. J. Cancer* 1999; 83: 456-64.) Sera from 2 sarcoma patients were used independently, at a dilution of 1:200, to immunoscreen the SW1045 and SW982 cDNA libraries. A total of $2.5-5.0 \times 10^5$ recombinants were screened per serum/cDNA library combination. Serum reactive phage clones were converted to plasmid forms and subjected to DNA sequencing (Cornell University DNA Services, Ithaca, N.Y.).

Determination of Serum Antibody Reactivity

Two assays were used to determine serological reactivity, an ELISA-based method 30 and a bacteriophage expression method. With regard to CT antigens, serum antibody reactivity was determined by ELISA as previously described (Stockert E, et al. 1998. A survey of the humoral immune response of cancer patients to a panel of human tumor antigens. J Exp Med 187:1349-54.) Briefly, recombinant proteins (NY-ESO-1, SSX-2, MAGE-A1, MAGE-A3, MAGE-A4, MAGE-A10, CT7 and CT10) were produced in *E. coli* by transfection with pQE30 expression vectors (Qiagen, Chatsworth, Calif.) according to the manufacturer's protocol. 10 ul of recombinant protein (lug/ml) was absorbed to TC microwell plates (Nalge Nunc International Corp., Naperville, Ill.) for 15 hours at 4° C. After washing with PBS, plates were then blocked with 2% BSA and incubated with diluted (1:100-1: 25,000) patient sera for 2 hours at room temperature. Following a PBS wash step, 10 ul of a 1:5000 dilution of alkaline phosphatase-conjugated goat anti-human IgG secondary antibody (Southern Biotechnology, Birmingham, Ala.) was added to each well and incubated for 1 hour at room temperature. Following a PBS wash step, plates were incubated with 10ul/well Attophose substrate (JBL Scientific, San Louis Obispo, Calif.) for 25 min, and the fluorescence was then read by a Cyto-Fluor 2350 (Millipore, Bedford, Mass.).

In the case of SEREX-defined sarcoma antigens, a previously described serum antibody detection array (SADA or spot immunoassay (Scanlan M J, et al. Humoral immunity to human breast cancer: antigen definition and quantitative analysis of mRNA expression. Cancer Immunity 1:4 [epub]; Scanlan M J. et al. 2002. Cancer-Related Serological Recognition of Human Colon Cancer: Identification of Potential Diagnostic and Immunotherapeutic Targets. In press)) was used to determine serological reactivity.

Preabsorbed serum samples from 39 sarcoma patients and 33 healthy blood donors were evaluated for the presence of IgG antibody reactive to a panel of 72 SEREX-defined sarcoma antigens, identified herein, in the following manner. Precut nitrocellulose membranes (80×120 mm) were precoated with a layer (approximately 0.2 mm) of growth media (NZY/0.7% Agarose/2.5 mM isopropyl-β-D-thiogalactopyranoside) and placed on a reservoir layer of NZY/0.7% Agarose in a 86×128 mm Omni Tray (Nalge Nunc). $3.0 \times 10^5$ pfu of bacteriophage encoding individual SEREX-defined tumor antigens, in a volume of 60 ul, were mixed with 60 ul of exponentially growing E. coli XL-1 Blue MRF' and spotted (0.7 ul aliquots) on the precoated nitrocellulose membranes using a 96 pin replicator (Nalge Nunc). Membranes were incubated for 15 hours at 37° C. and then processed as per the standard SEREX protocol (Scanlan, et al., Int. J. Cancer 1998; 76: 652-8; Scanlan, et al., Int. J. Cancer 1999; 83: 456-64). Briefly, plates were blocked in 0.5% non-fat dried milk; incubated in 10 ml of a 1:200 dilution of sera at room temperature for 15 hours; and then incubated in a 1:3000 dilution of alkaline phosphatase conjugated, Fe fragment specific, goat anti-human IgG (Jackson Immunoresearch laboratories Inc., West Grove Pa.). Serum IgG reactivity was detected with the alkaline phosphatase substrate, 4-nitro blue tetrazolium chloride/5-bromo-4-chloro-3-indolyl-phosphate.

Reverse Transcriptase-PCR (RT-PCR) Analysis

The cDNA preparations used as templates in the RT-PCR reactions were prepared using the Superscript first strand synthesis kit (Invitrogen Life Technologies, Carlsbad, Calif.) according to the manufacturer's instructions using 5 μg of total RNA in 40 μl reaction. For evaluation of CT antigens expression in sarcoma cell lines, PCR primers specific for ESO-1, LAGE-1, MAGE-1, MAGE-3, MAGE-4, MAGE-10, SCP-1, CT7, SSX-1, SSX-2, and SSX-4 were synthesized commercially (Invitrogen Life Technologies) using published primer sequences. PCR primers specific for SEREX-defined antigens NY-SAR-12, NY-SAR-35 and NY-SAR-41 were also synthesized commercially (Invitrogen Life Technologies) and their sequences are as follows: NY-SAR-12 forward, TggCgCAgAAAggAAAAggAAAAT (SEQ ID NO: 91); NY-SAR-12 reverse, AgAggTAgCTggCAggATgT-TAg (SEQ ID NO: 92); NY-SAR-35 forward,CTTggTgC-gATCAgCCTTAT (SEQ ID NO: 93); NY-SAR-35 reverse, TTgATgCATgAAAACAgAACTC (SEQ ID NO: 94); NY-SAR-41 forward, AgAATTggCAgAggCTCgTCATCA (SEQ ID NO: 95); NY-SAR-41 reverse, TTCCAATTTTgC-CTTCTCTAACTg (SEQ ID NO: 96).

RT-PCR was performed in the following manner. Twenty-five μl PCR reaction mixtures, consisting of 2 μl cDNA, 0.2 mM dNTP, 1.5 mM MgCl$_2$, 0.25 μM gene specific forward and reverse primers, and 2.5 U Platinum Taq DNA polymerase (Invitrogen Life Technologies), were heated to 94° C. for 2 min., followed by 34 thermal cycles of 94° C. for 30 seconds, 55° C. for 30 seconds and 72° C. for 1 min., and a final cycle of 94° C. for 30 seconds, 55° C. for 30 seconds and 72° C. for 5 min. Thermal cycling was performed using a GeneAmp PCR System 9700 (PE Biosystems, Foster City, Calif.). Resultant PCR products were analyzed in 2% Agarose/Tris-Acetate-EDTA gels.

Real-time Quantitative Reverse Transcription (RT)-PCR

The concentration of NY-SAR-35 mRNA transcripts in normal tissues was measured by real-time RT-PCR using 16 different normal tissue cDNA preparations that had been normalized for 6 housekeeping genes (Clontech). Gene-specific TaqMan probes and PCR primers were designed using Primer Express software (PE Biosystems). PCR reactions were prepared using 2.5 ul of cDNA diluted in TaqMan PCR Master Mix (PE Biosystems) supplemented with 200 nM 6-carboxy-fluorescein labeled gene-specific TaqMan probe, and a predetermined, optimum concentration of gene specific forward and reverse primers (300-900 nM). Triplicate PCR reactions were prepared for each cDNA sample. PCR consisted of 40 cycles of 95° C. denaturation (15 seconds) and 60° C. annealing/extension (60 seconds). Thermal cycling and fluorescent monitoring were performed using an ABI 7700 sequence analyzer (PE Biosystems). The point at which the PCR product is first detected above a fixed threshold, termed cycle threshold (Ct), was determined for each sample. The abundance of gene-specific transcripts in normal tissues was determined by comparison with a standard curve generated from the Ct values of known concentrations of plasmid DNA template encoding NY-SAR-35.

Northern Blot Analysis

A Northern blot containing poly A+ RNA (2 ug/lane) from various normal tissues was obtained commercially (Clontech). An NY-SAR-35 cDNA probe (bp 263-1029) was labeled using the Bright Star Psoralen-Biotin Kit (Ambion Inc., Austin, Tex.) and hybridized to the membrane for 15 hours at 68° C. After washing, the hybridization signal was developed using the Bright Star Bio-Detect Kit, according to the manufacturer's instructions (Ambion).

Southern Blot Analysis

Genomic DNA was extracted from normal human testis, and samples (10 ug) were independently digested with EcoRI, HindIII, and BamHI at 37° C. overnight. The DNA was then separated on 0.7% agarose gel and blotted onto a nylon transfer membrane. An NY-SAR-35 cDNA probe (bp 252-1029) was radiolabeled with $^{32}$P-dCTP using a random-primer DNA labeling kit (Roche Molecular Biochemicals, Indianapolis, Ind.). The blot was hybridized to a $^{32}$P labeled probe at 68° C. After 15 hours of hybridization, the membrane was washed under high stringency conditions (0.1×SSC, 0.5% SDS at 60° C.) and exposed for autoradiography.

RESULTS

Identification of Human Sarcoma Antigens by SEREX Analysis

Preliminary studies were carried out to determine optimum sources of target antigens and immunoreactive patient sera. Three sarcoma cell lines were typed for expression of NY-ESO-1, LAGE-1, MAGE-1, MAGE-3, MAGE-4, MAGE-10, BAGE, SCP-1, CT7, SSX-1, SSX-2, and SSX-4 transcripts by RT-PCR. As shown in Table 2, all 3 sarcoma cell lines expressed at least one of the transcripts in this panel. Specifically, the SW982 and SW1045 synovial sarcoma cell lines expressed 8 and 10 of the 12 CT antigen transcripts in the panel, respectively, while Fuji synovial sarcoma cells expressed 4/12 CT antigen transcripts.

TABLE 2

Cancer/Testis antigen expression in sarcoma cell lines

| | Cell Line | | |
|---|---|---|---|
| CT Antigen | SW982 (synovial) | SW1045 (synovial) | Fuji |
| NY-ESO-1 | + | + | + |
| LAGE-1 | Neg | + | + |
| MAGE-A1 | + | + | Neg |
| MAGE-A3 | + | + | Neg |
| MAGE-A4 | + | + | |
| MAGE-A10 | + | + | Neg |
| BAGE | + | + | Neg |
| SCP-1 | Neg | Neg | Neg |
| CT7 | + | + | Neg |
| SSX1 | Neg | + | Neg |
| SSX2 | Neg | Neg | |
| SSX4 | + | + | Neg |
| Totals | 8/12 | 10/12 | 4/12 |

In order to identify a subset of sarcoma patients that are actively mounting an immune response against tumor antigens, sera from 54 sarcoma patients (various histologies) were tested by ELISA (Stockert E, et al. 1998. A survey of the humoral immune response of cancer patients to a panel of human tumor antigens. J Exp Med 187:1349-54) for the presence of antibodies against a panel of 8 CT antigens consisting of: NY-ESO-1, SSX-2, MAGE-A1, MAGE-A3, MAGE-A4, MAGE-A10, CT7 and CT10. Only 2/54 sarcoma patients, a malignant fibrous histocytoma (MFH) and fibrosarcoma patient, had detectable serum antibodies against a CT antigen, while the remaining 52 patients lacked detectable anti-CT antigen antibodies. Both seropositive patients had antibodies to NY-ESO-1 but lacked antibodies to the other 7 CT antigens tested.

Although it was determined that CT antigen expression is frequent in sarcoma tissue, serum antibody responses were not as frequent. This lack of immunogenicity in sarcoma may be an indication of immune escape by sarcoma cells, whereby the immune system fails to recognize CT antigens and eliminate tumor cells expressing these antigens, resulting in the expansion of a homogenous population CT antigen expressing sarcoma cells. Relevant escape mechanisms include defective antigen presentation (35) and/or production of immuno-inhibitory cytokines, such as TGF-β and IL-10 (36). It is also possible that homogeneous NY-ESO-1 and MAGE expression in synovial sarcoma (20,21), as opposed to heterogeneous CT antigen expression observed in many other tumor types (33,34), may also be a contributing factor to immune escape.

These 2 patients were chosen as the serum sources for SEREX immunoscreening of cDNA libraries prepared from the SW982 and SW1045 synovial sarcoma cell lines. A total of 4 SEREX immunoscreenings were performed, leading to the identification of 72 distinct sarcoma antigens, designated NY-SAR-1 through NY-SAR-72. As shown in Table 3, immunoscreening with sera from an NY-ESO-1 serum antibody positive MFH patient led to the identification of 28 antigens, including 8 overlapping antigens derived from both the SW982 and SW1045 cDNA libraries, as well as 13 antigens derived solely from the SW982 cDNA library, and 7- antigens derived solely from the SW 1045 cDNA library. Immunoscreening with sera from an NY-ESO-1 serum antibody positive fibrosarcoma patient defined 46 antigens, including 2 overlapping antigens derived from both the SW982 and SW1045 cDNA libraries, as well as 25 antigens derived solely from the SW982 cDNA library, and 19 antigens derived solely from the SW1045 cDNA library. Two antigens, NY-SAR-4/FH and NY-SAR-17/LAGE-1 were identified with both the MFH and FS sera. These 72 antigens (Tables 4-6) represent 58 known proteins and 14 uncharacterized gene products.

TABLE 3

Immunoscreening of synovial sarcoma cDNA expression libraries with allogeneic sarcoma patient sera

| Sarcoma Serum | Synovial sarcoma cDNA expression library | Number of recombinants screened | Number of different antigens identified | Total number of distinct antigens |
|---|---|---|---|---|
| Malignant Fibrous Histocytoma | SW982 | $5 \times 10^5$ | 21 | 28 |
| | SW1045 | $5 \times 10^5$ | 15 | |
| Fibrosarcoma | SW982 | $2.5 \times 10^5$ | 27 | 46 |
| | SW1045 | $2.5 \times 10^5$ | 21 | |

TABLE 4

SEREX-defined sarcoma antigens: antigens reactive with sera from multiple cancer patients

| NY-SAR- Antigen | Identity (Unigene cluster) | Reactivity with Sarcoma Sera | Source of Reactive Sera[1] | SEREX Database ID Number[2] of Equivalent Isolate (Tumor Source[1]) |
|---|---|---|---|---|
| 2 | STAU (Hs.6113) | 2/39 | MFH (#3), OS (#2) | 614 (PRC), 1273 (BC) |
| 4 | FH (Hs.75653) | 5/39 | MFH (#3), OS (#4, #7), ES (#1), FS (#2) | No Match |
| 12 | NESG1 (Hs.158450) | 2/39 | MFH (#3), LS (#4) | No Match |
| 13 | ACTN1 (Hs.119000) | 1/39 | MFH (#3) | 855 (BC) |
| 15 | RBM6 (Hs.173993) | 1/39 | MFH (#3) | 76 (LC) |
| 16 | FLJ12785 (Hs.192742) | 1/39 | MFH (#3) | 756 (TALL) |
| 17 | LAGE-1a (Hs.87225) | 2/39 | MFH (#3), FS (#2) | 1160 (BC) |
| 18 | SSSCA1 (Hs.25723) | 1/39 | MFH (#3) | 1799 (CC) |

TABLE 4-continued

SEREX-defined sarcoma antigens: antigens reactive with sera from multiple cancer patients

| NY-SAR-Antigen | Identity (Unigene cluster) | Reactivity with Sarcoma Sera | Source of Reactive Sera[1] | SEREX Database ID Number[2] of Equivalent Isolate (Tumor Source[1]) |
|---|---|---|---|---|
| 28 | MGC: 9727 (Hs.11065) | 1/39 | MFH (#3) | 71 (BC) |
| 30 | SNK (Hs.3838) | 2/39 | FS (#2), RS (#1) | No Match |
| 44 | LGALS1 (Hs.227751) | 1/39 | FS (#2) | 704 (RC) |
| 47 | MIF (Hs.73798) | 1/39 | FS (#2) | 989 (MEL) |
| 50 | PYCR1 (Hs.79217) | 3/39 | FS (#2), MFH (#2, #4) | No Match |
| 71 | None (Hs.314941) | 1/39 | FS (#2) | 1938 (GL) |
| 72 | HSPE1 (Hs.1197) | 1/39 | FS (#2) | 882 (HC), 1202 (MEL) |

Antigens did not react with sera from normal blood donors (0/33).
[1] Abbreviations: BC, breast cancer; CC, colon cancer; ES, Ewing sarcoma; FS, fibrosarcoma; GC, gastric cancer; GL, glioma; HC, hepatocellular carcinoma; LC, lung cancer; LS, leimyosarcoma; MEL, melanoma; MFH, malignant fibrous histocytoma; OC, ovarian cancer; OS, osteosarcoma; PRC, prostate cancer; RC, renal cancer; RS, rhabdomyosarcoma; TALL, T-cell acute lymphocytic leukemia.
[2] SEREX database ID numbers from the LICR's SEREX database (licr.org/SEREX.html).

TABLE 5

SEREX-defined sarcoma antigens: antigens reactive with sera from both normal donors and sarcoma patients

| NY-SAR-Antigen | Identity (Unigene cluster) | SEREX Database ID Number[1] of Equivalent Isolate (Tumor Source[2]) | Reactivity with Normal Sera | Reactivity with Sarcoma Sera |
|---|---|---|---|---|
| 1 | TMF1 (Hs.267632) | 246 (G), 1241 (BC) | 2/33 | 3/39 |
| 3 | KIAA1536 (Hs.156667) | 89 (BR) | 2/33 | 3/39 |
| 6 | RHAMM (Hs.72550) | 1513 (OC) | 1/33 | 3/39 |
| 7 | PINCH (Hs.112378) | 344 (CC), 550 (GC), 1152 (RC), 1281 (BR) | 16/21 | 14/39 |
| 10 | KIAA0603 (Hs.173802) | No Match | 11/33 | 4/39 |
| 11 | U2AF1RS2 (Hs.171909) | 430 (RC), 786 (HD), 1236 (BC), 1334 (GC) | 6/33 | 17/39 |
| 14 | SC65 (Hs.207251) | NoMatch | 8/33 | 4/39 |
| 19 | HEF1 (Hs.80261) | 421 (RC) | 3/33 | 7/39 |
| 22 | NELIN (Hs.216381) | No Match | 4/33 | 19/39 |
| 29 | FLJ13441 (Hs.232146) | 974 (PC) | 6/33 | 3/39 |
| 31 | HUMAUANTIG (Hs.75528) | 1017 (BC), 1331 (GC), 1475 (OC) | 2/33 | 6/39 |
| 32 | PDAP1 (Hs.278426) | No Match | 4/33 | 8/39 |
| 33 | SURF6 (Hs.274430) | No Match | 2/33 | 2/39 |
| 41 | None (Hs.166670) | No Match | 1/33 | 1/39 |
| 45 | STIP1 (Hs.75612) | 430 (RC) | 4/33 | 2/39 |
| 53 | FXYD5 (Hs.333418) | No Match | 1/33 | 1/39 |
| 54 | LMOD1 (Hs.79386) | No Match | 7/33 | 13/39 |
| 55 | RBM10 (Hs.154583) | No Match | 1/33 | 1/39 |
| 58 | LIP8 (Hs.348012) | No Match | 1/33 | 3/39 |
| 61 | ZNF282 (Hs.58167) | No Match | 1/33 | 2/39 |
| 64 | USP16 (Hs.99819) | No Match | 2/33 | 2/39 |
| 65 | FDFT1 (Hs.48876) | No Match | 2/33 | 1/39 |

TABLE 5-continued

SEREX-defined sarcoma antigens: antigens reactive
with sera from both normal donors and sarcoma patients

| NY-SAR-Antigen | Identity (Unigene cluster) | SEREX Database ID Number[1] of Equivalent Isolate (Tumor Source[2]) | Reactivity with Normal Sera | Reactivity with Sarcoma Sera |
|---|---|---|---|---|
| 66 | ROCK1 (Hs.109450) | 444 (RC) | 1/33 | 1/39 |
| 68 | P38IP (Hs.333500) | No Match | 1/33 | 3/39 |

[1]The LICR's SEREX database ID numbers from licr.org/SEREX.html.
[2]Abbreviations: BC, breast cancer; CC, colon cancer; HD, Hodgkins disease; GC, gastric cancer; OC, ovarian cancer; PC, pancreatic cancer; RC, renal cancer

TABLE 6

SEREX-defined sarcoma antigens: antigens reactive
with sera from a single sarcoma patient

| NY-SAR-Antigen | Gene Identity (Unigene Cluster) |
|---|---|
| 5 | TBC1D1 (Hs.278586) |
| 8 | BIRC2 (Hs.289107) |
| 9 | ATP5B (Hs.25) |
| 20 | TCEB3 (Hs.155202) |
| 21 | GTF3C3 (Hs.90847) |
| 23 | C20orf81 (Hs.29341) |
| 24 | None (not clusted) |
| 25 | PDE4DIP (Hs.265848) |
| 26 | PIASX-BETA (Hs.111323) |
| 27 | FLJ10330 (Hs.342307) |
| 34 | SEC23B (Hs.173497) |
| 35 | None (Hs.128580) |
| 36 | SSX1 (Hs.194759) |
| 37 | MP1 (Hs.260116) |
| 38 | HMG20B (Hs.32317) |
| 39 | PSMD4 (Hs.148495) |
| 40 | INPP1 (Hs.32309) |
| 42 | BTG3 (Hs.77311) |
| 43 | SSX4 (Hs.278632) |
| 46 | ARNTL2 (Hs.222024) |
| 48 | MGC20533 (Hs.69280) |
| 49 | EMK1 (Hs.157199) |
| 51 | EDF1 (Hs.174050) |
| 52 | Actin (Hs.288061) |
| 56 | MLF1 (Hs.85195) |
| 57 | GCN5L2 (Hs.101067) |
| 59 | UPF3B (Hs.103832) |
| 60 | EGLN1 (Hs.6523) |
| 62 | AD034(Hs.281397) |
| 63 | USP19 (Hs.301373) |
| 67 | LUC7L (Hs.16803) |
| 69 | ARL1 (Hs.242894) |
| 70 | RPL10A (Hs.334895) |

[1]Antigens reacted with sera from single sarcoma patient (1/39), but not with sera from normal individuals (0/33). The antigens listed had no matches with existing entries in the SEREX database (licr.org/SEREX.html).

The nucleotide sequences of all uncharacterized gene products (NY-SAR-3, -10, -16, -22, -23, -24, -27, -28, -29, -35, -41, -48, -62, -71) have been deposited in the GenBank database (SEQ ID NOs: 1-14, respectively). The cDNA sequences encoding the 72 sarcoma antigens were also compared to sequences deposited in the SEREX database accessible through a website of the Ludwig Institute for Cancer Research (licr.org/SEREX.html). Examination of this database revealed that 21 of the 72 sarcoma antigens defined in this study (29%) were also identified through SEREX analysis of other tumor types (Tables 4 and 5).

Reactivity Patterns of Sera from Normal Individuals and Cancer Patients with SEREX-defined Sarcoma Antigens To determine whether immune recognition of the isolated antigens was cancer-related, allogeneic sera samples obtained from 33 normal blood donors and 39 sarcoma patients (various histologies) were tested for reactivity against the 72 sarcoma antigens defined in the current study using serum antibody detection arrays (SADA). Twenty-four of the 72 antigens (33%) had a serological profile that was not restricted to cancer patients, as evidenced by their reactivity with normal sera. These antigens have been listed in Table 5.

With one notable exception (NY-SAR-22/NELIN), the frequency of antibody responses to 23 of the 24 antigens associated with normal sera reactivity was similar in normal blood donors and cancer patients. In the case of NY-SAR-22/NELIN (UniGene cluster Hs.216381), the frequency of antibody responses was considerably higher in cancer patients, in which 19/39 (49%) of sarcoma patients and 4/33 (12%) of normal individuals had a detectable antibody response. The remaining 48 antigens had a cancer-related serological profile, reacting only with sera from cancer patients.

The 48 antigens having a cancer-related serological profile could be subdivided into 4 categories; a) antigens identified by serum from only a single sarcoma patient; b) antigens that reacted with sera from a single sarcoma patient and, as determined by an analysis of the SEREX database, with sera from patients having other forms of cancer; c) antigens that reacted exclusively with sera from 2 or more sarcoma patients; and d) antigens that reacted with sera from 2 or more sarcoma patients and with sera from patients having other forms of cancer. Of the 48 antigens having a cancer-related serological profile, 33 antigens reacted with sera from a single sarcoma patient (Table 6).

As shown in Table 4, the remaining 15 antigens reacted with sera from 2 or more cancer patients, but not with sera from normal individuals. Nine antigens reacted with sera from a single sarcoma patient, and with sera from patients with other tumor types (NY-SAR-13, -15, -16, -18, -28, -44, -47, -71, -72). Four antigens reacted exclusively with sera from 2 or more sarcoma patients (NY-SAR, -4, -12, -30, -50). The remaining two antigens, NY-SAR-2/STAU and the CT antigen, NY-SAR-17/LAGE-1A, reacted with sera from 2 or more sarcoma patients and with sera from patients with other types of cancer. A cancer-related serological response to NY-SAR-4/FH occurred most frequently. In this case, serum samples from 5/39 sarcoma patients were reactive with NY-SAR-4/FH, including 2/10 sera samples from osteosarcoma patients, 1/6 sera samples from malignant fibrous histiocytoma patients, 1/2 patients sera samples from fibrosarcoma patients, and 1/7 sera samples from Ewing sarcoma patients. No serological responses to NY-SAR-4/FH were detected in normal blood donors.

Expression Patterns of mRNA Encoding Serologically Defined Sarcoma Antigens in Normal and Malignant Tissues A preliminary in silico mRNA expression profile of all gene products identified in this study was carried out based on the tissue distribution of expressed sequence tags (ESTs) in the human EST database. Products with no EST matches, or those having EST matches limited to tumor tissue, fetal tissue, and/or less than 3 normal adult tissues were further examined by RT-PCR. Gene products with restricted EST profiles include the three well-characterized cancer-testis antigens, LAGE-1/NY-SAR-17, NY-SAR-36/SSX1, and NY-SAR-43/SSX4 which are expressed exclusively in normal testis and a range of different tumor types (Lethe B, et al. 1998. LAGE-1, a new gene with tumor specificity. Int. J. Cancer 76:903-8; Türeci Ö, et al. 1998. Expression of SSX genes in human tumors. Int. J. Cancer 77:19-23; Gure A O, et al. 1997. SSX: a multigene family with several members transcribed in normal testis and human cancer. Int. J. Cancer 72:965-971), and 3 putative tissue restricted antigens, including a known gene product, nasopharyngeal specific protein 1 (NESG1)/NY-SAR-12 (Li Z, Yao K, Cao Y. Molecular cloning of a novel tissue-specific gene from human nasopharyngeal epithelium. Gene Sep. 3, 1999;237(1):235-40), and 2 uncharacterized gene products, NY-SAR-35 (UniGene cluster Hs.128580) and NY-SAR-41 (UniGene cluster Hs.166670). With the exception of serum reactivity to NY-SAR-41 occurring in 1/33 normal blood donors, these differentially expressed antigens showed a cancer-related serological profile.

As shown in FIG. 1A, mRNA expression patterns of NY-SAR-12, -35, and -41 were examined in 17 different human tissues by RT-PCR. NESG1/NY-SAR-12 mRNA was detected in normal placenta, testis, colon, lung, and ovary (0/12 other normal tissues). NY-SAR-35 mRNA was detected only in normal testis (0/15 other normal tissues), while a lower molecular weight transcript was detected in normal ovary. NY-SAR-41 was detected in normal testis, fetal brain, colon, lung, and bladder (0/12 other normal tissues). As shown in FIG. 1B, the testis restricted expression pattern of NY-SAR-35 was confirmed by real time quantitative RT-PCR at 40 amplification cycles. In these studies, NY-SAR-35 was expressed in normal testis at a level corresponding to 83.2 ag, which was more than 1000 times the level detected in the remaining 15 normal tissues.

The expression of NY-SAR-35 mRNA was also examined in 26 sarcoma specimens of various histologies, and was detected in fibrosarcoma and rhabdomyosarcoma specimens (2/26), as well as the SW1045 synovial sarcoma cell line (Table 7 and FIG. 1C). With regard to other tumor types, transcripts encoding NY-SAR-35 were detected in 1/16 (6%) melanoma specimens, 6/29 (21%) lung cancer specimens, and 3/13 (23%) breast cancer specimens. NY-SAR-35 mRNA was not detected in small number of colon cancer specimens (0/9) or in small numbers of renal cancer specimens (0/8). Thus, on the basis of its immunogenicity in cancer patients, and its restricted mRNA expression profile, NY-SAR-35 can be considered a novel CT antigen.

TABLE 7

Expression of NY-SAR-35 in sarcoma, sarcoma cell lines and other malignant tissues

| Histology | Expression Frequency |
|---|---|
| Sarcomas | |
| Synovial sarcoma | 0/8 |
| Leimyosarcoma | 0/4 |
| Malignant Fibrous Histocytoma | 0/4 |
| Ewing Sarcoma | 0/2 |
| Osteosarcoma | 0/2 |
| Rhabdomyosarcoma | 1/1 |
| Fibrosarcoma | 1/1 |
| Liposarcoma | 0/1 |
| Neurosarcoma | 0/1 |
| Chondrosarcoma | 0/1 |
| DFSP | 0/1 |
| SW1045 synovial sarcoma cell line | positive |
| SW982 synovial sarcoma cell line | negative |
| Fuji synovial sarcoma cell line | negative |
| Other Malignancies | |
| Melanoma | 1/16 |
| Lung Cancer | 6/29 |
| Colon Cancer | 0/9 |
| Breast Cancer | 3/13 |
| Renal Cancer | 0/8 |
| Esophageal Cancer | 9/12 |
| Ovarian Cancer | 1/12 |
| Gastric Cancer | 5/6 |

The NY-SAR-35 Gene, Transcript and Putative Protein

An analysis of the human genome database, mapped the NY-SAR-35 cDNA sequence to Xq28, approximately 5.9 Mbp downstream (3') of the CT10/MAGE-E1 gene and 6.8 Mbp upstream (5') of the NY-ESO-1 gene. The NY-SAR-35 gene is approximately 44 kb in length and spans 6 exons. Analyses of the human genome databases (NCBI GenBank, ncbi.nlm.nih.gov/genome, and Celera Genomics, Rockville, Md., celera.com) revealed no homologous sequences. These results were verified by probing Southern blots of human genomic DNA with the NY-SAR-35 cDNA.

The present SEREX immunoscreening provided 4 overlapping NY-SAR-35 cDNA clones, ranging from 677-767 bp in length, all contained identical 3' sequences originating from the poly A region. The NY-SAR-35 cDNA sequence was identical to 3 ESTs, AA909915, AA906131, and AW593050, which were all derived from the NFL_T_G-BC_S1 mixed tissue (fetal lung, testis, germinal center B cell) cDNA library and found in UniGene cluster Hs.128580. As shown in FIG. 1D, Northern blot analysis revealed a single NY-SAR-35 mRNA transcript of 1.1 kB in normal testis, indicating the SEREX-defined clones and EST sequences represent partial transcripts. To obtain a full-length NY-SAR-35 transcript, 5' RACE was performed, yielding 262 bp of additional 5' DNA sequence. Thus, the total length of the NY-SAR-35 transcript is 1029 bp.

The NY-SAR-35 transcript encodes an open reading frame of 255 amino acids (bp 68-895) with a predicted molecular mass of 29.2 kDa. It is identical to a hypothetical protein, XM098959, predicted from Genefinder analysis of human chromosome X sequences. The putative NY-SAR-35 protein has a signal peptide, a transmembrane domain and a cysteine-rich trefoil/P-domain, found in several secreted proteins of the gastrointestinal tract (Hoffmann W, Hauser F. The P-domain or trefoil motif: a role in renewal and pathology of mucous epithelia? Trends Biochem Sci 1993 July;18(7):239-43). These data suggest that NY-SAR-35 is an extracellular protein.

REFERENCES 1. van der Bruggen P, et al. 1991. A gene encoding an antigen recognized by cytolytic T lymphocytes on a human melanoma. Science 254:1643-47.
2. Gaugler, B., Van den Eynde, B., van der Bruggen, P., Romero, P., Gaforio, J. J., De Plaen, E., Lethe, B., Brasseur, F., and Boon, T. Human gene MAGE-3 codes for an antigen recognized on a melanoma by autologous cytolytic T lymphocytes. J. Exp. Med. 1994; 179: 921-30.
3. Kawakami, Y., Eliyahu, S., Delgado, C. H., Robbins, P. F., Rivoltini, L., Topalian, S., L., Miki, T., and Rosenberg, S. A. Cloning of the gene for a shared human melanoma antigen recognized by autologous T cells infiltrating into tumor. Proc. Natl. Acad. Sci. USA. 1994; 91: 3515-19.
4. Chen, Y. -T., Scanlan, M. J., Sahin, U., Tureci, O., Gure, A. O., Tsang, S., Williamson, B., Stockert, E., Pfreundschuh, M., and Old, L. J. A testicular antigen aberrantly expressed in human cancers detected by autologous antibody screening. Proc. Natl. Acad. Sci. USA. 1997; 94:1914-18.
5. Jager D, Stockert E, Gure A O, Scanlan M J, Karbach J, Jager E, Knuth A, Old L J, Chen Y T. Identification of a tissue-specific putative transcription factor in breast tissue by serological screening of a breast cancer library. Cancer Res 2001 Mar 1;61(5):2055-61
6. Boel, P., Wildmann, C., Sensi, M. L., Brasseur, R., Renauld, J. C., Coulie, P., Boon, T., and van der Bruggen, P. BAGE: a new gene encoding an antigen recognized on human melanomas by cytolytic T lymphocytes. Immunity 1995; 2: 167-75. (PMID: 7895173)
7. Van den Eynde, B., Peeters, O., De Backer, O., Gaugler, B., Lucas, S., and Boon, T. A new family of genes coding for an antigen recognized by autologous cytolytic T lymphocytes on a human melanoma. J. Exp. Med. 1995; 182: 689-98. (PMID: 7544395)
8. Skipper J C, Hendrickson R C, Gulden P H, Brichard V, Van Pel A, Chen Y, Shabanowitz J, Wolfel T, Slingluff C L Jr, Boon T, Hunt D F, Engelhard V H. An HLA-A2-restricted tyrosinase antigen on melanoma cells results from post-translational modification and suggests a novel pathway for processing of membrane proteins. J Exp Med Feb. 1, 1996;183(2):527-34
9. Cox A L, Skipper J, Chen Y, Henderson R A, Darrow T L, Shabanowitz J, Engelhard V H, Hunt D F, Slingluff C L Jr. Identification of a peptide recognized by five melanoma-specific human cytotoxic T cell lines. Science Apr. 29, 1994;264(5159):716-9
10. Pascolo S, Schirle M, Guckel B, Dumrese T, Stumm S, Kayser S, Moris A, Wallwiener D, Rammensee H G, Stevanovic S. A MAGE-A1 HLA-A A*0201 epitope identified by mass spectrometry. Cancer Res May 15, 2001;61(10):4072-7
11. Sahin, U., Türeci, Ö, Schmitt, H., Cochlovius, B., Johannes, T., Schmits, R., Stenner, F., Luo, G., Schobert, I., and Pfreundschuh, M. Human neoplasms elicit multiple specific immune responses in the autologous host. Proc. Natl. Acad. Sci. USA 1995; 92: 11810-13.
12. Scanlan, M. J., Chen, Y. T., Williamson, B., Gure, A. O., Stockert, E., Gordan, J. D., Tureci, O., Sahin, U., Pfreundschuh, M., and Old, L. J. Characterization of human colon cancer antigens recognized by autologous antibodies. Int. J. Cancer 1998; 76: 652-8.
13. Scanlan, M. J., Gordan, J. D., Williamson, B., Stockert, E., Bander, N. H., Jongeneel, V., Gure, A. O., Jäger, D., Jäger, E., Knuth, A., Chen, Y. -T., and Old, L. J. Antigens recognized by autologous antibody in patients with renal-cell carcinoma. Int. J. Cancer 1999; 83: 456-64.
14. Scanlan M J, et al. Humoral immunity to human breast cancer: antigen definition and quantitative analysis of mRNA expression. Cancer Immunity 1:4 [epub]
15. Jager D, Stockert E, Jager E, Gure A O, Scanlan M J, Knuth A, Old L J, Chen Y T. Serological cloning of a melanocyte rab guanosine 5'-triphosphate-binding protein and a chromosome condensation protein from a melanoma complementary DNA library. Cancer Res Jul. 1, 2000;60(13):3584-91
16. Chen, Y. -T., Scanlan, M. J., Obata, Y., and Old, L. J. Identification of human tumor antigens by serological expression cloning. In: S. A. Rosenberg (ed.). Principles and Practice of Biologic Therapy of Cancer, pp. 557-570. Philadelphia: Lippincott Williams & Wilkins, 2000.
17. Sahin U, et al. 1998. Expression of multiple cancer/testis antigens in breast cancer and melanoma: basis for polyvalent CT vaccine strategies. Int J Cancer 78:387-89.
18. Scanlan M J et al. 2000. Expression of cancer-testis antigens in lung cancer: definition of bromodomain testis-specific gene (BRDT) as a new CT gene, CT9. Cancer Lett. 150:155-64.
19. Van den Eynde B J van der Bruggen P. 1997. T cell defined tumor antigens. Curr Opin Immunol 9:684-693.
20. Jungbluth A A, et al. 2001. Monophasic and biphasic synovial sarcomas abundantly express cancer/testis antigen NY-ESO-1 but not MAGE-AL or CT7. Int J Cancer 94:252-6.
21. Antonescu C R, Busam K J, Iversen K, Kolb D, Coplan K, Spagnoli G C, Ladanyi M, Old L J, Jungbluth A A. MAGE antigen expression in monophasic and biphasic synovial sarcoma. Hum Pathol 2002 February;33(2):225-9
22. Stockert E, et al. 1998. A survey of the humoral immune response of cancer patients to a panel of human tumor antigens. J Exp Med 187:1349-54.
23. Scanlan M J. et al. 2002. Cancer-Related Serological Recognition of Human Colon Cancer: Identification of Potential Diagnostic and Immunotherapeutic Targets. In press
24. Lethe B, et al. 1998. LAGE-1, a new gene with tumor specificity. Int. J. Cancer 76:903-8.
25. Türeci Ö, et al. 1998. Expression of SSX genes in human tumors. Int J Cancer 77:19-23.
26. Gure A O, et al. 1997. SSX: a multigene family with several members transcribed in normal testis and human cancer. Int J Cancer 72:965-971.
27. Li Z, Yao K, Cao Y. Molecular cloning of a novel tissue-specific gene from human nasopharyngeal epithelium. Gene Sep. 3, 1999;237(1):235-40
28. Hoffmann W, Hauser F. The P-domain or trefoil motif: a role in renewal and pathology of mucous epithelia? Trends Biochem Sci 1993 July; 18(7):239-43
29. Chen Y T, et al. 1998. Identification of multiple cancer/testis antigens by allogeneic antibody screening of a melanoma cell line library. Proc. Natl. Acad. Sci. USA. 95:6919-23.
30. Niwa M, Maruyama H, Fujimoto T, Dohi K, Maruyama I N. Affinity selection of cDNA libraries by lambda phage surface display. Gene Oct. 3, 2000;256(1-2):229-36
31. Le Naour F, Misek D E, Krause M C, Deneux L, Giordano T J, Scholl S, Hanash S M. Proteomics-based identification of RS/DJ-1 as a novel circulating tumor antigen in breast cancer. Clin Cancer Res 2001 November;7(11):3328-35

32. Yang X F, Wu C J, McLaughlin S, Chillemi A, Wang K S, Canning C, Alyea E P, Kantoff P, Soiffer R J, Dranoff G, Ritz J. CML66, a broadly immunogenic tumor antigen, elicits a humoral immune response associated with remission of chronic myelogenous leukemia. Proc Natl Acad Sci USA Jun. 19, 2001;98(13):7492-7
33. Jungbluth A A, et al. 2001. Immunohistochemical analysis of NY-ESO-1 antigen expression in normal and malignant human tissues. Int J Cancer 92:856-60.
34. Jungbluth A A, et al. 2000. Expression of MAGE-antigens in normal tissues and cancer. Int J Cancer 85:460-5.
35. Garrido F, Algarra I. MHC antigens and tumor escape from immune surveillance. Adv Cancer Res 2001;83:117-58
36. Conrad C T, Ernst N R, Dummer W, Brocker E B, Becker J C. Differential expression of transforming growth factor beta 1 and interleukin 10 in progressing and regressing areas of primary melanoma. J Exp Clin Cancer Res 1999 June; 18(2):225-32
37. Tomlinson I P, et al. Germline mutations in FH predispose to dominantly inherited uterine fibroids, skin leiomyomata and papillary renal cell cancer. Nat Genet 2002 April;30 (4):406-10
38. Ayyoub M, et al. 2002. Proteasome-assisted identification of a SSX-2-derived epitope recognized by tumor-reactive CTL infiltrating metastatic melanoma. J Immunol 168: 1717-22.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is:

1. A composition comprising an isolated nucleic acid molecule selected from the group consisting of:
   (a) a nucleic acid molecule consisting of a sequence set forth in SEQ ID NO: 10 and which codes for a polypeptide having a sequence set forth as SEQ ID NO: 55 or a fragment thereof that is at least eight amino acids in length,
   (b) nucleic acid molecules that only differ from the nucleic acid molecule of (a) in codon sequence due to the degeneracy of the genetic code, and
   (c) full-length complements of (a) or (b).

2. A composition comprising an isolated nucleic acid molecule, wherein the sequence of the isolated nucleic acid molecule comprises (a) the nucleotide sequence set forth as SEQ ID NO:10, (b) a nucleotide sequence which codes for a polypeptide having the sequence set forth as SEQ ID NO:55 that only differs from the sequence set forth as SEQ ID NO:10 due to the degeneracy of the genetic code or (c) a nucleotide sequence that is a full-length complement of (a) or (b).

3. An expression vector comprising an isolated nucleic acid molecule of the composition of claim 1 or 2 operably linked to a promoter.

4. A host cell transformed or transfected with the expression vector of the composition of claim 3.

5. The composition of claim 1 or 2, further comprising a pharmaceutically acceptable carrier.

6. The host cell of claim 4, wherein the host cell expresses a MHC molecule.

7. The host cell of claim 6, wherein the host cell expresses the MHC molecule recombinantly.

8. A kit, comprising:
   one or more nucleic acid molecules of the composition of claim 1 or 2.

9. The kit of claim 8, wherein the one or more nucleic acid molecules are detectably labeled.

10. The kit of claim 8, wherein the one or more nucleic acid molecules consist of a first primer and a second primer, wherein the first primer and the second primer are constructed and arranged to selectively amplify at least a portion of a nucleic acid molecule the sequence of which comprises the sequence set forth as SEQ ID NO: 10 or the full complement thereof.

11. The kit of claim 8, wherein the nucleic acids are bound to a substrate.

12. The composition of claim 1 or 2, further comprising an adjuvant or cytokine.

13. The composition of claim 1 or 2, further comprising a cytotoxic or chemotherapeutic agent.

14. The composition of claim 5, further comprising a cytotoxic or chemotherapeutic agent.

* * * * *